United States Patent
Ince et al.

(10) Patent No.: US 11,530,385 B2
(45) Date of Patent: Dec. 20, 2022

(54) HORMONE RESPONSIVE TISSUE CULTURE SYSTEM AND USES THEREOF

(71) Applicants: Whitehead Institute for Biomedical Research, Cambridge, MA (US); The Brigham and Women's Hospital, Inc., Boston, MA (US)

(72) Inventors: Tan A. Ince, Miami, FL (US); Robert A. Weinberg, Cambridge, MA (US)

(73) Assignees: Whitehead Institute for Biomedical Research, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 199 days.

(21) Appl. No.: 15/665,686

(22) Filed: Aug. 1, 2017

(65) Prior Publication Data

US 2018/0282691 A1    Oct. 4, 2018

Related U.S. Application Data

(63) Continuation of application No. 12/672,786, filed as application No. PCT/US2008/009639 on Aug. 11, 2008, now abandoned.

(60) Provisional application No. 60/964,271, filed on Aug. 10, 2007.

(51) Int. Cl.
  *C12N 5/09*   (2010.01)
  *C12N 5/071*   (2010.01)

(52) U.S. Cl.
  CPC ......... *C12N 5/0631* (2013.01); *C12N 5/0693* (2013.01); *C12N 2500/20* (2013.01); *C12N 2500/22* (2013.01); *C12N 2500/25* (2013.01); *C12N 2500/32* (2013.01); *C12N 2500/36* (2013.01); *C12N 2500/38* (2013.01); *C12N 2500/40* (2013.01); *C12N 2500/50* (2013.01); *C12N 2501/01* (2013.01); *C12N 2501/11* (2013.01); *C12N 2501/392* (2013.01); *C12N 2501/395* (2013.01); *C12N 2503/02* (2013.01); *C12N 2510/04* (2013.01)

(58) Field of Classification Search
  CPC .............. C12N 5/0631; C12N 2510/04; C12N 2500/20; C12N 2500/22; C12N 2500/25; C12N 2500/32; C12N 2500/36; C12N 2500/38; C12N 2500/40; C12N 2500/50; C12N 2501/01; C12N 2501/11; C12N 2501/392; C12N 2501/395; C12N 2503/02; C12N 5/0693
  See application file for complete search history.

(56) References Cited

U.S. PATENT DOCUMENTS

| | | |
|---|---|---|
| 4,657,866 A | 4/1987 | Kumar |
| 5,326,699 A | 7/1994 | Torishima et al. |
| 5,405,772 A | 4/1995 | Ponting |
| 5,443,954 A | 8/1995 | Reddel et al. |
| 5,529,920 A | 6/1996 | Cole et al. |
| 5,691,203 A * | 11/1997 | Katsuen et al. ............. 435/402 |
| 5,710,038 A | 1/1998 | Mes-Masson et al. |
| 5,712,163 A | 1/1998 | Parenteau et al. |
| 5,780,299 A | 7/1998 | Coon et al. |
| 5,814,511 A | 9/1998 | Chang et al. |
| 6,277,891 B1 | 8/2001 | Sanders et al. |
| 6,383,805 B1 | 5/2002 | Latimer |
| 6,451,601 B1 | 9/2002 | Baetge et al. |
| 8,252,591 B2 | 8/2012 | Ince et al. |
| 8,936,939 B2 | 1/2015 | Ince et al. |
| 2002/0119565 A1 | 8/2002 | Clarke et al. |
| 2004/0037815 A1 | 2/2004 | Clarke et al. |
| 2005/0123521 A1 | 6/2005 | Zern et al. |

(Continued)

FOREIGN PATENT DOCUMENTS

| | | | |
|---|---|---|---|
| EP | 1000541 A1 | 5/2000 | |
| RU | 2103352 C1 * | 1/1998 | ............... C12N 1/18 |

(Continued)

OTHER PUBLICATIONS

Ince T. A. et al., "Characterization of twenty-five ovarian tumour cell lines that phenocopy primary tumours", Nat. Commun., 6: 7419; doi:10.1038/ncomms8419 (2015); (NPL already provided on record by applicants on Apr. 28, 2022 as Exhibits A and B). (Year: 2015).*

(Continued)

*Primary Examiner* — Satyendra K Singh
(74) *Attorney, Agent, or Firm* — Foley Hoag LLP; David P. Halstead

(57) ABSTRACT

The invention provides tissue culture system for primary cells (e.g. normal mammalian primary epithelial progenitors). This system includes: a) a serum-free, chemically defined cell culture media; and, b) methods for isolation and in vitro long-term propagation of primary cells (e.g. primary epithelial cells). Primary cells so isolated and cultured can be kept undifferentiated and proliferate for many weeks (>15 weeks) or population doubling (>35 PD) without senescence, or any detectable genetic alterations. Upon changing media/culture conditions, these cells can be induced to differentiate.

The invention also provides methods to transform normal primary cells so cultured into "cancer stem cells." The genetically defined cancer stem cell tumor model mimics the behavior of the disease closely, e.g., the cells are invasive, hormone responsive and metastatic when injected into mice. The tumor cells express genes that are specific to cancer stem cells identified in patient samples.

6 Claims, 103 Drawing Sheets

(56) References Cited

U.S. PATENT DOCUMENTS

| | | | |
|---|---|---|---|
| 2005/0226856 A1* | 10/2005 | Ahlfors | 424/93.7 |
| 2006/0019256 A1 | 1/2006 | Clarke et al. | |
| 2006/0252073 A1 | 11/2006 | Yilmaz et al. | |
| 2008/0299540 A1 | 12/2008 | Ince et al. | |
| 2011/0244502 A1 | 10/2011 | Ince et al. | |
| 2013/0055417 A1 | 2/2013 | Ince et al. | |
| 2018/0155687 A1 | 6/2018 | Ince et al. | |

FOREIGN PATENT DOCUMENTS

| | | |
|---|---|---|
| RU | 2404244 C2 | 11/2010 |
| WO | WO-2000/073420 A2 | 12/2000 |
| WO | WO-2009/023194 A2 | 2/2009 |

OTHER PUBLICATIONS

Al-Hajj et al., "Prospective identification of tumorigenic breast cancer cells," Proc. Natl. Acad. Sci. U.S.A. 100(7):3983-8 (2003).
Alkhalaf et al., "Proliferation of Guinea-Pig Uterine Epithelial Cells in Serum-Free Culture Conditions: Effect of 17b-Estradiol, Epidermal Growth Factor and Insulin," J. Steroid Biochem. Molec. Biol. 38(3):345-350 (1991).
Anantamongkol et al., "Prolactin and Dexamethasone Regulate Second Messenger-Stimulated Cl- Secretion in Mammary Epithelia," Journal of Signal Transduction 1-15 (2012).
Bocker et al., "Common adult stem cells in the human breast give rise to glandular and myoepithelial cell lineages: a new cell biological concept," Lab Invest. 82(6):737-46 (2002).
Boyce et al., "Calcium-regulated differentiation of normal human epidermal keratinocytes in chemically defined clonal culture and serum-free serial culture," J Invest Dermatol. 81(1):33s-40 (1983).
Dick, "Breast cancer stem cells revealed," Proc. Natl. Acad. Sci. U.S.A. 100(7):3547-3549 (2003).
Dicken et al., "Blood Chemistry and CBC Analysis—Clinical Laboratory Testing From a Functional Perspective," Book published by Bear Mountain Publishing, Table of Contents and pp. 261-279 (2002).
Dixon et al., "Extracellular nucleotides stimulate proliferation in MCF-7 breast cancer cells via P2-purinoceptors," British Journal of Cancer 75(1):34-39 (1997).
Elenbaas et al., "Human breast cancer cells generated by oncogenic transformation of primary mammary epithelial cells," Genes Dev. 15(1):50-65 (2001).
Extended European Search Report from corresponding application EP 12761150.7.
Fitz "Regulation of Cellular ATP Release," Transactions of the American Clinical and Climatological Association 118:199-208 (2007).
Garcia I. et al., "Establishment of Two Rabbit Mammary Epithelial Cell Lines with Distinct Oncogenic Potential and Differentiated Phenotype after Microinjection of Transforming Genes", *Molecular and Cellular Biology*, 6(6): 1974-1982 (Jun. 1986).
Gordon et al., "Extracellular ATP: effects, sources and fate," Biochem. J. 233:309-319 (1986).
Gudjonsson et al. "Isolation, immortalization, and characterization of a human breast epithelial cell line with stem cell properties," Genes Dev. 16(6): 693-706 (2002).
HAM'S nutrient mixtures: Sigma-Aldrich, at the web—www.sigmaaldrich.com, see pp. 1-13 (print date Oct. 10, 2007).
Hammond et al., "Serum-free growth of human mammary epithelial cells: rapid clonal growth in defined medium and extended serial passage with pituitary extract," Proc. Natl. Acad. Sci. U.S.A. 81(17): 5435-9, 1984.
He et al., "Nucleotide, Supplements Alter Proliferation and Differentiation of Culture Human (Caco-2) and Rat (IEC-6) Intestinal Epithelial Cells1,2," Biochemical and Molecular Roles of Nutients, J. Nutr. 123:1017-1027 (1993).
Iguchi et al., "Growth of normal mouse vaginal epithelial cells in an on collagen gels," Proc. Natl. Acad. Sci. 80:3743-3747 (1983).

Imagawa et al., "Serum-free Growth of Normal and Tumor Mouse Mammary Epithelial Cells in Primary Culture," Proceedings of the National Academy of Sciences of the USA, 79:4074-4077 (1982).
Ince et al., "Transformation of different human breast epithelial cell types leads to distinct tumor phenotypes," Cancer Cell 12(2):160-170 (2007).
International Search Report and Written Opinion for PCT/US2012/030446 dated Jul. 19, 2012.
Khakh et al., "P2X receptors as cell-surface ATP sensors in health and disease," Nature 422(3):527-532 (2006).
Lechner et al., "A Serum-Free Method For Culturing Norman Human Bronchial Epithelialcells At Clonal Density," Journal Of Tissue Culture Methods 9(2):43-48 (1995).
Lee et al., "Clonal expansion of adult rat hepatic stem cell lines by suppression of asymmetric cell kinetics (SACK)," *Biotechnol. Bioeng.* 83(7):760-771 (2003).
Liu et al., "A Genetically Defined Model for Human Ovarian Cancer," *Cancer Res.* 64(5):1655-1663 (2004).
Lundberg et al., "Immortalization and transformation of primary human airway epithelial cells by gene transfer," *Oncogene* 21(29):4577-4586 (2002).
Marx, J. "Cancer research. Mutant Stem Cells May Seed Cancer," *Science* 301(5638):1308-1310 (2003).
Matouskova et al., "Temporal in vitro expansion ofthe luminal lineage of human mammary epithelial cells achieved with the 3T3 feeder layer technique," Breast Cancer Res. Treat. 60(3):241-249 (2000).
Moutsatou "The spectrum of phytoestrogens in nature: our knowledge is expanding," Hormones 6(3):173-193 (2007).
Musante et al., "Autocrine Regulation of Volume-sensitive Anion Channels in Airway Epithelial Cells by Adensone," The Journal of Biological Chemistry 271(17):11701-11707 (1999).
Occhiuto et al., "The phytoestrogenic isoflavones from *Trifolium pratense* L. (Red clover) protects human cortical neurons from glutamate toxicity," Phtomedicine 15(9):676-682 (2008).
Pechoux et al., "Human mammary luminal epithelial cells contain progenitors to myoepithelial cells," Dev. Biol. 206(1):88-99 (1999).
Penttinen et al., "Diet-Derived Polyphenol Metabolite Enterolactone Is a Tissue-Specific Estrogen Receptor Activator Endocrinology," 148(10):4875-4886 (2007).
Prie et al., "Role of adenosine on glucagon-induced cAMP in a human cortical collecting duct cell line," Kidney Intl, 47:1310-8 (1995).
Print out from http://www.tocris.com/pharmacologicalBrowser.php?ItemId=80335. Last visited on May 5, 2010.
Print-out from ftp://occams.dfci.harvard.edu/pub/bio/tgi/data/other/OCFNLER_manuscript_TAI_MM_1.27.2011.doc, p. 1-24.
Print-out from www.cambrex.com/catnav.oid.692.prodoid.Mammedia (last visited on Sep. 26, 2006).
Print-out from www.cambrex.com/RelatedCatNav.catorg.17100.oid.534.prodoid.HMEC (last visited on Sep. 26, 2006).
Print-out from www.lbl.gov/LBL-Programs/mrgs/review.html (last visited on Aug. 25, 2006).
Rambhatla et al., "Cellular Senescence: Ex Vivo p53-Dependent Asymmetric Cell Kinetics," J. Biomed. *Biotechnol.* 1(1):28-37 (2001).
Rangarajan et al., "Species and cell type-specific requirements for cellular transformation," Cancer Cell. 6(2):171-83 (2004).
Reigada et al., "Degradation of extracellular ATP by the retinal pigment epithelium," Am. J. Physiol Cell Physiol. 289:C617-C624 (2005).
Reya et al., "Stem cells, cancer, and cancer stem cells," Nature 414(6859):105-11 (2001).
Richards et al. "Response of end bud cells from immature rat mammary gland to hormones when cultured in collagen gel," Exp Cell Res. 147:95-109 (1983).
Sakuma et al., "Stimulation of cAMP production and cyclooxygenase-2 by prostaglandin E2 and selective prostaglandin receptor agonists in murine osteoblastic cells," Bone, 34:827-34 (2004).
Sherley et al., "Asymmetric cell kinetics genes: the key to expansion of adult stem cells in culture," Stem Cells 20(6):561-72 (2002).

(56) References Cited

OTHER PUBLICATIONS

Sherley et al., "Expression of the wild-type p53 antioncogene induces guanine nucleotide-dependent stem cell division kinetics," *Proc. Natl. Acad. Sci. U.S.A.* 92(1):136-40 (1995).

Sinelnik et al., "The Detergent Properties of the Bile Acids and Their Action on Bile Secretions," Fiziol Zh, 45(3): 18-27 (1999).

Speirs et al., "Short-term primary culture of epithelial cells derived from human breast tumours," Br. J. Cancer 78(11):1421-1429 (1998).

Stampfer et al. "Culture systems for study of human mammary epithelial cell proliferation, differentiation and transformation," Cancer Surv. 18:7-34 (1993).

Stampfer et al., "Human mammary epithelial cells in culture: differentiation and transformation," Cancer Treat Res. 40:1-24 (1988).

Stingl et al., "Characterization of bipotent mammary epithelial progenitor cells in normal adult human breast tissue," *Breast* Cancer Res. Treat. 67(2):93-109 (2001).

Suard et al., "Cell Proliferation and Milk Protein in Rabbit Mammary Cell Cultures," Journal of Cell Biology 96:1435-1442 (1983).

Tan et al., "Tranformation of different human breast epithelial cell types leads to distinct tumor phenotypes," Cancer Cell 12(2):160-170 (2007).

Wagner et al., "An adjunct mammary epithelial cell population in parous females: its role in functional adaptation and tissue renewal," Development 129(6):1377-86 (2002).

Wikipedia, "List of Human Blood Components," Wikipedia, retrieved from the Internet <http://en.wikipedia.org/wiki/List_of_human_blood_components, accessed on Oct. 26, 2015.

Yang et al., "Sustained growth in primary culture of normal mammary epithelial cells embedded in collagen gels," Proc. Natl. Acad. Sci, USA 77(4):2088-2092 (1980).

Zhao et al., "Neuroprotective and Neurotrophic Efficacy of Phytoestrogen in Cultured Hippocampal Neurons," Ex. Biol. Med. 227(7):509-519 (2002).

\* cited by examiner

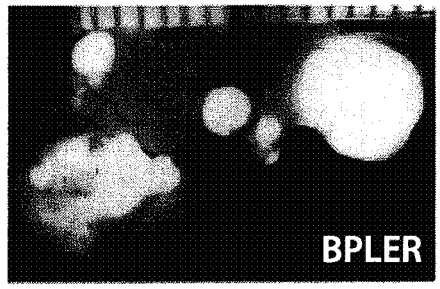
Fig. 20A
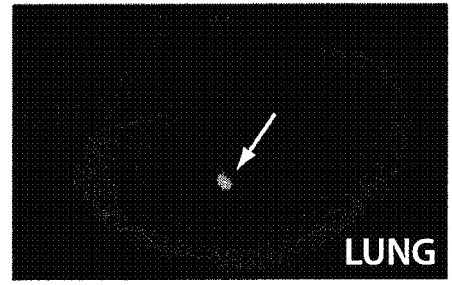
Fig. 20C
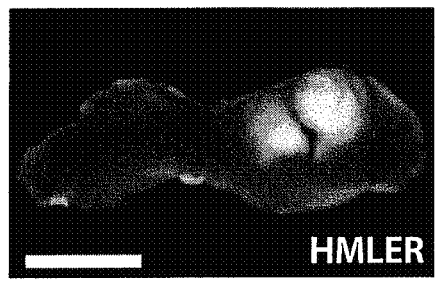
Fig. 20B
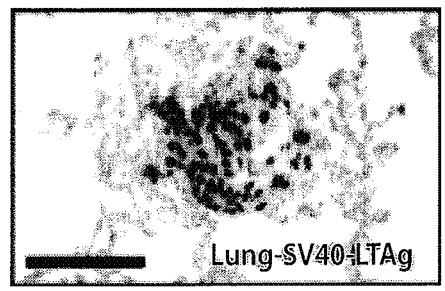
Fig. 20D
| FREQUENCY OF METASTASIS | BPLER-1 | BPLER-2 | HMLER |
|---|---|---|---|
| ORTHOTOPIC | 10 / 11 | 6 / 8 * | 0 / 8 * |
| SUBCUTANEOUS | 9 / 10 | 8 / 12 | 0 / 6 |
Fig. 20E

BPLER

| CELLS INJECTED | TUMORS / INJECTION | | |
|---|---|---|---|
| | 1 | 2 | 3 |
| $10^6$ | 9/9 | 9/9 | 9/9 |
| $10^5$ | 9/9 | 9/9 | 12/12 |
| $10^4$ | 9/9 | 9/9 | 12/12 |
| $10^3$ | 8/15 | 9/9 | 9/12 |
| $10^2$ | - | 10/12 | 4/9 |

Fig. 22A

HMLER

| CELLS INJECTED | TUMORS / INJECTION | |
|---|---|---|
| | MEGM | WIT |
| $10^6$ | 4/12 | 5/9 |
| $10^5$ | 0/12 | 1/12 |
| $10^4$ | 0/12 | 0/12 |
| $10^3$ | 0/12 | 0/12 |
| $10^2$ | - | - |

Fig. 22B

BPLER

| CELLS INJECTED | PRIMARY TUMOR/ INJECTION | LUNG METASTASIS | PRIMARY TUMOR BURDEN (gm) | TIME (WEEKS) |
|---|---|---|---|---|
| $10^5$ | 12/12 | 3/4 | 1.26 ± 0.11 | 10 wk. |
| $10^4$ | 12/12 | 3/4 | 1.12 ± 0.11 | 10 wk. |
| $10^3$ | 9/12 | 1/3 | 0.76 ± 0.24 | 10 wk. |
| $10^2$ | 8/12 | 2/4 | 2.04 ± 0.35 | 18 wk. |

Fig. 22C

BPLER

HMLER

BPLER

HMLER

HUMAN BREAST
ADENOCARCINOMA

HUMAN BREAST
ADENOCARCINOMA

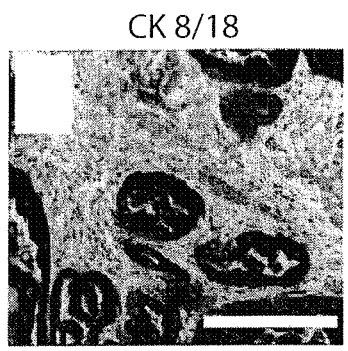
Fig. 27C CK 8/18
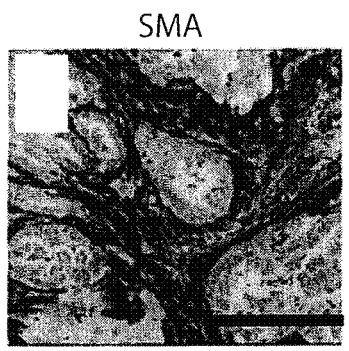
Fig. 27D SMA
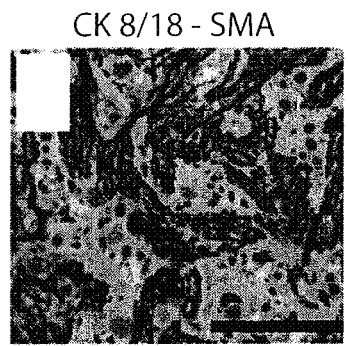
Fig. 27E CK 8/18 - SMA
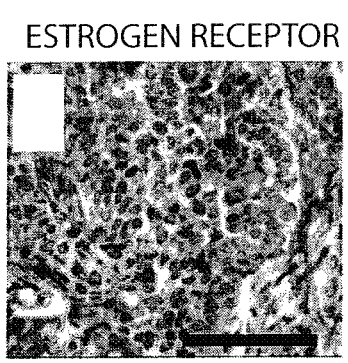
Fig. 27F ESTROGEN RECEPTOR
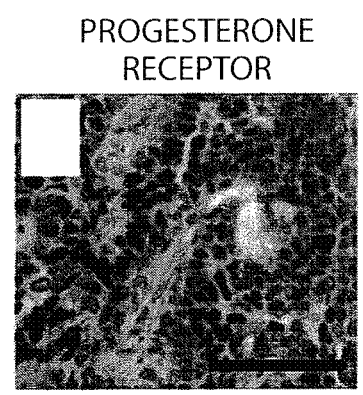
Fig. 27G PROGESTERONE RECEPTOR
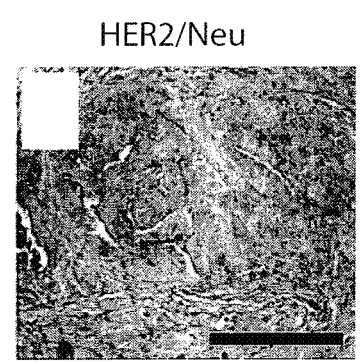
Fig. 27H HER2/Neu 1: The genes that are differentially expressed ≥ 2-fold between BPEC and HMEC populations (n=3).

| ACCESSION | UP REGULATED CLASS | T-TEST | FOLD CHANGE | BPEC MEAN | HMEC MEAN | GENE SYMBOL |
|---|---|---|---|---|---|---|
| 232082_x_at | BPEC | 1.8088 | 95.7343 | 2846.5 | 29.73 | |
| 218990_s_at | BPEC | 2.0942 | 56.7684 | 1388.93 | 24.47 | SPRR3 |
| 1553081_at | BPEC | 1.5638 | 46.2209 | 2301.8 | 49.8 | WFDC12 |
| 219990_at | BPEC | 5.6316 | 45.5233 | 292.87 | 6.43 | FLJ23311 |
| 210065_s_at | BPEC | 1.5322 | 37.8803 | 3313.27 | 87.47 | |
| 223861_at | BPEC | 1.1114 | 36.7702 | 197.33 | 5.37 | DKFZp434A1315 |
| 213796_at | BPEC | 4.1415 | 36.1989 | 22793.23 | 629.67 | |
| 230835_at | BPEC | 3.8266 | 28.1689 | 1495.77 | 53.1 | |
| 236119_s_at | BPEC | 1.0351 | 27.2777 | 1548.47 | 56.77 | |
| 206504_at | BPEC | 4.2644 | 26.9129 | 1647.07 | 61.2 | CYP24 |
| 224328_s_at | BPEC | 1.2178 | 24.5209 | 4106.43 | 167.47 | |
| 219911_s_at | BPEC | 5.7698 | 22.9341 | 347.83 | 15.17 | SLC21A12 |
| 204351_at | BPEC | 2.4755 | 19.9372 | 8814.23 | 442.1 | S100P |
| 210064_s_at | BPEC | 1.7668 | 19.6582 | 3370.07 | 171.43 | UPK1B |
| 211597_s_at | BPEC | 3.1209 | 19.0209 | 2461.3 | 129.4 | |
| 1560848_at | BPEC | 1.8141 | 18.9737 | 72.1 | 3.8 | |
| 209680_s_at | BPEC | 13.8288 | 18.3558 | 734.23 | 40 | |
| 206023_at | BPEC | 3.2078 | 18.0991 | 1479.9 | 81.77 | NMU |
| 206914_at | BPEC | 2.0125 | 18.0875 | 96.47 | 5.33 | CRTAM |
| 220620_at | BPEC | 2.7653 | 17.9967 | 5607.17 | 311.57 | NICE-1 |
| 223720_at | BPEC | 3.438 | 17.7564 | 413.13 | 23.27 | |
| 209773_s_at | BPEC | 4.2367 | 17.2775 | 6779.7 | 392.4 | |
| 208539_x_at | BPEC | 2.4879 | 16.8719 | 3385.07 | 200.63 | SPRR2B |
| 206193_s_at | BPEC | 1.1969 | 16.8413 | 2840.57 | 168.67 | CDSN |
| 215101_s_at | BPEC | 1.865 | 16.7652 | 368.83 | 22 | |
| 205625_s_at | BPEC | 13.2899 | 16.7381 | 2711.57 | 162 | |
| 235591_at | BPEC | 1.7951 | 16.4174 | 390.73 | 23.8 | |
| 1557842_at | BPEC | 3.1414 | 16.2059 | 36.73 | 2.27 | |
| 222223_s_at | BPEC | 3.3634 | 15.7097 | 425.73 | 27.1 | |
| 239680_at | BPEC | 9.994 | 15.2862 | 75.33 | 4.83 | |
| 201890_at | BPEC | 3.381 | 15.3557 | 6307.6 | 410.77 | |
| 222962_s_at | BPEC | 6.6718 | 15.2304 | 420.87 | 27.63 | HsMCM10 |
| 205626_s_at | BPEC | 11.9748 | 15.1025 | 1600.37 | 105.97 | CALB1 |
| 205403_at | BPEC | 4.4821 | 14.8676 | 1231.53 | 82.83 | IL1R2 |
| 219795_at | BPEC | 2.5299 | 14.786 | 3904.5 | 264.07 | SLC6A14 |
| 243871_at | BPEC | 2.1293 | 14.7538 | 545.4 | 36.97 | |
| 205900_at | BPEC | 1.8851 | 13.5503 | 713.2 | 52.63 | KRT1 |
| 231148_at | BPEC | 3.9227 | 13.5302 | 2577.5 | 190.5 | |

Fig. 31

| | | | | | | |
|---|---|---|---|---|---|---|
| 206336_at | BPEC | 2.7853 | 13.3535 | 788.3 | 59.03 | SCYB6 |
| 203418_at | BPEC | 4.3637 | 13.3444 | 1224.57 | 91.77 | CCNA2 |
| 223484_at | BPEC | 3.1451 | 13.2796 | 3123.37 | 235.2 | NMES1 |
| 205085_at | BPEC | 6.2219 | 13.0061 | 355.5 | 27.33 | ORC1L |
| 1566606_a_at | BPEC | 2.3038 | 12.9468 | 40.57 | 3.13 | |
| 220651_s_at | BPEC | 8.1006 | 12.8856 | 750.8 | 58.27 | PRO2249 |
| 1564007_at | BPEC | 2.1812 | 12.7402 | 53.93 | 4.23 | |
| 219650_at | BPEC | 5.5755 | 12.4169 | 505.37 | 40.7 | FLJ20105 |
| 219493_at | BPEC | 5.8173 | 12.4032 | 1518.57 | 122.43 | FLJ22009 |
| 203213_at | BPEC | 3.8748 | 12.1041 | 5349.2 | 441.93 | |
| 235706_at | BPEC | 5.8939 | 12.1004 | 184.73 | 15.27 | |
| 239230_at | BPEC | 7.3154 | 12.089 | 584.3 | 48.33 | |
| 203757_s_at | BPEC | 3.4844 | 11.9675 | 1485.17 | 124.1 | |
| 1554921_a_at | BPEC | 4.6583 | 11.7483 | 1496.73 | 127.4 | |
| 1569983_at | BPEC | 2.1391 | 11.7297 | 43.4 | 3.7 | |
| 223381_at | BPEC | 4.698 | 11.6891 | 823.3 | 70.43 | |
| 201650_at | BPEC | 1.6065 | 11.6879 | 7468.57 | 639 | KRT19 |
| 207442_at | BPEC | 2.9134 | 11.644 | 171.17 | 14.7 | CSF3 |
| 235272_at | BPEC | 2.8924 | 11.5079 | 3086.8 | 268.23 | |
| 214549_x_at | BPEC | 110.9876 | 11.4539 | 21466.2 | 1874.13 | SPRR1A |
| 203764_at | BPEC | 4.2496 | 11.4373 | 2494.87 | 218.13 | KIAA0008 |
| 243818_at | BPEC | 3.3302 | 11.3303 | 210.37 | 18.57 | |
| 219978_s_at | BPEC | 3.8916 | 11.3159 | 1242.87 | 109.83 | BM037 |
| 226707_at | BPEC | 0.9788 | 11.1136 | 326 | 29.33 | |
| 211657_at | BPEC | 3.5595 | 11.1105 | 2721.33 | 244.93 | NCA |
| 201710_at | BPEC | 2.5495 | 11.0722 | 414.1 | 37.4 | MYBL2 |
| 229551_x_at | BPEC | 5.7959 | 10.955 | 632.83 | 57.77 | |
| 1569850_at | BPEC | 2.774 | 10.9461 | 74.43 | 6.8 | |
| 220723_s_at | BPEC | 3.3719 | 10.83 | 3209.3 | 296.33 | FLJ21511 |
| 244111_at | BPEC | 4.5439 | 10.6779 | 127.07 | 11.9 | |
| 207752_x_at | BPEC | 1.9707 | 10.6671 | 511.67 | 47.97 | PRB1 |
| 206642_at | BPEC | 2.6744 | 10.6478 | 1592.2 | 149.53 | DSG1 |
| 205024_s_at | BPEC | 4.8459 | 10.5683 | 939.17 | 88.87 | RAD51 |
| 206884_s_at | BPEC | 6.525 | 10.5575 | 5056.7 | 478.97 | SCEL |
| 1566764_at | BPEC | 4.3102 | 10.5569 | 597.17 | 56.57 | |
| 1557196_a_at | BPEC | 3.2209 | 10.5047 | 112.4 | 10.7 | |
| 236534_at | BPEC | 9.4183 | 10.3785 | 273.3 | 26.33 | |
| 235019_at | BPEC | 3.1005 | 10.3195 | 165.8 | 16.07 | |
| 242856_at | BPEC | 3.4118 | 10.3041 | 192 | 18.63 | |
| 207165_at | BPEC | 5.4515 | 10.2975 | 2371.87 | 230.33 | HMMR |

Fig. 31 (Cont.)

| | | | | | | |
|---|---|---|---|---|---|---|
| 1559849_at | BPEC | 2.241 | 10.2593 | 27.7 | 2.7 | |
| 234855_at | BPEC | 4.0312 | 10.2316 | 64.8 | 6.33 | |
| 208134_x_at | BPEC | 1.3631 | 10.1634 | 394 | 38.77 | PSG2 |
| 232056_at | BPEC | 8.5014 | 10.1343 | 2196.43 | 216.73 | |
| 204886_at | BPEC | 8.1458 | 10.1055 | 376.93 | 37.3 | |
| 211814_s_at | BPEC | 4.7188 | 10.0756 | 231.07 | 22.93 | |
| 214974_x_at | BPEC | 1.4811 | 10.066 | 2573.53 | 255.67 | |
| 213693_s_at | BPEC | 1.72 | 10.0358 | 1964.33 | 195.73 | |
| 1553973_a_at | BPEC | 5.9415 | 10.0301 | 21172.1 | 2110.87 | |
| 232278_s_at | BPEC | 6.1414 | 10.0092 | 691.63 | 69.1 | sdp35 |
| 1566766_a_at | BPEC | 11.5545 | 9.9548 | 579.37 | 58.2 | |
| 210559_s_at | BPEC | 5.1046 | 9.6742 | 2416.93 | 249.83 | |
| 220724_at | BPEC | 5.1868 | 9.6361 | 2125.73 | 220.6 | FLJ21511 |
| 219148_at | BPEC | 5.1559 | 9.6039 | 3600.2 | 374.87 | TOPK |
| 220414_at | BPEC | 2.0414 | 9.6033 | 506.73 | 52.77 | CLSP |
| 203214_x_at | BPEC | 4.3079 | 9.5767 | 2140.07 | 223.47 | CDC2 |
| 205759_s_at | BPEC | 6.1087 | 9.4851 | 994.03 | 104.8 | SULT2B1 |
| 208017_s_at | BPEC | 1.7588 | 9.4575 | 174.33 | 18.43 | MCF2 |
| 202094_at | BPEC | 4.1506 | 9.4258 | 542.3 | 57.53 | |
| 231120_x_at | BPEC | 3.4818 | 9.3839 | 1254 | 133.63 | |
| 235545_at | BPEC | 13.8911 | 9.2912 | 671.13 | 72.23 | |
| 221521_s_at | BPEC | 4.4005 | 9.2564 | 1144.4 | 123.63 | |
| 209278_s_at | BPEC | 3.2939 | 9.2346 | 3665.83 | 396.97 | |
| 204822_at | BPEC | 7.9947 | 9.1918 | 1323 | 143.93 | TTK |
| 1555383_a_at | BPEC | 2.4638 | 9.1346 | 352.9 | 38.63 | |
| 202503_s_at | BPEC | 4.4805 | 9.046 | 9150.3 | 1011.53 | KIAA0101 |
| 237330_at | BPEC | 18.6899 | 9.0288 | 31.3 | 3.47 | |
| 223574_x_at | BPEC | 1.8725 | 9.0149 | 181.5 | 20.13 | |
| 212657_s_at | BPEC | 10.6808 | 8.9965 | 8525.97 | 947.7 | |
| 216243_s_at | BPEC | 3.0455 | 8.9208 | 2606.37 | 292.17 | |
| 243727_at | BPEC | 1.4788 | 8.8617 | 55.53 | 6.27 | |
| 211372_s_at | BPEC | 3.5612 | 8.8173 | 683.63 | 77.53 | |
| 1552619_a_at | BPEC | 4.4322 | 8.753 | 2512.7 | 287.07 | ANLN |
| 234233_s_at | BPEC | 3.0842 | 8.6364 | 164.67 | 19.07 | |

Fig. 31 (Cont.)

RELATIVE EXPRESSION OF MAMMARY LUMINAL-CELL-SPECIFIC GENES IN BPEC vs HMEC

| Affymetrix_ID | Grigoriadis myoepithelial/luminal log2 ratio | BPEC/HMEC (log2 ratio) | HMEC/BPEC (log2 ratio) | BPEC/HMEC (log2 ratio) | HMEC/BPEC (log2 ratio) | Gene Symbol |
|---|---|---|---|---|---|---|
| 214701_s_at | -2.58 | -6.62924492 | 6.62924492 | same | different | FN1 |
| 221577_x_at | -1.21 | -5.66367831 | 5.66367831 | same | different | GDF15 |
| 205206_at | -1.97 | -4.73634316 | 4.73634316 | same | different | KAL1 |
| 202295_s_at | -0.84 | -4.07359500 | 4.07359500 | same | different | CTSH |
| 209955_s_at | -1.03 | -4.04810260 | 4.04810260 | same | different | FAP |
| 215646_s_at | -2.20 | -3.72369249 | 3.72369249 | same | different | CSPG2 |
| 202672_s_at | -0.72 | -3.34656395 | 3.34656395 | same | different | ATF3 |
| 203423_at | -0.70 | -3.33338606 | 3.33338606 | same | different | RBP1 |
| 220407_s_at | -1.80 | -3.17337255 | 3.17337255 | same | different | TGFB2 |
| 209101_at | -0.70 | -2.88783255 | 2.88783255 | same | different | CTGF |
| 212503_s_at | -0.41 | -2.86213849 | 2.86213849 | same | different | DIP2C |
| 208868_s_at | -0.68 | -2.80769150 | 2.80769150 | same | different | GABARAPL1 |
| 226279_at | -0.70 | -2.78217529 | 2.78217529 | same | different | PRSS23 |
| 211138_s_at | 0.53 | -2.65513061 | 2.65513061 | different | same | KMO |
| 227529_s_at | -2.08 | -2.62716327 | 2.62716327 | same | different | AKAP12 |
| 221011_s_at | -1.23 | -2.56976395 | 2.56976395 | same | different | LBH |
| 222450_at | -0.86 | -2.54350354 | 2.54350354 | same | different | TMEPAI |
| 226403_at | -0.82 | -2.49404196 | 2.49404196 | same | different | TMC4 |
| 226122_at | -0.54 | -2.48845651 | 2.48845651 | same | different | PLEKHG1 |
| 209581_at | -0.44 | -2.43757372 | 2.43757372 | same | different | HRASLS3 |
| 202637_s_at | -0.72 | -2.43435527 | 2.43435527 | same | different | ICAM1 |
| 219232_s_at | -1.15 | -2.40762053 | 2.40762053 | same | different | EGLN3 |
| 1561969_at | -2.52 | -2.36584653 | 2.36584653 | same | different | ZPLD1 |
| 230708_at | -0.55 | -2.30991108 | 2.30991108 | same | different | PRICKLE1 |
| 205476_at | -0.92 | -2.27744119 | 2.27744119 | same | different | CCL20 |

Fig. 32A

| Gene Title | Entrez Gene |
|---|---|
| fibronectin 1 | 2335 |
| growth differentiation factor 15 | 9518 |
| Kallmann syndrome 1 sequence | 3730 |
| cathepsin H | 1512 |
| fibroblast activation protein, alpha | 2191 |
| chondroitin sulfate proteoglycan 2 (versican) | 1462 |
| activating transcription factor 3 | 467 |
| retinol binding protein 1, cellular | 5947 |
| transforming growth factor, beta 2 | 7042 |
| connective tissue growth factor | 1490 |
| DIP2 disco-interacting protein 2 homolog C (Drosophila) | 22982 |
| GABA(A) receptor-associated protein like 1 | 23710 |
| protease, serine, 23 | 11098 |
| kynurenine 3-monooxygenase (kynurenine 3-hydroxylase) | 8564 |
| A kinase (PRKA) anchor protein (gravin) 12 | 9590 |
| limb bud and heart development homolog (mouse) | 81606 |
| transmembrane, prostate androgen induced RNA | 56937 |
| transmembrane channel-like 4 | 147798 |
| pleckstrin homology domain containing, family G member 1 | 57480 |
| HRAS-like suppressor 3 | 11145 |
| intercellular adhesion molecule 1 (CD54), human rhinovirus receptor | 3383 |
| egl nine homolog 3 (C. elegans) | 112399 |
| zona pellucida-like domain containing 1 | 131368 |
| Prickle homolog 1 (Drosophila) | 144165 |
| chemokine (C-C motif) ligand 20 | 6364 |

Fig. 32A (Cont.)

| | | | | | |
|---|---|---|---|---|---|
| 224733_at | -0.70 | -2.26922311 | 2.26922311 | same | different | CMTM3 |
| 203325_s_at | -0.63 | -2.26781426 | 2.26781426 | same | different | COL5A1 |
| 201363_s_at | -0.62 | -2.26343093 | 2.26343093 | same | different | IVNS1ABP |
| 231236_at | -0.61 | -2.25596515 | 2.25596515 | same | different | ZFP57 |
| 211966_at | -1.22 | -2.25317566 | 2.25317566 | same | different | COL4A2 |
| 205659_at | -1.26 | -2.07841191 | 2.07841191 | same | different | HDAC9 |
| 211981_at | -1.58 | -2.05165046 | 2.05165046 | same | different | COL4A1 |
| 206382_s_at | -0.90 | -2.02204005 | 2.02204005 | same | different | BDNF |
| 235857_at | -0.44 | -2.01028075 | 2.01028075 | same | different | KCTD11 |
| 208084_at | -2.08 | -1.92457655 | 1.92457655 | same | different | ITGB6 |
| 202897_at | -0.45 | -1.90261167 | 1.90261167 | same | different | SIRPA |
| 209589_s_at | -1.40 | -1.88098746 | 1.88098746 | same | different | EPHB2 |
| 201242_s_at | -0.68 | -1.87105990 | 1.87105990 | same | different | ATP1B1 |
| 219049_at | -0.79 | -1.82024604 | 1.82024604 | same | different | ChGn |
| 218627_at | -0.43 | -1.71650389 | 1.71650389 | same | different | DRAM |
| 203872_at | -1.26 | -1.65467896 | 1.65467896 | same | different | ACTA1 |
| 219736_at | -0.89 | -1.64024660 | 1.64024660 | same | different | TRIM36 |
| 202531_at | -0.58 | -1.61973052 | 1.61973052 | same | different | IRF1 |
| 212122_at | -0.97 | -1.61772873 | 1.61772873 | same | different | RHOQ |
| 202086_at | -1.10 | -1.58976683 | 1.58976683 | same | different | MX1 |
| 208425_s_at | -1.41 | -1.58877933 | 1.58877933 | same | different | TANC2 |
| 209305_s_at | -1.23 | -1.53548172 | 1.53548172 | same | different | GADD45B |
| 206042_x_at | -0.81 | -1.49309651 | 1.49309651 | same | different | SNRPN |
| 203502_at | -1.50 | -1.47192869 | 1.47192869 | same | different | BPGM |
| 209529_at | -0.89 | -1.45196377 | 1.45196377 | same | different | PPAP2C |
| 225704_at | -0.35 | -1.43200611 | 1.43200611 | same | different | KIAA1545 |

Fig. 32A (Cont.)

| Gene | ID |
|---|---|
| CKLF-like MARVEL transmembrane domain containing 3 | 123920 |
| collagen, type V, alpha 1 | 1289 |
| influenza virus NS1A binding protein | 10625 |
| zinc finger protein 57 homolog (mouse) | 346171 |
| collagen, type IV, alpha 2 | 1284 |
| histone deacetylase 9 | 9734 |
| collagen, type IV, alpha 1 | 1282 |
| brain-derived neurotrophic factor | 627 |
| potassium channel tetramerisation domain containing 11 | 147040 |
| integrin, beta 6 | 3694 |
| signal-regulatory protein alpha | 140885 |
| EPH receptor B2 | 2048 |
| ATPase, Na+/K+ transporting, beta 1 polypeptide | 481 |
| chondroitin beta1,4 N-acetylgalactosaminyltransferase | 55790 |
| damage-regulated autophagy modulator | 55332 |
| actin, alpha 1, skeletal muscle | 58 |
| tripartite motif-containing 36 | 55521 |
| interferon regulatory factor 1 | 3659 |
| ras homolog gene family, member Q | 23433 |
| myxovirus (influenza virus) resistance 1, interferon-inducible protein p78 (mouse) | 4599 |
| myxovirus (influenza virus) resistance | |
| tetratricopeptide repeat, ankyrin repeat and coiled-coil containing 2 | 26115 |
| growth arrest and DNA-damage-inducible, beta | 4616 |
| small nuclear ribonucleoprotein polypeptide N /// SNRPN upstream reading frame | 6638 /// 8926 |
| 2,3-bisphosphoglycerate mutase /// 2,3-bisphosphoglycerate mutase | 669 |
| phosphatidic acid phosphatase type 2C | 8612 |
| KIAA1545 protein | 57666 |

Fig. 32A (Cont.)

| | | | | |
|---|---|---|---|---|
| 219429_at | -0.87 | 1.51997764 | -1.51997764 | different | same | FA2H |
| 211258_s_at | -2.01 | 1.52834249 | -1.52834249 | different | same | TGFA |
| 211889_x_at | -1.08 | 1.56828019 | -1.56828019 | different | same | CEACAM1 |
| 226726_at | -0.61 | 1.57752827 | -1.57752827 | different | same | MBOAT2 |
| 201428_at | -0.94 | 1.61020148 | -1.61020148 | different | same | CLDN4 |
| 203815_at | -0.76 | 1.65488092 | -1.65488092 | different | same | GSTT1 |
| 228221_at | -0.82 | 1.72053691 | -1.72053691 | different | same | SLC44A3 |
| 225987_at | -0.52 | 1.75487349 | -1.75487349 | different | same | STEAP4 |
| 233565_s_at | -0.84 | 1.76892096 | -1.76892096 | different | same | SDCBP2 |
| 204015_s_at | -0.89 | 1.83200680 | -1.83200680 | different | same | DUSP4 |
| 205466_s_at | -0.84 | 1.84152752 | -1.84152752 | different | same | HS3ST1 |
| 209276_s_at | -0.86 | 1.85115906 | -1.85115906 | different | same | GLRX |
| 210130_s_at | -0.81 | 1.88073599 | -1.88073599 | different | same | TM7SF2 |
| 225177_at | -0.99 | 1.96226612 | -1.96226612 | different | same | RAB11FIP1 |
| 1555733_s_at | -1.93 | 1.96572612 | -1.96572612 | different | same | AP1S3 |
| 209366_x_at | -0.38 | 2.08702186 | -2.08702186 | different | same | CYB5A |
| 219529_at | -0.83 | 2.17010634 | -2.17010634 | different | same | CLIC3 /// RABEP |
| 202838_at | -1.07 | 2.17574832 | -2.17574832 | different | same | FUCA1 |
| 219225_at | -1.80 | 2.19655478 | -2.19655478 | different | same | PGBD5 |
| 213172_at | -1.33 | 2.22618138 | -2.22618138 | different | same | TTC9 |
| 227804_at | -0.61 | 2.26658844 | -2.26658844 | different | same | TLCD1 |

Fig. 32A (Cont.)

| Gene | ID |
|---|---|
| fatty acid 2-hydroxylase | 79152 |
| transforming growth factor, alpha | 7039 |
| carcinoembryonic antigen-related cell adhesion molecule 1 (biliary glycoprotein) | 634 |
| membrane bound O-acyltransferase domain containing 2 | 129642 |
| claudin 4 | 1364 |
| glutathione S-transferase theta 1 | 2952 |
| solute carrier family 44, member 3 | 126969 |
| STEAP family member 4 | 79689 |
| syndecan binding protein (syntenin) 2 | 27111 |
| dual specificity phosphatase 4 | 1846 |
| heparan sulfate (glucosamine) 3-O-sulfotransferase 1 | 9957 |
| glutaredoxin (thioltransferase) | 2745 |
| transmembrane 7 superfamily member 2 | 7108 |
| RAB11 family interacting protein 1 (class I) | 80223 |
| adaptor-related protein complex 1, sigma 3 subunit | 130340 |
| cytochrome b5 type A (microsomal) | 1528 |
| chloride intracellular channel 3 /// rabaptin, RAB GTPase binding effector protein 1 | 9022 /// 9135 |
| fucosidase, alpha-L-1, tissue | 2517 |
| piggyBac transposable element derived 5 | 79605 |
| tetratricopeptide repeat domain 9 | 23508 |
| TLC domain containing 1 | 116238 |

Fig. 32A (Cont.)

| Probe | Value1 | Value2 | Value3 | Gene |
|---|---|---|---|---|
| 215101_s_at | -2.24 | 2.28644504 | -2.28644504 | different | same | CXCL5 |
| 220414_at | -1.87 | 2.33580673 | -2.33580673 | different | same | CALML5 |
| 207388_s_at | -1.05 | 2.33977829 | -2.33977829 | different | same | PTGES |
| 213568_at | -0.99 | 2.38580280 | -2.38580280 | different | same | OSR2 |
| 201830_s_at | -1.88 | 2.43174622 | -2.43174622 | different | same | NET1 |
| 204803_s_at | -1.17 | 2.51317652 | -2.51317652 | different | same | RRAD |
| 205627_at | -1.36 | 2.56389205 | -2.56389205 | different | same | CDA |
| 219836_at | -1.70 | 2.84690160 | -2.84690160 | different | same | ZBED2 |
| 214091_s_at | -1.85 | 2.92170017 | -2.92170017 | different | same | GPX3 |
| 210397_at | -0.74 | 2.99920027 | -2.99920027 | different | same | DEFB1 |
| 230323_s_at | -0.51 | 3.05392889 | -3.05392889 | different | same | TMEM45B |
| 219127_at | -0.53 | 3.07720043 | -3.07720043 | different | same | ATAD4 |
| 205568_at | -0.82 | 3.09110915 | -3.09110915 | different | same | AQP9 |
| 220979_s_at | -0.85 | 3.51079773 | -3.51079773 | different | same | ST6GALNAC5 |
| 228010_at | -0.61 | 3.74246962 | -3.74246962 | different | same | PPP2R2C |
| 215729_s_at | -1.84 | 3.91256000 | -3.91256000 | different | same | VGLL1 |
| 1555812_a_at | -0.75 | 3.98722915 | -3.98722915 | different | same | ARHGDIB |
| 220724_at | -0.95 | 4.01353054 | -4.01353054 | different | same | FLJ21511 |
| 220431_at | -0.80 | 4.26075324 | -4.26075324 | different | same | TMPRSS11E |
| 231120_x_at | -1.54 | 4.35176303 | -4.35176303 | different | same | PKIB |
| 231849_at | -1.67 | 4.64911479 | -4.64911479 | different | same | KRT80 |
| 204614_at | -0.68 | 4.71700832 | -4.71700832 | different | same | SERPINB2 |
| 218990_s_at | -0.65 | 4.91570922 | -4.91570922 | different | same | SPRR3 |
| 206504_at | -1.26 | 5.72328641 | -5.72328641 | different | same | CYP24A1 |
| Num up > 2-fold | 1 | 74 | 81 | 80 | 75 | |
| Num down > 2-fold | 154 | 81 | 74 | 75 | 80 | |

Fig. 32A (Cont.)

| Gene | ID |
|---|---|
| chemokine (C-X-C motif) ligand 5 | 6374 |
| calmodulin-like 5 | 51806 |
| prostaglandin E synthase | 9536 |
| odd-skipped related 2 (Drosophila) | 116039 |
| neuroepithelial cell transforming gene 1 | 10276 |
| Ras-related associated with diabetes | 6236 |
| cytidine deaminase | 978 |
| zinc finger, BED-type containing 2 | 79413 |
| glutathione peroxidase 3 (plasma) | 2878 |
| defensin, beta 1 | 1672 |
| transmembrane protein 45B | 120224 |
| ATPase family, AAA domain containing 4 | 79170 |
| aquaporin 9 | 366 |
| ST6 (alpha-N-acetyl-neuraminyl-2,3-beta-galactosyl-1,3)-N-acetylgalactosaminide alpha-2,6-sialyltransferase 5 /// ST6 | 81849 |
| protein phosphatase 2 (formerly 2A), regulatory subunit B (PR 52), gamma isoform | 5522 |
| vestigial like 1 (Drosophila) | 51442 |
| Rho GDP dissociation inhibitor (GDI) beta | 397 |
| hypothetical protein FLJ21511 | 80157 |
| transmembrane protease, serine 11E ///similar to transmembraneprotease, serine 11E | 28983 /// 729884 |
| protein kinase (cAMP-dependent, catalytic) inhibitor beta | 5570 |
| keratin 80 | 144501 |
| serpin peptidase inhibitor, clade B (ovalbumin), member 2 | 5055 |
| small proline-rich protein 3 | 6707 |
| cytochrome P450, family 24, subfamily A, polypeptide 1 | 1591 |

Fig. 32A (Cont.)

RELATIVE EXPRESSION OF MAMMARY MYOEPITHELIAL-CELL-SPECIFIC GENES IN BPEC vs HMEC

| Affymetrix_ID | Grigoriadis myoepithelial/ luminal log2 ratio | BPEC/HMEC (log2 ratio) | HMEC/BPEC (log2 ratio) | BPEC/HMEC (log2 ratio) | HMEC/BPEC (log2 ratio) | Probe Set ID |
|---|---|---|---|---|---|---|
| 210809_s_at | 5.46 | -6.392837808 | 6.392837781 | different | same | 210809_s_at |
| 221729_at | 2.94 | -3.62327226 | 3.62327226 | different | same | 221729_at |
| 227048_at | 1.43 | -3.703612815 | 3.703612815 | different | same | 227048_at |
| 203434_s_at | 1.56 | -4.959476521 | 4.959476521 | different | same | 203434_s_at |
| 209167_at | 1.70 | -1.537268434 | 1.537268434 | different | same | 209167_at |
| 201141_at | 2.14 | -5.335565665 | 5.335565665 | different | same | 201141_at |
| 204646_at | 0.91 | -1.901104046 | 1.901104046 | different | same | 204646_at |
| 202363_at | 0.69 | -2.652894565 | 2.852894565 | different | same | 202363_at |
| 226771_at | 1.35 | -1.260720742 | 1.260720742 | different | same | 226771_at |
| 212353_at | 1.81 | -1.130836889 | 1.130836889 | different | same | 212353_at |
| 204421_s_at | 0.87 | -2.239232386 | 2.239232239 | different | same | 204421_s_at |
| 203889_at | 1.15 | -3.687756462 | 3.687756462 | different | same | 203889_at |
| 203989_x_at | 0.62 | -2.075138276 | 2.075138276 | different | same | 203989_x_at |
| 227059_at | 1.37 | -4.280725473 | 4.280725473 | different | same | 227059_at |
| 209656_s_at | 0.70 | -2.818258656 | 2.818258656 | different | same | 209656_s_at |
| 204466_s_at | 1.91 | -2.013458898 | 2.013458898 | different | same | 204466_s_at |
| 213093_at | 1.60 | -2.347469502 | 2.347469502 | different | same | 213093_at |
| 213325_at | 0.58 | -1.145097369 | 1.145097369 | different | same | 213325_at |
| 218723_s_at | 1.31 | -1.999548638 | 1.999548864 | different | same | 218723_s_at |
| 202237_at | 1.14 | -1.953036147 | 1.953036615 | different | same | 202237_at |
| 204955_at | 1.02 | -1.418944735 | 1.418944474 | different | same | 204955_at |
| 212813_at | 1.15 | -1.040174493 | 1.040174449 | different | same | 212813_at |
| 202718_at | 1.96 | -2.351373449 | 2.351373345 | different | same | 202718_at |
| 212667_at | 1.80 | -2.311011701 | 2.3110117 | different | same | 212667_at |
| 37408_at | 0.91 | -3.096970582 | 3.096970758 | different | same | 37408_at |

Fig. 32B

| Gene Symbol | Gene Title | Entrez Gene |
|---|---|---|
| POSTN | periostin, osteoblast specific factor | 10631 |
| COL5A2 | collagen, type V, alpha 2 | 1290 |
| LAMA1 | laminin, alpha 1 | 284217 |
| MME | membrane metallo-endopeptidase (neutral endopeptidase, enkephalinase) | 4311 |
| GPM6B | glycopritein m6b | 2824 |
| GPNMB | glycoprotein (transmembrane) nmb | 10457 |
| DPYD | dihydropyrimidine dehydrogenase | 1806 |
| SPOCK1 | sparc/osteonectin, cwcv and kazal-like domains proteoglycan (testican) 1 | 6695 |
| ATP8B2 | ATPase, Class I, type 8B, member 2 | 57198 |
| SULF1 | sulfatase 1 | 23213 |
| FGF2 | fibroblast growth factor 2 (basic) | 2247 |
| SCG5 | secretogranin V (7B2 protein) | 6447 |
| F2R | coagulation factor II (thrombin) receptor | 2149 |
| GPC6 | Glypican 6 | 10082 |
| TMEM47 | transmembrane protein 47 | 83604 |
| SNCA | synuclein, alpha (non A4 component of amyloid precursor) /// synuclein, alpha (non A4 component of amyloid precu | 6622 |
| PRKCA | protein kinase C, alpha | 5578 |
| PVRL3 | poliovirus receptor-related 3 | 25945 |
| RGC32 | response gene to complement 32 | 28984 |
| NNMT | nicotinamide N-methyltransferase | 4837 |
| SRPX | sushi-repeat-containing protein, X-linked | 8406 |
| JAM3 | junctional adhesion molecule 3 | 83700 |
| IGFBP2 | insulin-like growth factor binding protein 2, 36kDa | 3485 |
| SPARC | secreted protein, acidic, cysteine-rich 9osteonectin) | 6678 |
| MRC2 | mannose receptor. C type 2 | 9902 |

Fig. 32B (Cont.)

| | | | |
|---|---|---|---|
| 219355_at | 1.27 | -1.159809464 | 1.159809464 |
| 209383_at | 0.62 | -3.781048506 | 3.78104851 |
| 214247_s_at | 3.08 | -2.286131639 | 2.28613164 |
| 213369_at | 0.63 | -2.055350801 | 2.0553508 |
| 208763_s_at | 0.95 | -3.634273489 | 3.63427349 |
| 209610_s_at | 1.73 | -4.683853221 | 4.68385322 |
| 209875_s_at | 1.76 | -1.888219731 | 1.88821973 |
| 207387_s_at | 1.52 | -1.329958448 | 1.32995845 |
| 210139_s_at | 0.55 | -1.836718743 | 1.83671874 |
| 227846_at | 1.37 | -1.764857917 | 1.76485792 |
| 203140_at | 0.97 | -1.08254904 | 1.08254904 |
| 209230_s_at | 1.13 | -2.783572743 | 2.78357274 |
| 227070_at | 1.70 | -1.44168561 | 1.44168561 |
| 202948_at | 0.42 | -1.164099536 | 1.16409954 |
| 214763_s_at | 0.96 | -8.262087928 | 8.26208793 |
| 202436_s_at | 1.65 | -1.285421731 | 1.28542173 |
| 208901_at | 0.65 | -2.525935741 | 2.52593574 |
| 204726_at | 2.07 | -1.823589558 | 1.82358956 |
| 227080_at | 1.32 | -2.706300055 | 2.70630055 |
| 208962_s_at | 0.63 | -1.276754934 | 1.27675493 |
| 212158_at | 1.42 | -2.729090032 | 2.72909032 |
| 212249_at | 0.90 | -1.364479067 | 1.36447907 |
| 201471_s_at | 0.61 | -1.905433416 | 1.90543342 |
| 218248_at | 0.55 | 1.224083064 | -1.22240831 |
| 222962_s_at | 1.21 | 3.755955045 | -3.755955 |
| 223720_at | 1.30 | 2.868150078 | -2.08681501 |
| 205749_at | 1.13 | 1.060419789 | -1.0604198 |
| 210145_at | 0.86 | 2.706627613 | -2.7066276 |

| | |
|---|---|
| different | same | 219355_at
| different | same | 209383_at
| different | same | 214247_s_at
| different | same | 213369_at
| different | same | 208763_s_at
| different | same | 209610_s_at
| different | same | 209875_s_at
| different | same | 207387_s_at
| different | same | 210139_s_at
| different | same | 227846_at
| different | same | 203140_at
| different | same | 209230_s_at
| different | same | 227070_at
| different | same | 202948_at
| different | same | 214763_s_at
| different | same | 202436_s_at
| different | same | 208901_at
| different | same | 204726_at
| different | same | 227080_at
| different | same | 208962_s_at
| different | same | 212158_at
| different | same | 212249_at
| different | same | 201471_s_at
| same | different | 218248_at
| same | different | 222962_s_at
| same | different | 223720_at
| same | different | 205749_at
| same | different | 210145_at

Fig. 32B (Cont.)

| Symbol | Description | Number |
|---|---|---|
| CXorf57 | chromosome X open reading frame 57 | 55086 |
| DDIT3 | DNA-damage-inducible transcript 3 | 1649 |
| DKK3 | dickkopf homolog 3 (Xenopus laevis) | 27122 |
| PCDH21 | protocadherin 21 | 92211 |
| TSC22D3 | TSC22 domain family, member 3 | 1831 |
| SLC1A4 | solute carrier family 1 (glutamate/neutral amino acid transporter), member 4 | 6509 |
| SPP1 | secreted phosphoprotein 1 (osteopontin, bone sialoprotein I, early T-lymphocyte activation 1) | 6696 |
| GK | glycerol kinase | 2710 |
| PMP22 | peripheral myelin protein 22 | 5376 |
| GPR176 | G protein-coupled receptor 176 | 11245 |
| BCL6 | B-cell CLL/lymphoma 6 (zinc finger 51) /// B-cell CLL/lymphoma 6 (zinc finger protein 51) | 604 |
| NUPR1 | nuclear protein 1 | 26471 |
| GLT8D2 | glycosyltransferase 8 domain containing 2 | 83468 |
| IL1R1 | interleukin 1 receptor, type I | 3554 |
| FBXO32 | F-box protein 32 | 114907 |
| CYP1B1 | cytochrome P450, family 1, subfamily B, polypeptide 1 | 1545 |
| PLSCR4 | phospholipid scramblase 4 | 57088 |
| CDH13 | cadherin 13, H-cadherin (heart) | 1012 |
| ZNF697 | zinc finger protein 697 | 90874 |
| FADS1 | fatty acid desaturase 1 | 3992 |
| SDC2 | syndecan 2 (heparan sulfate proteoglycan 1, cell surface-associated, fibroglycan) | 6383 |
| PIK3R1 | phosphoinositide-3-kinase, regulatory subunit 1 (p85 alpha) | 5295 |
| SQSTM1 | sequestosome 1 | 8878 |
| FAM111A | family with sequence similarity 111, member A | 63901 |
| MCM10 | MCM10 minichromosome maintenance deficient 10 (S. cerevisiae) | 55388 |
| SPINK7 | serine peptidase inhibitor, Kazal type 7 (putative) | 54651 |
| CYP1A1 | cytochrome P450, family 1, subfamily A, polypeptide 1 | 1543 |
| PLA2G4A | phospholipase A2, group IVA (cytosolic, calcium-dependent) | 5321 |

Fig. 32B (Cont.)

| | | | | | | |
|---|---|---|---|---|---|---|
| 223832_s_at | 0.77 | 1.310380859 | -1.3103809 | same | different | 223832_s_at |
| 225687_at | 0.80 | 4.426987448 | -4.4269874 | same | different | 225687_at |
| 202917_s_at | 2.09 | 3.365745045 | -3.365745 | same | different | 202917_s_at |
| 205909_at | 0.69 | 4.019263249 | -4.0192632 | same | different | 205909_at |
| 203535_at | 0.80 | 2.89253411 | -2.8925341 | same | different | 203535_at |
| 209891_at | 1.11 | 4.596286112 | -45962861 | same | different | 209891_at |
| 205067_at | 0.64 | 1.428583257 | -1.4285833 | same | different | 205067_at |
| 206170_at | 0.89 | 2.544611425 | -2.5446114 | same | different | 206170_at |
| 203798_s_at | 2.47 | 1.420514692 | -1.4205147 | same | different | 203798_s_at |
| 230188_at | 0.98 | 1.292112984 | -1.292113 | same | different | 230188_at |
| 220027_s_at | 0.57 | 2.637723064 | -2.6377231 | same | different | 220027_s_at |
| 235272_at | 1.88 | 4.454731128 | -4.4547311 | same | different | 235272_at |
| 206023_at | 0.67 | 5.579501464 | -5.5795015 | same | different | 206023_at |
| 205185_at | 1.93 | 2.506329682 | -2.5063297 | same | different | 205185_at |
| 231148_at | 0.94 | 5.707515427 | -5.7075154 | same | different | 231148_at |
| 230835_at | 2.49 | 5.284051257 | -5.2840513 | same | different | 230835_at |
| 205916_at | 3.78 | 3.255715272 | -3.2557153 | same | different | 205916_at |
| 41469_at | 1.65 | 3.673305619 | -3.6733056 | same | different | 41469_at |
| 213796_at | 2.91 | 7.318994544 | -7.3189945 | same | different | 213796_at |

| | | | | | |
|---|---|---|---|---|---|
| Num up > 2-fold | 356 | 111 | 246 | 112 | 245 Same direction |
| Num down > 2-fold | 1 | 246 | 111 | 245 | 112 Different direction |

Fig. 32B (Cont.)

| | | |
|---|---|---|
| CAPNS2 | calpain, small subunit 2 | 84290 |
| FAM83D | family with sequence similarity 83, member D | 81610 |
| S100A8 | s100 calcium binding protein a8 | 6279 |
| POLE2 | polymerase (DNA directed), epsilon 2 (p59 subunit) | 5427 |
| S100A9 | S100 calcium binding protein A9 | 6280 |
| SPBC25 | spindle pole body component 25 homolog (S. cerevisiae) | 57405 |
| IL1B | intrtleukin 1, beta | 3553 |
| ADRB2 | adrenergic, beta-2-, receptor, surface | 154 |
| VSNL1 | visinin-like 1 | 7447 |
| ICHTHYIN | ichthyin protein | 348938 |
| RASIP1 | Ras interacting protein 1 | 54922 |
| SBSN | suprabasin | 374897 |
| NMU | neuromedin U | 10874 |
| SPINK5 | serine peptidase inhibitor, Kazal type 5 | 11005 |
| IGFL2 | IGF-like family member 2 | 147920 |
| UNQ467 | KIPV467 | 388533 |
| S100A7 | S100 calcium binding protein A7 | 6278 |
| PI3 | peptidase inhibitor 3, skin-derived (SKALP) | 5266 |
| SPRR1A | small proline-rich protein 1A | 6698 |

Fig. 32B (Cont.)

The genes that are differentially expressed in BPEC-hTERT vs. HMEC-hTERT (≥2-Fold)

| M = log2 (BPEC-hTERT/ HMEC-hTERT) | adj.P .Val | Gene Symbol | Gene Title | Entrez Gene | Representative Public ID |
|---|---|---|---|---|---|
| 9.33 | 0.11 | SPRR1A | small proline-rich protein 1A | 6698 | AI923984 |
| 8.82 | 0.04 | PI3 | peptidase inhibitor 3, skin-derived (SKALP) | 5266 | L10343 |
| 8.05 | 0.03 | PI3 | peptidase inhibitor 3, skin-derived (SKALP) /// peptidase inhibitor 3, skin-derived (SKALP) | 5266 | NM_002638 |
| 7.32 | 0.10 | CALB1 | calbindin 1, 28kDa | 793 | AW014927 |
| 7.29 | 0.03 | MAFB | v-maf musculoaponeurotic fibrosarcoma oncogene homolog B (avian) | 9935 | NM_005461 |
| 7.20 | 0.11 | CALB1 | calbindin 1, 28kDa | 793 | NM_004929 |
| 7.08 | 0.21 | KLK10 | kallikrein 10 | 5655 | BC002710 |
| 6.97 | 0.03 | SPRR3 | small proline-rich protein 3 | 6707 | BF575466 |
| 6.95 | 0.08 | S100P | S100 calcium binding protein P | 6286 | NM_005980 |
| 6.83 | 0.02 | GPX3 | glutathione peroxidase 3 (plasma) | 2878 | NM_002084 |
| 6.72 | 0.13 | LYPD3 | LY6/PLAUR domain containing 3 | 27076 | NM_014400 |
| 6.54 | 0.05 | SLC6A14 | solute carrier family 6 (amino acid transporter), member 14 | 11254 | NM_007231 |
| 6.53 | 0.09 | DSG1 | desmoglein 1 | 1828 | NM_001942 |
| 6.44 | 0.04 | MAFB | v-maf musculoaponeurotic fibrosarcoma oncogene homolog B (avian) | 9935 | AW135013 |
| 6.43 | 0.02 | S100A7 | S100 calcium binding protein A7 (psoriasin 1) | 6278 | NM_002963 |
| 6.04 | 0.23 | MFAP5 | microfibrillar associated protein 5 | 8076 | U37283 |
| 6.02 | 0.17 | KRT24 | keratin 24 | 192666 | NM_019016 |
| 5.95 | 0.34 | KLK7 | kallikrein 7 (chymotryptic, stratum corneum) | 5650 | NM_005046 |
| 5.88 | 0.24 | TACSTD1 | tumor-associated calcium signal transducer 1 | 4072 | NM_002354 |
| 5.87 | 0.29 | KLK5 | kallikrein 5 | 25818 | AF243527 |
| 5.83 | 0.04 | SPRR2B | small proline-rich protein 2B | 6701 | NM_006945 |
| 5.61 | 0.23 | KLK8 | kallikrein 8 (neuropsin/ovasin) | 11202 | NM_007196 |

Fig. 32C

| | | | | |
|---|---|---|---|---|
| 5.60 | EHF | Ets homologous factor | 26298 | AAI763378 |
| 5.55 | SERPINB13 | serpin peptidase inhibitor, clade B (ovalbumin), member 13 | 5275 | AJ001698 |
| 5.53 | ARHGDIB | Rho GDP dissociation inhibitor (GDI) beta | 397 | AF498927 |
| 5.53 | PPP2R2C | protein phosphatase 2 (formerly 2A), regulatory subunit B (PR 52), gamma isoform | 5522 | AI669212 |
| 5.50 | SCEL | sciellin | 8796 | NM_003843 |
| 5.50 | MFAP5 | microfibrillar associated protein 5 | 8076 | AW665892 |
| 5.50 | MFAP5 | microfibrillar associated protein 5 | 8076 | AW665892 |
| 5.46 | A2ML1 | alpha-2-macroglobulin-like 1 | 144568 | AL832750 |
| 5.45 | GJB6 | gap junction protein, beta 6 (connexin 30) | 10804 | AI694073 |
| 5.45 | IL1RN | interleukin 1 receptor antagonist | 3557 | U65590 |
| 5.39 | IGFL1 | insulin growth factor-like family member 1 | 374918 | AA195677 |
| 5.36 | GPX3 | glutathione peroxidase 3 (plasma) | 2878 | AW149846 |
| 5.31 | SLPI | secretory leukocyte peptidase inhibitor | 6590 | NM_003064 |
| 5.27 | HOP | homeodomain-only protein /// homeodomain-only protein | 84525 | AB059408 |
| 5.26 | IFI27 | interferon, alpha-inducible protein 27 | 3429 | NM_005532 |
| 5.24 | RAB25 | RAB25, member RAS oncogene family | 57111 | NM_020387 |
| 5.19 | IL1R2 | interleukin 1 receptor, type II | 7850 | NM_004633 |
| 5.18 | UNQ467 | KIPV467 | 388533 | W69083 |
| 5.15 | LCN2 | lipocalin 2 (oncogene 24p3) | 3934 | NM_005564 |
| 5.12 | SCEL | sciellin | 8796 | AW470178 |
| 5.11 | SPRR3 | small proline-rich protein 3 | 6707 | NM_005416 |
| 5.09 | ARHGDIB | Rho GDP dissociation inhibitor (GDI) beta | 397 | NM_001175 |
| 5.08 | SULT2B1 | sulfotransferase family, cytosolic, 2B, member 1 | 6820 | NM_004605 |
| 5.04 | AQP3 | aquaporin 3 (Gill blood group) | 360 | N74607 |
| 4.99 | CLDN7 | claudin 7 | 1366 | NM_001307 |
| 4.97 | KRT1 | keratin 1 (epidermolytic hyperkeratosis) | 3848 | NM_006121 |

Fig. 32C (Cont.)

| | | | | |
|---|---|---|---|---|
| 4.89 | CNTN1 | Contactin 1 | 1272 | AI091445 |
| 4.89 | IGFL2 | insulin growth factor-like family member 2 | 147920 | AI806131 |
| 4.88 | LCE3D | late cornified envelope 3D /// late cornified envelope 3D | 84648 | AB048288 |
| 4.87 | C1orf42 | chromosome 1 open reading frame 42 | 54544 | NM_019060 |
| 4.85 | SPRR1A | small proline-rich protein 1A | 6698 | NM_005987 |
| 4.84 | SERPINB2 | serpin peptidase inhibitor, clade B (ovalbumin), member 2 | 5055 | NM_002575 |
| 4.79 | CXADR | coxsackie virus and adenovirus receptor | 1525 | NM_001338 |
| 4.79 | DSC2 | desmocollin 2 | 1824 | BF196457 |
| 4.75 | SERPINB13 | serpin peptidase inhibitor, clade B (ovalbumin), member 13 | 5275 | AJ001696 |
| 4.75 | PPP2R2C | protein phosphatase 2 (formerly 2A), regulatory subunit B (PR 52), gamma isoform | 5522 | AF086924 |
| 4.75 | KLK7 | kallikrein 7 (chymotryptic, stratum corneum) | 5650 | AU155415 |
| 4.74 | ANKRD22 | ankyrin repeat domain 22 | 118932 | AI925518 |
| 4.70 | SPRR1B | small proline-rich protein 1B (cornifin) | 6699 | NM_003125 |
| 4.68 | IL1RN | interleukin 1 receptor antagonist | 3557 | BE563442 |
| 4.67 | SLAMF9 | SLAM family member 9 | 89886 | NM_033438 |
| 4.64 | GALNT6 | UDP-N-acetyl-alpha-D-galactosamine:polypeptide N-acetylgalactosaminyltransferase 6 (GalNAc-T6) | 11226 | NM_007210 |
| 4.58 | ENTPD3 | ectonucleoside triphosphate diphosphohydrolase 3 | 956 | NM_001248 |
| 4.56 | CDSN | corneodesmosin | 1041 | NM_001264 |
| 4.55 | BBOX1 | butyrobetaine (gamma), 2-oxoglutarate dioxygenase (gamma-butyrobetaine hydroxylase) 1 | 8424 | NM_003986 |
| 4.55 | GRHL1 | grainyhead-like 1 (Drosophila) | 29841 | BE566136 |
| 4.55 | TPD52 | tumor protein D52 | 7163 | AA524023 |
| 4.47 | NMU | neuromedin U | 10874 | NM_006681 |
| 4.46 | EHF | ets homologous factor | 26298 | NM_012153 |
| 4.45 | --- | Full length insert cDNA clone Y140A07 | --- | AI819863 |

Fig. 32C (Cont.)

| | | | | |
|---|---|---|---|---|
| 4.40 | SPINK5 | serine peptidase inhibitor, Kazal type 5 | 11005 | NM_006846 |
| 4.40 | PROM2 | prominin 2 | 150696 | NM_144707 |
| 4.36 | KLK11 | kallikrein 11 | 11012 | NM_006853 |
| 4.36 | VGLL1 | vestigial like 1 (Drosophila) | 51442 | BE542323 |
| 4.35 | MALL | mal, T-cell differentiation protein-like | 7851 | BC003179 |
| 4.34 | MAL2 | mal, T-cell differentiation protein 2 | 114569 | AL117612 |
| 4.33 | CYB5A | cytochrome b5 type A (microsomal) | 1528 | NM_001914 |
| 4.27 | TMEM79 | transmembrane protein 79 | 84283 | BC005094 |
| 4.27 | CXADR | Coxsackie virus and adenovirus receptor | 1525 | BG260087 |
| 4.27 | TPD52 | tumor protein D52 | 7163 | BG389015 |
| 4.25 | SCEL | sciellin | 8796 | BC020726 |
| 4.25 | TPD52 | tumor protein D52 | 7163 | BE974098 |
| 4.24 | HIST1H2BC | histone 1, H2bc | 8347 | NM_003526 |
| 4.18 | WFDC12 | WAP four-disulfide core domain 12 | 128488 | NM_080869 |
| 4.18 | FAM83A | family with sequence similarity 83, member A | 84985 | BG438092 |
| 4.15 | MLZE | melanoma-derived leucine zipper, extra-nuclear factor | 56169 | AJ245876 |
| 4.15 | CYB5A | cytochrome b5 type A (microsomal) | 1528 | M22865 |
| 4.13 | IVL | involucrin | 3713 | NM_005547 |
| 4.11 | MYO5B | myosin VB | 4645 | AI991160 |
| 4.11 | SPINK6 | serine peptidase inhibitor, Kazal type 6 | 404203 | BC032003 |
| 4.05 | NCF2 | neutrophil cytosolic factor 2 (65kDa, chronic granulomatous disease, autosomal 2) | 4688 | BC001606 |
| 4.05 | CLIC3 | chloride intracellular channel 3 | 9022 | NM_004669 |
| 4.05 | PTHLH | Parathyroid hormone-like hormone | 5744 | M31157 |
| 4.04 | MAPK13 | mitogen-activated protein kinase 13 | 5603 | BC000433 |
| 4.04 | SERPINB3 | serpin peptidase inhibitor, clade B (ovalbumin), member 3 | 6317 | U19556 |
| 3.95 | SERPINB3 | serpin peptidase inhibitor, clade B (ovalbumin), member 3 | 6317 | BC005224 |

Fig. 32C (Cont.)

| | | | | |
|---|---|---|---|---|
| 3.90 | ADAM8 | ADAM metallopeptidase domain 8 | 101 | NM_001109 |
| 3.87 | GRHL3 | grainyhead-like 3 (Drosophila) | 57822 | AL137763 |
| 3.85 | CYB5A | cytochrome b5 type A (microsomal) | 1528 | M22976 |
| 3.85 | C15orf48 | chromosome 15 open reading frame 48 | 84419 | AF228422 |
| 3.84 | PRRG4 | Proline rich Gla (G-carboxyglutamic acid) 4 (transmembrane) | 79056 | BF905445 |
| 3.83 | THBD | thrombomodulin | 7056 | NM_000361 |
| 3.83 | GPRC5A | G protein-coupled receptor, family C, group 5, member A | 9052 | NM_003979 |
| 3.80 | HIST1H2BC | histone 1, H2bc | 8347 | AA037483 |
| 3.78 | KRT16 | keratin 16 (focal non-epidermolytic palmoplantar keratoderma) | 3868 | AF061812 |
| 3.76 | SBSN | suprabasin | 374897 | AI814274 |
| 3.76 | PKIB | protein kinase (cAMP-dependent, catalytic) inhibitor beta | 5570 | AF225513 |
| 3.75 | THBD | thrombomodulin | 7056 | NM_000361 |
| 3.74 | MYO5C | myosin VC | 55930 | NM_018728 |
| 3.73 | TSPAN1 | tetraspanin 1 | 10103 | AF133425 |
| 3.72 | OCLN | Occludin | 4950 | AI829721 |
| 3.71 | IL1R2 | interleukin 1 receptor, type II | 7850 | U64094 |
| 3.71 | KLK8 | kallikrein 8 (neuropsin/ovasin) | 11202 | NM_144506 |
| 3.67 | RBM35A | RNA binding motif protein 35A | 54845 | BF001941 |
| 3.66 | FXYD3 | FXYD domain containing ion transport regulator 3 | 5349 | BC005238 |
| 3.65 | CDH1 | cadherin 1, type 1, E-cadherin (epithelial) | 999 | L08599 |
| 3.65 | TGM1 | transglutaminase 1 (K polypeptide epidermal type I, protein-glutamine-gamma-glutamyltransferase) | 7051 | NM_000359 |
| 3.65 | AMPD3 | adenosine monophosphate deaminase (isoform E) | 272 | NM_000480 |
| 3.65 | RBM35A | RNA binding motif protein 35A | 54845 | NM_017697 |
| 3.63 | GAL | galanin | 51083 | AL556409 |
| 3.63 | EHF | ets homologous factor | 26298 | AF124438 |
| 3.63 | C10orf58 | chromosome 10 open reading frame 58 /// chromosome 10 open reading frame 58 | 84293 | BC005871 |

Fig. 32C (Cont.)

| | | | | |
|---|---|---|---|---|
| 3.63 | DSC2 | desmocollin 2 | 1824 | NM_004949 |
| 3.60 | FAM83A | family with sequence similarity 83, member A | 84985 | AI590662 |
| 3.59 | LPAAT-THETA | lysophosphatidic acid acyltransferase theta /// lysophosphatidic acid acyltransferase theta | 84803 | BC006236 |
| 3.56 | IL1RN | interleukin 1 receptor antagonist | 3557 | AW083357 |
| 3.55 | TRAF3IP3 | TRAF3 interacting protein 3 | 80342 | AI922337 |
| 3.54 | LASS3 | LAG1 longevity assurance homolog 3 (S. cerevisiae) | 204219 | BC034500 |
| 3.54 | SERPINB13 | serpin peptidase inhibitor, clade B (ovalbumin), member 13 | 5275 | BE148534 |
| 3.53 | IGSF9 | immunoglobulin superfamily, member 9 | 57549 | AB037776 |
| 3.53 | TMEM45B | transmembrane protein 45B | 120224 | AI282982 |
| 3.52 | HOOK1 | hook homolog 1 (Drosophila) | 51361 | AA618420 |
| 3.51 | LAD1 | ladinin 1 | 3898 | U58994 |
| 3.51 | SERPINB1 | serpin peptidase inhibitor, clade B (ovalbumin), member 1 | 1992 | AI554300 |
| 3.51 | CBLC | Cas-Br-M (murine) ecotropic retroviral transforming sequence c | 23624 | NM_012116 |
| 3.47 | DAPP1 | dual adaptor of phosphotyrosine and 3-phosphoinositides | 27071 | AI632216 |
| 3.46 | EPB41L5 | erythrocyte membrane protein band 4.1 like 5 | 57669 | AI652872 |
| 3.46 | NALP2 | NACHT, leucine rich repeat and PYD containing 2 | 55655 | AF298547 |
| 3.46 | FAM83A | family with sequence similarity 83, member A | 84985 | BE157240 |
| 3.45 | GPR110 | G protein-coupled receptor 110 | 266977 | BG426455 |
| 3.44 | SERPINB1 | serpin peptidase inhibitor, clade B (ovalbumin), member 1 | 1992 | NM_030666 |
| 3.44 | EPS8L1 | EPS8-like 1 | 54869 | AI219073 |
| 3.44 | DAPP1 | dual adaptor of phosphotyrosine and 3-phosphoinositides | 27071 | AA150186 |
| 3.42 | BCL11B | B-cell CLL/lymphoma 11B (zinc finger protein) | 64919 | AA918317 |
| 3.42 | CEACAM6 | carcinoembryonic antigen-related cell adhesion molecule 6 (non-specific cross reacting antigen) | 4680 | M18728 |
| 3.42 | SLCO4A1 | solute carrier organic anion transporter family, member 4A1 | 28231 | NM_016354 |
| 3.40 | EPPK1 | epiplakin 1 | 83481 | AL137725 |
| 3.40 | SERPINB13 | serpin peptidase inhibitor, clade B (ovalbumin), member 13 | 5275 | AF169949 |
| 3.39 | TGFA | transforming growth factor, alpha | 7039 | M31172 |

Fig. 32C (Cont.)

Relative expression of Mammary Luminal-Cell-Specific genes in BPEC-hTERT vs. HMEC-hTERT

| Affymetrix_ID | Grigoriadis myoepithelial/ luminal log2 ratio | Coef. BPEC-hTERT/ HMEC-hTERT | Coef. HMEC-hTERT/ BPEC-hTERT | Coef. BPEC-hTERT/ HMEC-hTERT | Coef. HMEC-hTERT/ BPEC-hTERT |
|---|---|---|---|---|---|
| 214701_s_at | -2.58 | -5.3113 | 5.3113 | same | different |
| 221577_x_at | -1.21 | -5.6412 | 5.6412 | same | different |
| 202295_s_at | -0.84 | -2.3275 | 2.3275 | same | different |
| 209955_s_at | -1.03 | -4.6916 | 4.6916 | same | different |
| 215646_s_at | -2.20 | -5.9178 | 5.9178 | same | different |
| 202672_s_at | -0.72 | -1.4369 | 1.4369 | same | different |
| 203423_at | -0.70 | -1.4114 | 1.4114 | same | different |
| 220407_s_at | -1.80 | -3.3712 | 3.3712 | same | different |
| 209101_at | -0.70 | -2.5591 | 2.5591 | same | different |
| 212503_s_at | -0.41 | -2.9174 | 2.9174 | same | different |
| 209581_at | -0.44 | -1.2378 | 1.2378 | same | different |
| 202637_s_at | -0.72 | -1.4859 | 1.4859 | same | different |
| 224733_at | -0.70 | -2.0874 | 2.0874 | same | different |
| 211966_at | -1.22 | -2.0511 | 2.0511 | same | different |
| 205659_at | -1.26 | -3.566 | 3.566 | same | different |
| 211981_at | -1.58 | -1.8803 | 1.8803 | same | different |
| 201242_s_at | -0.68 | -1.5369 | 1.5369 | same | different |
| 218627_at | -0.43 | -1.2423 | 1.2423 | same | different |
| 208425_s_at | -1.41 | -1.314 | 1.314 | same | different |
| 209305_s_at | -1.23 | -1.3155 | 1.3155 | same | different |
| 209529_at | -0.89 | -1.3769 | 1.3769 | same | different |
| 221523_s_at | -1.11 | -3.1177 | 3.1177 | same | different |
| 223315_at | -1.19 | -1.8967 | 1.8967 | same | different |

Fig. 33

Relative expression of Mammary Luminal-Cell-Specific genes in BPEC-hTERT vs. HMEC-hTERT

| Gene Symbol | Gene Title | Entrez Gene |
|---|---|---|
| FN1 | fibronectin 1 | 2335 |
| GDF15 | growth differentiation factor 15 | 9518 |
| CTSH | cathepsin H | 1512 |
| FAP | fibroblast activation protein, alpha | 2191 |
| CSPG2 | chondroitin sulfate proteoglycan 2 (versican) | 1462 |
| ATF3 | activating transcription factor 3 | 467 |
| RBP1 | retinol binding protein 1, cellular | 5947 |
| TGFB2 | transforming growth factor, beta 2 | 7042 |
| CTGF | connective tissue growth factor | 1490 |
| DIP2C | DIP2 disco-interacting protein 2 homolog C (Drosophila) | 22982 |
| HRASLS3 | HRAS-like suppressor 3 | 11145 |
| ICAM1 | intercellular adhesion molecule 1 (CD54), human rhinovirus receptor | 3383 |
| CMTM3 | CKLF-like MARVEL transmembrane domain containing 3 | 123920 |
| COL4A2 | collagen, type IV, alpha 2 | 1284 |
| HDAC9 | histone deacetylase 9 | 9734 |
| COL4A1 | collagen, type IV, alpha 1 | 1282 |
| ATP1B1 | ATPase, Na+/K+ transporting, beta 1 polypeptide | 481 |
| DRAM | damage-regulated autophagy modulator | 55332 |
| TANC2 | tetratricopeptide repeat, ankyrin repeat and coiled-coil containing 2 | 26115 |
| GADD45B | growth arrest and DNA-damage-inducible, beta | 4616 |
| PPAP2C | phosphatidic acid phosphatase type 2C | 8612 |
| RRAGD | Ras-related GTP binding D | 58528 |
| NTN4 | netrin 4 | 59277 |

Fig. 33 (Cont.)

| | | | | |
|---|---|---|---|---|
| 210764_s_at | -1.09 | -1.774 | 1.774 | same | different |
| 201124_at | -0.62 | -2.9959 | 2.9959 | same | different |
| 207265_s_at | -0.72 | -1.1773 | 1.1773 | same | different |
| 218211_s_at | -1.10 | -3.1273 | 3.1273 | same | different |
| 218066_at | -0.41 | -2.8261 | 2.8261 | same | different |
| 213069_at | -0.47 | -2.5968 | 2.5968 | same | different |
| 209894_at | -0.84 | -2.1337 | 2.1337 | same | different |
| 231779_at | -0.42 | -2.0806 | 2.0806 | same | different |
| 226017_at | -0.51 | -1.8218 | 1.8218 | same | different |
| 205640_at | -0.72 | -1.8181 | 1.8181 | same | different |
| 205122_at | -0.77 | -1.5908 | 1.5908 | same | different |
| 222528_s_at | -0.50 | -1.5065 | 1.5065 | same | different |
| 223158_s_at | -0.51 | -1.4197 | 1.4197 | same | different |
| 231955_s_at | -0.82 | -1.3382 | 1.3382 | same | different |
| 203335_at | -0.51 | -1.338 | 1.338 | same | different |
| 201825_s_at | -0.45 | -1.2857 | 1.2857 | same | different |
| 205174_s_at | -0.52 | -1.2151 | 1.2151 | same | different |
| 204519_s_at | -0.84 | -1.1935 | 1.1935 | same | different |
| 201647_s_at | -0.95 | -1.165 | 1.165 | same | different |
| 213839_at | -0.65 | -1.1413 | 1.1413 | same | different |
| 210176_at | -0.53 | -1.126 | 1.126 | same | different |
| 208702_x_at | -0.56 | -1.1204 | 1.1204 | same | different |
| 233496_s_at | -0.71 | -1.1183 | 1.1183 | same | different |
| 208092_s_at | -0.73 | -1.1145 | 1.1145 | same | different |
| 235521_at | -0.84 | -1.1133 | 1.1133 | same | different |
| 226324_s_at | -0.91 | -1.0838 | 1.0838 | same | different |
| 207334_s_at | -2.16 | -1.073 | 1.073 | same | different |

Fig. 33 (Cont.)

| | | |
|---|---|---|
| CYR61 | cysteine-rich, angiogenic inducer, 61 | 3491 |
| ITGB5 | integrin, beta 5 | 3693 |
| KDELR3 | KDEL (Lys-Asp-Glu-Leu) endoplasmic reticulum protein retention receptor 3 | 11015 |
| MLPH | melanophilin | 79083 |
| SLC12A7 | solute carrier family 12 (potassium/chloride transporters), member 7 | 10723 |
| HEG1 | HEG homolog 1 (zebrafish) | 57493 |
| LEPR | leptin receptor | 3953 |
| IRAK2 | interleukin-1 receptor-associated kinase 2 | 3656 |
| CMTM7 | CKLF-like MARVEL transmembrane domain containing 7 | 112616 |
| ALDH3B1 | aldehyde dehydrogenase 3 family, member B1 | 221 |
| TMEFF1 | transmembrane protein with EGF-like and two follistatin-like domains 1 | 8577 |
| SLC25A37 | solute carrier family 25, member 37 | 51312 |
| NEK6 | NIMA (never in mitosis gene a)-related kinase 6 | 10783 |
| HIBADH | 3-hydroxyisobutyrate dehydrogenase | 11112 |
| PHYH | phytanoyl-CoA 2-hydroxylase | 5264 |
| SCCPDH | saccharopine dehydrogenase (putative) | 51097 |
| QPCT | glutaminyl-peptide cyclotransferase (glutaminyl cyclase) | 25797 |
| PLLP | plasma membrane proteolipid (plasmolipin) | 51090 |
| SCARB2 | scavenger receptor class B, member 2 | 950 |
| KIAA0500 | KIAA0500 protein | 57237 |
| TLR1 | toll-like receptor 1 | 7096 |
| APLP2 | amyloid beta (A4) precursor-like protein 2 | 334 |
| CFL2 | cofilin 2 (muscle) | 1073 |
| FAM49A | family with sequence similarity 49, member A | 81553 |
| HOXA3 | homeobox A3 | 3200 |
| IFT172 | intraflagellar transport 172 homolog (Chlamydomonas) | 26160 |
| TGFBR2 | transforming growth factor, beta receptor II (70/80kDa) | 7048 |

Fig. 33 (Cont.)

| | | | | |
|---|---|---|---|---|
| 205538_at | -0.61 | -1.0622 | 1.0622 | same |
| 225355_at | -1.37 | -1.0586 | 1.0586 | same |
| 1553995_a_at | -1.15 | -1.0409 | 1.0409 | same |
| 209645_s_at | -0.99 | -1.0352 | 1.0352 | same |
| 238932_at | -1.16 | -1.0143 | 1.0143 | same |
| 231236_at | -0.61 | 1.5788 | -1.5788 | different |
| 235857_at | -0.44 | 1.9711 | -1.9711 | different |
| 208084_at | -2.08 | 1.8397 | -1.8397 | different |
| 202086_at | -1.10 | 2.8981 | -2.8981 | different |
| 204972_at | -1.24 | 2.5973 | -2.5973 | different |
| 204415_at | -0.77 | 3.0397 | -3.0397 | different |
| 201340_s_at | -1.46 | 1.467 | -1.467 | different |
| 203153_at | -1.29 | 1.052 | -1.052 | different |
| 219749_at | -0.56 | 2.134 | -2.134 | different |
| 230006_s_at | -0.55 | 2.6169 | -2.6169 | different |
| 238065_at | -0.42 | 1.1959 | -1.1959 | different |
| 204364_s_at | -0.84 | 1.1294 | -1.1294 | different |
| 218182_s_at | -0.91 | 2.6009 | -2.6009 | different |
| 211026_s_at | -1.73 | 1.1675 | -1.1675 | different |
| 225299_at | -1.02 | 3.549 | -3.549 | different |
| 1559361_at | -2.30 | 2.629 | -2.629 | different |
| 224650_at | -0.49 | 4.292 | -4.292 | different |
| 202411_at | -0.60 | 5.0709 | -5.0709 | different |
| 218756_s_at | -0.63 | 1.2485 | -1.2485 | different |
| 220800_s_at | -1.38 | 1.3249 | -1.3249 | different |
| 205778_at | -1.15 | 5.8337 | -5.8337 | different |
| 203585_at | -0.51 | 2.413 | -2.413 | different | | same |
| | | | | | different |
| | | | | | different |
| | | | | | different |
| | | | | | different |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |
| | | | | | same |

Fig. 33 (Cont.)

| Symbol | Description | Number |
|---|---|---|
| CORO2A | coronin, actin binding protein, 2A | 7464 |
| DKFZP761M1511 | hypothetical protein DKFZP761M1511 | 54492 |
| NT5E | 5'-nucleotidase, ecto (CD73) | 4907 |
| ALDH1B1 | aldehyde dehydrogenase 1 family, member B1 | 219 |
| TSC22D2 | TSC22 domain family, member 2 | 9819 |
| ZFP57 | zinc finger protein 57 homolog (mouse) | 346171 |
| KCTD11 | potassium channel tetramerisation domain containing 11 | 147040 |
| ITGB6 | integrin, beta 6 | 3694 |
| MX1 | myxovirus (influenza virus) resistance 1, interferon-inducible protein p78 (mouse) | 4599 |
| OAS2 | 2'-5'-oligoadenylate synthetase 2, 69/71kDa | 4939 |
| IFI6 | interferon, alpha-inducible protein 6 | 2537 |
| ENC1 | ectodermal-neural cortex (with BTB-like domain) | 8507 |
| IFIT1 | interferon-induced protein with tetratricopeptide repeats 1 | 3434 |
| SH2D4A | SH2 domain containing 4A | 63898 |
| DKFZp313A2432 | hypothetical protein DKFZp313A2432 | 258010 |
| TPM3 | tropomyosin 3 | 7170 |
| REEP1 | receptor accessory protein 1 | 65055 |
| CLDN1 | claudin 1 | 9076 |
| MGLL | monoglyceride lipase | 11343 |
| MYO5B | myosin VB | 4645 |
| RPL21 | Ribosomal protein L21 | 6144 |
| MAL2 | mal, T-cell differentiation protein 2 | 114569 |
| IFI27 | interferon, alpha-inducible protein 27 | 3429 |
| MGC4172 | short-chain dehydrogenase/reductase | 79154 |
| TMOD3 | tropomodulin 3 (ubiquitous) | 29766 |
| KLK7 | kallikrein-related peptidase 7 | 5650 |
| ZNF185 | zinc finger protein 185 (LIM domain) | 7739 |

Fig. 33 (Cont.)

| | | | | |
|---|---|---|---|---|
| 212531_at | -1.27 | 5.1461 | -5.1461 | different | same |
| 211258_s_at | -2.01 | 2.8987 | -2.8987 | different | same |
| 201428_at | -0.94 | 2.5305 | -2.5305 | different | same |
| 203815_at | -0.76 | 1.3776 | -1.3776 | different | same |
| 228221_at | -0.82 | 2.0077 | -2.0077 | different | same |
| 225987_at | -0.52 | 1.1764 | -1.1764 | different | same |
| 233565_s_at | -0.84 | 2.6743 | -2.6743 | different | same |
| 205466_s_at | -0.84 | 1.8495 | -1.8495 | different | same |
| 209276_s_at | -0.86 | 2.0626 | -2.0626 | different | same |
| 210130_s_at | -0.81 | 2.0878 | -2.0878 | different | same |
| 225177_at | -0.99 | 2.7987 | -2.7987 | different | same |
| 1555733_s_at | -1.93 | 1.2138 | -1.2138 | different | same |
| 209366_x_at | -0.38 | 4.0386 | -4.0386 | different | same |
| 219529_at | -0.83 | 3.8543 | -3.8543 | different | same |
| 219225_at | -1.80 | 2.7846 | -2.7846 | different | same |
| 227804_at | -0.61 | 1.3783 | -1.3783 | different | same |
| 207388_s_at | -1.05 | 2.6014 | -2.6014 | different | same |
| 213568_at | -0.99 | 2.2751 | -2.2751 | different | same |
| 204803_s_at | -1.17 | 2.7733 | -2.7733 | different | same |
| 214091_s_at | -1.85 | 5.5233 | -5.5233 | different | same |
| 210397_at | -0.74 | 2.4683 | -2.4683 | different | same |
| 230323_s_at | -0.51 | 3.1805 | -3.1805 | different | same |
| 219127_at | -0.53 | 1.3779 | -1.3779 | different | same |
| 205568_at | -0.82 | 1.0223 | -1.0223 | different | same |
| 220979_s_at | -0.85 | 2.6019 | -2.6019 | different | same |
| 228010_at | -0.61 | 5.5112 | -5.5112 | different | same |
| 215729_s_at | -1.84 | 4.2983 | -4.2983 | different | same |

Fig. 33 (Cont.)

| Symbol | Description | Number |
|---|---|---|
| LCN2 | lipocalin 2 (oncogene 24p3) | 3934 |
| TGFA | transforming growth factor, alpha | 7039 |
| CLDN4 | claudin 4 | 1364 |
| GSTT1 | glutathione S-transferase theta 1 | 2952 |
| SLC44A3 | solute carrier family 44, member 3 | 126969 |
| STEAP4 | STEAP family member 4 | 79689 |
| SDCBP2 | syndecan binding protein (syntenin) 2 | 27111 |
| HS3ST1 | heparan sulfate (glucosamine) 3-O-sulfotransferase 1 | 9957 |
| GLRX | glutaredoxin (thioltransferase) | 2745 |
| TM7SF2 | transmembrane 7 superfamily member 2 | 7108 |
| RAB11FIP1 | RAB11 family interacting protein 1 (class I) | 80223 |
| AP1S3 | adaptor-related protein complex 1, sigma 3 subunit | 130340 |
| CYB5A | cytochrome b5 type A (microsomal) | 1528 |
| CLIC3 | chloride intracellular channel 3 /// rabaptin, RAB GTPase binding effector protein 1 | 9022 |
| PGBD5 | piggyBac transposable element derived 5 | 79605 |
| TLCD1 | TLC domain containing 1 | 116238 |
| PTGES | prostaglandin E synthase | 9536 |
| OSR2 | odd-skipped related 2 (Drosophila) | 116039 |
| RRAD | Ras-related associated with diabetes | 6236 |
| GPX3 | glutathione peroxidase 3 (plasma) | 2878 |
| DEFB1 | defensin, beta 1 | 1672 |
| TMEM45B | transmembrane protein 45B | 120224 |
| ATAD4 | ATPase family, AAA domain containing 4 | 79170 |
| AQP9 | aquaporin 9 | 366 |
| ST6GALNAC5 | ST6 (alpha-N-acetyl-neuraminyl-2,3-beta galactosyl-1,3)-N-acetylgalactosaminide alpha-2,6-sialyltransferase 5 | 81849 |
| PPP2R2C | protein phosphatase 2 (formerly 2A), regulatory subunit B (PR 52), gamma isoform | 5522 |
| VGLL1 | vestigial like 1 (Drosophila) | 51442 |

Fig. 33 (Cont.)

| | | | | |
|---|---|---|---|---|
| 1555812_a_at | -0.75 | 5.613 | -5.613 | different | same |
| 220724_at | -0.95 | 5.2627 | -5.2627 | different | same |
| 220431_at | -0.80 | 1.7165 | -1.7165 | different | same |
| 231120_x_at | -1.54 | 2.1303 | -2.1303 | different | same |
| 231849_at | -1.67 | 1.4253 | -1.4253 | different | same |
| 204614_at | -0.68 | 4.8838 | -4.8838 | different | same |
| 218990_s_at | -0.65 | 5.2054 | -5.2054 | different | same |
| 206504_at | -1.26 | 2.6454 | -2.6454 | different | same |
| 226603_at | -0.94 | 1.0033 | -1.0033 | different | same |
| 217208_s_at | -1.76 | 1.0213 | -1.0213 | different | same |
| 228152_s_at | -1.04 | 1.0246 | -1.0246 | different | same |
| 218432_at | -0.45 | 1.0386 | -1.0386 | different | same |
| 202670_at | -0.69 | 1.1391 | -1.1391 | different | same |
| 242625_at | -1.80 | 1.1446 | -1.1446 | different | same |
| 225095_at | -0.34 | 1.1733 | -1.1733 | different | same |
| 209369_at | -0.51 | 1.1918 | -1.1918 | different | same |
| 224175_s_at | -0.46 | 1.2037 | -1.2037 | different | same |
| 1563933_a_at | -1.39 | 1.2117 | -1.2117 | different | same |
| 1552502_s_at | -0.81 | 1.2313 | -1.2313 | different | same |
| 228061_at | -0.91 | 1.2387 | -1.2387 | different | same |
| 207717_s_at | -0.59 | 1.255 | -1.255 | different | same |
| 223058_at | -0.51 | 1.2753 | -1.2753 | different | same |
| 202770_s_at | -0.85 | 1.2923 | -1.2923 | different | same |
| 228013_at | -0.51 | 1.3215 | -1.3215 | different | same |
| 224018_s_at | -1.05 | 1.334 | -1.334 | different | same |
| 232977_x_at | -0.54 | 1.3508 | -1.3508 | different | same |
| 235390_at | -0.46 | 1.3558 | -1.3558 | different | same |

Fig. 33 (Cont.)

| Gene | Description | ID |
|---|---|---|
| ARHGDIB | Rho GDP dissociation inhibitor (GDI) beta | 397 |
| FLJ21511 | hypothetical protein FLJ21511 | 80157 |
| TMPRSS11E | transmembrane protease, serine 11E /// similar to transmembrane protease, serine 11E | 28983 |
| PKIB | protein kinase (cAMP-dependent, catalytic) inhibitor beta | 5570 |
| KRT80 | keratin 80 | 144501 |
| SERPINB2 | serpin peptidase inhibitor, clade B (ovalbumin), member 2 | 5055 |
| SPRR3 | small proline-rich protein 3 | 6707 |
| CYP24A1 | cytochrome P450, family 24, subfamily A, polypeptide 1 | 1591 |
| SAMD9L | sterile alpha motif domain containing 9-like | 219285 |
| DLG1 | tumor necrosis factor receptor superfamily, member 11b (osteoprotegerin) | 1739 |
| FLJ31033 | hypothetical protein FLJ31033 | 91351 |
| FBXO3 | F-box protein 3 | 26273 |
| MAP2K1 | mitogen-activated protein kinase kinase 1 | 5604 |
| RSAD2 | radical S-adenosyl methionine domain containing 2 | 91543 |
| SPTLC2 | Serine palmitoyltransferase, long chain base subunit 2 | 9517 |
| ANXA3 | annexin A3 | 306 |
| TRIM34 | tripartite motif-containing 34 /// tripartite motif-containing 6 and tripartite motif-containing 34 | 445372 |
| PLD5 | phospholipase D family, member 5 | 200150 |
| RHBDL2 | rhomboid, veinlet-like 2 (Drosophila) | 54933 |
| CCDC126 | coiled-coil domain containing 126 | 90693 |
| PKP2 | plakophilin 2 | 5318 |
| FAM107B | family with sequence similarity 107, member B | 83641 |
| CCNG2 | cyclin G2 | 901 |
| PPP2R2A | Protein phosphatase 2 (formerly 2A), regulatory subunit B (PR 52), alpha isoform | 5520 |
| SCD5 | stearoyl-CoA desaturase 5 | 79966 |
| MYH14 | myosin, heavy chain 14 | 79784 |
| P18SRP | P18SRP protein | 285672 |

Fig. 33 (Cont.)

| | | | | |
|---|---|---|---|---|
| 214440_at | -0.73 | 1.385 | -1.385 | different | same |
| 211725_s_at | -0.80 | 1.4286 | -1.4286 | different | same |
| 216074_x_at | -1.09 | 1.4414 | -1.4414 | different | same |
| 218986_s_at | -1.15 | 1.4729 | -1.4729 | different | same |
| 211078_s_at | -0.79 | 1.4788 | -1.4788 | different | same |
| 206284_x_at | -0.67 | 1.4875 | -1.4875 | different | same |
| 204368_at | -0.48 | 1.5089 | -1.5089 | different | same |
| 238649_at | -0.69 | 1.5779 | -1.5779 | different | same |
| 219634_at | -0.67 | 1.6203 | -1.6203 | different | same |
| 217979_at | -0.88 | 1.6632 | -1.6632 | different | same |
| 214453_s_at | -1.00 | 1.6659 | -1.6659 | different | same |
| 205660_at | -0.78 | 1.6697 | -1.6697 | different | same |
| 203557_s_at | -0.71 | 1.6771 | -1.6771 | different | same |
| 223333_s_at | -1.33 | 1.6915 | -1.6915 | different | same |
| 209124_at | -0.48 | 1.6943 | -1.6943 | different | same |
| 1562378_s_at | -0.42 | 1.7018 | -1.7018 | different | same |
| 230660_at | -0.62 | 1.7214 | -1.7214 | different | same |
| 209193_at | -0.69 | 1.8218 | -1.8218 | different | same |
| 205691_at | -0.75 | 1.8666 | -1.8666 | different | same |
| 224836_at | -0.58 | 1.9699 | -1.9699 | different | same |
| 228302_x_at | -1.16 | 2.0021 | -2.0021 | different | same |
| 213524_s_at | -0.83 | 2.0363 | -2.0363 | different | same |
| 205483_s_at | -1.15 | 2.0612 | -2.0612 | different | same |
| 1555829_at | -1.63 | 2.2148 | -2.2148 | different | same |
| 210609_s_at | -0.58 | 2.2206 | -2.2206 | different | same |

Fig. 33 (Cont.)

| | | |
|---|---|---|
| NAT1 | N-acetyltransferase 1 (arylamine N-acetyltransferase) | 9 |
| BID | BH3 interacting domain death agonist /// BH3 interacting domain death agonist | 637 |
| WWC1 | WW and C2 domain containing 1 | 23286 |
| FLJ20035 | hypothetical protein FLJ20035 | 55601 |
| STK3 | serine/threonine kinase 3 (STE20 homolog, yeast) | 6788 |
| CLTB | clathrin, light chain (Lcb) | 1212 |
| SLCO2A1 | solute carrier organic anion transporter family, member 2A1 | 6578 |
| PITPNC1 | phosphatidylinositol transfer protein, cytoplasmic 1 | 26207 |
| CHST11 | carbohydrate (chondroitin 4) sulfotransferase 11 | 50515 |
| TSPAN13 | Tetraspanin 13 | 27075 |
| IFI44 | interferon-induced protein 44 | 10561 |
| OASL | 2'-5'-oligoadenylate synthetase-like | 8638 |
| PCBD1 | pterin-4 alpha-carbinolamine dehydratase/dimerization cofactor of HNF 1 alpha (TCF1) | 5092 |
| ANGPTL4 | angiopoietin-like 4 | 51129 |
| MYD88 | myeloid differentiation primary response gene (88) | 4615 |
| PROM2 | prominin 2 | 150696 |
| SERTAD4 | SERTA domain containing 4 | 56256 |
| PIM1 | pim-1 oncogene | 5292 |
| SYNGR3 | synaptogyrin 3 | 9143 |
| TP53INP2 | tumor protein p53 inducible nuclear protein 2 | 58476 |
| CAMK2N1 | calcium/calmodulin-dependent protein kinase II inhibitor 1 | 55450 |
| G0S2 | G0/G1switch 2 | 50486 |
| ISG15 | ISG15 ubiquitin-like modifier | 9636 |
| FAM62B | family with sequence similarity 62 (C2 domain containing) member B | 57488 |
| TP53I3 | tumor protein p53 inducible protein 3 | 9540 |

Fig. 33 (Cont.)

| | | | | |
|---|---|---|---|---|
| 226701_at | -1.18 | 2.2973 | -2.2973 | different | same |
| 223454_at | -0.76 | 2.3519 | -2.3519 | different | same |
| 225955_at | -0.69 | 2.3753 | -2.3753 | different | same |
| 213711_at | -0.62 | 2.4756 | -2.4756 | different | same |
| 227609_at | -1.13 | 2.5156 | -2.5156 | different | same |
| 219209_at | -0.52 | 2.6705 | -2.6705 | different | same |
| 232682_at | -0.55 | 2.7196 | -2.7196 | different | same |
| 227919_at | -0.77 | 2.7197 | -2.7197 | different | same |
| 202525_at | -0.64 | 2.9947 | -2.9947 | different | same |
| 228964_at | -0.44 | 3.1809 | -3.1809 | different | same |
| 202708_s_at | -0.38 | 3.2961 | -3.2961 | different | same |
| 229292_at | -0.60 | 3.3182 | -3.3182 | different | same |
| 201462_at | -0.45 | 3.3395 | -3.3395 | different | same |
| 222859_s_at | -1.47 | 3.4812 | -3.4812 | different | same |
| 209114_at | -0.65 | 3.5344 | -3.5344 | different | same |
| 201130_s_at | -1.19 | 3.5381 | -3.5381 | different | same |
| 201688_s_at | -1.27 | 4.26 | -4.26 | different | same |
| 222242_s_at | -0.84 | 5.7399 | -5.7399 | different | same |
| Num down > 2-fold | 173 | 55 | 118 | 118 | 55 |
| Num up > 2-fold | 0 | 119 | 55 | 55 | 119 |

Fig. 33 (Cont.)

| | | |
|---|---|---|
| GJA5 | gap junction protein, alpha 5, 40kDa (connexin 40) | 2702 |
| CXCL16 | chemokine (C-X-C motif) ligand 16 | 58191 |
| MED25 | mediator of RNA polymerase II transcription, subunit 25 homolog (S. cerevisiae) | 284207 |
| KRT81 | keratin 81 | 3887 |
| EPSTI1 | epithelial stromal interaction 1 (breast) | 94240 |
| IFIH1 | interferon induced with helicase C domain 1 | 64135 |
| MREG | melanoregulin | 55686 |
| UCA1 | urothelial cancer associated 1 | 652995 |
| PRSS8 | protease, serine, 8 (prostasin) | 5652 |
| PRDM1 | PR domain containing 1, with ZNF domain | 639 |
| HIST2H2BE | histone cluster 2, H2be | 8349 |
| EPB41L5 | erythrocyte membrane protein band 4.1 like 5 | 57669 |
| SCRN1 | secernin 1 | 9805 |
| DAPP1 | dual adaptor of phosphotyrosine and 3-phosphoinositides | 27071 |
| TSPAN1 | tetraspanin 1 | 10103 |
| CDH1 | cadherin 1, type 1, E-cadherin (epithelial) | 999 |
| TPD52 | tumor protein D52 | 7163 |
| KLK5 | kallikrein-related peptidase 5 | 25818 |

Fig. 33 (Cont.)

Relative expression of Mammary Myoepithelial-Cell-Specific genes in BPEC-hTERT vs. HMEC-hTERT

| Affymetrix_ID | Grigoriadis myoepithelial/ luminal log2 ratio | Coef. BPEC-hTERT/ HMEC-hTERT | Coef. HMEC-hTERT/ BPEC-hTERT | Coef. BPEC-hTERT/ HMEC-hTERT | Coef. HMEC-hTERT/ BPEC-hTERT |
|---|---|---|---|---|---|
| 210809_s_at | 5.46 | -9.1951 | 9.1951 | different | same |
| 221729_at | 2.94 | -6.4666 | 6.4666 | different | same |
| 227048_at | 1.43 | -6.3533 | 6.3533 | different | same |
| 203434_s_at | 1.56 | -5.738 | 5.738 | different | same |
| 209167_at | 1.70 | -5.3377 | 5.3377 | different | same |
| 201141_at | 2.14 | -5.2605 | 5.2605 | different | same |
| 206026_s_at | 1.35 | -5.2191 | 5.2191 | different | same |
| 202746_at | 1.05 | -5.0715 | 5.0715 | different | same |
| 204646_at | 0.91 | -4.5337 | 4.5337 | different | same |
| 202363_at | 0.69 | -4.4565 | 4.4565 | different | same |
| 226771_at | 1.35 | -4.2409 | 4.2409 | different | same |
| 212353_at | 1.81 | -3.9229 | 3.9229 | different | same |
| 204421_s_at | 0.87 | -3.9045 | 3.9045 | different | same |
| 203889_at | 1.15 | -3.9014 | 3.9014 | different | same |
| 203989_x_at | 0.62 | -3.8583 | 3.8583 | different | same |
| 227059_at | 1.37 | -3.821 | 3.821 | different | same |
| 219789_at | 1.75 | -3.8051 | 3.8051 | different | same |
| 209656_s_at | 0.70 | -3.5551 | 3.5551 | different | same |
| 204466_s_at | 1.91 | -3.2222 | 3.2222 | different | same |
| 213093_at | 1.50 | -3.1701 | 3.1701 | different | same |
| 213325_at | 0.58 | -3.1146 | 3.1146 | different | same |
| 218723_s_at | 1.31 | -3.0962 | 3.0962 | different | same |
| 202237_at | 1.14 | -3.0853 | 3.0853 | different | same |

Fig. 33 (Cont.)

Relative expression of Mammary Myoepithelial-Cell-Specific genes in BPEC-hTERT vs. HMEC-hTERT

| Gene Symbol | Gene Title | Entrez Gene |
|---|---|---|
| POSTN | periostin, osteoblast specific factor | 10631 |
| COL5A2 | collagen, type V, alpha 2 | 1290 |
| LAMA1 | laminin, alpha 1 | 284217 |
| MME | membrane metallo-endopeptidase (neutral endopeptidase, enkephalinase) | 4311 |
| GPM6B | glycoprotein M6B | 2824 |
| GPNMB | glycoprotein (transmembrane) nmb | 10457 |
| TNFAIP6 | tumor necrosis factor, alpha-induced protein 6 | 7130 |
| ITM2A | integral membrane protein 2A | 9452 |
| DPYD | dihydropyrimidine dehydrogenase | 1806 |
| SPOCK1 | sparc/osteonectin, cwcv and kazal-like domains proteoglycan (testican) 1 | 6695 |
| ATP8B2 | ATPase, Class I, type 8B, member 2 | 57198 |
| SULF1 | sulfatase 1 | 23213 |
| FGF2 | fibroblast growth factor 2 (basic) | 2247 |
| SCG5 | secretogranin V (7B2 protein) | 6447 |
| F2R | coagulation factor II (thrombin) receptor | 2149 |
| GPC6 | Glypican 6 | 10082 |
| NPR3 | natriuretic peptide receptor C/guanylate cyclase C (atrionatriuretic peptide receptor C) | 4883 |
| TMEM47 | transmembrane protein 47 | 83604 |
| SNCA | synuclein, alpha (non A4 component of amyloid precursor) | 6622 |
| PRKCA | protein kinase C, alpha | 5578 |
| PVRL3 | poliovirus receptor-related 3 | 25945 |
| RGC32 | response gene to complement 32 | 28984 |
| NNMT | nicotinamide N-methyltransferase | 4837 |

Fig. 33 (Cont.)

| | | | |
|---|---|---|---|
| 204955_at | 1.02 | -3.0214 | 3.0214 | different | same |
| 212813_at | 1.15 | -3.0197 | 3.0197 | different | same |
| 202718_at | 1.96 | -3.0089 | 3.0089 | different | same |
| 212667_at | 1.80 | -2.8354 | 2.8354 | different | same |
| 37408_at | 0.91 | -2.8795 | 2.8795 | different | same |
| 201426_s_at | 0.61 | -2.7698 | 2.7698 | different | same |
| 211709_s_at | 0.88 | -2.6902 | 2.6902 | different | same |
| 222162_s_at | 0.74 | -2.6739 | 2.6739 | different | same |
| 219355_at | 1.27 | -2.6641 | 2.6641 | different | same |
| 209383_at | 0.62 | -2.6627 | 2.6627 | different | same |
| 214247_s_at | 3.08 | -2.6451 | 2.6451 | different | same |
| 211896_s_at | 2.79 | -2.6163 | 2.6163 | different | same |
| 226665_at | 0.56 | -2.5977 | 2.5977 | different | same |
| 213369_at | 0.63 | -2.596 | 2.596 | different | same |
| 208763_s_at | 0.95 | -2.5709 | 2.5709 | different | same |
| 209610_s_at | 1.73 | -2.5623 | 2.5623 | different | same |
| 209875_s_at | 1.76 | -2.5614 | 2.5614 | different | same |
| 236277_at | 1.10 | -2.5274 | 2.5274 | different | same |
| 207387_s_at | 1.52 | -2.4922 | 2.4922 | different | same |
| 210139_s_at | 0.55 | -2.4721 | 2.4721 | different | same |
| 221898_at | 1.10 | -2.4585 | 2.4585 | different | same |
| 227846_at | 1.37 | -2.4436 | 2.4436 | different | same |
| 203140_at | 0.97 | -2.4328 | 2.4328 | different | same |
| 209230_s_at | 1.13 | -2.4176 | 2.4176 | different | same |
| 204115_at | 2.16 | -2.3557 | 2.3557 | different | same |
| 227070_at | 1.70 | -2.331 | 2.331 | different | same |
| 203980_at | 0.80 | -2.3222 | 2.3222 | different | same |

Fig. 33 (Cont.)

| Gene | Description | ID |
|---|---|---|
| SRPX | sushi-repeat-containing protein, X-linked | 8406 |
| JAM3 | junctional adhesion molecule 3 | 83700 |
| IGFBP2 | insulin-like growth factor binding protein 2, 36kDa | 3485 |
| SPARC | secreted protein, acidic, cysteine-rich (osteonectin) | 6678 |
| MRC2 | mannose receptor, C type 2 | 9902 |
| VIM | vimentin | 7431 |
| CLEC11A | C-type lectin domain family 11, member A /// C-type lectin domain family 11, member A | 6320 |
| ADAMTS1 | ADAM metallopeptidase with thrombospondin type 1 motif, 1 | 9510 |
| CXorf57 | chromosome X open reading frame 57 | 55086 |
| DDIT3 | DNA-damage-inducible transcript 3 | 1649 |
| DKK3 | dickkopf homolog 3 (Xenopus laevis) | 27122 |
| DCN | decorin | 1634 |
| AHSA2 | AHA1, activator of heat shock 90kDa protein ATPase homolog 2 (yeast) | 130872 |
| PCDH21 | protocadherin 21 | 92211 |
| TSC22D3 | TSC22 domain family, member 3 | 1831 |
| SLC1A4 | solute carrier family 1 (glutamate/neutral amino acid transporter), member 4 | 6509 |
| SPP1 | secreted phosphoprotein 1 (osteopontin, bone sialoprotein I, early T-lymphocyte activation 1) | 6696 |
| PAK3 | P21 (CDKN1A)-activated kinase 3 | 5063 |
| GK | glycerol kinase | 2710 |
| PMP22 | peripheral myelin protein 22 | 5376 |
| PDPN | podoplanin | 10630 |
| GPR176 | G protein-coupled receptor 176 | 11245 |
| BCL6 | B-cell CLL/lymphoma 6 (zinc finger protein 51) /// B-cell CLL/lymphoma 6 (zinc finger protein 51) | 604 |
| NUPR1 | nuclear protein 1 | 26471 |
| GNG11 | guanine nucleotide binding protein (G protein), gamma 11 | 2791 |
| GLT8D2 | glycosyltransferase 8 domain containing 2 | 83468 |
| FABP4 | fatty acid binding protein 4, adipocyte | 2167 |

Fig. 33 (Cont.)

| | | | | |
|---|---|---|---|---|
| 202948_at | 0.42 | -2.286 | 2.286 | different same |
| 241763_s_at | 0.96 | -2.2131 | 2.2131 | different same |
| 202436_s_at | 1.65 | -2.2084 | 2.2084 | different same |
| 221911_at | 2.18 | -2.1831 | 2.1831 | different same |
| 218901_at | 0.65 | -2.1745 | 2.1745 | different same |
| 218573_at | 0.66 | -2.1523 | 2.1523 | different same |
| 204726_at | 2.07 | -2.1477 | 2.1477 | different same |
| 227080_at | 1.32 | -2.0924 | 2.0924 | different same |
| 208962_s_at | 0.63 | -2.0808 | 2.0808 | different same |
| 212158_at | 1.42 | -2.0735 | 2.0735 | different same |
| 212249_at | 0.90 | -2.0504 | 2.0504 | different same |
| 201471_s_at | 0.61 | -2.0301 | 2.0301 | different same |
| 212915_at | 1.78 | -1.9999 | 1.9999 | different same |
| 204112_s_at | 0.50 | -1.9507 | 1.9507 | different same |
| 219469_at | 0.83 | -1.9029 | 1.9029 | different same |
| 202555_s_at | 2.59 | -1.898 | 1.898 | different same |
| 207469_s_at | 1.00 | -1.8294 | 1.8294 | different same |
| 219077_s_at | 0.47 | -1.8024 | 1.8024 | different same |
| 212636_at | 1.28 | -1.7907 | 1.7907 | different same |
| 205880_at | 1.25 | -1.7845 | 1.7845 | different same |
| 219682_s_at | 1.56 | -1.7841 | 1.7841 | different same |
| 219561_at | 0.51 | -1.7768 | 1.7768 | different same |
| 218656_s_at | 0.95 | -1.7416 | 1.7416 | different same |
| 226419_s_at | 0.53 | -1.7377 | 1.7377 | different same |
| 203837_at | 0.55 | -1.7312 | 1.7312 | different same |
| 213800_at | 0.76 | -1.73 | 1.73 | different same |
| 202368_s_at | 1.06 | -1.6994 | 1.6994 | different same |

Fig. 33 (Cont.)

| Gene | Description | ID |
|---|---|---|
| IL1R1 | interleukin 1 receptor, type I | 3554 |
| FBXO32 | F-box protein 32 | 114907 |
| CYP1B1 | cytochrome P450, family 1, subfamily B, polypeptide 1 | 1545 |
| ETV1 | ets variant gene 1 | 2115 |
| PLSCR4 | phospholipid scramblase 4 | 57088 |
| MAGEH1 | melanoma antigen family H, 1 | 28986 |
| CDH13 | cadherin 13, H-cadherin (heart) | 1012 |
| ZNF697 | zinc finger protein 697 | 90874 |
| FADS1 | fatty acid desaturase 1 | 3992 |
| SDC2 | syndecan 2 (heparan sulfate proteoglycan 1, cell surface-associated, fibroglycan) | 6383 |
| PIK3R1 | phosphoinositide-3-kinase, regulatory subunit 1 (p85 alpha) | 5295 |
| SQSTM1 | sequestosome 1 | 8878 |
| PDZRN3 | PDZ domain containing RING finger 3 | 23024 |
| HNMT | histamine N-methyltransferase | 3176 |
| DYNC2H1 | dynein, cytoplasmic 2, heavy chain 1 | 79659 |
| MYLK | myosin, light chain kinase /// myosin, light chain kinase | 4638 |
| PIR | pirin (iron-binding nuclear protein) | 8544 |
| WWOX | WW domain containing oxidoreductase | 51741 |
| QKI | quaking homolog, KH domain RNA binding (mouse) | 9444 |
| PRKD1 | protein kinase D1 | 5587 |
| TBX3 | T-box 3 (ulnar mammary syndrome) | 6926 |
| COPZ2 | coatomer protein complex, subunit zeta 2 | 51226 |
| LHFP | lipoma HMGIC fusion partner | 10186 |
| FLJ44342 | hypothetical LOC645460 | 645460 |
| MAP3K5 | mitogen-activated protein kinase kinase kinase 5 | 4217 |
| CFH | complement factor H | 3075 |
| TRAM2 | translocation associated membrane protein 2 | 9697 |

Fig. 33 (Cont.)

| | | | | |
|---|---|---|---|---|
| 211340_s_at | 0.54 | -1.6522 | 1.6522 | different | same |
| 235737_at | 1.87 | -1.6467 | 1.6467 | different | same |
| 226989_at | 0.64 | -1.6398 | 1.6398 | different | same |
| 223165_s_at | 0.61 | -1.6349 | 1.6349 | different | same |
| 222494_at | 0.37 | -1.6302 | 1.6302 | different | same |
| 213413_at | 2.22 | -1.6199 | 1.6199 | different | same |
| 1558117_s_at | 0.91 | -1.5984 | 1.5984 | different | same |
| 225990_at | 1.90 | -1.5931 | 1.5931 | different | same |
| 218651_s_at | 0.63 | -1.5747 | 1.5747 | different | same |
| 218589_at | 1.81 | -1.5571 | 1.5571 | different | same |
| 209732_at | 1.49 | -1.5537 | 1.5537 | different | same |
| 203688_at | 0.96 | -1.5485 | 1.5485 | different | same |
| 212614_at | 1.24 | -1.5283 | 1.5283 | different | same |
| 219855_at | 1.52 | -1.5226 | 1.5226 | different | same |
| 201666_at | 1.20 | -1.5168 | 1.5168 | different | same |
| 209355_s_at | 1.35 | -1.5096 | 1.5096 | different | same |
| 44783_s_at | 1.04 | -1.5013 | 1.5013 | different | same |
| 218824_at | 1.78 | -1.5005 | 1.5005 | different | same |
| 224694_at | 1.22 | -1.4876 | 1.4876 | different | same |
| 229900_at | 1.03 | -1.486 | 1.486 | different | same |
| 203574_at | 0.59 | -1.4776 | 1.4776 | different | same |
| 225782_at | 1.44 | -1.4744 | 1.4744 | different | same |
| 202242_at | 0.84 | -1.4544 | 1.4544 | different | same |
| 219759_at | 0.64 | -1.4527 | 1.4527 | different | same |
| 226908_at | 0.92 | -1.4345 | 1.4345 | different | same |
| 201292_at | 1.15 | -1.433 | 1.433 | different | same |
| 218469_at | 1.67 | -1.4236 | 1.4236 | different | same |

Fig. 33 (Cont.)

| Gene | Description | ID |
|---|---|---|
| MCAM | melanoma cell adhesion molecule | 4162 |
| TSLP | thymic stromal lymphopoietin | 85480 |
| RGMB | RGM domain family, member B | 285704 |
| IHPK2 | inositol hexaphosphate kinase 2 | 51447 |
| CHES1 | checkpoint suppressor 1 | 1112 |
| STON1 | stonin 1 | 11037 |
| USP31 | ubiquitin specific peptidase 31 | 57478 |
| BOC | Boc homolog (mouse) | 91653 |
| LARP6 | La ribonucleoprotein domain family, member 6 | 55323 |
| P2RY5 | purinergic receptor P2Y, G-protein coupled, 5 | 10161 |
| CLEC2B | C-type lectin domain family 2, member B /// CMT1A duplicated region transcript 15 pseudogene | 94158 |
| PKD2 | polycystic kidney disease 2 (autosomal dominant) | 5311 |
| ARID5B | AT rich interactive domain 5B (MRF1-like) | 84159 |
| NUDT11 | nudix (nucleoside diphosphate linked moiety X)-type motif 11 | 55190 |
| TIMP1 | TIMP metallopeptidase inhibitor 1 | 7076 |
| PPAP2B | phosphatidic acid phosphatase type 2B | 8613 |
| HEY1 | hairy/enhancer-of-split related with YRPW motif 1 | 23462 |
| FLJ10781 | hypothetical protein FLJ10781 | 55228 |
| ANTXR1 | anthrax toxin receptor 1 | 84168 |
| CD109 | CD109 molecule | 135228 |
| NFIL3 | nuclear factor, interleukin 3 regulated | 4783 |
| MSRB3 | methionine sulfoxide reductase B3 | 253827 |
| TSPAN7 | tetraspanin 7 | 7102 |
| LRAP | leukocyte-derived arginine aminopeptidase | 64167 |
| LRIG3 | leucine-rich repeats and immunoglobulin-like domains 3 | 121227 |
| TOP2A | topoisomerase (DNA) II alpha 170kDa | 7153 |
| GREM1 | gremlin 1, cysteine knot superfamily, homolog (Xenopus laevis) | 26585 |

Fig. 33 (Cont.)

| | | | | |
|---|---|---|---|---|
| 223494_at | 0.50 | -1.4113 | 1.4113 | different | same |
| 225664_at | 1.62 | -1.377 | 1.377 | different | same |
| 228365_at | 1.34 | -1.3713 | 1.3713 | different | same |
| 209537_at | 0.47 | -1.3656 | 1.3656 | different | same |
| 212624_s_at | 0.64 | -1.3508 | 1.3508 | different | same |
| 204011_at | 0.93 | -1.3494 | 1.3494 | different | same |
| 203935_at | 0.43 | -1.347 | 1.347 | different | same |
| 223734_at | 0.93 | -1.3429 | 1.3429 | different | same |
| 225303_at | 1.30 | -1.3428 | 1.3428 | different | same |
| 214293_at | -0.42 | -1.3224 | 1.3224 | same | different |
| 209337_at | 0.85 | -1.3184 | 1.3184 | different | same |
| 226066_at | 0.53 | -1.3055 | 1.3055 | different | same |
| 228519_x_at | 0.45 | -1.2941 | 1.2941 | different | same |
| 223393_s_at | 1.14 | -1.2888 | 1.2888 | different | same |
| 206400_at | 2.90 | -1.2799 | 1.2799 | different | same |
| 204688_at | 1.33 | -1.2385 | 1.2385 | different | same |
| 231772_x_at | 0.50 | -1.2365 | 1.2365 | different | same |
| 221728_x_at | 0.44 | -1.2281 | 1.2281 | different | same |
| 224995_at | 0.41 | -1.2245 | 1.2245 | different | same |
| 203518_at | 0.53 | -1.2241 | 1.2241 | different | same |
| 223496_s_at | 2.17 | -1.2206 | 1.2206 | different | same |
| 218902_at | 0.88 | -1.2196 | 1.2196 | different | same |
| 235944_at | 1.37 | -1.2161 | 1.2161 | different | same |
| 202283_at | 2.64 | -1.2119 | 1.2119 | different | same |
| 227249_at | 1.02 | -1.2086 | 1.2086 | different | same |
| 212299_at | 0.45 | -1.1962 | 1.1962 | different | same |
| 217678_at | 2.37 | -1.1949 | 1.1949 | different | same |

Fig. 33 (Cont.)

| Gene | Description | ID |
|---|---|---|
| MGEA5 | meningioma expressed antigen 5 (hyaluronidase) | 10724 |
| COL12A1 | collagen, type XII, alpha 1 | 1303 |
| CPNE8 | copine VIII | 144402 |
| EXTL2 | exostoses (multiple)-like 2 | 2135 |
| CHN1 | chimerin (chimaerin) 1 | 1123 |
| SPRY2 | sprouty homolog 2 (Drosophila) | 10253 |
| ACVR1 | activin A receptor, type I | 90 |
| OSAP | ovary-specific acidic protein | 84709 |
| KIRREL | kin of IRRE like (Drosophila) | 55243 |
| SEPT11 | Septin 11 | 55752 |
| PSIP1 | PC4 and SFRS1 interacting protein 1 | 11168 |
| MITF | microphthalmia-associated transcription factor | 4286 |
| CIRBP | cold inducible RNA binding protein | 1153 |
| TSHZ3 | teashirt family zinc finger 3 | 57616 |
| LGALS7 | lectin, galactoside-binding, soluble, 7 (galectin 7) | 3963 |
| SGCE | sarcoglycan, epsilon | 8910 |
| CENPH | centromere protein H | 64946 |
| XIST | X (inactive)-specific transcript | 7503 |
| SPIRE1 | spire homolog 1 (Drosophila) | 56907 |
| LYST | lysosomal trafficking regulator | 1130 |
| CCDC8 | coiled-coil domain containing 8 | 83987 |
| NOTCH1 | Notch homolog 1, translocation-associated (Drosophila) | 4851 |
| HMCN1 | hemicentin 1 | 83872 |
| SERPINF1 | serpin peptidase inhibitor, clade F (alpha-2 antiplasmin, pigment epithelium derived factor), member 1 | 5176 |
| NDE1 | NudE nuclear distribution gene E homolog 1 (A. nidulans) | 54820 |
| NEK9 | NIMA (never in mitosis gene a)- related kinase 9 | 91754 |
| SLC7A11 | solute carrier family 7, (cationic amino acid transporter, y+ system) member 11 | 23657 |

Fig. 33 (Cont.)

| | | | | |
|---|---|---|---|---|
| 221805_at | 1.64 | -1.1828 | 1.1828 | different | same |
| 213428_s_at | 0.70 | -1.1809 | 1.1809 | different | same |
| 209160_at | 1.43 | -1.1752 | 1.1752 | different | same |
| 219249_s_at | 0.84 | -1.1596 | 1.1596 | different | same |
| 226695_at | 2.11 | -1.1589 | 1.1589 | different | same |
| 212761_at | 0.65 | -1.1355 | 1.1355 | different | same |
| 206237_s_at | 1.94 | -1.1151 | 1.1151 | different | same |
| 213455_at | -0.64 | -1.107 | 1.107 | same | different |
| 203865_s_at | 0.96 | -1.1003 | 1.1003 | different | same |
| 225627_s_at | 1.61 | -1.0954 | 1.0954 | different | same |
| 204418_x_at | 0.63 | -1.0718 | 1.0718 | different | same |
| 228783_at | 0.60 | -1.0595 | 1.0595 | different | same |
| 238482_at | 0.95 | -1.0575 | 1.0575 | different | same |
| 205003_at | 0.92 | -1.0557 | 1.0557 | different | same |
| 224397_s_at | 1.43 | -1.0492 | 1.0492 | different | same |
| 216250_s_at | 1.02 | -1.0324 | 1.0324 | different | same |
| 205573_s_at | 0.38 | -1.0303 | 1.0303 | different | same |
| 207076_s_at | 0.54 | -1.0219 | 1.0219 | different | same |
| 205891_at | 0.65 | -1.0176 | 1.0176 | different | same |
| 230075_at | 1.46 | -1.0065 | 1.0065 | different | same |
| 227961_at | 0.71 | -1.0024 | 1.0024 | different | same |
| 205534_at | 2.58 | 1.011 | -1.011 | same | different |
| 209270_at | 0.67 | 1.0378 | -1.0378 | same | different |
| 204633_s_at | 0.50 | 1.0509 | -1.0509 | same | different |
| 204469_at | 2.07 | 1.0946 | -1.0946 | same | different |
| 1559607_s_at | 0.56 | 1.1027 | -1.1027 | same | different |
| 210355_at | 1.49 | 1.1338 | -1.1338 | same | different |

Fig. 33 (Cont.)

| | | |
|---|---|---|
| NEFL | neurofilament, light polypeptide 68kDa | 4747 |
| COL6A1 | collagen, type VI, alpha 1 | 1291 |
| AKR1C3 | aldo-keto reductase family 1, member C3 (3-alpha hydroxysteroid dehydrogenase, type II) | 8644 |
| FKBP10 | FK506 binding protein 10, 65 kDa | 60681 |
| PRRX1 | paired related homeobox 1 | 5396 |
| TCF7L2 | transcription factor 7-like 2 (T-cell specific, HMG-box) | 6934 |
| NRG1 | neuregulin 1 | 3084 |
| FAM114A1 | family with sequence similarity 114, member A1 | 92689 |
| ADARB1 | adenosine deaminase, RNA-specific, B1 (RED1 homolog rat) | 104 |
| CACHD1 | cache domain containing 1 | 57685 |
| GSTM2 | glutathione S-transferase M2 (muscle) | 2946 |
| BVES | blood vessel epicardial substance | 11149 |
| KLF7 | Kruppel-like factor 7 (ubiquitous) | 8609 |
| DOCK4 | dedicator of cytokinesis 4 | 9732 |
| TMTC1 | transmembrane and tetratricopeptide repeat containing 1 | 83857 |
| LPXN | leupaxin | 9404 |
| SNX7 | sorting nexin 7 | 51375 |
| ASS1 | argininosuccinate synthetase 1 | 445 |
| ADORA2B | adenosine A2b receptor | 136 |
| RAB39B | RAB39B, member RAS oncogene family | 116442 |
| CTSB | cathepsin B | 1508 |
| PCDH7 | BH-protocadherin (brain-heart) | 5099 |
| LAMB3 | laminin, beta 3 | 3914 |
| RPS6KA5 | ribosomal protein S6 kinase, 90kDa, polypeptide 5 | 9252 |
| PTPRZ1 | protein tyrosine phosphatase, receptor-type, Z polypeptide 1 | 5803 |
| GBP6 | Guanylate binding protein family, member 6 | 163351 |
| PTHLH | parathyroid hormone-like hormone | 5744 |

Fig. 33 (Cont.)

| | | | |
|---|---|---|---|
| 217966_s_at | 1.94 | 1.2228 | -1.2228 | same | different |
| 218248_at | 0.55 | 1.2251 | -1.2251 | same | different |
| 213924_at | 1.03 | 1.2428 | -1.2428 | same | different |
| 222962_s_at | 1.21 | 1.25 | -1.25 | same | different |
| 223720_at | 1.30 | 1.2762 | -1.2762 | same | different |
| 208885_at | 0.99 | 1.2786 | -1.2786 | same | different |
| 205109_s_at | 1.11 | 1.3231 | -1.3231 | same | different |
| 206034_at | 0.71 | 1.3681 | -1.3681 | same | different |
| 241937_s_at | 0.66 | 1.3884 | -1.3884 | same | different |
| 202597_at | 0.82 | 1.3954 | -1.3954 | same | different |
| 223707_at | 0.93 | 1.3955 | -1.3955 | same | different |
| 218804_at | 1.76 | 1.4486 | -1.4486 | same | different |
| 226271_at | 0.42 | 1.4548 | -1.4548 | same | different |
| 205749_at | 1.13 | 1.4949 | -1.4949 | same | different |
| 225078_at | 1.53 | 1.5059 | -1.5059 | same | different |
| 210145_at | 0.86 | 1.5059 | -1.5059 | same | different |
| 219532_at | 0.89 | 1.5064 | -1.5064 | same | different |
| 223832_s_at | 0.77 | 1.5524 | -1.5524 | same | different |
| 225687_at | 0.80 | 1.5803 | -1.5803 | same | different |
| 223497_at | 0.54 | 1.5831 | -1.5831 | same | different |
| 202917_s_at | 2.09 | 1.5934 | -1.5934 | same | different |
| 205909_at | 0.69 | 1.613 | -1.613 | same | different |
| 232035_at | 1.25 | 1.6582 | -1.6582 | same | different |
| 231022_at | -0.41 | 1.6687 | -1.6687 | different | same |
| 203535_at | 0.80 | 1.74 | -1.74 | same | different |
| 203638_s_at | 1.42 | 1.75 | -1.75 | same | different |
| 204039_at | 0.77 | 1.8274 | -1.8274 | same | different |

Fig. 33 (Cont.)

| | | |
|---|---|---|
| FAM129A | family with sequence similarity 129, member A | 116496 |
| FAM111A | family with sequence similarity 111, member A | 63901 |
| MPPE1 | Metallophosphoesterase 1 | 65258 |
| MCM10 | MCM10 minichromosome maintenance deficient 10 (S. cerevisiae) | 55388 |
| SPINK7 | serine peptidase inhibitor, Kazal type 7 (putative) | 84651 |
| LCP1 | lymphocyte cytosolic protein 1 (L-plastin) | 3936 |
| ARHGEF4 | Rho guanine nucleotide exchange factor (GEF) 4 | 50649 |
| SERPINB8 | serpin peptidase inhibitor, clade B (ovalbumin), member 8 | 5271 |
| WDR4 | WD repeat domain 4 | 10785 |
| IRF6 | interferon regulatory factor 6 | 3664 |
| MGC10850 | hypothetical protein MGC10850 | 84736 |
| TMEM16A | transmembrane protein 16A | 55107 |
| GDAP1 | ganglioside-induced differentiation-associated protein 1 | 54332 |
| CYP1A1 | cytochrome P450, family 1, subfamily A, polypeptide 1 | 1543 |
| EMP2 | epithelial membrane protein 2 | 2013 |
| PLA2G4A | phospholipase A2, group IVA (cytosolic, calcium-dependent) | 5321 |
| ELOVL4 | elongation of very long chain fatty acids (FEN1/Elo2, SUR4/Elo3, yeast)-like 4 | 6785 |
| CAPNS2 | calpain, small subunit 2 | 84290 |
| FAM83D | family with sequence similarity 83, member D | 81610 |
| KIAA1411 | KIAA1411 | 57579 |
| S100A8 | S100 calcium binding protein A8 | 6279 |
| POLE2 | polymerase (DNA directed), epsilon 2 (p59 subunit) | 5427 |
| HIST1H4H | histone cluster 1, H4h | 8365 |
| NAIP | similar to Occludin | 647859 |
| S100A9 | S100 calcium binding protein A9 | 6280 |
| FGFR2 | fibroblast growth factor receptor 2 | 2263 |
| CEBPA | CCAAT/enhancer binding protein (C/EBP), alpha | 1050 |

Fig. 33 (Cont.)

| | | | | | |
|---|---|---|---|---|---|
| 207023_x_at | 0.60 | 1.8884 | -1.8884 | same | different |
| 223541_at | 1.47 | 1.913 | -1.913 | same | different |
| 235075_at | 0.88 | 2.0638 | -2.0638 | same | different |
| 209891_at | 1.11 | 2.075 | -2.075 | same | different |
| 241355_at | 0.75 | 2.1197 | -2.1197 | same | different |
| 204475_at | 1.84 | 2.1385 | -2.1385 | same | different |
| 207030_s_at | 1.77 | 2.2274 | -2.2274 | same | different |
| 220026_at | 1.87 | 2.2331 | -2.2331 | same | different |
| 219683_at | 0.84 | 2.2505 | -2.2505 | same | different |
| 231867_at | 3.14 | 2.3209 | -2.3209 | same | different |
| 202504_at | 1.17 | 2.3553 | -2.3553 | same | different |
| 1553602_at | 2.01 | 2.3687 | -2.3687 | same | different |
| 205067_at | 0.64 | 2.3692 | -2.3692 | same | different |
| 206170_at | 0.89 | 2.3704 | -2.3704 | same | different |
| 226499_at | 0.59 | 2.404 | -2.404 | same | different |
| 203798_s_at | 2.47 | 2.4371 | -2.4371 | same | different |
| 222484_s_at | 2.48 | 2.5693 | -2.5693 | same | different |
| 230188_at | 0.98 | 2.5704 | -2.5704 | same | different |
| 212977_at | 0.91 | 2.6511 | -2.6511 | same | different |
| 218677_at | 0.69 | 2.6561 | -2.6561 | same | different |

Fig. 33 (Cont.)

| Gene | Description | ID |
|---|---|---|
| KRT10 | keratin 10 (epidermolytic hyperkeratosis; keratosis palmaris et plantaris) | 3858 |
| HAS3 | hyaluronan synthase 3 | 3038 |
| DSG3 | desmoglein 3 (pemphigus vulgaris antigen) | 1830 |
| SPBC25 | spindle pole body component 25 homolog (S. cerevisiae) | 57405 |
| HR | hairless homolog (mouse) | 55806 |
| MMP1 | matrix metallopeptidase 1 (interstitial collagenase) | 4312 |
| CSRP2 | cysteine and glycine-rich protein 2 | 1466 |
| CLCA4 | chloride channel, calcium activated, family member 4 | 22802 |
| FZD3 | frizzled homolog 3 (Drosophila) | 7976 |
| ODZ2 | odz, odd Oz/ten-m homolog 2 (Drosophila) | 57451 |
| TRIM29 | tripartite motif-containing 29 | 23650 |
| SBEM | small breast epithelial mucin | 118430 |
| IL1B | interleukin 1, beta | 3553 |
| ADRB2 | adrenergic, beta-2-, receptor, surface | 154 |
| MGC61598 | Similar to ankyrin-repeat protein Nrarp | 441478 |
| VSNL1 | visinin-like 1 | 7447 |
| CXCL14 | chemokine (C-X-C motif) ligand 14 | 9547 |
| ICHTHYIN | ichthyin protein | 348938 |
| CXCR7 | chemokine (C-X-C motif) receptor 7 | 57007 |
| S100A14 | S100 calcium binding protein A14 | 57402 |

Fig. 33 (Cont.)

| | | | | | |
|---|---|---|---|---|---|
| 205680_at | 1.89 | 3.0649 | -3.0649 | same | different |
| 220027_s_at | 0.57 | 3.1762 | -3.1762 | same | different |
| 202831_at | 1.46 | 3.4439 | -3.4439 | same | different |
| 235272_at | 1.88 | 3.8513 | -3.8513 | same | different |
| 209719_x_at | 1.17 | 4.151 | -4.151 | same | different |
| 206023_at | 0.67 | 4.284 | -4.284 | same | different |
| 211361_s_at | 2.80 | 4.4226 | -4.4226 | same | different |
| 205185_at | 1.93 | 4.5687 | -4.5687 | same | different |
| 231148_at | 0.94 | 5.1523 | -5.1523 | same | different |
| 231771_at | 1.69 | 5.5097 | -5.5097 | same | different |
| 230835_at | 2.49 | 5.8362 | -5.8362 | same | different |
| 205916_at | 3.78 | 6.5583 | -6.5583 | same | different |
| 41469_at | 1.65 | 8.8434 | -8.8434 | same | different |
| 213796_at | 2.91 | 9.2705 | -9.2705 | same | different |
| Num up > 2-fold | 218 | 67 | 152 | 68 | 151 |
| Num down > 2-fold | 3 | 152 | 67 | 151 | 68 |

Fig. 33 (Cont.)

| | | |
|---|---|---|
| MMP10 | matrix metallopeptidase 10 (stromelysin 2) | 4319 |
| RASIP1 | Ras interacting protein 1 | 54922 |
| GPX2 | glutathione peroxidase 2 (gastrointestinal) | 2877 |
| SBSN | suprabasin | 374897 |
| SERPINB3 | serpin peptidase inhibitor, clade B (ovalbumin), member 3 | 6317 |
| NMU | neuromedin U | 10874 |
| SERPINB13 | serpin peptidase inhibitor, clade B (ovalbumin), member 13 | 5275 |
| SPINK5 | serine peptidase inhibitor, Kazal type 5 | 11005 |
| IGFL2 | IGF-like family member 2 | 147920 |
| GJB6 | gap junction protein, beta 6 (connexin 30) | 10804 |
| UNQ467 | KIPV467 | 388533 |
| S100A7 | S100 calcium binding protein A7 | 6278 |
| PI3 | peptidase inhibitor 3, skin-derived (SKALP) | 5266 |
| SPRR1A | small proline-rich protein 1A | 6698 |

Fig. 33 (Cont.)

The genes that are differentially expressed in BPEC-hTERT vs. HMEC-hTERT (≥2-Fold)

| M = log2 (BPEC-hTERT/ HMEC-hTERT) | adj.P .Val | Gene Symbol | Gene Title | Entrez Gene | Representative Public ID |
|---|---|---|---|---|---|
| 9.33 | 0.11 | SPRR1A | small proline-rich protein 1A | 6698 | AI923984 |
| 8.82 | 0.04 | PI3 | peptidase inhibitor 3, skin-derived (SKALP) | 5266 | L10343 |
| 8.05 | 0.03 | PI3 | peptidase inhibitor 3, skin-derived (SKALP) /// peptidase inhibitor 3, skin-derived (SKALP) | 5266 | NM_002638 |
| 7.32 | 0.10 | CALB1 | calbindin 1, 28kDa | 793 | AW014927 |
| 7.29 | 0.03 | MAFB | v-maf musculoaponeurotic fibrosarcoma oncogene homolog B (avian) | 9935 | NM_005461 |
| 7.20 | 0.11 | CALB1 | calbindin 1, 28kDa | 793 | NM_004929 |
| 7.08 | 0.21 | KLK10 | kallikrein 10 | 5655 | BC002710 |
| 6.97 | 0.03 | SPRR3 | small proline-rich protein 3 | 6707 | BF575466 |
| 6.95 | 0.08 | S100P | S100 calcium binding protein P | 6286 | NM_005980 |
| 6.83 | 0.02 | GPX3 | glutathione peroxidase 3 (plasma) | 2878 | NM_002084 |
| 6.72 | 0.13 | LYPD3 | LY6/PLAUR domain containing 3 | 27076 | NM_014400 |
| 6.54 | 0.05 | SLC6A14 | solute carrier family 6 (amino acid transporter), member 14 | 11254 | NM_007231 |
| 6.53 | 0.09 | DSG1 | desmoglein 1 | 1828 | NM_001942 |
| 6.44 | 0.04 | MAFB | v-maf musculoaponeurotic fibrosarcoma oncogene homolog B (avian) | 9935 | AW135013 |
| 6.43 | 0.02 | S100A7 | S100 calcium binding protein A7 (psoriasin 1) | 6278 | NM_002963 |
| 6.04 | 0.23 | MFAP5 | microfibrillar associated protein 5 | 8076 | U37283 |
| 6.02 | 0.17 | KRT24 | keratin 24 | 192666 | NM_019016 |
| 5.95 | 0.34 | KLK7 | kallikrein 7 (chymotryptic, stratum corneum) | 5650 | NM_005046 |
| 5.88 | 0.24 | TACSTD1 | tumor-associated calcium signal transducer 1 | 4072 | NM_002354 |
| 5.87 | 0.29 | KLK5 | kallikrein 5 | 25818 | AF243527 |
| 5.83 | 0.04 | SPRR2B | small proline-rich protein 2B | 6701 | NM_006945 |
| 5.61 | 0.23 | KLK8 | kallikrein 8 (neuropsin/ovasin) | 11202 | NM_007196 |

Fig. 33 (Cont.)

| | | | | |
|---|---|---|---|---|
| 5.60 | EHF | Ets homologous factor | 26298 | AA1763378 |
| 5.55 | SERPINB13 | serpin peptidase inhibitor, clade B (ovalbumin), member 13 | 5275 | AJ001698 |
| 5.53 | ARHGDIB | Rho GDP dissociation inhibitor (GDI) beta | 397 | AF498927 |
| 5.53 | PPP2R2C | protein phosphatase 2 (formerly 2A), regulatory subunit B (PR 52), gamma isoform | 5522 | AI669212 |
| 5.50 | SCEL | sciellin | 8796 | NM_003843 |
| 5.50 | MFAP5 | microfibrillar associated protein 5 | 8076 | AW665892 |
| 5.50 | MFAP5 | microfibrillar associated protein 5 | 8076 | AW665892 |
| 5.46 | A2ML1 | alpha-2-macroglobulin-like 1 | 144568 | AL832750 |
| 5.45 | GJB6 | gap junction protein, beta 6 (connexin 30) | 10804 | AI694073 |
| 5.45 | IL1RN | interleukin 1 receptor antagonist | 3557 | U65590 |
| 5.39 | IGFL1 | insulin growth factor-like family member 1 | 374918 | AA195677 |
| 5.36 | GPX3 | glutathione peroxidase 3 (plasma) | 2878 | AW149846 |
| 5.31 | SLPI | secretory leukocyte peptidase inhibitor | 6590 | NM_003064 |
| 5.27 | HOP | homeodomain-only protein /// homeodomain-only protein | 84525 | AB059408 |
| 5.26 | IFI27 | interferon, alpha-inducible protein 27 | 3429 | NM_005532 |
| 5.24 | RAB25 | RAB25, member RAS oncogene family | 57111 | NM_020387 |
| 5.19 | IL1R2 | interleukin 1 receptor, type II | 7850 | NM_004633 |
| 5.18 | UNQ467 | KIPV467 | 388533 | W69083 |
| 5.15 | LCN2 | lipocalin 2 (oncogene 24p3) | 3934 | NM_005564 |
| 5.12 | SCEL | sciellin | 8796 | AW470178 |
| 5.11 | SPRR3 | small proline-rich protein 3 | 6707 | NM_005416 |
| 5.09 | ARHGDIB | Rho GDP dissociation inhibitor (GDI) beta | 397 | NM_001175 |
| 5.08 | SULT2B1 | sulfotransferase family, cytosolic, 2B, member 1 | 6820 | NM_004605 |
| 5.04 | AQP3 | aquaporin 3 (Gill blood group) | 360 | N74607 |
| 4.99 | CLDN7 | claudin 7 | 1366 | NM_001307 |
| 4.97 | KRT1 | keratin 1 (epidermolytic hyperkeratosis) | 3848 | NM_006121 |

Fig. 33 (Cont.)

| | | | | |
|---|---|---|---|---|
| 4.89 | CNTN1 | Contactin 1 | 1272 | AI091445 |
| 4.89 | IGFL2 | insulin growth factor-like family member 2 | 147920 | AI806131 |
| 4.88 | LCE3D | late cornified envelope 3D /// late cornified envelope 3D | 84648 | AB048288 |
| 4.87 | C1orf42 | chromosome 1 open reading frame 42 | 54544 | NM_019060 |
| 4.85 | SPRR1A | small proline-rich protein 1A | 6698 | NM_005987 |
| 4.84 | SERPINB2 | serpin peptidase inhibitor, clade B (ovalbumin), member 2 | 5055 | NM_002575 |
| 4.79 | CXADR | coxsackie virus and adenovirus receptor | 1525 | NM_001338 |
| 4.79 | DSC2 | desmocollin 2 | 1824 | BF196457 |
| 4.75 | SERPINB13 | serpin peptidase inhibitor, clade B (ovalbumin), member 13 | 5275 | AJ001696 |
| 4.75 | PPP2R2C | protein phosphatase 2 (formerly 2A), regulatory subunit B (PR 52), gamma isoform | 5522 | AF086924 |
| 4.75 | KLK7 | kallikrein 7 (chymotryptic, stratum corneum) | 5650 | AU155415 |
| 4.74 | ANKRD22 | ankyrin repeat domain 22 | 118932 | AI925518 |
| 4.70 | SPRR1B | small proline-rich protein 1B (cornifin) | 6699 | NM_003125 |
| 4.68 | IL1RN | interleukin 1 receptor antagonist | 3557 | BE563442 |
| 4.67 | SLAMF9 | SLAM family member 9 | 89886 | NM_033438 |
| 4.64 | GALNT6 | UDP-N-acetyl-alpha-D-galactosamine:polypeptide N-acetylgalactosaminyltransferase 6 (GalNAc-T6) | 11226 | NM_007210 |
| 4.58 | ENTPD3 | ectonucleoside triphosphate diphosphohydrolase 3 | 956 | NM_001248 |
| 4.56 | CDSN | corneodesmosin | 1041 | NM_001264 |
| 4.55 | BBOX1 | butyrobetaine (gamma), 2-oxoglutarate dioxygenase (gamma-butyrobetaine hydroxylase) 1 | 8424 | NM_003986 |
| 4.55 | GRHL1 | grainyhead-like 1 (Drosophila) | 29841 | BE566136 |
| 4.55 | TPD52 | tumor protein D52 | 7163 | AA524023 |
| 4.47 | NMU | neuromedin U | 10874 | NM_006681 |
| 4.46 | EHF | ets homologous factor | 26298 | NM_012153 |
| 4.45 | --- | Full length insert cDNA clone YI40A07 | --- | AI819863 |

Fig. 33 (Cont.)

| | | | | |
|---|---|---|---|---|
| 4.40 | SPINK5 | serine peptidase inhibitor, Kazal type 5 | 11005 | NM_006846 |
| 4.40 | PROM2 | prominin 2 | 150696 | NM_144707 |
| 4.36 | KLK11 | kallikrein 11 | 11012 | NM_006853 |
| 4.36 | VGLL1 | vestigial like 1 (Drosophila) | 51442 | BE542323 |
| 4.35 | MALL | mal, T-cell differentiation protein-like | 7851 | BC003179 |
| 4.34 | MAL2 | mal, T-cell differentiation protein 2 | 114569 | AL117612 |
| 4.33 | CYB5A | cytochrome b5 type A (microsomal) | 1528 | NM_001914 |
| 4.27 | TMEM79 | transmembrane protein 79 | 84283 | BC005094 |
| 4.27 | CXADR | Coxsackie virus and adenovirus receptor | 1525 | BG260087 |
| 4.27 | TPD52 | tumor protein D52 | 7163 | BG389015 |
| 4.25 | SCEL | sciellin | 8796 | BC020726 |
| 4.25 | TPD52 | tumor protein D52 | 7163 | BE974098 |
| 4.24 | HIST1H2BC | histone 1, H2bc | 8347 | NM_003526 |
| 4.18 | WFDC12 | WAP four-disulfide core domain 12 | 128488 | NM_080869 |
| 4.18 | FAM83A | family with sequence similarity 83, member A | 84985 | BG438092 |
| 4.15 | MLZE | melanoma-derived leucine zipper, extra-nuclear factor | 56169 | AJ245876 |
| 4.15 | CYB5A | cytochrome b5 type A (microsomal) | 1528 | M22865 |
| 4.13 | IVL | involucrin | 3713 | NM_005547 |
| 4.11 | MYO5B | myosin VB | 4645 | AI991160 |
| 4.11 | SPINK6 | serine peptidase inhibitor, Kazal type 6 | 404203 | BC032003 |
| 4.05 | NCF2 | neutrophil cytosolic factor 2 (65kDa, chronic granulomatous disease, autosomal 2) | 4688 | BC001606 |
| 4.05 | CLIC3 | chloride intracellular channel 3 | 9022 | NM_004669 |
| 4.05 | PTHLH | Parathyroid hormone-like hormone | 5744 | M31157 |
| 4.04 | MAPK13 | mitogen-activated protein kinase 13 | 5603 | BC000433 |
| 4.04 | SERPINB3 | serpin peptidase inhibitor, clade B (ovalbumin), member 3 | 6317 | U19556 |
| 3.95 | SERPINB3 | serpin peptidase inhibitor, clade B (ovalbumin), member 3 | 6317 | BC005224 |

Fig. 33 (Cont.)

| | | | | |
|---|---|---|---|---|
| 3.90 | ADAM8 | ADAM metallopeptidase domain 8 /// ADAM metallopeptidase domain 8 | 101 | NM_001109 |
| 3.87 | GRHL3 | grainyhead-like 3 (Drosophila) | 57822 | AL137763 |
| 3.85 | CYB5A | cytochrome b5 type A (microsomal) | 1528 | M22976 |
| 3.85 | C15orf48 | chromosome 15 open reading frame 48 | 84419 | AF228422 |
| 3.84 | PRRG4 | Proline rich Gla (G-carboxyglutamic acid) 4 (transmembrane) | 79056 | BF905445 |
| 3.83 | THBD | thrombomodulin | 7056 | NM_000361 |
| 3.83 | GPRC5A | G protein-coupled receptor, family C, group 5, member A | 9052 | NM_003979 |
| 3.80 | HIST1H2BC | histone 1, H2bc | 8347 | AA037483 |
| 3.78 | KRT16 | keratin 16 (focal non-epidermolytic palmoplantar keratoderma) | 3868 | AF061812 |
| 3.76 | SBSN | suprabasin | 374897 | AI814274 |
| 3.76 | PKIB | protein kinase (cAMP-dependent, catalytic) inhibitor beta | 5570 | AF225513 |
| 3.75 | THBD | thrombomodulin | 7056 | NM_000361 |
| 3.74 | MYO5C | myosin VC | 55930 | NM_018728 |
| 3.73 | TSPAN1 | tetraspanin 1 | 10103 | AF133425 |
| 3.72 | OCLN | Occludin | 4950 | AI829721 |
| 3.71 | IL1R2 | interleukin 1 receptor, type II | 7850 | U64094 |
| 3.71 | KLK8 | kallikrein 8 (neuropsin/ovasin) | 11202 | NM_144506 |
| 3.67 | RBM35A | RNA binding motif protein 35A | 54845 | BF001941 |
| 3.66 | FXYD3 | FXYD domain containing ion transport regulator 3 | 5349 | BC005238 |
| 3.65 | CDH1 | cadherin 1, type 1, E-cadherin (epithelial) | 999 | L08599 |
| 3.65 | TGM1 | transglutaminase 1 (K polypeptide epidermal type I, protein-glutamine-gamma-glutamyltransferase) | 7051 | NM_000359 |
| 3.65 | AMPD3 | adenosine monophosphate deaminase (isoform E) | 272 | NM_000480 |
| 3.65 | RBM35A | RNA binding motif protein 35A | 54845 | NM_017697 |
| 3.63 | GAL | galanin | 51083 | AL556409 |
| 3.63 | EHF | ets homologous factor | 26298 | AF124438 |
| 3.63 | C10orf58 | chromosome 10 open reading frame 58 /// chromosome 10 open reading frame 58 | 84293 | BC005871 |

Fig. 33 (Cont.)

| | | | | |
|---|---|---|---|---|
| 3.63 | DSC2 | desmocollin 2 | 1824 | NM_004949 |
| 3.60 | FAM83A | family with sequence similarity 83, member A | 84985 | AI590662 |
| 3.59 | LPAAT-THETA | lysophosphatidic acid acyltransferase theta /// lysophosphatidic acid acyltransferase theta | 84803 | BC006236 |
| 3.56 | IL1RN | interleukin 1 receptor antagonist | 3557 | AW083357 |
| 3.55 | TRAF3IP3 | TRAF3 interacting protein 3 | 80342 | AI922337 |
| 3.54 | LASS3 | LAG1 longevity assurance homolog 3 (S. cerevisiae) | 204219 | BC034500 |
| 3.54 | SERPINB13 | serpin peptidase inhibitor, clade B (ovalbumin), member 13 | 5275 | BE148534 |
| 3.53 | IGSF9 | immunoglobulin superfamily, member 9 | 57549 | AB037776 |
| 3.53 | TMEM45B | transmembrane protein 45B | 120224 | AI282982 |
| 3.52 | HOOK1 | hook homolog 1 (Drosophila) | 51361 | AA618420 |
| 3.51 | LAD1 | ladinin 1 | 3898 | U58994 |
| 3.51 | SERPINB1 | serpin peptidase inhibitor, clade B (ovalbumin), member 1 | 1992 | AI554300 |
| 3.51 | CBLC | Cas-Br-M (murine) ecotropic retroviral transforming sequence c | 23624 | NM_012116 |
| 3.47 | DAPP1 | dual adaptor of phosphotyrosine and 3-phosphoinositides | 27071 | AI632216 |
| 3.46 | EPB41L5 | erythrocyte membrane protein band 4.1 like 5 | 57669 | AI652872 |
| 3.46 | NALP2 | NACHT, leucine rich repeat and PYD containing 2 | 55655 | AF298547 |
| 3.46 | FAM83A | family with sequence similarity 83, member A | 84985 | BE157240 |
| 3.45 | GPR110 | G protein-coupled receptor 110 | 266977 | BG426455 |
| 3.44 | SERPINB1 | serpin peptidase inhibitor, clade B (ovalbumin), member 1 | 1992 | NM_030666 |
| 3.44 | EPS8L1 | EPS8-like 1 | 54869 | AI219073 |
| 3.44 | DAPP1 | dual adaptor of phosphotyrosine and 3-phosphoinositides | 27071 | AA150186 |
| 3.42 | BCL11B | B-cell CLL/lymphoma 11B (zinc finger protein) | 64919 | AA918317 |
| 3.42 | CEACAM6 | carcinoembryonic antigen-related cell adhesion molecule 6 (non-specific cross reacting antigen) /// carcino | 4680 | M18728 |
| 3.42 | SLCO4A1 | solute carrier organic anion transporter family, member 4A1 | 28231 | NM_016354 |
| 3.40 | EPPK1 | epiplakin 1 | 83481 | AL137725 |
| 3.40 | SERPINB13 | serpin peptidase inhibitor, clade B (ovalbumin), member 13 | 5275 | AF169949 |
| 3.39 | TGFA | transforming growth factor, alpha | 7039 | M31172 |

Fig. 33 (Cont.)

| Affymetrix_ID | BPE log mean | BPLER log mean | HME log mean | HMLER log mean | > 2-fold BPE/HME |
|---|---|---|---|---|---|
| 58916_at | 4.58 | 6.40 | 4.31 | 7.01 | |
| 48808_at | 8.34 | 9.93 | 7.05 | 10.02 | 48808_at |
| 45633_at | 6.26 | 7.70 | 5.42 | 7.23 | |
| 44563_at | 6.23 | 7.37 | 6.18 | 7.60 | |
| 38158_at | 6.62 | 7.65 | 5.65 | 7.52 | |
| 33304_at | 5.23 | 7.07 | 4.60 | 8.04 | |
| 244780_at | 5.16 | 2.61 | 3.49 | 2.42 | 244780_at |
| 244317_at | 6.21 | 4.28 | 5.46 | 2.64 | |
| 244107_at | 8.24 | 6.87 | 7.45 | 4.42 | |
| 243386_at | 5.35 | 4.25 | 4.48 | 3.31 | |
| 243299_at | 7.36 | 6.23 | 6.82 | 5.58 | |
| 242890_at | 6.56 | 7.90 | 5.73 | 9.12 | |
| 242750_at | 3.99 | 2.99 | 5.68 | 3.34 | 242750_at |
| 242625_at | 4.51 | 6.07 | 3.37 | 7.02 | 242625_at |
| 242442_x_at | 4.85 | 3.85 | 4.07 | 2.94 | |
| 242260_at | 4.41 | 5.92 | 5.08 | 6.43 | |
| 242064_at | 5.32 | 3.89 | 7.90 | 3.11 | 242064_at |
| 242005_at | 3.26 | 5.10 | 2.93 | 7.62 | |
| 241994_at | 10.09 | 8.75 | 9.78 | 7.81 | |
| 241813_at | 8.64 | 6.83 | 6.93 | 5.42 | 241813_at |
| 241455_at | 7.52 | 5.89 | 4.39 | 2.67 | 241455_at |
| 239381_at | 11.33 | 10.24 | 6.73 | 4.36 | 239381_at |
| 239007_at | 4.91 | 3.70 | 5.86 | 3.93 | |
| 238778_at | 7.44 | 6.03 | 6.66 | 4.28 | |
| 238716_at | 5.94 | 4.91 | 7.28 | 5.96 | 238716_at |
| 238601_at | 7.31 | 6.03 | 8.25 | 5.99 | |
| 238482_at | 6.57 | 5.36 | 7.63 | 3.61 | 238482_at |
| 238451_at | 5.42 | 4.03 | 4.84 | 3.18 | |
| 238028_at | 7.67 | 6.48 | 4.69 | 3.35 | 238028_at |
| 238017_at | 7.69 | 6.06 | 4.70 | 2.98 | 238017_at |
| 237867_s_at | 4.90 | 3.84 | 6.72 | 3.89 | 237867_s_at |
| 237411_at | 6.34 | 7.57 | 6.45 | 7.64 | |
| 236347_at | 5.73 | 4.70 | 6.26 | 5.25 | |
| 236277_at | 4.81 | 6.24 | 7.34 | 9.23 | 236277_at |
| 235964_x_at | 6.32 | 8.07 | 4.42 | 8.95 | 235964_x_at |
| 235911_at | 6.38 | 7.80 | 7.48 | 8.53 | 235911_at |
| 235775_at | 6.34 | 4.96 | 5.61 | 4.42 | |
| 235740_at | 4.59 | 3.27 | 7.90 | 4.76 | 235740_at |
| 235727_at | 7.53 | 6.47 | 8.02 | 6.87 | |
| 235638_at | 7.50 | 5.70 | 8.40 | 2.59 | |
| 235609_at | 5.84 | 7.25 | 5.21 | 7.64 | |

Fig. 34

| Figure 6B.a:<br>≥ 2-fold<br>BPLER/BPE | Figure 6B.c:<br>≥ 2-fold<br>HMLER/HME | Figure 6B.b:<br>≥ 2-fold both<br>and same<br>direction | Group 6C.b:<br>> 2-fold<br>BPLER/HMLER | Group 6C.a:<br>> 2-fold both<br>and same<br>direction |
|---|---|---|---|---|
| 58916_at | 58916_at | 58916_at | | |
| 48808_at | 48808_at | 48808_at | | |
| 45633_at | 45633_at | 45633_at | | |
| 44563_at | 44563_at | 44563_at | | |
| 38158_at | 38158_at | 38158_at | | |
| 33304_at | 33304_at | 33304_at | | |
| 244780_at | 244780_at | 244780_at | | |
| 244317_at | 244317_at | 244317_at | 244317_at | |
| 244107_at | 244107_at | 244107_at | 244107_at | |
| 243386_at | 243386_at | 243386_at | | |
| 243299_at | 243299_at | 243299_at | | |
| 242890_at | 242890_at | 242890_at | 242890_at | |
| 242750_at | 242750_at | 242750_at | | |
| 242625_at | 242625_at | 242625_at | | |
| 242442_x_at | 242442_x_at | 242442_x_at | | |
| 242260_at | 242260_at | 242260_at | | |
| 242064_at | 242064_at | 242064_at | | |
| 242005_at | 242005_at | 242005_at | 242005_at | |
| 241994_at | 241994_at | 241994_at | | |
| 241813_at | 241813_at | 241813_at | 241813_at | 241813_at |
| 241455_at | 241455_at | 241455_at | 241455_at | 241455_at |
| 239381_at | 239381_at | 239381_at | 239381_at | 239381_at |
| 239007_at | 239007_at | 239007_at | | |
| 238778_at | 238778_at | 238778_at | 238778_at | |
| 238716_at | 238716_at | 238716_at | 238716_at | 238716_at |
| 238601_at | 238601_at | 238601_at | | |
| 238482_at | 238482_at | 238482_at | 238482_at | |
| 238451_at | 238451_at | 238451_at | | |
| 238028_at | 238028_at | 238028_at | 238028_at | 238028_at |
| 238017_at | 238017_at | 238017_at | 238017_at | 238017_at |
| 237867_s_at | 237867_s_at | 237867_s_at | | |
| 237411_at | 237411_at | 237411_at | | |
| 236347_at | 236347_at | 236347_at | | |
| 236277_at | 236277_at | 236277_at | 236277_at | 236277_at |
| 235964_x_at | 235964_x_at | 235964_x_at | | |
| 235911_at | 235911_at | 235911_at | | |
| 235775_at | 235775_at | 235775_at | | |
| 235740_at | 235740_at | 235740_at | 235740_at | 235740_at |
| 235727_at | 235727_at | 235727_at | | |
| 235638_at | 235638_at | 235638_at | 235638_at | |
| 235609_at | 235609_at | 235609_at | | |

Fig. 34 (Cont.)

| Gene Symbol | Gene Title |
|---|---|
| KCTD14 | potassium channel tetramerisation domain containing 14 |
| DHFR / | dihydrofolate reductase /// similar to Dihydrofolate reductase |
| GINS3 | GINS complex subunit 3 (Psf3 homolog) |
| WDR79 | WD repeat domain 79 |
| ESPL1 | extra spindle poles like 1 (S. cerevisiae) |
| ISG20 | interferon stimulated exonuclease gene 20kDa |
| SGPP2 | sphingosine-1-phosphate phosphotase 2 |
| KIAA1324L | KIAA1324-like |
| --- | --- |
| SRG | survival-related gene |
| VRK2 | Vaccinia related kinase 2 |
| HELLS | Helicase, lymphoid-specific |
| MMAA | Methylmalonic aciduria (cobalamin deficiency) cblA type |
| RSAD2 | radical S-adenosyl methionine domain containing 2 |
| RG9MTD2 | RNA (guanine-9-) methyltransferase domain containing 2 |
| MATR3 | Matrin 3 |
| SDK2 | sidekick homolog 2 (chicken) |
| --- | --- |
| XDH | xanthine dehydrogenase |
| MBD1 | methyl-CpG binding domain protein 1 |
| --- | Transcribed locus, strongly similar to XP_371820.3 PREDICTED: similar to Al661453 protein [Homo sapiens] |
| KLK7 | kallikrein 7 (chymotryptic, stratum corneum) |
| ZNF616 | zinc finger protein 616 |
| MPP7 | membrane protein, palmitoylated 7 (MAGUK p55 subfamily member 7) |
| --- | Homo sapiens, clone IMAGE:5396854, mRNA |
| --- | Transcribed locus |
| KLF7 | Kruppel-like factor 7 (ubiquitous) |
| MPP7 | membrane protein, palmitoylated 7 (MAGUK p55 subfamily member 7) |
| FLJ90086 | similar to Al661453 protein |
| RDHE2 | retinal short chain dehydrogenase reductase isoform 1 |
| FLJ20701 | hypothetical protein FLJ20701 |
| ADAMTS6 | ADAM metallopeptidase with thrombospondin type 1 motif, 6 |
| MMAA | methylmalonic aciduria (cobalamin deficiency) cblA type |
| PAK3 | P21 (CDKN1A)-activated kinase 3 |
| C20orf118 | Chromosome 20 open reading frame 118 |
| MFI2 | Antigen p97 (melanoma associated) identified by monoclonal antibodies 133.2 and 96.5 |
| TMTC2 | transmembrane and tetratricopeptide repeat containing 2 |
| MCTP1 | Multiple C2 domains, transmembrane 1 |
| BTBD5 | BTB (POZ) domain containing 5 |
| RASSF6 | Ras association (RalGDS/AF-6) domain family 6 |
| --- | Transcribed locus |

Fig. 34 (Cont.)

| | | | | | |
|---|---|---|---|---|---|
| 235529_x_at | 7.14 | 9.03 | 5.55 | 9.72 | 235529_x_at |
| 235352_at | 6.74 | 4.71 | 7.64 | 6.56 | |
| 235301_at | 7.11 | 4.84 | 6.65 | 3.34 | |
| 235266_at | 6.53 | 8.67 | 6.41 | 8.57 | |
| 235113_at | 9.00 | 10.45 | 9.12 | 10.37 | |
| 235075_at | 13.05 | 11.82 | 10.98 | 6.67 | 235075_at |
| 235065_at | 5.43 | 3.68 | 6.27 | 4.27 | |
| 235000_at | 5.03 | 4.00 | 5.39 | 4.36 | |
| 234995_at | 6.30 | 7.46 | 6.38 | 7.98 | |
| 234987_at | 5.45 | 8.25 | 3.78 | 8.58 | 234987_at |
| 234977_at | 6.13 | 4.94 | 6.28 | 5.11 | |
| 234331_s_at | 7.32 | 5.16 | 4.93 | 3.34 | 234331_s_at |
| 233955_x_at | 4.39 | 6.53 | 6.05 | 8.75 | 233955_x_at |
| 233565_s_at | 8.17 | 6.12 | 5.50 | 3.13 | 233565_s_at |
| 233230_s_at | 6.65 | 5.38 | 6.79 | 5.09 | |
| 232449_at | 3.25 | 2.19 | 5.84 | 2.16 | 232449_at |
| 232202_at | 11.20 | 10.15 | 8.74 | 7.20 | 232202_at |
| 232101_s_at | 7.33 | 5.75 | 6.90 | 4.95 | |
| 232056_at | 8.98 | 7.20 | 4.12 | 2.69 | 232056_at |
| 231929_at | 7.38 | 6.11 | 7.67 | 6.20 | |
| 231873_at | 7.46 | 6.11 | 8.09 | 6.75 | |
| 231867_at | 10.87 | 9.35 | 8.55 | 3.63 | 231867_at |
| 231148_at | 9.21 | 4.36 | 4.06 | 2.88 | 231148_at |
| 231067_s_at | 3.14 | 4.48 | 3.09 | 7.98 | |
| 231035_s_at | 6.73 | 5.57 | 7.68 | 5.48 | |
| 231033_at | 8.26 | 4.43 | 3.63 | 2.34 | 231033_at |
| 230839_at | 6.92 | 3.90 | 7.90 | 5.16 | |
| 230746_s_at | 5.82 | 8.07 | 4.50 | 12.44 | 230746_s_at |
| 230559_x_at | 6.60 | 5.58 | 7.05 | 5.27 | |
| 230492_s_at | 8.25 | 7.00 | 8.32 | 5.77 | |
| 230398_at | 11.48 | 10.22 | 10.84 | 9.21 | |
| 230345_at | 5.47 | 6.70 | 5.56 | 7.37 | |
| 230316_at | 5.73 | 4.25 | 5.49 | 4.34 | |
| 230130_at | 4.90 | 6.33 | 4.04 | 5.47 | |
| 230076_at | 8.26 | 5.58 | 8.51 | 5.65 | |
| 230063_at | 6.25 | 5.13 | 6.33 | 5.25 | |
| 229975_at | 5.55 | 3.51 | 5.17 | 4.11 | |
| 229927_at | 6.97 | 4.85 | 5.68 | 3.11 | 229927_at |
| 229886_at | 5.65 | 6.69 | 6.54 | 7.71 | |
| 229797_at | 3.11 | 5.39 | 3.71 | 5.72 | |
| 229700_at | 5.95 | 6.98 | 6.58 | 7.76 | |
| 229666_s_at | 8.16 | 9.19 | 8.51 | 11.33 | |
| 229551_x_at | 6.33 | 7.99 | 6.20 | 8.47 | |
| 229546_at | 4.49 | 3.17 | 4.63 | 2.85 | |
| 229518_at | 9.04 | 7.24 | 6.91 | 4.89 | 229518_at |
| 229498_at | 7.70 | 6.30 | 7.76 | 4.44 | |

Fig. 34 (Cont.)

| | | | | |
|---|---|---|---|---|
| 235529_x_at | 235529_x_at | 235529_x_at | | |
| 235352_at | 235352_at | 235352_at | 235352_at | |
| 235301_at | 235301_at | 235301_at | 235301_at | |
| 235266_at | 235266_at | 235266_at | | |
| 235113_at | 235113_at | 235113_at | | |
| 235075_at | 235075_at | 235075_at | 235075_at | 235075_at |
| 235065_at | 235065_at | 235065_at | | |
| 235000_at | 235000_at | 235000_at | | |
| 234995_at | 234995_at | 234995_at | | |
| 234987_at | 234987_at | 234987_at | | |
| 234977_at | 234977_at | 234977_at | | |
| 234331_s_at | 234331_s_at | 234331_s_at | 234331_s_at | 234331_s_at |
| 233955_x_at | 233955_x_at | 233955_x_at | 233955_x_at | 233955_x_at |
| 233565_s_at | 233565_s_at | 233565_s_at | 233565_s_at | 233565_s_at |
| 233230_s_at | 233230_s_at | 233230_s_at | | |
| 232449_at | 232449_at | 232449_at | | |
| 232202_at | 232202_at | 232202_at | 232202_at | 232202_at |
| 232101_s_at | 232101_s_at | 232101_s_at | | |
| 232056_at | 232056_at | 232056_at | 232056_at | 232056_at |
| 231929_at | 231929_at | 231929_at | | |
| 231873_at | 231873_at | 231873_at | | |
| 231867_at | 231867_at | 231867_at | 231867_at | 231867_at |
| 231148_at | 231148_at | 231148_at | 231148_at | 231148_at |
| 231067_s_at | 231067_s_at | 231067_s_at | 231067_s_at | |
| 231035_s_at | 231035_s_at | 231035_s_at | | |
| 231033_at | 231033_at | 231033_at | 231033_at | 231033_at |
| 230839_at | 230839_at | 230839_at | 230839_at | |
| 230746_s_at | 230746_s_at | 230746_s_at | 230746_s_at | |
| 230559_x_at | 230559_x_at | 230559_x_at | | |
| 230492_s_at | 230492_s_at | 230492_s_at | 230492_s_at | |
| 230398_at | 230398_at | 230398_at | 230398_at | |
| 230345_at | 230345_at | 230345_at | | |
| 230316_at | 230316_at | 230316_at | | |
| 230130_at | 230130_at | 230130_at | | |
| 230076_at | 230076_at | 230076_at | | |
| 230063_at | 230063_at | 230063_at | | |
| 229975_at | 229975_at | 229975_at | | |
| 229927_at | 229927_at | 229927_at | 229927_at | 229927_at |
| 229886_at | 229886_at | 229886_at | 229886_at | |
| 229797_at | 229797_at | 229797_at | | |
| 229700_at | 229700_at | 229700_at | | |
| 229666_s_at | 229666_s_at | 229666_s_at | 229666_s_at | |
| 229551_x_at | 229551_x_at | 229551_x_at | | |
| 229546_at | 229546_at | 229546_at | | |
| 229518_at | 229518_at | 229518_at | 229518_at | 229518_at |
| 229498_at | 229498_at | 229498_at | 229498_at | |

Fig. 34 (Cont.)

| | |
|---|---|
| C20orf118 | Chromosome 20 open reading frame 118 |
| --- | CDNA FLJ31593 fis, clone NT2RI2002481 |
| KIAA1324L | KIAA1324-like |
| ATAD2 | ATPase family, AAA domain containing 2 |
| PPIL5 | peptidylprolyl isomerase (cyclophilin)-like 5 |
| DSG3 | desmoglein 3 (pemphigus vulgaris antigen) |
| --- | Full length insert cDNA clone ZE05E03 |
| --- | CDNA FLJ30652 fis, clone DFNES2000011 |
| CCDC52 | coiled-coil domain containing 52 |
| C20orf118 | Chromosome 20 open reading frame 118 |
| ZADH2 | zinc binding alcohol dehydrogenase, domain containing 2 |
| --- | --- |
| CXXC5 | CXXC finger 5 |
| SDCBP2 | syndecan binding protein (syntenin) 2 |
| KIAA1458 | KIAA1458 protein |
| BCDO2 | beta-carotene dioxygenase 2 |
| FAM83B | Family with sequence similarity 83, member B |
| PIGN | phosphatidylinositol glycan, class N |
| SCEL | sciellin |
| --- | Transcribed locus |
| BMPR2 | bone morphogenetic protein receptor, type II (serine/threonine kinase) |
| ODZ2 | odz, odd Oz/ten-m homolog 2 (Drosophila) |
| IGFL2 | insulin growth factor-like family member 2 |
| AKAP12 | A kinase (PRKA) anchor protein (gravin) 12 |
| --- | Transcribed locus |
| --- | Full length insert cDNA clone YI40A07 |
| PRMT8 | protein arginine methyltransferase 8 |
| STC1 | Stanniocalcin 1 |
| FGD4 | FYVE, RhoGEF and PH domain containing 4 |
| RP5-1022P6.2 | hypothetical protein KIAA1434 |
| TNS4 | tensin 4 |
| --- | Transcribed locus, weakly similar to XP_864747.1 |
| SEC14L2 | SEC14-like 2 (S. cerevisiae) |
| SLIT2 | Slit homolog 2 (Drosophila) |
| --- | --- |
| --- | Transcribed locus |
| --- | Transcribed locus |
| LEMD1 | LEM domain containing 1 |
| FLJ32363 | FLJ32363 protein |
| MCOLN3 | mucolipin 3 |
| LOC148203 | hypothetical protein LOC148203 |
| CSTF3 | cleavage stimulation factor, 3' pre-RNA, subunit 3, 77kDa |
| ZNF367 | zinc finger protein 367 |
| LOC653602 | hypothetical LOC653602 |
| FAM46B | family with sequence similarity 46, member B |
| --- | MRNA; cDNA DKFZp779M2422 (from clone DKFZp779M2422) |

Fig. 34 (Cont.)

| | | | | | |
|---|---|---|---|---|---|
| 229450_at | 4.27 | 7.65 | 3.63 | 10.18 | |
| 229352_at | 6.67 | 4.96 | 9.34 | 4.73 | 229352_at |
| 229331_at | 7.52 | 6.50 | 8.61 | 7.01 | 229331_at |
| 229147_at | 9.77 | 8.00 | 10.28 | 3.95 | |
| 229125_at | 5.52 | 2.96 | 5.70 | 2.29 | |
| 228977_at | 6.95 | 8.01 | 4.63 | 5.81 | 228977_at |
| 228968_at | 5.62 | 4.38 | 7.24 | 5.33 | 228968_at |
| 228904_at | 3.78 | 5.47 | 3.70 | 7.26 | |
| 228854_at | 3.49 | 2.39 | 8.42 | 7.06 | 228854_at |
| 228771_at | 5.98 | 4.61 | 4.43 | 3.14 | 228771_at |
| 228708_at | 11.71 | 9.88 | 12.43 | 8.79 | |
| 228702_at | 2.58 | 3.64 | 2.94 | 5.16 | |
| 228653_at | 5.99 | 4.57 | 6.97 | 5.22 | |
| 228617_at | 4.64 | 5.65 | 3.43 | 7.05 | 228617_at |
| 228559_at | 7.32 | 8.61 | 7.60 | 9.15 | |
| 228497_at | 6.59 | 5.26 | 8.54 | 6.01 | 228497_at |
| 228416_at | 5.03 | 3.82 | 6.06 | 4.43 | 228416_at |
| 228401_at | 7.00 | 8.68 | 6.56 | 8.34 | |
| 228347_at | 3.81 | 4.93 | 4.21 | 8.55 | |
| 228341_at | 5.27 | 4.24 | 6.86 | 5.75 | 228341_at |
| 228335_at | 3.12 | 6.79 | 3.10 | 8.98 | |
| 228328_at | 7.98 | 6.71 | 8.51 | 7.15 | |
| 228325_at | 5.00 | 3.82 | 5.89 | 3.46 | |
| 228320_x_at | 6.71 | 5.22 | 6.81 | 5.45 | |
| 228318_s_at | 6.54 | 5.22 | 7.01 | 5.32 | |
| 228256_s_at | 4.72 | 2.35 | 4.68 | 1.99 | |
| 228188_at | 8.86 | 7.06 | 9.52 | 6.75 | |
| 228153_at | 10.34 | 9.34 | 9.64 | 7.91 | |
| 228115_at | 7.00 | 4.62 | 7.10 | 5.15 | |
| 228082_at | 9.22 | 7.13 | 10.40 | 9.25 | 228082_at |
| 228065_at | 8.40 | 7.30 | 7.65 | 6.21 | |
| 228033_at | 8.31 | 9.82 | 8.36 | 10.00 | |
| 227949_at | 4.79 | 3.51 | 4.14 | 2.77 | |
| 227948_at | 7.56 | 6.37 | 8.00 | 6.52 | |
| 227936_at | 6.96 | 8.24 | 5.56 | 8.41 | 227936_at |
| 227921_at | 5.55 | 6.88 | 5.85 | 7.84 | |
| 227917_at | 5.85 | 4.74 | 7.66 | 5.76 | 227917_at |
| 227905_s_at | 8.70 | 7.66 | 9.63 | 8.39 | |
| 227867_at | 3.76 | 5.09 | 5.14 | 6.19 | 227867_at |
| 227752_at | 9.21 | 6.32 | 7.97 | 6.06 | 227752_at |

Fig. 34 (Cont.)

| | | | | |
|---|---|---|---|---|
| 229450_at | 229450_at | 229450_at | 229450_at | |
| 229352_at | 229352_at | 229352_at | | |
| 229331_at | 229331_at | 229331_at | | |
| 229147_at | 229147_at | 229147_at | 229147_at | |
| 229125_at | 229125_at | 229125_at | | |
| 228977_at | 228977_at | 228977_at | 228977_at | 228977_at |
| 228968_at | 228968_at | 228968_at | | |
| 228904_at | 228904_at | 228904_at | 228904_at | |
| 228854_at | 228854_at | 228854_at | 228854_at | 228854_at |
| 228771_at | 228771_at | 228771_at | 228771_at | 228771_at |
| 228708_at | 228708_at | 228708_at | 228708_at | |
| 228702_at | 228702_at | 228702_at | 228702_at | |
| 228653_at | 228653_at | 228653_at | | |
| 228617_at | 228617_at | 228617_at | 228617_at | |
| 228559_at | 228559_at | 228559_at | | |
| 228497_at | 228497_at | 228497_at | | |
| 228416_at | 228416_at | 228416_at | | |
| 228401_at | 228401_at | 228401_at | | |
| 228347_at | 228347_at | 228347_at | 228347_at | |
| 228341_at | 228341_at | 228341_at | 228341_at | 228341_at |
| 228335_at | 228335_at | 228335_at | 228335_at | |
| 228328_at | 228328_at | 228328_at | | |
| 228325_at | 228325_at | 228325_at | | |
| 228320_x_at | 228320_x_at | 228320_x_at | | |
| 228318_s_at | 228318_s_at | 228318_s_at | | |
| 228256_s_at | 228256_s_at | 228256_s_at | | |
| 228188_at | 228188_at | 228188_at | | |
| 228153_at | 228153_at | 228153_at | 228153_at | |
| 228115_at | 228115_at | 228115_at | | |
| 228082_at | 228082_at | 228082_at | 228082_at | 228082_at |
| 228065_at | 228065_at | 228065_at | 228065_at | |
| 228033_at | 228033_at | 228033_at | | |
| 227949_at | 227949_at | 227949_at | | |
| 227948_at | 227948_at | 227948_at | | |
| 227936_at | 227936_at | 227936_at | | |
| 227921_at | 227921_at | 227921_at | | |
| 227917_at | 227917_at | 227917_at | 227917_at | 227917_at |
| 227905_s_at | 227905_s_at | 227905_s_at | | |
| 227867_at | 227867_at | 227867_at | 227867_at | 227867_at |
| 227752_at | 227752_at | 227752_at | | |

Fig. 34 (Cont.)

| | |
|---|---|
| --- | --- |
| SPESP1 | sperm equatorial segment protein 1 |
| SPATA18 | spermatogenesis associated 18 homolog (rat) |
| --- | Transcribed locus, strongly similar to NP_958834.1 |
| ANKRD38 | ankyrin repeat domain 38 |
| IL17D | Interleukin 17D |
| ZNF449 | zinc finger protein 449 |
| HOXB3 | homeobox B3 |
| --- | Transcribed locus |
| ADRBK2 | adrenergic, beta, receptor kinase 2 |
| RAB27B | RAB27B, member RAS oncogene family |
| FLJ43663 | hypothetical protein FLJ43663 |
| RP5-875H10.1 | SAM domain containing 1 |
| BIRC4BP | XIAP associated factor-1 |
| C16orf60 | Chromosome 16 open reading frame 60 |
| SLC22A15 | solute carrier family 22 (organic cation transporter), member 15 |
| ACVR2A | activin A receptor, type IIA |
| ATAD2 | ATPase family, AAA domain containing 2 |
| SIX1 | Sine oculis homeobox homolog 1 (Drosophila) |
| --- | CDNA FLJ34034 fis, clone FCBBF2004671 |
| CLDN11 | claudin 11 (oligodendrocyte transmembrane protein) |
| --- | CDNA FLJ33653 fis, clone BRAMY2024715 |
| KIAA0146 | KIAA0146 |
| CCDC64 | coiled-coil domain containing 64 |
| FLJ34443 | hypothetical protein FLJ34443 |
| EPB41L4A | erythrocyte membrane protein band 4.1 like 4A |
| --- | --- |
| IBRDC2 | IBR domain containing 2 |
| --- | Full length insert cDNA clone ZE05E03 |
| ASAM | adipocyte-specific adhesion molecule |
| BCL9L | B-cell CLL/lymphoma 9-like |
| E2F7 | E2F transcription factor 7 |
| PHACTR3 | phosphatase and actin regulator 3 |
| FGD4 | FYVE, RhoGEF and PH domain containing 4 |
| TMEM68 | transmembrane protein 68 |
| --- | --- |
| --- | Homo sapiens, clone IMAGE:5396854, mRNA |
| AZI2 | 5-azacytidine induced 2 |
| LOC129293 | hypothetical protein LOC129293 |
| SPTLC2L | serine palmitoyltransferase, long chain base subunit 2-like (aminotransferase 2) |

Fig. 34 (Cont.)

| | | | | | |
|---|---|---|---|---|---|
| 227542_at | 9.49 | 8.29 | 9.17 | 7.26 | |
| 227530_at | 3.66 | 6.28 | 2.76 | 9.98 | |
| 227529_s_at | 2.74 | 4.42 | 2.58 | 8.38 | |
| 227443_at | 8.06 | 6.53 | 9.01 | 6.61 | |
| 227350_at | 7.71 | 9.55 | 6.91 | 9.96 | |
| 227347_x_at | 5.40 | 6.55 | 3.81 | 5.08 | 227347_x_at |
| 227260_at | 5.65 | 6.74 | 5.82 | 7.98 | |
| 227259_at | 4.31 | 5.41 | 4.75 | 5.81 | |
| 227195_at | 10.35 | 8.43 | 10.02 | 6.98 | |
| 227152_at | 5.81 | 4.46 | 5.77 | 4.10 | |
| 227143_s_at | 6.44 | 8.11 | 5.85 | 7.35 | |
| 227134_at | 8.82 | 7.37 | 8.84 | 7.19 | |
| 227049_at | 7.71 | 6.29 | 8.16 | 6.99 | |
| 226978_at | 5.97 | 4.81 | 6.29 | 4.83 | |
| 226948_at | 7.32 | 5.96 | 7.16 | 6.09 | |
| 226939_at | 9.54 | 8.03 | 9.14 | 6.92 | |
| 226863_at | 10.42 | 9.28 | 7.66 | 6.04 | 226863_at |
| 226853_at | 8.31 | 7.00 | 7.58 | 6.43 | |
| 226817_at | 12.64 | 11.16 | 9.69 | 7.01 | 226817_at |
| 226757_at | 4.40 | 6.82 | 4.15 | 9.71 | |

Fig. 34 (Cont.)

| | | | | |
|---|---|---|---|---|
| 227542_at | 227542_at | 227542_at | 227542_at | |
| 227530_at | 227530_at | 227530_at | 227530_at | |
| 227529_s_at | 227529_s_at | 227529_s_at | 227529_s_at | |
| 227443_at | 227443_at | 227443_at | | |
| 227350_at | 227350_at | 227350_at | | |
| 227347_x_at | 227347_x_at | 227347_x_at | 227347_x_at | 227347_x_at |
| 227260_at | 227260_at | 227260_at | 227260_at | |
| 227259_at | 227259_at | 227259_at | | |
| 227195_at | 227195_at | 227195_at | 227195_at | |
| 227152_at | 227152_at | 227152_at | | |
| 227143_s_at | 227143_s_at | 227143_s_at | | |
| 227134_at | 227134_at | 227134_at | | |
| 227049_at | 227049_at | 227049_at | | |
| 226978_at | 226978_at | 226978_at | | |
| 226948_at | 226948_at | 226948_at | | |
| 226939_at | 226939_at | 226939_at | 226939_at | |
| 226863_at | 226863_at | 226863_at | 226863_at | 226863_at |
| 226853_at | 226853_at | 226853_at | | |
| 226817_at | 226817_at | 226817_at | 226817_at | 226817_at |
| 226757_at | 226757_at | 226757_at | 226757_at | |

Fig. 34 (Cont.)

| | |
|---|---|
| --- | cDNA FLJ14294 fis, clone PLACE1008181 |
| AKAP12 | A kinase (PRKA) anchor protein (gravin) 12 |
| AKAP12 | A kinase (PRKA) anchor protein (gravin) 12 |
| C9orf150 | chromosome 9 open reading frame 150 |
| HELLS | Helicase, lymphoid-specific |
| HES4 | hairy and enhancer of split 4 (Drosophila) |
| ANKRD10 | Ankyrin repeat domain 10 |
| CD47 | CD47 molecule |
| ZNF503 | zinc finger protein 503 |
| C12orf35 | chromosome 12 open reading frame 35 |
| BID | BH3 interacting domain death agonist |
| SYTL1 | synaptotagmin-like 1 |
| ZADH2 | zinc binding alcohol dehydrogenase, domain containing 2 |
| PPARA | peroxisome proliferative activated receptor, alpha |
| RHBDD1 | rhomboid domain containing 1 |
| CPEB2 | cytoplasmic polyadenylation element binding protein 2 |
| FAM110C | Family with sequence similarity 110 member C |
| BMP2K | BMP2 inducible kinase |
| DSC2 | desmocollin 2 |
| IFIT2 | interferon-induced protein with tetratricopeptide repeats 2 |

Fig. 34 (Cont.)

HORMONE RESPONSIVE TISSUE CULTURE SYSTEM AND USES THEREOF

RELATED APPLICATIONS

This application is a continuation of U.S. application Ser. No. 12/672,786, filed on May 27, 2011, which is a national stage application under 35 U.S.C. § 371 of International Application PCT/US2008/009639, filed Aug. 11, 2008, which claims the benefit of the filing date of U.S. provisional application 60/964,271, entitled "Hormone Responsive Tissue Culture System and Uses Thereof" filed Aug. 10, 2007. This application is related to U.S. provisional application 60/569,005, entitled "Contribution of Target Cell Type to Epithelial Tumor Phenotypes," filed May 7, 2004 and U.S. provisional application 60/630,934, entitled "Hormone Responsive Tissue Culture System and Uses Thereof," filed Nov. 24, 2004. The entire teachings of the referenced applications are expressly incorporated herein by reference.

GOVERNMENT SUPPORT

The invention was made with government support under K08-CA-92013, awarded by the National Cancer Institute. The government has certain rights in the invention.

BACKGROUND OF THE INVENTION

Recent work comparing transformation and tumorigenicity of rodent and human cells has established significant differences between species. Therefore, it will be important to use human cells in creating tumor models that are relevant to human cancers.

The histopathological and clinical behavior differences among epithelial cancer subtypes arising within a single organ can be as large as those arising in different organs. For instance, more than a dozen distinct histopathological subclasses of breast cancer are encountered in the clinic (Rosen 2001), and subtypes with differing patient outcomes have also been defined through gene expression profiling (Gusterson et al., 2005; Sorlie et al., 2001). The phenotypic diversity of tumors has been generally ascribed to subtype-specific genetic and epigenetic alterations. However, some have suggested that the heterogeneity among of human breast cancers is also due to their derivation from a variety of distinct normal epithelial cell types (Bocker et al., 2002; Dontu et al., 2003; Welm et al., 2003), this notion being supported both by mouse tumor models (Dimri et al., 2005; Li et al., 2003) and by expression profiling of human breast tumors (Sorlie et al., 2003). While it seems evident based on clinical observations that cells from different organs give rise to distinct tumors, it has been less clear whether transformation of neighboring epithelial cells residing within a single organ can lead to different tumor phenotypes.

It has been difficult to retrospectively identify the precise cell type that gives rise to a particular tumor in clinical samples or rodent tumor models, since the normal cell from which the tumor arose is already transformed and no longer available in its original state. This suggests that prospective transformation of different cell subtypes from the same normal epithelium is essential to uncover the influence of the normal cell phenotype on the phenotype of a tumor derived from a particular normal cell population. In the case of human breast tissue, a specific culture medium (termed MEGM or MCDB-170) has been widely used to propagate a sub-population human mammary epithelial cells in vitro since its development more than two decades ago (Hammond et al., 1984; Stampfer et al., 2000). It has been previously reported that experimental transformation of HMECs grown in MEGM medium resulted in tumorigenic breast epithelial cells that gave rise, after implantation into immunocompromised host mice, to poorly differentiated carcinomas with areas of squamous differentiation (Elenbaas et al., 2001). This particular tumor phenotype is rare among naturally occurring human breast cancers, representing less than 1% of human breast tumors. It has also been reported previously that the normal HMEC population from which these tumors were derived is equally rare in vivo (Brenner et al., 1998; Holst et al., 2003; Tlsty et al., 2004; Yaswen et al., 2001).

Therefore, there is a need to develop alternative means of propagating normal human mammary epithelial cells in vitro.

SUMMARY OF THE INVENTION

The present invention provides a medium formulation, methods of making such media and methods of using such media to identify, isolate, or enrich primary cells and progenitor cells, and to proliferate such cells (e.g. normal primary mammary epithelial progenitors or stem cells, and other primary glandular epithelial cells, etc.).

The invention also provides methods of creating genetically defined tumor cells, including "tumor stem cells" that differentiate into metastatic adenocarcinomas.

A) Medium and Tissue Culture:

The medium of the present invention supports the growth of primary mammary epithelial progenitor cells that can give rise to a luminal epithelial phenotype and simultaneously suppresses the growth of other cell types. Thus, primary cells isolated using such a medium/system is essentially free of other cell types, especially those undesirable cell types, such as myoepithelial, stromal, and basal epithelial cell types.

Primary cells isolated and cultured using the methods and media of the invention can grow and proliferate in an undifferentiated state for many weeks (at least about 4 weeks, and usually more than about 15 weeks) or through many population doublings (PD; at least about 15 PD, usually more than 35 PD) without senescence or detectable genetic alterations. These cells can also be induced to undergo differentiation by changing media and culture conditions. In the case of mammary epithelial progenitors, the cells can differentiate in 3-D culture into epithelial cells of luminal phenotype characterized by luminal epithelial cell marker expression.

In certain embodiments of the invention, "about" or "approximately" refers to a number that varies by up to 5%, or in other embodiments up to 10%, and in other embodiments up to 25%, from the number being referred to.

In a specific embodiment, the tissue culture medium of the invention is a chemically defined serum-free medium that is substantially free of animal serum and/or tissue or organ extracts (e.g. Bovine Pituatary Extact).

As used herein, the term "serum-free" refers to the fact that the medium contains essentially no serum. In certain embodiments, there is 0% (completely free), or less than about 0.001%, 0.005%, 0.01%, 0.025%, 0.05%, 0.1%, 1.0%, or 10.0% total serum in the subject medium. The most common types of serums include: various forms of bovine serum (calf serum, fetal bovine serum, bovine calf serum, donor bovine calf serum, newborn bovine calf serum, etc.), horse serum and human serum.

In certain embodiments, there is 1-5% total serum in the subject medium. Such medium may be used for differentiating breast epithelial cells, as well as for propagating other cell hypes, such as mesothelial cells.

"Chemically defined" means the structures, chemical formulae, and the percentage of the various individual components within a chemical composition are known or can be defined. Various tissue extracts, such as bovine pituitary extracts, are not chemically defined, at least partly because not all individual components of the extract are known. For those known components, the amount and the relative percentages of the various components could (and usually do) vary from one batch to another. This is partly caused by the fact that individual animals may have inherently different levels of various chemical compositions, even in the same tissue, depending on such factors a general health, nutrition, mood, pathological infections, trauma, etc.

In certain embodiments, the medium of the instant invention does not contain any animal serum products prepared for tissue culture purposes. Nor does it contain any tissue extracts with unknown/undefined chemical components. Instead, all essential components necessary to support the desired growth/proliferation of desired cell types are chemically defined. Most, if not all, of these individual components can be readily purchased as commercial products from various venders, such as Sigma-Aldrich Corp. (St. Louis, Mo.), GIBCO-Invitrogen Corp. (Carlsbad, Calif.); Calbiochem, and/or BD Biosciences (San Jose, Calif.), etc.

In certain other embodiments, the presence in the subject medium of serum and/or tissue extracts, especially in trace amounts, would not substantially interfere with the characteristics of the medium, such as inhibiting the ability of the subject medium to support long-term undifferentiated cell growth and/or proliferation without a significant decrease in differentiation potential.

The invention also provides normal primary cells produced and/or isolated using the subject methods and media.

B) Transformation of Primary Cells and Creation of Tumor Xenografts:

1) Tumor Stem Cells

The invention also provides methods to transform normal primary cells so cultured into engineered tumorigenic cells; when injected into immuno-compromised xenograft animals, the engineered tumorigenic cells are tumorigenic and recapitulate properties of breast cancer stem cells described in human tumors. In the case of mammary epithelial progenitor cells, more than 90% of the isolated cell population express CD44, CD24 and ESA (epithelial cell surface antigen). Upon transformation, more than 95% of the transformed cells express CD44, CD24 and ESA and the number (e.g., about 10-100) of such transformed cells that need to be injected into immuno-compromised xenografted animals to generate tumors in about 50% of the injected animals is less than that needed using presently-available techniques. This number of cells is about 10,000-fold lower than the number of tumor cells needed in a traditional xenografted transplantation.

In tumor cells isolated from such xenografted animals, a mixed population of tumor cells with mixed $CD44^{+/-}$, $ESA^{+/-}$ and $CD24^{+/-}$ expression is obtained. When tissue cultured transformed cells or tumor cells isolated from explanted tumors are isolated, separated into $CD44^+$, $CD44^-$, $CD24^+$ and $CD24^-$ fractions, and reinjected into nude mice, only $CD44^+$ and $CD24^-$ fractions are capable of forming tumors. These results observed in this experimental model recapitulates the behavior of human tumor stem cells that were isolated from naturally occurring human tumors by al Hajj et. al.

2) Tumor Phenotype

In addition, this genetically defined cancer stem cell tumor model mimics the behavior of human tumors; Most human carcinomas retain some form of normal glandular architecture of the tissue they rise in such as breast, prostate, colon, lung etc., which explains their classification as ductal adenocarcinomas. Moreover, many human tumors are associated with a desmoplastic stromal response, which is composed of a newly formed extracellular matrix and multiple non-neoplastic cell types, in particular, abundant α-Smooth muscle actin (α-SMA)-positive myofibroblasts. Both the ductal architecture and the stromal response seen in human tumors are absent in most commonly used tumor xenograft models.

In contrast the tumorigenic cells are prepared according to the invention here in recapitulate the morphologic (histopathology) features of human tumors, i.e; they form ductal structures of human adenocarcinomas that cause a robust desmoplastic reaction. Furthermore, these transformed cells recapitulate the behavior of human tumors i.e; the tumor cells are highly invasive, hormone responsive, and metastatic to distant sites when injected into xenografted animals. This type of an adenocarcinoma phenotype has been difficult to recapitulate in many tumor xenograft models (Cardiff et al., 2000; Liu et al., 2004; Lundberg et al., 2002), even though this tumor type constitutes the great majority of the tumors arising in a variety of visceral tissues, including breast, lung, ovary, colon and prostate. We point out that, in contrast, the presently described tissue culture and xenograft model system has indeed been able to phenocopy many aspects of naturally occurring human adenocarcinomas, including their metastatic behavior. These tumor cells also express gene products that are specific to cancer stem cells identified in patient samples.

Thus, the invention also provides transformed primary cells that are tumorigenic in immuno-compromised animals. Such transformed cells are useful for establishing a tumor model that mimics characteristics of cancers as they occur in patients, in terms of invasiveness, hormone responsiveness and metastasis.

The invention also provides such a tumor model and the use of the tumor cells and tumor models in methods of screening for candidate agents or drug leads specifically targeting stem cell-like cancer cells. While previous work identified tumor stem cells in patient samples, no methods of in vitro expansion of these cells were developed. Therefore, to our knowledge our system is the only one in which in vitro drug screening is possible in human tumor stem cells and their normal counterparts.

Furthermore, in most tumor xenograft experiments using established tumor cell lines, injection of at least $10^6$ tumor cells is required in order to observe tumor growth. In contrast, our system allows tumor formation using as low as 10 cells. Therefore, instead of the traditional one reagent (or one condition) per animal model, our system can screen a plurality of reagents or conditions an single animal model.

The tumorigenic cells and tumor models of the invention can be further used to compare various characteristics of normal cells (e.g., the untransformed normal parental cells) and theirtumorigenic derivatives, both in vitro and in vivo. In practice, any characteristics that can be measured or studied can be compared between these normal and tumor cell populations. For illustration only, and without limitation, these include the following properties/behavior/characteristics of the cells: in vivo growth, in vitro proliferation, invasion and metastasis, anchorage-independent growth, cell cycle progression, apoptosis, senescence, drug resistance, immunogenicity, sensitivity to chemo-/radiotherapy, differentiation potential, expression of various markers, etc.

The invention also provides a method to carry out a pharmaceutical/biotechnology product discovery and development, comprising of creation of tumor models derived from various normal cell types isolated and propagated using the media and methods of the instant invention, and screening for drug molecule or lead compound libraries in order to identify molecules that target tumor cells but not their normal precursor cells. The business method may further include licensing the rights to such tumor cell/tumor model/drug candidates to third party. The business method may further comprise marketing of such established tumor cells/tumor models for sale or licensing.

Thus, one aspect of the invention relates to a culture medium comprising: (1) one or more lipid synthesis precursors; (2) one or more protein synthesis precursors (at least the essential amino acids, optionally also including non-essential amino acids); (3) one or more carbohydrate synthesis precursors and energy metabolism precursors; (4) one or more cations (e.g. monovalent and divalent), ions, trace metals and enzyme cofactors/vitamins; (5) one or more agents that induce increased intracellular 3'-5' cyclic adenosine monophosphate (cAMP) levels, and, optionally, (6) one or more antioxidants; (7) one or more nucleotide salvage pathway synthesis precursors; (8) one or more buffers; (9) one or more carrier proteins (such as bovine serum albumin); (10) one or more detergents (such as Tween 80); (11) one or more non-insulin hormones, growth factors or growth factor peptides and their inhibitors, cytokines and interleukins; (12) differentiation inducing reagents and, (13) insulin and glucose, wherein the medium supports undifferentiated growth and/or proliferation of primary epithelial progenitor cells for at least about 4 weeks (e.g., at least about 6 weeks) or at least about 15 population doubling (PD) in vitro (e.g., at least about 30 PD), without a significant decrease in differentiation potential.

In another embodiment, the invention relates to a culture medium comprising: (1) one or more lipid synthesis precursors; (2) one or more protein synthesis precursors; (3) one or more carbohydrate synthesis and energy metabolism precursors; (4) one or more monovalent and/or divalent cations, ions, trace metals and enzyme cofactors/vitamins; and, (5) insulin, wherein the medium supports undifferentiated growth and/or proliferation of primary epithelial progenitor cells transformed by telomerase catalytic subunit (e.g. hTERT) for at least about 4 weeks (e.g., at least about 6 weeks) or at least about 15 population doubling (PD) in vitro (e.g., at least about 30 PD), without a significant decrease in differentiation potential.

The invention provides cell culture medium comprising: (a) one or more lipid synthesis precursors; (b) one or more protein synthesis precursors; (c) one or more carbohydrate synthesis and energy metabolism precursors; (d) one or more monovalent and/or divalent cations, ions, trace metals and enzyme cofactors/vitamins; and (e) insulin, wherein the medium supports undifferentiated growth and/or proliferation of primary epithelial progenitor cells transformed by telomerase catalytic subunit for at least about 4 weeks or at least about 15 population doubling (PD) in vitro, without a significant decrease in differentiation potential.

The invention provides cell culture medium comprising (a) None or trace amount of calf/fetal bovine serum; (b) Epidermal Growth Factor at a final concentration of about 10 ng/mL; (c) Hydrocortisone at a final concentration of about 0.5 μg/mL; (d) Cholera toxin at a final concentration of about 100 ng/mL; (e) Insulin at a final concentration of about 20 μg/mL, wherein the medium supports undifferentiated growth and/or proliferation of human primary breast cells for at least about 4 weeks or at least about 15 population doubling (PD) in vitro, without a significant decrease in differentiation potential.

The invention provides cell culture medium comprising (a) none or trace amount of calf/fetal bovine serum; (b) epidermal growth factor at a final concentration of about 10 ng/mL; (c) hydrocortisone at a final concentration of about 0.5 μg/mL; (d) cholera toxin at a final concentration of about 25 ng/mL; (e) insulin at a final concentration of about 20 μg/mL; wherein the medium supports undifferentiated growth and/or proliferation of human ovarian and/or fallopian tube epithelial cells for at least about 4 weeks or at least about 15 population doubling (PD) in vitro, without a significant decrease in differentiation potential.

The invention provides culture medium comprising: (a) calf/fetal bovine serum at a final concentration of about 0.1%-0.2% by volume; (b) epidermal growth factor at a final concentration of about 10 ng/mL; (c) hydrocortisone at a final concentration of about 0.5 μg/mL; (d) cholera toxin at a final concentration of about 25 ng/mL; (e) insulin at a final concentration of about 20 μg/mL; wherein the medium supports undifferentiated growth and/or proliferation of human mesothelial cells for at least about 4 weeks or at least about 15 population doubling (PD) in vitro, without a significant decrease in differentiation potential.

The invention provides the above medium that supports undifferentiated growth and/or proliferation of the relevant cells for at least about 6 weeks or at least about 30 PD in vitro, without a significant decrease in differentiation potential. The invention further provides cells cultured in media of the invention.

Energy metabolism precursors are usually carbohydrates; they may overlap with carbohydrate synthesis precursors, such as glucose. However, since amino acids and lipids may also be energy metabolism precursors, such composition may also overlap with lipid synthesis precursors and/or protein synthesis precursors.

In certain embodiments of any of the media of the invention, one or more lipids or fatty acids serve as lipid synthesis precursors; one or more amino acids serve as protein synthesis precursors; and/or one or more sugars serve as carbohydrate synthesis and/or energy metabolism precursors.

Many enzymes use cofactors (e.g. nonprotein component of enzymes). If the cofactor is organic, then it is called a coenzyme. Many of the coenzymes are derived from vitamins, including vitamins A, B1 (thiamin), B12, D, E, K, and folic acid. Other enzyme cofactors include niacin, pantothenic acid, and riboflavin, etc.

In certain embodiments, the medium also comprises one or more of the following: (1) one or more antioxidants; (2) one or more nucleotide salvage pathway synthesis precursors; (3) one or more buffers; (4) one or more carrier proteins (such as bovine serum albumin); (5) one or more detergents (such as Tween 80); (6) one or more non-insulin hormones and growth factors.

In certain embodiments, the medium also comprises at least 10 of the components listed as optional in Table II or at least 10 of the components listed in the medium of Example XIX. In certain embodiments, the medium also comprises the at least one component listed in Table XI (Medium 199) at between 0.3 and 3 times the listed concentration. In preferred embodiments, the medium comprises all or at least 90% of the components listed in Table XI (Medium 199) at between 0.3 and 3 times the listed concentrations.

In certain embodiments, the medium of the instant invention has the composition of combining F12 medium with M199 medium. The amount of F12 medium is preferably between 30% and 70% by volume (e.g., 40%-60% or 45%-55%), with the remaining being M199 medium. In an exemplary embodiment, the subject medium comprises 50% (by volume) of F12 medium and 50% (by volume) of Medium 199. Although the media of the invention may be obtained by mixing F12 and M199 at the specified percentage (by volume), the invention is not limited to obtaining a particular medium composition by mixing fully-prepared F12 and M199. Those of ordinary skill in the art may calculate the concentration of each component of a particular medium composition and prepare accordingly, without preparing M199 and F12 first.

Certain embodiments of the subject medium are described in the examples and referred to as "WIT medium."

The invention also encompasses embodiments in which any one or more of the components of such medium listed (e.g. at least 5, 6, 7, 8, 9, 10, at least 90% or all of the components) are added in the listed concentrations (or in amounts independently ranging from 0.1 to 10 times, or 0.3 to 3 times of the listed concentration), to a medium having the composition of combining F12 medium with M199 medium. The amount of F12 medium is preferably between 30% and 70% by volume (e.g., 40%-60% or 45%-55%), with the remaining being M199 medium. The medium may be used, without limitation, for any of the purposes and in any of the methods described herein.

In certain embodiments, the medium supports growth and/or proliferation of primary breast epithelial progenitor cells without detectable genetic alterations. In certain embodiments, the genetic alteration is p16 inactivation. In certain embodiments, the medium does not support survival or sustained growth or proliferation of fibroblasts and breast stromal cells. In certain embodiments, the medium supports growth and/or proliferation of cells which are substantially free of expression of stress indicator genes, such as p53 and/or p16. In certain embodiments, the medium is substantially free of at least one member selected from the group consisting of: serum, heparin, fibroblast growth factor (FGF), and bovine pituitary extract (BPE). In certain embodiments, the medium supports growth and/or proliferation of cells which are substantially free of expression of epithelial differentiation markers and mesenchymal differentiation markers. In certain embodiments, the epithelial differentiation markers comprise at least one member selected from the group consisting of: keratin 8, keratin 10, keratin 14, keratin 18, keratin 19, E-cadherin, p63, smooth muscle actin (SMA), and β-catenin. In certain embodiments, the mesenchymal differentiation marker is vimentin.

In certain embodiments, the one or more antioxidants comprise at least one antioxidant selected from the group consisting of: glutathione (reduced), dithiothreitol (DTT), vitamin E, vitamin K3, vitamin D2 or calciferol, niacin, niacinamide, and ascorbic acid. In certain embodiments, the one or more nucleotide salvage pathway synthesis precursors are selected from the group consisting of: hypoxanthine, xanthine, adenine, guanine, and thymidine. In certain embodiments, the one or more lipid synthesis precursors are selected from the group consisting of: cholesterol, linoleic acid, lipoic acid, and o-phosphoryl ethanolamine. In certain embodiments, the one or more hormones are selected from the group consisting of: progesterone, testosterone, hydrocortisone, triiodothyronine (thyroid hormone), and estrogen. In certain embodiments, the one or more growth factors are selected from the group consisting of: insulin and epidermal growth factor (EGF). In certain embodiments, the agents that induce increased intracellular cAMP levels directly increase intracellular cAMP levels. In certain embodiments, the one or more agents that induce(s) increased intracellular cAMP levels inhibit a cAMP phosphodiesterase. In certain embodiments, the one or more agents that induce(s) increased intracellular cAMP levels are selected from the group consisting of: a ß-adrenergic receptor agonist, dibutyryl cAMP, isobutylmethylxanthine, theophylline, isoproterenol, cholera toxin and forskolin.

In certain embodiments, the medium further comprises at least one buffer, such as N-[2-hydroxyethyl]piperazine-N'-[2-ethanesulfonic acid] (HEPES) buffer, sodium bicarbonate buffer, or a combination of both. In certain embodiments the medium comprises an alternate buffer component substantially nontoxic to mammalian cells.

In certain embodiments, the medium comprises the components listed in Table II. In a specific embodiment, the medium includes the components listed in Table II, each present in the concentration shown or within the listed concentration range. In other embodiments, the medium includes the components listed in Table II, with at least one of the components present at a concentration that is about 5%, 10%, 20%, 50%, 100% higher or lower than the listed maximum or minimum concentration.

In certain embodiments, the medium comprises about 50% Medium 199 (M199) and about 50% F12 (Ham) medium, supplemented with glutamine, EGF, transferrin, insulin, progesterone, testosterone, 17B-estrodiol, O-phosphorylethanolamine, selenious acid, lionleic acid, BSA, triiodothyronine, hydrocortizone, cholera toxin, HEPES, and other components to approximately their corresponding concentrations as listed in Table II.

In certain embodiments, the medium supports undifferentiated growth and/or proliferation of primary epithelial progenitor cells transfected with telomerase, for at least about 15 months in vitro, without a substantial decrease in differentiation potential.

In certain embodiments, the medium supports growth, proliferation, and/or differentiation of primary epithelial progenitor cells induced to express: (1) telomerase catalytic subunit, (2) a first polypeptide that functions in the same signaling pathway(s) as the SV40 large T antigen, and (3) a second polypeptide that functions in the same signaling pathway as the mutant H-ras oncogene product, for at least about 15 weeks or at least about 35 population doubling (PD) in vitro, without losing tumorigenicity.

In certain embodiments, the medium comprises the components listed in Table I. In certain embodiments, the medium comprises about 50% Medium 199 (M199) and about 50% F12 (Ham) medium, supplemented with glutamine, EGF, transferrin, insulin, 17β-estrodiol, o-phosphorylethanolamine, selenious acid, lionleic acid, BSA, triiodothyronine, hydrocortizone, cholera toxin, and HEPES, to approximately their corresponding concentrations listed in Table I. In certain embodiments, the medium further comprises one or more antibiotics, such as penicillin and/or streptomycin. In certain embodiments, the medium is a 1× medium formulation, or a concentrated medium formulation of about 2×, 5×, or 10× formulation. In certain embodiments, at least some components of the medium is a concentrated formulation of about 2×, 5×, 10×, 100×, or 1000×. In certain embodiments, at least some or all components of the medium are in liquid/aqueous form. In certain embodiments, at least some or all components of the medium is in solid, powder, or frozen form.

In certain embodiments, the medium supports the growth, proliferation, and/or differentiation of mammalian cells. In certain embodiments, the mammalian cells are non-human mammalian cells. In certain embodiments, the non-human mammalian cells are from mouse, rat, non-human primate (e.g. monkey), rabbit, dog, or cat. In certain embodiments, the medium supports the growth, proliferation, and/or differentiation of cells from normal glandular epithelial cells of an organ/tissue selected from: breast, prostate, ovary, pancreas, stomach, intestine, colon, endocervix, kidney, skin, lung, uterus, parotid gland, or fallopian tube. In certain embodiments, the medium supports the growth, proliferation, and/or differentiation of endometrial cells or cervical cells. In certain embodiments, the medium supports the differentiation of breast glandular epithelial cells to luminal phenotype, but not basaloid phenotype. In certain embodiments, the luminal phenotype is characterized by specific keratin expression profiles typical of luminal mammary epithelial cells. In certain embodiments, the medium is substantially free of bovine pituitary extract (BPE), or other tissue/organ extracts with undefined chemical composition. In certain embodiments, the medium supports undifferentiated growth and proliferation of the cells for at least about 5, 6, 7, 8, 9, 10, 11, 12, 13, 14, or 15 weeks in culture. In certain embodiments, the medium supports undifferentiated growth and proliferation of a population of breast progenitor cells characterized by expression of CD44, CD24, and ESA in >85% of the cells.

Another aspect of the invention relates to a culture medium comprising: (a) one or more lipid synthesis precursors; (b) one or more protein synthesis precursors; (c) one or more carbohydrate synthesis and energy metabolism precursors; (d) one or more monovalent and/or divalent cations, ions, trace metals and enzyme cofactors/vitamins; and (e) insulin, wherein the medium supports undifferentiated growth and/or proliferation of primary epithelial progenitor cells transformed by telomerase catalytic subunit for at least about 4 weeks or at least about 15 population doubling (PD) in vitro, without a significant decrease in differentiation potential.

Another aspect of the invention relates to a culture medium comprising: (a) None or trace amount of calf/fetal bovine serum; (b) Epidermal Growth Factor at a final concentration of about 10 ng/mL; (c) Hydrocortisone at a final concentration of about 0.5 µg/mL; (d) Cholera toxin at a final concentration of about 100 ng/mL; (e) Insulin at a final concentration of about 20 µg/mL, wherein the medium supports undifferentiated growth and/or proliferation of human primary breast cells for at least about 4 weeks or at least about 15 population doubling (PD) in vitro, without a significant decrease in differentiation potential.

Another aspect of the invention relates to a culture medium comprising: (a) none or trace amount of calf/fetal bovine serum; (b) epidermal growth factor at a final concentration of about 10 ng/mL; (c) hydrocortisone at a final concentration of about 0.5 µg/mL; (d) cholera toxin at a final concentration of about 25 ng/mL; (e) insulin at a final concentration of about 20 µg/mL, wherein the medium supports undifferentiated growth and/or proliferation of human ovarian & fallopian tube epithelial cells for at least about 4 weeks or at least about 15 population doubling (PD) in vitro, without a significant decrease in differentiation potential.

Another aspect of the invention relates to a culture medium comprising: calf/fetal bovine serum at a final concentration of about 0.1%-0.2% by volume; (b) epidermal growth factor at a final concentration of about 10 ng/mL; (c) hydrocortisone at a final concentration of about 0.5 µg/mL; (d) cholera toxin at a final concentration of about 25 ng/mL; (e) insulin at a final concentration of about 20 µg/mL, wherein the medium supports undifferentiated growth and/or proliferation of human mesothelial cells for at least about 4 weeks or at least about 15 population doubling (PD) in vitro, without a significant decrease in differentiation potential.

Another aspect of the invention provides a composition comprising solid form chemicals which, when dissolved in an aqueous solvent, produce a culture medium described or claimed herein.

The invention further relates to a method of isolating mammalian primary cells, comprising: (a) providing tissues containing the primary cells from a mammal; (b) plating primary cells obtained from the tissue on a tissue culture container with mixed (+/−) charge surface, in culture medium for between 3 days to 4 weeks with medium change at reasonable frequency, wherein said medium change optionally occurs at least once every 12 hours to 3 days; and; (c) harvesting primary cells and transferring the harvested the primary cells to a new tissue culture container with mixed (+/−) charge surface in the medium of claim 1, thereby isolating the primary cells from the mammal.

In certain embodiments, the method further comprises, before (d), removing residual cells other than the primary cells by selective trypsin digestion using low concentration of trypsin over a period of 1-3 days.

In certain embodiments, the primary cells are primary glandular epithelial cells.

In certain embodiments, the tissues are from: breast, prostate, ovary, pancreas, stomach, intestine, colon, endocervix, kidney, skin, lung, uterus, mesothelium, bone marrow, or fallopian tube.

In certain embodiments, the other cells are stromal cells and/or myoepithelial cells.

In certain embodiments, step (b) is effectuated by collagenase digestion of the tissues overnight at 37° C., optionally followed by three consecutive rounds of centrifugation for 5 minutes each at 300×g, 100×g, and 50×g, respectively, or some other suitable centrifugation or cell collection process, such processes being known to one of skill in the art.

In certain embodiments, the tissue culture container is a PRIMARIA™ container made from surface-modified polystyrene.

Another aspect of the invention provides a primary cell isolated using the method of the invention, wherein the primary cells grow and/or proliferate in the subject medium for at least about 4 weeks or at least about 15 population doubling (PD) in vitro, without any detectable genetic alterations, or losing differentiation potential.

In certain embodiments, the primary cell is a primary glandular epithelial cell.

In certain embodiments, the primary glandular epithelial cell is from a tissue/organ selected from: breast, prostate, ovary, pancreas, stomach, intestine, colon, endocervix, kidney, skin, lung, uterus, mesothelium, bone marrow, or fallopian tube.

In certain embodiments, the primary cell grows and/or proliferates in the subject medium for at least about 15 weeks or at least about 35 population doubling (PD) in vitro.

In certain embodiments, the genetic alterations comprise p16 inactivation.

In certain embodiments, the primary cell is substantially free of fibroblasts and stromal cells.

In certain embodiments, the primary cell is substantially free of stress gene (e.g. p16, p53) expression.

In certain embodiments, the primary cell is substantially free of epithelial differentiation markers expression and mesenchymal differentiation markers expression.

In certain embodiments, the primary cell is hormone responsive before and during culturing in the medium.

The invention further relates to a tumorigenic cell derived from the subject primary cell, wherein the tumorigenic cell expresses: (1) a telomerase catalytic subunit; (2) a first polypeptide functions in the same signaling pathway(s) as does the SV40 large T antigen; and, (3) a second polypeptide functions in the same signaling pathway as does the mutant H-ras oncogene product. Optionally, the tumorigenic cell also expresses SV40 small t antigen, or has diminished level of target proteins of the small t antigen in the cell (such as PP2A etc.) The diminished level of SV40 large and/or small t antigens may be brought about by any means, including siRNA or antibody against the target protein(s). The function of SV40 large T antigen may also be replaced by HPV E6 and E7 proteins.

In certain embodiments, about 10-100 of the subject cell, when injected into each xenograft animals, generate tumors in at least about 40-50% of the animals.

In certain embodiments, the tumorigenic cells are at least about 88% $CD44^+$, $CD24^+$, and $ESA^+$, and have essentially no vimentin expression.

In certain embodiments, the tumorigenic cell, which generates tumors in a xenografted animal, gives rise to a mixed population of tumor cells with mixed expression of CD44, CD24, ESA, vimentin, E-cadherin, or keratin 18. In certain embodiments, xenograft tumors arising from the injected tumorigenic cells form glandular structures similar to those seen in human tumors. In certain embodiments, xenograft tumors arising from the injected tumorigenic cells are invasive into adjacent tissues, such as skeletal muscle. In certain embodiments, xenograft tumors arising from the injected tumorigenic cells are metastatic. In certain embodiments, xenograft tumors arising from the injected tumorigenic cells metastasize to lung in >95% of the host xenograft animals.

In certain embodiments, xenograft tumors arising from the injected tumorigenic cells express at least one of progesterone, testosterone, and/or estrogen receptors, and are responsive to treatment with at least one of progesterone, testosterone, and/or estrogen.

Another aspect of the invention provides a method of subculturing isolated primary cells from a mammal, the method comprising: (1) harvesting isolated and cultured primary cells with trypsin or other cell dissociation techniques, (2) resuspending the harvested primary glandular epithelial cells in the subject medium supplemented with a trypsin inhibitor; (3) plating the resuspended primary glandular epithelial cells on a tissue culture container with mixed (+/−) charge surface; (4) replacing the medium with fresh subject medium after the primary glandular epithelial cells have attached to the surface of the tissue culture container. It should be noted during subculturing, it is not necessary to always resuspend the harvested cells in the subject medium. The harvested cells can be resuspended and plated in any suitable medium known in the art and/or PBS buffer, so long as the medium is replaced with the subject medium after the cells have attached to the subculturing container. The technique of subculturing is well known in the art.

In certain embodiments, the primary cells are primary glandular epithelial cells.

In certain embodiments, the trypsin inhibitor is calf serum (CS).

Another aspect of the invention provides a method for long-term culturing and maintenance of hormone-responsive primary cells from a mammal, the method comprising: (1) isolating primary cells from the mammal using the subject method; (2) using the subject method to culture and subculture the primary cells isolated in (1) in the subject medium.

In certain embodiments, the primary cells are primary glandular epithelial cells.

In certain embodiments, the method further comprises introducing ectopic genetic materials into the hormone-responsive primary cells or primary glandular epithelial cells.

In certain embodiments, the method further comprises stimulating the primary cells or the primary glandular epithelial cells with one or more hormone(s).

In certain embodiments, the method further comprises contacting the hormone-responsive glandular epithelial cells with one or more agent(s) or drug candidate(s).

Another aspect of the invention provides a method for inducing differentiation of isolated mammary epithelial progenitor cells to epithelial cells of luminal phenotype, comprising: (1) isolating and culturing the mammary epithelial progenitor cells according to the subject method; (2) inducing the differentiation of the mammary epithelial progenitor cells to epithelial cells of luminal phenotype.

In certain embodiments, step (2) of the method is effectuated by culturing cells in 3-D culture with EHS.

In certain embodiments, the differentiation is characterized by expression of markers specific for luminal phenotype or myoepithelial.

In certain embodiments, the markers include one or more of: keratin 8, keratin 18, keratin 19, keratin 14, E-cadherin, caludin-4, CD-10 and β-catenin.

Another aspect of the invention provides a method for enriching tumor stem cells in vitro, comprising culturing and subculturing tumorigenic cells of invention in culture medium comprising: (a) one or more lipid synthesis precursors; (b) one or more protein synthesis precursors; (c) one or more carbohydrate synthesis and energy metabolism precursors; (d) one or more monovalent and/or divalent cations, ions, trace metals and enzyme cofactors/vitamins; (e) one or more agents that induce increased intracellular 3'-5' cyclic adenosine monophosphate (cAMP) levels; and (f) insulin. In certain embodiment, the tumor stem cells are enriched at least 1,000 fold in vitro.

The invention also relates to a kit for isolating and culturing glandular epithelial cells from a mammal, the kit comprising a carrier means having in close confinement therein one or more container means: (1) wherein a first container means contains any of the subject medium; (2) an instruction for isolating and subculturing glandular epithelial cells from the mammal.

In certain embodiments, the kit further comprises collagenase and/or trypsin.

In certain embodiments, the collagenase is supplied in Hank's buffered saline solution (HBSS).

In certain embodiments, the trypsin is supplied in a high concentration of about 0.075%-0.35%. In certain embodiments, the trypsin is supplied at a low concentration of about 0-0.025%.

The invention also relates to a kit for isolating and culturing glandular epithelial cells from a mammal, the kit comprising a carrier means having in close confinement therein one or more container means: (1) wherein a plurality of the container means each individually contain, in proportion, solid forms of the components for any of the subject medium, such as that listed in Table II; (2) an instruction for making any one of the subject medium; (3) an instruction for isolating and subculturing glandular epithelial cells from the mammal.

In certain embodiments, at least some of the components of the kit are stored at different temperatures as that for other of the components.

In certain embodiments, at least some of the components of the kit are stored as liquid.

In certain embodiments, at least some of the components of the kit are stored as solid powder.

In further embodiments, the invention relates to a method for in vitro comparison of the characteristics of normal glandular epithelial cells and abnormal glandular epithelial cells derived therefrom, comprising: (1) isolating normal (primary) glandular epithelial cells using the subject method; (2) culturing the isolated normal glandular epithelial cells under the same condition as that of the abnormal (e.g. genetically modified, in tumor or genetic transformation) glandular epithelial cells; (3) comparing the behavior of the normal glandular epithelial cells and abnormal glandular epithelial cells.

In certain embodiments, the condition includes treatment by a hormone to which the normal glandular epithelial cells respond.

In certain embodiments, the abnormal glandular epithelial cells are derived from the normal glandular epithelial cells by introducing one or more ectopic genes therein.

In certain embodiments, the ectopic genes include: (1) a telomerase catalytic subunit; (2) a first polypeptide functions in the same signaling pathway(s) as does the SV40 large T antigen; and, (3) a second polypeptide functions in the same signaling pathway as does the mutant H-ras oncogene product.

In certain embodiments, the abnormal glandular epithelial cells are derived from a tumor/cancer/diseased tissue from which the normal glandular epithelial cells are obtained.

Another aspect of the invention provides a method of producing tumorigenic cells from corresponding normal primary cells, the method comprising: (1) isolating normal primary cells using the subject method; (2) introducing into the isolated cells exogenous DNA which, when expressed in the isolated cells, transforms the cells into tumorigenic cells which form tumors in immunocompromised mice into which they are introduced.

In certain embodiments, the exogenous DNA comprises: (a) DNA that encodes human telomerase catalytic subunit; (b) DNA that encodes a first oncogene or inhibitor of a first tumor suppressor (TS) gene; and, (c) DNA that encodes a second oncogene or inhibitor of a second TS gene, wherein the first oncogene/the first TS gene and the second oncogene/second TS gene function in two distinct biochemical pathways in human somatic cells.

In certain embodiments, the DNA of (a) is cDNA which encodes human telomerase catalytic subunit; the DNA of (b) is cDNA that encodes a first oncogene; and the DNA of (c) is cDNA that encodes a second oncogene, wherein the first oncogene and the second oncogene function in two distinct biochemical pathways in primary cells.

In certain embodiments, the biochemical pathways are signaling pathways and the cDNA of (b) encodes an oncogene which functions in the same signaling pathway as does the ras oncogene product, and the cDNA of (c) encodes an oncogene which functions in the same signaling pathways as does the SV40 LT antigen oncoprotein, wherein function of the oncogene encoded by the cDNA of (b) and function of the oncogene encoded by the cDNA of (c) in their respective signaling pathways in the normal human somatic cells in which human telomerase catalytic subunit is ectopically expressed results in production of tumorigenic human somatic cells.

In certain embodiments, the DNA of (b) is cDNA that encodes the H-ras oncogene product, and the DNA of (c) is cDNA that encodes the SV40 large T oncogene product.

In certain embodiments, the tumorigenic human somatic cells produced from tumors in immunocompromised mice into which they are introduced and the tumors formed are invasive and/or metastatic in the mice.

Another aspect of the invention provides a tumorigenic cell produced by the subject method. In certain embodiments, the tumorigenic cell is a human cell.

Another aspect of the invention provides an in vitro method of identifying an agent which reduces proliferation of tumorigenic cells, comprising: (1) contacting the subject tumorigenic cells, or tumorigenic cells produced by the subject method, with a candidate agent to be assessed for its ability to reduce proliferation of the tumorigenic cells, under conditions appropriate for the agent to enter cells; (2) determining the extent to which proliferation of the tumorigenic cells occurs in the presence of the candidate agent to be assessed; and, (3) comparing the extent determined with the extent to which proliferation of the tumorigenic cells occurs under the same conditions, but in the absence of the candidate agent to be assessed. If proliferation occurs to a lesser extent in the presence of the candidate agent to be assessed than in its absence, the candidate agent to be assessed is an agent which reduces proliferation of tumorigenic human somatic cells. In certain embodiments, the tumorigenic cells form a tumor in an immunocompromised xenografted animal model. In certain embodiments, the tumor is invasive and/or metastatic.

Another aspect of the invention provides an in vitro method of identifying an agent which inhibits or negatively affects one or more characteristics of tumorigenic cells, the characteristics including: cell viability, growth, proliferation, invasiveness, ability to metastasize, anchorage-independent growth, or angiogenesis, the method comprising: (1) contacting the subject tumorigenic cells, or tumorigenic cells produced by the subject method, with a candidate agent to be assessed for its ability to inhibit or negatively affect the one or more characteristics of the tumorigenic cells, under conditions appropriate for the agent to enter cells; (2) determining the extent to which the characteristics is inhibited or negatively affected in the presence of the candidate agent to be assessed; and, (3) comparing the extent determined with the characteristics of the tumorigenic cells under the same conditions, but in the absence of the candidate agent to be assessed. If the characteristics is substantially inhibited or negatively affected in the presence of the candidate agent to be assessed than in its absence, the candidate agent to be assessed is an agent which inhibits or negatively affects one or more the characteristics of the tumorigenic cells.

In certain embodiments, the one or more characteristics is inhibited or negatively affected by at least about 20%, 40%, 50%, 60%, 70%, 80%, 90%, or 100% in the presence of the candidate agent to be assessed than in its absence.

In certain embodiments, the method further comprises using the identified agent as a lead molecule to identify additional agents that more potently inhibit or negatively affect the characteristics. Another aspect of the invention provides an agent identified by the subject method. Another aspect of the invention provides a pharmaceutical composition comprising an effective amount of the subject agent, and one or more pharmaceutically acceptable excipient or salt.

Another aspect of the invention provides an in vitro method of identifying an agent which enhances or positively affects one or more characteristics of tumorigenic cells, the characteristics including: differentiation, apoptosis, sensitivity to chemotherapy/radiotherapy, or senescence, the method comprising: (1) contacting the subject tumorigenic cells, or tumorigenic cells produced by the subject method, with a candidate agent to be assessed for its ability to enhance or positively affect the one or more characteristics of the tumorigenic cells, under conditions appropriate for the agent to enter cells; (2) determining the extent to which the characteristics is enhanced or positively affected in the presence of the candidate agent to be assessed; and, (3) comparing the extent determined with the characteristics of the tumorigenic cells under the same conditions, but in the absence of the candidate agent to be assessed. If the characteristics is substantially enhanced or positively affected in the presence of the candidate agent to be assessed than in its absence, the candidate agent to be assessed is an agent which enhances or positively affects one or more the characteristics of the tumorigenic cells.

Another aspect of the invention provides an in vivo method of identifying an agent which inhibits or negatively affects one or more characteristics of tumor generated by tumorigenic cells in a tumor model, the characteristics including: tumor stem cell frequency, tumor growth, tumor differentiation, invasiveness, metastasis, or angiogenesis, the method comprising: (1) introducing to test animals the subject tumorigenic cells, or tumorigenic cells produced by the subject method, to generate tumors; (2) administering a candidate agent to the test animals to assess its ability to inhibit or negatively affect the one or more characteristics of the tumor; and, (3) determining the extent to which the characteristics is inhibited or negatively affected in the presence of the candidate agent. If the characteristics is substantially inhibited or negatively affected in the presence of the candidate agent to be assessed than in its absence, the candidate agent to be assessed is an agent which inhibits or negatively affects one or more the characteristics of the tumor.

Another aspect of the invention provides an in vivo method of determining the effect of at least two candidate agents which potentially affect one or more characteristics of tumor generated by tumorigenic cells in a tumor model, the characteristics including: tumor stem cell frequency, tumor growth, tumor differentiation invasiveness, metastasis, or angiogenesis, the method comprising: (a) associating each candidate agent with a unique detectable marker, wherein presence of the detectable marker substantially matches the presence of the candidate agent; (b) dividing tumorigenic cells of claim 14 into separate groups according to the number of candidate agents to be tested; (c) contacting one group of tumorigenic cells with one candidate agent; (d) introducing to test animals tumorigenic cells of step (c) to generate tumors; (e) determining the extent to which the one or more characteristics is affected in the presence of the candidate agent; (f) determining the presence of detectable markers; wherein the presence of a candidate agent is determined by the presence of its associated detectable marker, and wherein if the one or more characteristics is substantially affected in the presence of the candidate agent than in its absence, the candidate agent is an agent which affects one or more the characteristics of the tumor. In certain embodiments, each group of tumorigenic cells comprises 100 or less tumorigenic cells. In certain embodiments, the detectable marker is a DNA bar code. In certain embodiments, the detectable marker is a fluorescent marker. In certain embodiments, the agent is an RNAi molecule. In certain embodiments, the agent is an siRNA molecule. In certain embodiments, the agent is a chemical compound.

Another aspect of the invention provides a method of identifying a gene whose expression in a tumorigenic cell is related to/involved in metastasis of such cells in vivo, comprising: (1) introducing a candidate gene into the subject tumorigenic cells, or tumorigenic cells produced by the subject method, thereby producing modified tumorigenic cells; (2) introducing the modified tumorigenic cells to test animals; (3) maintaining the test animals under conditions appropriate for formation of tumors and metastasis to occur; and (4) determining whether metastasis of the modified tumorigenic cells occurs. If metastasis occurs, the candidate gene is a gene whose expression in a tumorigenic cell is related to/involved in metastasis of such cells in vivo.

Another aspect of the invention provides a method of identifying a gene whose expression in a tumorigenic cell is related to/involved in invasion of such cells in vivo, comprising: (1) introducing a candidate gene into the subject tumorigenic cells, or tumorigenic cells produced by the subject method, thereby producing modified tumorigenic cells; (2) introducing the modified tumorigenic cells to test animals; (3) maintaining the test animals under conditions appropriate for formation of tumors and invasion to occur; and (4) determining whether invasion of the modified tumorigenic cells occurs. If invasion occurs, the candidate gene is a gene whose expression in a tumorigenic cell is related to/involved in invasion of such cells in vivo.

Another aspect of the invention provides a method of identifying a gene product which is expressed in tumor cells but not in normal cells of the same type, or a gene product which is not expressed in tumor cells but is expressed in normal cells of the same type, comprising: (1) analyzing the subject tumorigenic cells, or tumorigenic cells produced by the subject method; (2) analyzing normal parental cells of which the tumorigenic cells are a variant for gene products; and, (3) comparing gene products produced by the tumorigenic cells and the normal parental cells, whereby a gene product which is expressed in tumorigenic cells but not in normal parental cells, or a gene product which is not expressed in tumorigenic cells but is expressed in normal parental cells is identified, thereby identifying a gene product which is expressed in tumor cells but not in normal cells of the same type, or a gene product which is not expressed in tumorigenic cells but is expressed in normal cells of the same type.

Another aspect of the invention provides a method of obtaining mammalian primary cells, comprising: (a) culturing primary cells obtained from a mammal in a first tissue culture container with a mixed (+/−) charge surface for a suitable period of time; (b) harvesting at least some of the primary cells; (c) plating the harvested primary cells in a second tissue culture container with a mixed (+/−) charge surface; and (d) culturing the transferred cells in the medium of claim 1, thereby obtaining mammalian primary cells. In certain embodiments, step (b) comprises culturing the cells for at least 1 week. In certain embodiments, step (b) comprises culturing the cells for between 1-4 weeks. In certain embodiments, the cells of step (a) are obtained by providing mammalian tissue containing cells and separating organoids containing the primary cells from at least some cells from other cells in the tissue. In certain embodiments, the cells of step (c) are plated at a density of at least $10^4$ cells/cm$^2$.

Another aspect of the invention provides an in vitro method of identifying an agent which inhibits or negatively affects one or more characteristics of tumorigenic cells, the characteristics including: cell viability, growth, proliferation, invasiveness, ability to metastasize, anchorage-independent growth, or angiogenesis, the method comprising: (a) contacting tumorigenic cells of claim 14 or 27 with a candidate agent to be assessed for its ability to inhibit or negatively affect the one or more characteristics of the tumorigenic cells; (b) determining whether the one or more characteristics is inhibited or negatively affected in cells contacted with the candidate agent to be assessed to a greater extent than would be expected in cells not contacted with the candidate agent. If the one or more characteristics is inhibited or negatively affected to a greater extent in cells contacted with the candidate agent than would be expected in cells not contacted with the candidate agent, the candidate agent is identified as an agent which inhibits or negatively affects one or more characteristics of the tumorigenic cells. The afore-mentioned method can be practiced using other tumorigenic cells described herein or tumorigenic cells isolated or generated using a method described herein.

Applicants note that subsequent to filing of the provisional application to which priority is claimed herein, their scientific article describing certain embodiments of the instant invention has been published (Ince T A, Richardson A L, Bell G W, Saitoh M, Godar S, Kamoub A E, Iglehart J D, Weinberg R A. Transformation of different human breast epithelial cell types leads to distinct tumor phenotypes. Cancer Cell. 2007 August; 12(2):160-70). Since the publication of this initial paper, at least two additional papers that use embodiments of the inventive media and BPLER cells have been published, which lend additional indication of the utility of the inventive media and model system(s). These two references are: (I) Godar S, Ince T A, Bell G W, Feldser D, Donaher J L, Bergh J, Liu A, Miu K, Watnick R S, Reinhardt F, McAllister S S, Jacks T, Weinberg R A. Growth-inhibitory and tumor-suppressive functions of p53 depend on its repression of CD44 expression. Cell. 2008 Jul. 11; 134(1):62-73; (II) McAllister S S, Gifford A M, Greiner A L, Kelleher S P, Saelzler M P, Ince T A, Reinhardt F, Harris L N, Hylander B L, Repasky E A, Weinberg R A. Systemic endocrine instigation of indolent tumor growth requires osteopontin. Cell. 2008 Jun. 13; 133(6):994-1005.

BRIEF DESCRIPTION OF THE DRAWINGS

FIG. 7B shows that BPLER tumors recapitulate glandular structures similar to Invasive Ductal Carcinoma of the breast from a human tumor sample, which is shown in FIG. 7A. In contrast, FIG. 7C shows that HMLER tumors were either undifferentiated due to complete lack of ductal structures or clear epithelial morphology; while FIG. 7D shows HMLER tumors that are focally Squamous Carcinomas due to presence of extracellular keratinization. This indicates that the subject tumor model is a close approximation of clinical tumor.

FIG. 16A: Comparison of population doublings of mammary epithelial cells simultaneously cultured from organoids isolated from the same donor in WIT (●) medium on Primaria plates or in MEGM (■) medium on regular culture plates. Cells that were cultured in MEGM growth arrested after 5 to 6 population doublings; in contrast cells that were cultured in WIT proliferated past 40 population doublings. FIG. 16B: Comparison of p53 and p16 protein expression levels in mammary epithelial cells cultured in WIT medium on Primaria plates vs. MEGM medium on regular plates on day 21, immediately prior to growth arrest of cells in MEGM medium, using Western blot; β-actin was probed simultaneous as control. FIG. 16C: Comparison of p16INK4A gene promoter methylation analysis by using DNA methylation-specific PCR primers: (U) unmethylated, (M) methylated, (W) wild-type. p16INK4A promoter DNA-specific primers produce a single PCR product of different sizes with a complete chemical modification reaction; U primers amplify only unmethylated DNA (154 bp), M primers amplify only methylated DNA (145 bp) and W primers amplify only DNA which is not chemically modified, or "wild type" (142 bp).

FIG. 17A: The comparison of luminal- and myoepithelial-specific expression signatures with genes that are differentially expressed ≥2-fold between HMEC and BPEC populations. Each bar represents the number of luminal- or myoepithelial specific transcripts expressed at a higher level (≥2-fold) in one cell type relative to the other; open bar (BPEC), filled bar (HMEC), luminal-specific (columns at left) myoepithelial-specific genes (columns at right). The mRNA from three independently derived BPECs and HMECs was analyzed, and compared to the luminal- or myoepithelial-cell-specific transcripts identified in the supplemental online table in "additional File 9" from Grigoriadis et. al., 2006. A full list of genes that are differentially expressed between BPECs and HMECs, and the list of genes that correspond to each specific bar in this figure is available in FIGS. 31 and 32A-32C. FIG. 17B: Comparison of luminal-specific claudin-4 and myoepithelial-specific CD-10 protein expression in HME and BPE cells, using Western blot; β-actin was probed simultaneous as control. FIG. 17C: Immunoperoxidase staining of formalin-fixed paraffin embedded normal human breast tissue with luminal-specific claudin-4 (left panel) and myoepithelial-specific CD-10 antibodies (middle panel). Double immunostaining (right panel) was performed by sequential Claudin-4-HRP staining (brown) followed by CD-10-alkaline phosphatase (red) staining. FIG. 17D shows a schematic representation of a mechanism for the derivation of the two normal in vitro breast epithelial cell populations via selection of pre-existing cell types, while FIG. 17E shows a schematic representation of a mechanism for the derivation of the two normal in vitro breast epithelial cell populations via in vitro differentiation form a single in vivo cell type.

FIG. 18A: Schematic steps for the creation of two breast cancer cell types (BPLER and HMLER) with defined genetic elements. FIG. 18B: Comparison of SV40-Large T Ag (LT) and H-Ras (RAS) protein expression levels in BPLER and HMLER cells, in vitro culture (western blot, β-actin as loading control). The difference between the two cell populations was less than two-fold, based on serial dilutions (see FIG. 25A). FIG. 18C: Comparison of ectopic hTERT mRNA expression levels in BPLER and HMLER cells with RT-PCR shows similar expression levels in both cells. Primers for GADPH was used as internal control, first lane was a control RT-PCR reaction with mRNA from HMECs without ectopic hTERT. FIG. 18D: SV40-Large T Ag (LT), H-Ras (RAS) and hTERT protein expression levels in BPLER and HMLER cells, in vitro culture (immuno-fluorescence). SV40-LT and hTERT were detected in the nucleus and Ras in the cytoplasm (Red: signal; blue: nuclear counter stain, bar=15 micrometer, see FIG. 25B for corresponding DAPI nuclear stains).

FIGS. 20A-20E illustrate the differences in primary tumor growth pattern and metastasis of BPLER and HMLER cells. Fluorescence dissecting microscopic images of nodules composed of tumor cells expressing green fluorescent protein (GFP). FIG. 20A: BPLER cells; multifocal growth of 5 tumor nodules ranging 0.1 to 0.6 cm in diameter, in mammary fat pad of NOD/SCID mice, 4 weeks post-injection (1×, ruler at the top edge of the image has 1 mm increments). FIG. 20B: HMLER cells; single 0.6 cm diameter primary tumor nodule of in mammary fat pad of NOD/SCID mice, 4 weeks post-injection (1×, bar=0.5 centimeter). FIG. 20C: BPLER metastasis to lungs from a mammary fat pad primary tumor; single 0.05 cm diameter green metastatic tumor nodule (white arrow), 10 weeks post-injection. FIG. 20D: Detection of metastatic BPLER cells (from panel C) with SV40-LT immunohistochemical staining of formalin-fixed, paraffin embedded lung sections (bar=250 micrometer). FIG. 20E: Frequency of BPLER and HMLER lung metastasis from orthotopic (mammary fat pad) and subcutaneous injection sites 10 weeks post-injection. BPLER1 and 2 were derived from two different individuals. (*) There was no statistically significant difference in tumor burden between these groups (BPLER-2: 0.74 gm±0.14; HMLER: 0.75 gm±0.06).

FIG. 21A: Hierarchical clustering: Each column represents a cell line sample and each row demonstrates the results of a different gene. Clustering orders the samples according to greatest similarity of gene expression, shown by the dendrogram at the top, and orders genes by similarity of expression level among the sample set, shown by the dendrogram along the side. Mean levels of expression are depicted in black, over-expression in red, and under-expression in green for each probeset that was present and exhibited differential expression. Expression values were compared to the mean expression value across all replicates and log 2-transformed. FIG. 21B: Transformation specific gene expression differences—tumorigenic cell vs. precursor cells: To the left is a heatmap in which each column represents a cell line sample and each row demonstrates the results of a different gene. Mean levels of expression are depicted in black, over-expression in red, and under-expression in green. To the right is a Venn diagram demonstrating the overlap of gene expression differences between in vitro cultured cell lines (BPLER vs. BPE) vs. (HMLER vs. HME). The full list of corresponding genes is available in FIG. 34. In vitro transformation induced changes that are cell-type-dependent; a) (BPLER/BPE, tumorigenic cells vs. hTERT-expressing cell origin): The genes with mRNA expression levels that change ≥2-fold upon transformation in BPE vs. BPLER but not in HME vs. HMLER (n=770). b) (HMLER/HME, tumorigenic cells vs. hTERT-expressing cell origin): The genes with mRNA expression levels that change ≥2-fold upon transformation in HME vs. HMLER but not in BPE vs. BPLER (n=2,456). In vitro transformation induced changes that are cell-type-independent; c) The genes with concordant ≥2-fold mRNA expression level change with transformation in both BPE and HME cell types (n=566). The number of probe sets that were statistically different in each group were (a) 43, (b) 7 and (c) 1952; p<0.05. FIG. 21C: Tumor-specific gene expression differences—tumorigenic vs. tumorigenic cells: To the left is a heatmap in which each column represents a sample from in vitro cultured cell line and each row demonstrates the results of a different gene. Mean levels of expression are depicted in black, over-expression in red, and under-expression in green. To the right is a Venn diagram demonstrating the overlap of gene expression differences between in vitro cultured cell lines (BPLER vs. HMLER) vs. (BPE vs. HME). The full list of corresponding genes is available in FIG. 34. a) Shaded bar: The genes with concordant greater than or equal to 2-fold difference in their mRNA expression level between tumorigenic vs. tumorigenic cells (BPLER/HMLER) and between the untransformed hTERT-immortalized cell origin (BPE/HME) (n=1, 265). Among this group of genes 287 probe sets were different statistically (p<0.05). b) Open bar: The genes with greater than or equal to 2-fold difference in their mRNA expression level between tumorigenic vs. tumorigenic cells (BPLER/HMLER) but not between the untransformed hTERT-expressing cell origin (BPE/HME) (n=1,948 genes). Among this group of genes 308 probe sets were different statistically (p<0.05).

FIGS. 22A-22C summarize number of BPLER cells required for tumor initiation and metastasis FIG. 22A: Three independent BPLER cell lines (1, 2 and 3) derived from normal mammary epithelial cells isolated from three different donors were injected subcutaneously into nude mice at the indicated numbers, ranging from 102 to 106 cells per injection site. Three injections were made in each mouse and tumor formation was assessed up to 10 weeks after injections. Injection of 102 cells from two independent single-cell clones of BPLER was tumorigenic in 8/12 and 11/12 mice 9 (data not shown). FIG. 22B: HMLER cells that were simultaneously grown in MEGM and WIT medium for three weeks were injected subcutaneously into nude mice at the indicated numbers, ranging from 102 to 106 cells per injection site. Three injections were made in each mouse (n=4) and tumor formation was assessed up to 24 weeks after injections. FIG. 22C: BPLER cells that were injected subcutaneously into nude mice at the indicated numbers, ranging from 102 to 105 cells, per injection site. Three injections were made in each mouse (n=4) and tumor formation. Lung metastasis was assessed at 10 weeks in mice injected with 103-105 cells and at 18 weeks in mice injected with 102 cells.

FIG. 23A. Transfer of primary BPE cells that had been grown in WIT medium and on tissue culture plates with a modified attachment surface (Primaria) during the initial three weeks of in vitro culture (left) into MEGM medium and on regular tissue culture plastic resulted in rapid senescence of the entire cell population within 5-7 days (right, bar=10 micrometer). FIG. 23B. Transfer of primary BPE cells that had been grown in WIT medium and on tissue culture plates with a modified attachment surface (Primaria) during the initial three weeks of in vitro culture (left) onto tissue culture plates with a regular plastic attachment surface in WIT medium resulted in rapid death of the entire cell population within 48 h (right, bar=10 micrometer). FIG. 23C. Transfer of primary HME cells that had been grown in MEGM medium and on regular plastic during the initial three weeks of in vitro culture (left) into WIT medium and on Primaria plates resulted in rapid death of the entire cell population within 24-48 h (right, bar=250 micrometer).

FIG. 25A: Comparison of SV40-Large T Ag (LT) and H-Ras (RAS) protein expression levels in BPLER and HMLER cells, in vitro culture (western blot, β-actin as loading control). The difference between the two cell populations was less than two-fold, based on multiple dilutions. FIG. 25B: SV40-Large T Ag (SV40-LT), H-Ras (RAS) and hTERT protein expression levels in BPLER and HMLER cells, in vitro culture (immuno-fluorescence). SV40-LT and hTERT were detected in the nucleus and Ras in the cytoplasm (Red: specific signal; blue: nuclear DAPI stain).

FIGS. 26A and 26B show that t BPLER tumors focally formed well-differentiated epithelial ductal structures with a central lumen surrounded by a desmoplastic stroma typical of ductal adenocarcinoma of the breast.

FIGS. 26B and 26D show that HMLER tumors grew as a solid mass of cells with little desmoplastic reaction and formed keratin pearls—a typical feature of squamous differentiation. No ductal or glandular structures, which are characteristically present in breast adenocarcinomas, were apparent. FIGS. 26E and 26F show Human Breast Adenocarcinoma. An example of a typical human breast adenocarcinoma with glandular/ductal structures and desmoplastic reaction. All histological sections were prepared from tumor tissue explanted 4 to 6 weeks after implantation of tumorigenic cells from tissue culture into the mammary fat pad of NOD/SCID mice.

FIGS. 27A-27H are photographs showing the phenotype of BPLER xenografts. The BPLER xenograft tumors contained poorly differentiated areas (FIG. 27A) with highly infiltrative cells that invaded adjacent skeletal muscle (FIG. 27B). Immunohistochemical staining of BPLER tumors highlights well-differentiated epithelial ductal structures that express cytokeratin 8/18 (FIG. 27C), and a strongly SMA-positive desmoplastic response (FIG. 27D). A double immunostain for Large T-Ag (red) and SMA (brown) highlights all the BPLER tumor cell nuclei (red) and mouse myofibroblasts (brown). The mutually exclusive staining pattern of the two markers confirms that SMA is expressed by stromal non-neoplastic cells only, and not by BPLER cells (FIG. 27E). Immunohistochemical staining for estrogen receptor (FIG. 27F), progesterone receptor (FIG. 27G) and Her2 (FIG. 27H) showed focal weak staining in less than 1-5% of the tumor cells in occasional BPLER tumors. This low level of staining would be categorized as (ER/PR/HER2) triple-negative according to current diagnostic criteria used for histopathological and clinical classification of human breast tumors. HMLER tumors were completely negative for these three markers.

FIG. 30A: Transformation specific gene expression differences—tumorigenic cells vs. precursor cells: To the left is a heatmap in which each column represents a cell line sample and each row demonstrates the results of a different gene. Mean levels of expression are depicted in black, over-expression in red, and under-expression in green. To the right is a Venn diagram demonstrating the overlap of gene expression differences between in vitro cultured cell lines (BPLER vs. BPEC) vs. (HMLER vs. HMEC). In vitro transformation induced changes that are cell-type-dependent; a) (BPLER/BPEC, tumorigenic cells vs. normal cell origin): The genes with mRNA expression levels that change ≥2-fold upon transformation in BPEC vs.

BPLER but not in HME vs. HMLER (n=969). b) (HMLER/ HMEC, tumorigenic cells vs. normal cell origin): The genes with mRNA expression levels that change ≥2-fold upon transformation in HME vs. HMLER but not in BPE vs. BPLER (n=4184). In vitro transformation induced changes that are cell-type-independent; c) The genes with concordant ≥2-fold mRNA expression level change with transformation in both BPECs and HMECs (n=987). FIG. 30B: Tumor-specific gene expression differences—tumorigenic vs. tumorigenic cells: To the left is a heatmap in which each column represents a sample from in vitro cultured cell line and each row demonstrates the results of a different gene. Mean levels of expression are depicted in black, over-expression in red, and under-expression in green. To the right is a Venn diagram demonstrating the overlap of gene expression differences between in vitro cultured cell lines (BPLER vs. HMLER) vs. (BPEC vs. HMEC). a) Shaded bar: Shaded bar: The genes with concordant greater than or equal to 2-fold difference in their mRNA expression level between tumorigenic vs. tumorigenic cells (BPLER/HMLER) and between the normal cell origin (BPEC/HMEC) (n=813). b) Open bar: The genes with greater than or equal to 2-fold difference in their mRNA expression level between tumorigenic vs. tumorigenic cells (BPLER/HMLER) but not between the normal cell origin (BPE/HME) (n=3487 genes).

FIG. 31 is a table listing genes that are differentially expressed in BPECs and HMECs.

FIGS. 32A-32C are tables compare the gene expression level of BPEC-hTERT and HMEC-hTERT cells. In FIG. 32A, the table shows the relative expression of Mammary Luminal-Cell-Specific genes in BPEC-hTERT and HMEC-hTERT cells. In FIG. 32B, the table shows the relative expression of Mammary Myoepithelial-Cell-Specific genes in BPEC-hTERT vs. HMEC-hTERT. In FIG. 32C, the table shows the genes that are differentially expressed BPEC-hTERT vs. HMEC-hTERT (≥2-Fold).

FIG. 33 is a table listing genes that are differentially expressed in BPEC-hTERT and HMEC-hTERT cells.

FIG. 34 summarizes a full list of genes showing gene expression differences between in vitro cultured cell lines (BPLER vs. BPE) vs. (HMLER vs. HME).

DETAILED DESCRIPTION OF THE INVENTION

I. Formulation of Culture Media

Figure 1:
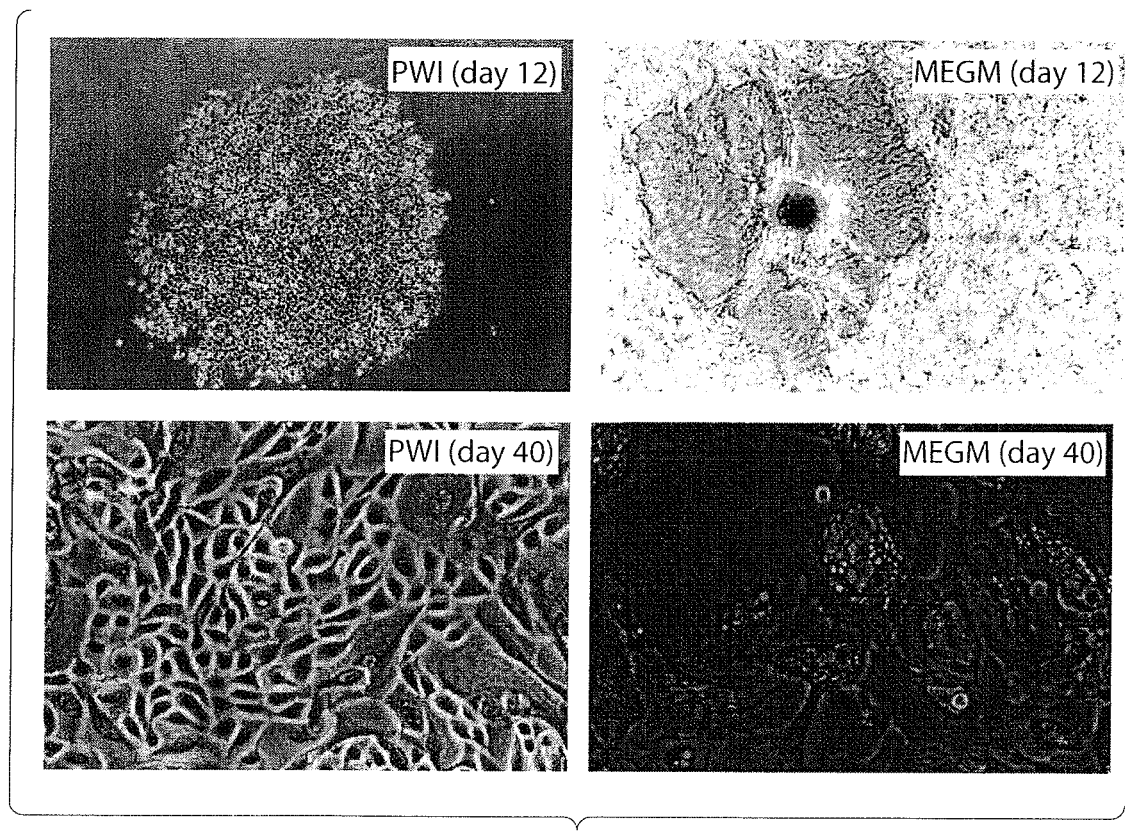
FIG. 1 illustrates that on day 12, while primary organoid cultures result in homogenous uniform colonies in the subject medium (e.g. PWI), there are multiple cell types forming a bi-phasic appearance in MEGM. Moreover, on day 40, cells in PWI are small and proliferating. But in MEGM medium, the cells have the typical flat, enlarged, and vacuolated appearance of senescent cells.

The subject invention relates to a medium that supports long-term, undifferentiated, growth and proliferation of primary cells (including primary mammalian epithelial cells) in vitro. In a specific embodiment, such medium is essentially free of serum, tissue/organ extracts, FGF, heparan, etc. In certain embodiments, FGF final concentration in the subject medium is less than about 0.0001 mg/L, about 0.001 mg/L, or about 0.005 mg/L. The phrases "cell culture medium," "culture medium" (plural "media" in each case) and "medium formulation" refer to a nutritive solution for cultivating cells and may be used interchangeably.

In one embodiment, such primary mammalian epithelial cells can grow for at least 4 weeks (or 15 population doublings), up to several months, in such a culture medium without losing differentiation potential. In a specific embodiment, the subject medium supports long-term undifferentiated growth and proliferation of primary breast epithelial cells transfected with telomerase, for at least about 15 weeks or at least about 35 population doubling (PD) in vitro, without any additional detectable genetic alterations, or losing differentiation potential.

In another embodiment, the subject medium supports undifferentiated growth and proliferation of primary cells for at least 5, 6, 7, 8, 9, 10, 11, 12, 13, 14, 15 weeks or more in culture.

The cell culture media of the present invention are aqueous-based (but can be reconstituted from dry powder and/or frozen components), comprising a number of ingredients in a solution of deionized, distilled water.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

In one embodiment, the tissue culture medium of the invention comprises: (1) one or more antioxidants; (2) one or more nucleotide salvage pathway synthesis precursors; (3) one or more lipid synthesis precursors; (4) one or more protein synthesis precursors; (5) one or more carbohydrate synthesis and energy metabolism precursors; (6) one or more buffers (not essential); (7) one or more cations (monovalent and/or divalent), ions, trace metals and enzyme cofactors; (8) one or more carrier proteins (such as bovine serum albumin); (9) one or more detergents (such as tween 80); (10) one or more agents that induce increased intracellular 3'-5' cyclic adenosine monophosphate (cAMP) levels; and/or (11) one or more hormones and growth factors, wherein the medium supports undifferentiated growth and/ or proliferation of primary epithelial progenitor cells for at least about 4 weeks or at least about 15 population doubling (PD) in vitro, without a significant decrease in differentiation potential. An example of such medium is illustrated below in Table II.

In other embodiments, one or more of the above-listed categories of components may be omitted, provided that the resulting medium supports undifferentiated growth and/or proliferation of primary epithelial progenitor cells for at least about 4 weeks or at least about 15 population doubling (PD) in vitro, without a significant decrease in differentiation potential.

Thus, the medium of the invention comprises one or more antioxidants; nucleotide synthesis and salvage pathway precursors; lipid synthesis precursors; agonists of intracellular cAMP level; and, hormones and growth factors. The medium may additionally comprise other components such as amino acid supplements, vitamins necessary for cell growth/proliferation, trace minerals, inorganic salts, energy sources (e.g. for glycolysis), and other components such as pH indicators, etc. In other words, ingredients of the present invention may include amino acids, vitamins, inorganic salts, adenine, D-glucose, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, triiodothyronine (T3), thymidine and transferrin. Each of these ingredients may be obtained commercially, for example from Sigma (Saint Louis, Mo.).

While not wishing to be bound by any particular theory, antioxidants generally help to quench free-radicals, which are thought to be detrimental to cell growth in general. The antioxidants of the invention may include, without limitation, one or more of the following: beta-carotene, vitamin E, vitamin C (ascorbic acid), vitamin K3, glutathione (reduced), niacin (or niacinamide), or DTT (dithiothreitol). The antioxidants may optionally be supplemented with trace metals, including Zn, Se, Cr, Cu, Mg, or Mn.

Again, without wishing to be bound by theory, trace minerals may be necessary for the constitution of certain enzymes. For example glutathione peroxidase uses selenium and glutathione superoxide uses copper as a cofactor. It was postulated that in diseases where there is a large free radical load, there may be deficiencies of these trace elements in a particular microenvironment. The presence of trace minerals may be helpful to enzymatic antioxidants (which may have been devoid of the cofactors). Thus the presence of the trace minerals may allow effective use of the enzymatic antioxidants by the host. Since it is known that zinc can up-regulate superoxide dismutase and selenium can up-regulate glutathione peroxidase, increasing trace minerals in a given microenvironment would produce a net increase in enzymatic antioxidants in the microenvironment. A net increase in the enzymatic antioxidants and increasing amphipathic antioxidant would further reduce oxidative damage to tissue or cells, as well as other deleterious effects due to free radicals.

Thus many inorganic salt ingredients, cations, ions, trace metals, and vitamins, which may be beneficial in the media of the present invention include a calcium salt (e.g., $CaCl_2$), $CuSO_4$, $FeSO_4$, KCl, a magnesium salt (e.g., $MgCl_2$), Sodium acetate, NaCl, $NaHCO_3$, $Na_2HPO_4$, $Na_2SO_4$ and ions of the trace elements selenium, and zinc. Optionally, additional inorganic salt ingredients may include a manganese salt (e.g., $MnCl_2$), silicon, molybdenum, vanadium, nickel, and tin.

These trace elements may be provided in a variety of forms, preferably in the form of salts such as $Na_2SeO_3$, and ZnSO (or $Na_2SiO_3$, $(NH_4)_6Mo_7O_{24}$, $NH_4VO_3$, $NiSO_4$, SnCl for optional salts). These inorganic salts and trace elements may be obtained commercially, for example from Sigma (Saint Louis, Mo.).

Vitamin ingredients which may be included in the media of the present invention include biotin, choline chloride, D-$Ca^{++}$-pantothenate, folic acid, i-inositol, niacinamide, pyridoxine, riboflavin, thiamine and vitamins A and B12. These vitamins may be obtained commercially, for example from Sigma (Saint Louis, Mo.).

Protein synthesis precursors include amino acid ingredients. In one embodiment, the amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Alternatively, in some other embodiments, only essential amino acids are included in the media of the present invention. Certain cells, such as human cells must have adequate amounts of 9 amino acids to survive. These so called "essential" amino acids cannot be synthesized from other precursors. However, cysteine can partially meet the need for methionine (they both contain sulfur), and tyrosine can partially substitute for phenylalanine. Such essential amino acids include: Histidine, Isoleucine, Leucine, Lysine, Methionine (and/or cysteine), Phenylalanine (and/or tyrosine), Threonine, Tryptophan, and Valine. In certain embodiments, only Histidine, Isoleucine, Leucine, Lysine, Threonine, Tryptophan, and Valine are included.

Some or all of the above ingredients, when admixed together in solution, can form a "basal medium." To this basal medium, other components, such as at least one nucleotide synthesis and/or salvage pathway precursors (e.g. hypoxanthine), epidermal growth factor (EGF), at least one agent increasing intracellular cyclic adenosine monophosphate (cAMP) levels, and at least one antioxidants, are added to formulate the complete culture media of the present invention. These latter added components, such as EGF and the cAMP-increasing agent(s) may be added to freshly formulated basal medium, or they may be admixed as in a stock solution stored frozen, preferably at about −20° C. to about −70° C., until being added to basal medium to formulate the complete medium of the present invention. This complete medium does not depend on BPE or other organ/gland extracts in animal cell culture media to achieved the desired cell growth/proliferation. The admixture may also be prepared as a 1-1000× formulation, most preferably as a 1×, 100×, 500× or 1000× formulation, which is then diluted appropriately into culture medium to provide a 1× final formulation in the complete media of the present invention.

The medium of the invention may also include one or more hormones, such as: progesterone, testosterone, hydrocortisone, and estrogen, and one or more growth factors such as: insulin and EGF (epidermal growth factor).

For example, the medium of the invention may comprise EGF, which may be natural or recombinant, and may be human or rodent. EGF available commercially (e.g., from GIBCO/LTI, Gaithersburg, Md.), isolated from natural sources or produced by recombinant DNA techniques (U.S. Pat. No. 4,743,679) according to methodologies that are routine in the art. To formulate the medium of the present invention, EGF should be added to the basal medium shown in Table II at a concentration of about 0.00001-10 mg/L, preferably about 0.0005-1 mg/L.

The medium of the invention may also include nucleotide analogs or precursors, such as hypoxanthine, xanthine, adenine, guanine, and thymidine that can be used in the salvage pathway synthesis of nucleotides.

The medium of the invention may also include lipid synthesis precursors, such as: cholesterol, linoleic acid, lipoic acid, or O-phosphoryl ethanolamine.

The medium of the invention also includes one or more cAMP agonists or agents that increase intracellular cAMP levels. A variety of such agents may be used in formulating the media of the present invention. Included are agents which induce a direct increase in intracellular cAMP levels (e.g., dibutyryl cAMP), agents which cause an increase in intracellular cAMP levels by an interaction with a cellular G-protein (e.g., cholera toxin and forskolin), agents which cause an increase in intracellular cAMP levels by acting as agonists of ß-adrenergic receptors (e.g., isoproterenol) and agents which cause an increase in intracellular cAMP levels by inhibiting the activities of cAMP phosphodiesterases (e.g., isobutylmethylxanthine (IBMX) and theophylline). Most preferable for use in formulating the media of the present invention is cholera toxin. These cAMP-increasing agents are available commercially, e.g. from Sigma (St.

Louis, Mo.), and are used at concentrations approximating those described in Green (Proc. Natl. Acad. Sci. USA 15:801-811 (1978)). For example, cholera toxin is added to the basal medium described above at a concentration of about 0-0.01 mg/L, preferably about 0-0.001 mg/L, and most preferably about 0-0.0001 mg/L. Dibutyryl cAMP, IBM, isoproterenol etc. can be added to achieve the same level of cAMP as cholera toxin.

It is also desirable to increase intracellular cAMP level by using agents such as cholera toxin, forskolin, G protein-coupled receptor agonists, PKC agonists. In addition, cells may have increased cAMP in response to the beta-adrenergic agonist isoproterenol (Iso), prostaglandin E(2) (PGE(2)), certain prostanoid receptor-selective agonists (beraprost, butaprost), and an adenosine receptor agonist. In addition, overexpression of AC type 6 or agents inhibiting cyclic nucleotide phosphodiesterases increased cellular cAMP levels.

The subject medium may also comprise one or more carbohydrate synthesis and energy metabolism precursors, such as D-glucose, sodium pyruvate, etc.

The subject medium may also comprise one or more carrier proteins, such as bovine serum albumin (BSA). Carrier protein may be a protein which transports specific substances through the cell membrane in which it is embedded and into the cell. Different carrier proteins may be required to transport different substances, as each one is designed to recognize only one substance, or group of similar substances. Certain carrier proteins may bind to one or more media components (such as growth factors, etc.) and confer them extra stability in the media, or to facilitate certain biological processes (e.g. acyl-carrier protein, sterol carrier protein, hormone carrier protein, etc.).

The subject medium may also comprise one or more carrier proteins, such as nonionic surfactants Tween 60 or Tween 80. Again, without wishing to be bound by any particular theory, such detergent components may help to wet, solubilize, emulsify, or disperse certain media components. For example, they may prevent aggregation of proteins such as BSA, increase solubility of certain components, and may even enhance the function of certain enzymes.

Although not considered essential, the subject medium may additionally comprise one or more buffer systems, such as HEPES and sodium bicarbonate buffer systems, such that a balanced pH is maintained in long-term culture. Frequent, constant or continuous change of culture medium may also help to restore medium pH in fast growing cells.

To illustrate, Table II below shows the composition of a medium formulation of the instant invention that supports long-term undifferentiated growth and proliferation of primary breast epithelial cells for at least about 4 weeks or at least about 15 population doubling (PD) in vitro, without any detectable genetic alterations, or losing differentiation potential. Primary mammalian epithelial cells can grow in such a medium for at least 4 weeks (or 15 population doublings), and up to several months, without any detectable genetic alterations, or losing differentiation potential. Wherever the term "Table II" is used herein, it should be understood to disclose embodiments in which the media has a composition listed in Table IIA and to disclose embodiments in which the media has a composition listed in Table IIB. It will be appreciated that the formulas listed in Tables IIA and IIB are generally similar but have some differences in the concentrations or concentration ranges of certain components.

In contrast, on average, cells isolated from similar tissues, when growing in other media, including the only commercially available medium MEGM® from Clonetics® (Cambrex Corp., East Rutherford, N.J.) at best support 4 weeks or less than 15 population doublings in vitro. Although a minor population of cell clones eventually escape (about $1 \times 10^{-5}$), such clones appear to have lost p16 activity, and may have additional genetic alterations that enable their escape from senescence.

In one embodiment, the subject medium does not support the growth or proliferation of fibroblasts and stromal cells. In fact, the subject medium may select against the growth or proliferation of these cells, possibly because of the absence of serum or tissue extracts in the subject medium formulation. Thus, the percentage of fibroblasts and other stromal cells decreases sharply after a few passages and population doublings, to the extent that no appreciable amount of fibroblast and stromal cell differentiation markers (e.g. vimentin) can be detected.

For example, the epithelial differentiation markers may include keratin 8, keratin 10, keratin 14, keratin 18, keratin 19, E-cadherin, p63, SMA (smooth muscle actin), and (3-catenin.

Ex vivo tissue culture exposes cells to oxidative damage, metabolic stress and DNA damage that induce p53 and p16 genes, which in turn induce cell-cycle arrest, senescence and/or apoptosis limiting the life-span cultured cells. In another embodiment, the media of the invention supports long-term stress-free growth and proliferation of primary cells. One indication of such stress-free growth in the subject medium is indicated by the low/undetectable expression level of CDK inhibitor p16 and tumor suppressor p53. These two proteins are typically induced to express at a high level in stressed cells, but not healthy growing cells in tissue culture media. In this embodiment the cells can be grown at 37° C., 5% $CO_2$ and varying $O_2$ concentrations, 1%, 3% or ambient air.

In another embodiment, the media of the invention is substantially free of at least one member selected from the group consisting of: serum, heparin, fibroblast growth factor (FGF), and bovine pituitary extract (BPE). In certain embodiments, none of the above listed components are present in the subject medium.

However, to the extent that such components do not substantially affect the performance of the medium in terms of supporting undifferentiated primary cell growth and proliferation, the subject medium may in certain embodiments include and tolerate the presence of one or more of such components.

Table I below is an example of a medium formula that can be used for short-term transport and/or storage of isolated primary cells, and may support undifferentiated growth of such cells to a lesser extent. The medium contains fewer components, which is easier and less expensive to make. Such medium can also be made by mixing about 50% Medium 199 (M199) and about 50% F12 (Ham) medium, and supplementing with glutamine, EGF, transferrin, insulin, 17B-estrodiol, o-phosphorylethanolamine, selenious acid, linoleic acid, BSA, hydrocortisone, cholera toxin, and HEPES, to approximately their corresponding concentrations listed in Table I. In some embodiments, the medium further comprises triiodothyronine. In some embodiments, the cholera toxin concentration range of the media of Table I is 0-0.0001 mg/L. In some embodiments, the insulin concentration range of the media of Table I is 10-15 mg/L.

The invention provides embodiments of the media of Table I and II in which any one or more of the components having a concentration range with a lower limit of 0 are absent and embodiments in which such component is present. For example, the invention provides embodiments of the media of Table I in which cholera toxin is absent and other embodiments in which cholera toxin is present.

It should be understood that the medium of the invention as listed in Tables I and II are merely for illustrative purposes only. Although the medium itself is sufficient for certain intended purposes, especially culturing primary mammary epithelial cells, not all components listed in these Tables may be necessary or even optimum for their intended purposes. A skilled artisan, partly depending on the need for the specific primary cells in question, could readily determine if any listed component is necessary and/or optimum by, for example, eliminating one component or changing the concentration of one component at a time and comparing the growth/proliferation of specific type of cultured cells in such a modified medium with the original medium. One or more components may also be substituted by other chemicals of similar properties when necessary. Such modified medium without one or more non-essential/unnecessary components are within the scope of the invention. Similarly, a skilled artisan could also determine the optimal level of any given component for a particular cell type, by, for example, testing a range of concentrations (e.g., 10%, 25%, 50%, 75%, 100%, 2-, 5-, 10-, 20-, 50-, 100-, 200-, 500-, 1000-fold higher, or 10%, 25%, 50%, 75%, 100%, 2-, 5-, 10-, 20-, 50-, 100-, 200-, 500-, 1000-fold lower) for each listed component based on or starting from the listed concentration of that particular component. Some components have a listed range of concentrations. The proper or optimal concentration for any particular cell types can also be determined similarly starting from the listed concentration. In doing such tests, initial broad-range concentration tests may be narrowed down later based on the outcomes of the initial experiments. For example, for an initial test, the concentration of one component of interest may be changed to $10^{-3}$, $10^{-2}$, $10^{-1}$, 10-fold, 100-fold, and 1000-fold of the concentration listed in Table I. If the $10^{-2}$ test still supports the desired growth, while $10^{-3}$ fails to, then the 10-fold concentration difference between $10^{-2}$ and $10^{-3}$ may be further explored in the second round of test to pin-point the best ranges. Thus, media so optimized for specific cell types are also within the scope of the instant invention.

As will be readily apparent to one of ordinary skill in the art, the concentration of a given ingredient can be increased or decreased beyond the range disclosed and the effect of the increased or decreased concentration can be determined using only routine experimentation. The optimization of the present media formulations for any specific cell type can be carried out using approaches described by Ham (Ham, *Methods for Preparation of Media, Supplements and Substrata for Serum-Free Animal Culture*, Alan R. Liss, Inc., New York, pp. 3-21, 1984) and Waymouth (Waymouth, C., *Methods for Preparation of Media, Supplements and Substrata for Serum-Free Animal Culture*, Alan R. Liss, Inc., New York, pp. 23-68, 1984). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

It will be understood that certain vitamins and hormones listed herein can exist in different forms, as known in the art (e.g., different naturally occurring or non-naturally occurring forms), and can be used as substitutes for one another. It will also be appreciated that where the instant application discloses a vitamin or hormone, the invention should be understood to encompass embodiments in which any form of such vitamin or hormone having similar biological activity (or compound(s) that can be modified or metabolized in cell culture medium or intracellularly to provide a biologically active form) is used in the inventive media and/or method(s).

It will be appreciated that compounds such as estrogen, progesterone, thyroid hormone, hydrocortisone, insulin, etc., can be substituted in whole or in part by other compounds (naturally occurring or non-naturally occurring, isolated from natural sources or at least in part chemically synthesized) that are agonists of the estrogen receptor, progesterone receptor, thyroid hormone receptor, glucocorticoid receptor, insulin receptor, respectively. A number of such compounds are known in the art.

The medium ingredients can be dissolved in a liquid carrier or maintained in dry form. If dissolved in a liquid carrier at the preferred concentrations shown above (i.e., a "1× formulation"), the pH of the medium should be adjusted to about 7.0-7.6, preferably about 7.1-7.5, and most preferably about 7.2-7.4. The osmolarity of the medium should also be adjusted to about 275-350 mOsm, preferably about 285-325 mOsm, and most preferably about 280-310 mOsm. The type of liquid carrier and the method used to dissolve the ingredients into solution vary and can be determined by one of ordinary skill in the art with no more than routine experimentation. Typically, the medium ingredients can be added in any order.

A cell culture medium is composed of a number of ingredients and these ingredients vary from one culture medium to another. A "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic aced. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See Methods For Preparation of Media, Supplements and Substrate For Serum-Free Animal Cell Culture Allen R. Liss, N.Y. (1984), which is incorporated by reference herein in its entirety. The osmolarity and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare 1× formulation, above). A "10× formulation" may contain a number of additional ingredients at a concentration about 10 times that found in the 1× culture medium. As will be readily apparent, "25× formulation," "50× formulation," "100× formulation," "500× formulation," and "1000× formulation" designate solutions that contain ingredients at about 25-, 50-, 100-, 500-, or 1000-fold concentrations, respectively, as compared to a 1× cell culture medium. Again, the osmolarity and pH of the media formulation and concentrated solution may vary.

Preferably, the solutions comprising ingredients are more concentrated than the concentration of the same ingredients in a 1× media formulation. The ingredients can be 10-fold more concentrated (10× formulation), 25-fold more concentrated (25× formulation), 50-fold more concentrated (50× concentration), or 100-fold more concentrated (100× formulation). More highly concentrated formulations can be made, provided that the ingredients remain soluble and stable. See U.S. Pat. No. 5,474,931 (entire contents incorporated herein by reference), which is directed to methods of solubilizing culture media components at high concentrations.

If the media ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1-1.0 m pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1× sterile medium formulation. Autoclaving or other elevated temperature-based methods of sterilization are not favored, since many of the components of the present culture media are heat labile and will be irreversibly degraded by temperatures such as those achieved during most heat sterilization methods.

As will be readily apparent to one of ordinary skill in the art, each of the components of the culture medium may react with one or more other components in the solution. Thus, the present invention encompasses the formulations disclosed in Tables I and II, supplemented as described above, as well as any reaction mixture which forms after these ingredients are combined.

Many tissue culture media typically contain one or more antibiotics, which are not necessary for cell growth/proliferation per se, but are present to inhibit the growth of other undesirable microbes, such as bacteria and/or fungi.

Antibiotics are natural chemical substances of relatively low molecular weight produced by various species of microorganisms, such as bacteria (including *Bacillus* species), actinomycetes (including *Streptomyces*) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are: (1) the p3-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Thus for convenience and other practical reasons, the subject media may be additionally supplemented by one or more antibiotics or other substances that inhibit the growth/proliferation of undesirable bacteria/fungi/virus. In other embodiments, however, the subject medium may be free of any antibiotics to ensure optimum growth of primary cells. Extra care should be taken when handling cells growing in antibiotic-free medium in order to avoid possible contamination.

TABLE I

Secondary Culture Medium without Optional Components

| Components | Concentration (mg/L)* |
|---|---|
| 2-deoxy-D-ribose | 0.25 |
| Adenine sulfate | 5 |
| Adenosine 5'-phosphate | 0.1 |
| Adenosine 5'-triphosphate | 0.5 |
| Ascorbic acid | 0.025 |
| Biotin | 0.00865 |
| Bovine serum albumin (BSA) | 900-1250 |
| Calcium chloride (anhydrous) | 16.61 |
| Calcium chloride ($CaCl_2$) | 100 |
| Cholera toxin | 0-0.1 |
| Choline chloride | 7.25 |
| Cupric sulfate ($CuSO_4 \cdot 5H_2O$) | 0.00125 |
| D-Calcium pantothenate | 0.255 |
| D-Glucose | 1000-4000 |
| Epidermal Growth Factor (EGF) | 0.0005-1.0 |
| Ferric nitrate ($Fe(NO_3)_2 \cdot 9H_2O$) | 0.35 |
| Ferric sulfate ($FeSO_4 \cdot 7H_2O$) | 0.417 |
| Folic Acid | 0.655 |
| Glycine | 28.75 |
| Guanine hydrochloride | 0.15 |
| Hydrocortisone | 0.00043-0.5 |

TABLE I-continued

Secondary Culture Medium without Optional Components

| Components | Concentration (mg/L)* |
|---|---|
| Hypoxanthine Na | 2.585-13.6 |
| i-Inositol | 9.025 |
| Insulin | 10-20 |
| L-Alanine | 16.95 |
| L-Arginine hydrochloride | 140.5 |
| L-Asparagine•H$_2$O | 7.505 |
| L-Aspartic Acid | 21.65 |
| L-Cysteine-HCl•H$_2$O | 17.61 |
| L-Cystine-2HCl | 13 |
| L-Glutamic Acid | 44.85 |
| L-Glutamine | 269 |
| L-Histidine-HCl•H$_2$O | 21.44 |
| L-Hydroxyproline | 5 |
| Linoleic Acid | 5.39 |
| Lipoic Acid | 0.105 |
| L-Isoleucine | 22 |
| L-Leucine | 36.55 |
| L-Lysine hydrochloride | 53.25 |
| L-Methionine | 9.75 |
| L-Phenylalanine | 15 |
| L-Proline | 37.25 |
| L-Serine | 17.75 |
| L-Threonine | 20.95 |
| L-Tryptophan | 6.02 |
| L-Tyrosine 2Na•2H$_2$O | 23.9 |
| L-Valine | 18.35 |
| Magnesium Chloride (anhydrous) | 28.61 |
| Magnesium sulfate (MgSO$_4$) | 48.835 |
| Niacin | 0.0125 |
| Niacinamide | 0.0305 |
| Para-aminobenzoic acid | 0.025 |
| Potassium chloride (KCl) | 311.8 |
| Putrescine-2HCl | 0.0805 |
| Pyridoxal hydrochloride | 0.0125 |
| Pyridoxine hydrochloride | 0.0425 |
| Riboflavin | 0.0235 |
| Ribose | 0.25 |
| Selenous acid | 0.0078 |
| Sodium acetate | 25 |
| Sodium bicarbonate (NaHCO$_3$) | 1688 |
| Sodium chloride (NaCl) | 7199.5 |
| Sodium phosphate (NaH$_2$PO$_4$•H$_2$O) | 70 |
| Sodium phosphate, dibas (anhydrous) | 71 |
| Thiamine hydrochloride | 0.155 |
| Thymidine | 0.35 |
| Thymine | 0.15 |
| Transferrin | 11.25 |
| Uracil | 0.15 |
| Zinc sulfate (ZnSO$_4$•7H$_2$O) | 0.431 |

*concentrations are expressed as units/total volume.

Note:
the concentrations listed above are not absolute and invariable. Since different cell types may have different growth needs, it is contemplated that generally, a 2-10 fold variation (increase or decrease) for each value is an acceptable range of concentration (supra). Some components may tolerate an even larger variation of final concentration (See Example below). Further optimization can be achieved using these starting concentrations (see above). One of the media prepared according to Table I is named "WIT medium" in Example IV below. Such a medium typically does not need to contain cholera toxin or other agents that increase intracellular cAMP levels, and is suitable, for example, for primary cells transformed (immortalized) by telomerase catalytic subunits and SV40 large T antigen.

TABLE IIA

Primary Culture Medium with Optional Components

| Components | Concentration (mg/L*) |
|---|---|
| *17-beta-estradiol | 0.00034-0.0034 |
| 2-deoxy-D-ribose | 0.25 |
| Adenine sulfate | 5 |
| Adenosine 5'-phosphate | 0.1 |
| Adenosine 5'-triphosphate | 0.5 |
| *Alpha-tocopherol acetate | 0-2 |
| *Alpha-tocopherol phosphate | 0.005 |
| Ascorbic acid | 0.025 |
| Biotin | 0.00865 |
| Bovine serum albumin (BSA) | 1250-9000 |
| *Calciferol (Vitamin D2) | 0.05 |
| Calcium chloride (anhydrous) | 2-16.61 |
| Calcium chloride (CaCl$_2$) | 5-100 |
| Cholera toxin | 0-0.1 |
| *Cholesterol | 0.1-2.2 |
| Choline chloride | 7.25 |
| Cupric sulfate (CuSO$_4$•5H$_2$O) | 0.00125 |
| D-Calcium pantothenate | 0.255 |
| D-Glucose | 1000-2000 |
| Epidermal Growth Factor (EGF) | 0.0005-0.01 |
| Ferric nitrate (Fe(NO$_3$)$_2$•9H$_2$O) | 0.35 |
| Ferric sulfate (FeSO$_4$•7H$_2$O) | 0.417 |
| Folic Acid | 0.655 |
| *Glutathione (reduced) | 0.025-1.0 |
| Glycine | 28.75 |
| Guanine hydrochloride | 0.15 |
| *HEPES pH 7.5 | 10 mM |
| *Hydrocortisone | 0.00043-0.5 |
| Hypoxanthine Na | 2.585-13.6 |
| i-Inositol | 9.025 |
| Insulin | 10-20 |
| L-Alanine | 16.95 |
| L-Arginine hydrochloride | 140.5 |
| L-Asparagine•H$_2$O | 7.505 |
| L-Aspartic Acid | 21.65 |
| L-Cysteine-HCl•H$_2$O | 17.61 |
| L-Cystine-2HCl | 13 |
| L-Glutamic Acid | 44.85 |
| L-Glutamine | 269 |
| L-Histidine-HCl•H$_2$O | 21.44 |
| L-Hydroxyproline | 5 |
| Linoleic Acid | 5.39 |
| Lipoic Acid | 0.105 |
| L-Isoleucine | 22 |
| L-Leucine | 36.55 |
| L-Lysine hydrochloride | 53.25 |
| L-Methionine | 9.75 |
| L-Phenylalanine | 15 |
| L-Proline | 37.25 |
| L-Serine | 17.75 |
| L-Threonine | 20.95 |
| L-Tryptophan | 6.02 |
| L-Tyrosine 2Na•2H$_2$O | 23.9 |
| L-Valine | 18.35 |
| Magnesium Chloride (anhydrous) | 28.61 |
| Magnesium sulfate (MgSO$_4$) | 48.835 |
| *Menadione (Vitamin K3) | 0.005 |
| Niacin | 0.0125 |
| Niacinamide | 0.0305 |
| *O-phosphoryl ethanolamine | 5.65 |
| Para-aminobenzoic acid | 0.025 |
| *Phenol red | 10.6 |
| Potassium chloride (KCl) | 311.8 |
| *Progesterone | 0.0004 |
| Putrescine-2HCl | 0.0805 |
| Pyridoxal hydrochloride | 0.0125 |
| Pyridoxine hydrochloride | 0.0425 |
| Riboflavin | 0.0235 |
| Ribose | 0.25 |
| Selenous acid | 0.0078 |
| Sodium acetate | 25 |
| Sodium bicarbonate (NaHCO$_3$) | 1688 |
| Sodium chloride (NaCl) | 7199.5 |
| Sodium phosphate (NaH$_2$PO$_4$•H$_2$O) | 70 |
| Sodium phosphate, dibas (anhydrous) | 71 |
| *Sodium pyruvate | 55 |
| *Testosterone | 0.00036 |
| Thiamine hydrochloride | 0.155 |
| *Thriiodothyronine | 0-0.168 × 10$^{-6}$ |
| Thymidine | 0.35 |
| Thymine | 0.15 |
| Transferrin | 11.25 |
| *Tween 80 | 10 |

TABLE IIA-continued

Primary Culture Medium with Optional Components

| Components | Concentration (mg/L*) |
|---|---|
| Uracil | 0.15 |
| *Vitamine A (acetate) | 0.05 |
| *Vitamine B12 | 0.7 |
| *Xanthine-Na | 0.17 |
| Zinc sulfate (ZnSO$_4$•7H$_2$O) | 0.431 |

*concentrations are expressed as units/total volume.

TABLE IIB

Primary Culture Medium with Optional Components

| Components | Concentration (mg/L*) |
|---|---|
| *17-beta-estradiol | 0.0004-0.004 |
| 2-deoxy-D-ribose | 0.25 |
| Adenine sulfate | 5 |
| Adenosine 5'-phosphate | 0.1 |
| Adenosine 5'-triphosphate | 0.5 |
| *Alpha-tocopherol acetate | 0-2 |
| *Alpha-tocopherol phosphate | 0.01-0.005 |
| Ascorbic acid | 0.01-0.03 |
| Biotin | 0.05-0.01 |
| Bovine serum albumin (BSA) | 1250-600 |
| *Calciferol (Vitamin D2) | 0.05 |
| *Calcium chloride (anhydrous) | 16 |
| Calcium chloride (CaCl$_2$) | 5-120 |
| Cholera toxin | 0-0.1 |
| Cholesterol | 0.1-2.2 |
| Choline chloride | 7.25 |
| Cupric sulfate (CuSO$_4$•5H$_2$O) | 0.00125 |
| D-Calcium pantothenate | 0.255 |
| D-Glucose | 1000-2000 |
| Epidermal Growth Factor (EGF) | 0.0005-0.01 |
| Ferric nitrate (Fe(NO$_3$)$_2$•9H$_2$O) | 0.35 |
| Ferric sulfate (FeSO$_4$•7H$_2$O) | 0.417 |
| Folic Acid | 0.655 |
| *Glutathione (reduced) | 0.025-1.0 |
| Glycine | 28.75 |
| Guanine hydrochloride | 0.15 |
| *HEPES pH 7.5 | 10 mM |
| Hydrocortisone | 0.0005-0.5 |
| Hypoxanthine Na | 2.585-13.6 |
| i-Inositol | 9.025 |
| Insulin | 10-20 |
| L-Alanine | 16.95 |
| L-Arginine hydrochloride | 140.5 |
| L-Asparagine•H$_2$O | 7.505 |
| L-Aspartic Acid | 21.65 |
| L-Cysteine-HCl•H$_2$O | 17.61 |
| L-Cystine-2HCl | 13 |
| L-Glutamic Acid | 44.85 |
| L-Glutamine | 123-269 |
| L-Histidine-HCl•H$_2$O | 21.44 |
| L-Hydroxyproline | 5 |
| Linoleic Acid | 5 |
| Lipoic Acid | 0.105 |
| L-Isoleucine | 22 |
| L-Leucine | 36.55 |
| L-Lysine hydrochloride | 53.25 |
| L-Methionine | 9.75 |
| L-Phenylalanine | 15 |
| L-Proline | 37.25 |
| L-Serine | 17.75 |
| L-Threonine | 20.95 |
| L-Tryptophan | 6.02 |
| L-Tyrosine 2Na•2H$_2$O | 23.9 |
| L-Valine | 18.35 |
| Magnesium Chloride (anhydrous) | 28 |
| Magnesium sulfate (MgSO$_4$) | 48.84 |
| *Menadione (Vitamin K3) | 0.005 |
| Niacin | 0.0125 |
| Niacinamide | 0.0305 |
| o-phosphoryl ethanolamine | 5.5 |

TABLE IIB-continued

Primary Culture Medium with Optional Components

| Components | Concentration (mg/L*) |
|---|---|
| Para-aminobenzoic acid | 0.025 |
| *Phenol red | 10.6 |
| Potassium chloride (KCl) | 311.8 |
| *Progesterone | 0.0004 |
| Putrescine-2HCl | 0.0805 |
| Pyridoxal hydrochloride | 0.0125 |
| Pyridoxine hydrochloride | 0.0425 |
| Riboflavin | 0.0235 |
| Ribose | 0.25 |
| Selenous acid | 0.008 |
| Sodium acetate | 25 |
| Sodium bicarbonate (NaHCO$_3$) | 1688 |
| Sodium chloride (NaCl) | 7199.5 |
| Sodium phosphate (NaH$_2$PO$_4$•H$_2$O) | 70 |
| Sodium phosphate, dibas (anhydrous) | 71 |
| *Sodium pyruvate | 55 |
| *Testosterone | 0.0004 |
| Thiamine hydrochloride | 0.155 |
| Thriiodothyronine | $0\text{-}0.2 \times 10^{-6}$ |
| Thymidine | 0.35 |
| Thymine | 0.15 |
| Transferrin | 10 |
| *Tween 80 | 10 |
| Uracil | 0.15 |
| *Vitamine A (acetate) | 0.05 |
| Vitamine B12 | 0.7 |
| *Xanthine-Na | 0.17 |
| Zinc sulfate (ZnSO$_4$•7H$_2$O) | 0.431 |

Note:
components with asterisks (*) are optional components. All optional components do not need to be present in the final medium at least for short term - as few as 1 to a maximum of 19 optional components might be present in the final medium. Certain media of the present invention contain all 19 optional components. In certain embodiments of the media of Table II, O-phosphorylethanolamine is a required component.

The medium of the instant invention can be made from individual components separately purchased from various chemical venders. Alternatively, certain commercial medium may be conveniently mixed and supplemented by additional components for make the subject medium. For example, in one embodiment, the subject medium may comprise about 50% Medium 199 (M199) and about 50% F12 (Ham) medium, supplemented with glutamine, EGF, transferrin, insulin, progesterone, testosterone, 17B-estrodiol, O-phosphorylethanolamine, selenious acid, lionleic acid, BSA, triiodothyronine, hydrocortizone, cholera toxin, HEPES, and other components to approximately their corresponding concentrations as listed in Table II. The invention thus provides methods of making a tissue culture medium comprising supplementing a commercially available cell culture medium or mixture of two or more such media by adding one or more of the optional components disclosed herein.

In some embodiments the subject medium has the same concentrations of components as would be obtained by starting with 100% M199, 100% F12, or a combination of M199 and F12 in any proportion, and then adding any one or more additional components to bring the concentrations of said components to the levels disclosed in Example IX or XIX. The percentage of media proportions here are by volume. In some embodiments the medium has the same concentration of components as would be obtained by combining between 10% and 90% M199, with the remainder of the medium being F12, and supplementing with any one or more additional components to bring the concentrations of said components to the levels disclosed in Example IX or XIX. In some embodiments the medium has the same concentration of components as would be obtained by combining between 20% and 80% M199, or between 30% and 70% M199, or between 40% and 60% M199, with the remainder of the medium in each case being F12, and supplementing with any one or more additional components to bring the concentrations of said components to the levels disclosed in Example IX or XIX. In some embodiments the medium has the same concentration of components as would be obtained by combining between 20% and 80% M199, or between 30% and 70% M199, or between 40% and 60% M199, with the remainder of the medium in each case being F12, and supplementing with any one or more additional component(s) to bring the concentrations of said component(s) to the levels disclosed in Example IX or XIX. In some embodiments the medium has the same concentrations of component(s) as would be achieved by combining 45-55% M199 with the balance being F12, and supplementing with any one or more additional component(s) to bring the concentrations of said component(s) to the levels disclosed in Example IX or XIX. In some embodiments the medium has the same concentrations of component(s) as would be achieved by combining 48-52% M199 (e.g., 50% M199) with the balance being F12, and supplementing with any one or more additional component(s) to bring the concentrations of said component(s) to the levels disclosed in Example IX or XIX. In some embodiments the final concentration of any one or more of the added components differs from that listed in Example IX or XIX by a factor of up to 10, by which is meant that the relevant concentration may range from 0.1 to 10 times that listed in Example IX or XIX. In some embodiments the final concentration of any one or more of the added components differs from that listed in Example IX or XIX by a factor of up to 3, by which is meant that the relevant concentration may range from 0.3 to 3 times that listed in Example IX or XIX. In some embodiments the final concentration of any one or more of the added components differs from that listed in Example IX or XIX by a factor of up to 2, by which is meant that the relevant concentration may range from 0.5 to 2 times that listed in Example IX or XIX. In some embodiments the added concentration of any one or more of the added components differs from those listed in Example IX or XIX by up to 10%, 20%, or 50% from the value listed in Example IX or XIX, respectively.

Although the media of the invention may be obtained by mixing F12 and M199 at the specified percentage (by volume), the invention is not limited to obtaining a particular medium composition by mixing fully-prepared F12 and M199. Those of ordinary skill in the art may calculate the concentration of each component of a particular medium composition and prepare accordingly, without preparing M199 and F12 first.

The invention also encompasses embodiments in which any one or more of the components of such medium listed (e.g. at least 5, 6, 7, 8, 9, 10, at least 90% or all of the components) are added in the listed concentrations (or in amounts independently ranging from 0.1 to 10 times, or 0.3 to 3 times of the listed concentration), to a medium having the composition of combining F12 medium with M199 medium. The amount of F12 medium is preferably between 30% and 70% by volume (e.g., 40%-60% or 45%-55%), with the remaining being M199 medium. The medium may be used, without limitation, for any of the purposes and in any of the methods described herein.

The invention encompasses embodiments in which any 1, 2, 3, 4, or 5 component(s) is/are not added to the medium. In some embodiments the medium is supplemented with insulin, EGF, hydrocortisone, and cholera toxin. Optionally the medium is further supplemented with serum, e.g., between 0.1% and 10% calf serum or fetal bovine serum.

The invention provides basal WIT medium as disclosed in Example XIX, containing insulin (10 µg/mL), EGF (0.5 ng/mL), and hydrocortisone (0.5 ng/ml). For culturing BPECs the basal WIT medium may be supplemented so as to achieve the following concentrations of insulin, EGF, hydrocortisone, and cholera toxin: insulin (20 µg/mL), EGF (10 ng/mL), hydrocortisone (0.5 µg/mL) and cholera toxin (100 ng/ml).

Certain embodiments of the invention comprise the components listed in Example XIX, in amounts effective to support undifferentiated growth and/or proliferation of primary epithelial progenitor cells, e.g., breast epithelial progenitor cells, for at least about 4 weeks or at least about 15 population doubling (PD) in vitro, without a significant decrease in differentiation potential. In certain embodiments of the invention, any specific ingredient listed in Example XIX is replaced at least in part by an alternate ingredient capable of fulfilling the same function. Such substitutions may be made with respect to any one or more listed ingredients (e.g., 1, 2, 3, 4, 5, 6, 7, 8, 9, 10, or more of the ingredients may be substituted by alternate ingredients capable of fulfilling the same function). In one embodiment, the buffer component is substituted. In another embodiment, the detergent or surfactant component is substituted. In another embodiment the carrier protein component is substituted. The specification provides nonlimiting examples of suitable substitutes.

In some embodiments, the subject medium disclosed in Example XIX is modified as described in detail below. Without limitation, such modifications may be of use for culturing cells isolated or derived from tissues other than the breast, e.g., culturing mesothelial cells and/or surface epithelial cells. The invention further provides methods of culturing and using said non-breast derived cells. In certain embodiments the methods are analogous to the methods described herein for breast-derived cells. For example, the methods may be used to identify and/or isolate or enrich for cancer stem cells and/or to screen for compounds that affect (e.g., inhibit) the survival and/or proliferation of such cells in vitro and/or in vivo. It will be appreciated that details of these methods may vary relative to those applicable for breast-derived cells. For example, said cells may be plated at different densities, on different tissue culture surfaces, for different time periods, and/or optimally harvested and/or replated using methods that differ in their details than those disclosed for breast-derived cells. The invention further provides cells of mesothelial or surface epithelial origin that have been cultured in the inventive medium. In some embodiments said cells are derived by obtaining primary cells and culturing them for various periods of time in the subject medium, thereby enriching for cells having one or more desired properties (e.g., cells that more closely replicate the morphological and/or other phenotypic characteristics of human tumors when introduced into an animal, relative to cells cultured in alternative medium). The cells may be genetically modified, e.g., by introduction of one or more oncogene(s) or other genes (e.g., hTERT catalytic subunit), by knockout or inhibition of one or more tumor suppressor genes, etc., as described elsewhere herein or known in the art.

For culturing mesothelial cells the invention provides a medium having the composition of basal WIT medium supplemented with 1% serum (e.g., calf serum or fetal bovine serum) and the same amounts of EGF, insulin, hydrocortisone, and cholera toxin as for BPECs (i.e., insulin (20 µg/mL), EGF (10 ng/mL), hydrocortisone (0.5 µg/mL) and cholera toxin (100 ng/mL). Mesothelial cells may be obtained from the membranous lining of any of several body cavities: the pleura (thoracal cavity), peritoneum (abdominal cavity) and pericardium (heart sac). Mesothelial tissue also surrounds the male internal reproductive organs (the tunica vaginalis testis) and covers the internal reproductive organs of women (the tunica serosa uteri). Without limitation, the media and methods of the invention may be used for culturing normal (e.g., primary) mesothelial cells and mesothelial cancer cells, e.g., mesothelioma. For culturing ovarian surface epithelium and fallopian tube epithelium the invention provides a medium having the composition of basal WIT medium supplemented with 25 ng/ml cholera toxin (rather than 100 ng/ml) and the same amounts of EGF, insulin, hydrocortisone, and cholera toxin as for BPECs (i.e., insulin (20 µg/mL), EGF (10 ng/mL), hydrocortisone (0.5 µg/mL)). Suitable concentrations for culturing human cells (or, in certain embodiments, other mammalian, e.g., mouse cells) of various types are summarized in the following table:

TABLE III

Suitable concentrations for culturing various human cell types

| Components (final concentration) | Human Primary Breast Cells | Human Ovarian & Fallopian Tube Epithelial Cells | Human Mesothelial Cells |
|---|---|---|---|
| Calf/Fetal Bovine Serum | None | None | 0.1-5.0% |
| Epidermal Growth Factor | 10 ng/mL | 10 ng/mL | 10 ng/mL |
| Hydrocortisone | 0.5 µg/mL | 0.5 µg/mL | 0.5 µg/mL |
| Cholera toxin | 100 ng/mL | 25 ng/mL | 25 ng/mL |
| Insulin | 20 µg/mL | 20 µg/mL | 20 µg/mL |

The invention provides a tissue culture medium comprising the components listed in the above table and sufficient standard tissue culture medium components (e.g., nutrients, salts, etc.) to support the growth of cells. The composition of these media may be varied. For example, the concentration of any of the components may be independently varied by up to 10%, 20%, 30%, 40%, or 50%, or by up to a factor of up to 2-3 fold, relative to the concentrations listed in the table. In one embodiment, the concentrations of each of the above 4 components varies by not more than 10% from the listed value. In one embodiment, the concentrations of each of the above 4 components varies by not more than 25% from the listed value. In one embodiment, the concentrations of each of the above 4 components varies by not more than 10% from the listed value. In one embodiment, the concentrations of each of the above 4 components varies by not more than 25% from the listed value. In one embodiment, the concentrations of each of the above 4 components varies by not more than 50% from the listed value. In some embodiments, the concentration range of serum in media for culturing human mesothelial cells is 0.1%-2%.

Unless otherwise indicated, as used herein, variation by up to X % means variation by ±X % with respect to the listed value. For example, if the listed value is 100 ng/ml, variation by 25% means that the value can range between 75 ng/ml and 125 ng/ml (i.e., 75-125 ng/ml). Unless otherwise indicated, where a range of values is disclosed, endpoints are included within the range. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate to any intervening value or range defined by any two values in the series, where the lowest value may be taken as a minimum and the greatest value may be taken as a maximum. For any embodiment of the invention in which a value is prefaced by the term "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

It will be appreciated that certain of the components may be provided as salts, esters, biologically active metabolites or derivatives, or as precursors that are metabolized, processed, or broken down by the cell or in the medium to yield a biologically active form of certain of the components disclosed herein. "Biologically active" in this context refers to the ability of the component to exert its desired effect on a cell when present in a cell culture medium.

The medium of the instant invention may be liquid or solid powder, or a combination of both. The liquid form may be a complete medium, which contains all the components sufficient to support the growth/proliferation of the target cells. Alternatively, the liquid media may be stored as separate packages, such that each individual package may be stored at its appropriate conditions (temperature, humidity, etc.). For example, most of the components listed in the tables (or Examples), if desired to be in a medium of the instant invention, can be pre-dissolved in a single solution and stored at appropriate conditions (e.g. 4° C. in a dark and dry place, etc.). Other components, which could be unstable at the storage conditions for the other components, or which could react slowly with other components, or which is otherwise better kept as a separate stock, may be stored under a different set of conditions (e.g. −20° C. or −80° C., etc.). It is only shortly or immediately before use are these separately stored components brought together to constitute the whole medium. Each separate package may be marketed or sold separately, or as different concentrated stocks (e.g. 2×, 5×, 10×, 100×, 1000×, etc.). In some embodiments, a medium of the instant invention is marketed or sold together with one or more cell lines (e.g., one or more cell line(s) disclosed herein, for whose culture said medium is suitable.

Similarly, the complete medium or individual components, packages thereof could be in the form of dry powder, which, upon reconstitution with an aqueous solution (such as water), will yield the desired medium, or its concentrated stocks (2×, 5×, or 10×, etc.).

Components that can be, or better kept as separate stocks just prior to use include: growth factors (e.g. Epidermal Growth Factor), hormones (e.g. progesterone, testosterone), other unstable enzymes/proteins (e.g. transferrin, insulin, cholera toxin, etc.), steroids (e.g. hydrocortisone, cholesterol), vitamins (Vitamins A, $B_{12}$, $K_3$), pH indicators (e.g. phenol red), one or more buffer components (e.g. sodium biocarbonate, HEPES) and other chemicals (e.g. glutathione, 17-β-estradiol, O-phosphoryl ethanolamine, etc.).

In certain embodiments, at least some or all components of the medium is in liquid/aqueous form. In other embodiments, at least some or all components of the medium is in solid/powder form.

The media of the invention are suitable for a variety of primary glandular epithelial cells, including epithelial cells from breast (luminal), prostate, lung, GI tract (e.g. salivary gland, small and large intestine, colon, stomach, pancreas, liver, gall bladder, etc.), cervix, endometrium/uterus, and ovary. The media may also be suitable for culturing primary endothelial cells.

In addition, the subject medium is also suitable to support long-term growth, proliferation, and/or differentiation of primary breast epithelial cells induced to express: (1) telomerase catalytic subunit, (2) a first polypeptide functions in the same signaling pathway(s) as does the SV40 large T antigen (such as SV40 Large T antigen), and (3) a second polypeptide functions in the same signaling pathway as does the mutant H-ras oncogene product (such as H-Ras), for at least about 15 weeks or at least about 35 population doubling (PD) in vitro, without losing tumorigenicity.

The media of the invention are suitable for a variety of primary glandular epithelial cells from different mammals, including human and other non-human mammals. The latter further includes: non-human primates (e.g. monkey, gorilla, etc.), mouse, rat, rabbit, domestic cattle, horse, pig, sheep, goat, dog, and cat.

In certain embodiments, the medium supports the growth, proliferation, and/or differentiation of cells from normal glandular epithelial cells of an organ/tissue selected from: breast, prostate, ovary, pancreas, stomach, intestine, colon, endocervix, kidney, skin, lung, uterus, parotid gland, or fallopian tube.

In certain embodiments, the medium supports the growth, proliferation, and/or differentiation of endometrial cells or cervical cells.

In certain embodiments, the medium supports the differentiation of breast glandular epithelial cells to luminal phenotype, but not basoid phenotype. Such luminal phenotype is characterized by specific keratin expression profiles typical of luminal mammary epithelial cells.

In certain embodiments, the subject medium supports undifferentiated growth and proliferation of a population of breast progenitor cells characterized by expression of CD44, CD24 and ESA (epithelial cell surface antigen) in at least about 85% of the cells, or at least about 88%, 90%, 95% 99% or near 100% of the cells.

Another aspect of the invention relates to a culture medium comprising: (a) one or more lipid synthesis precursors; (b) one or more protein synthesis precursors; (c) one or more carbohydrate synthesis and energy metabolism precursors; (d) one or more monovalent and/or divalent cations, ions, trace metals and enzyme cofactors/vitamins; and (e) insulin, wherein the medium supports undifferentiated growth and/or proliferation of primary epithelial progenitor cells transformed by telomerase catalytic subunit for at least about 4 weeks or at least about 15 population doubling (PD) in vitro, without a significant decrease in differentiation potential.

Another aspect of the invention relates to a culture medium comprising: (a) None or trace amount of calf/fetal bovine serum; (b) Epidermal Growth Factor at a final concentration of about 10 ng/mL; (c) Hydrocortisone at a final concentration of about 0.5 µg/mL; (d) Cholera toxin at a final concentration of about 100 ng/mL; (e) Insulin at a final concentration of about 20 µg/mL, wherein the medium supports undifferentiated growth and/or proliferation of human primary breast cells for at least about 4 weeks or at least about 15 population doubling (PD) in vitro, without a significant decrease in differentiation potential.

Another aspect of the invention relates to a culture medium comprising: (a) none or trace amount of calf/fetal bovine serum; (b) epidermal growth factor at a final concentration of about 10 ng/mL; (c) hydrocortisone at a final concentration of about 0.5 µg/mL; (d) cholera toxin at a final concentration of about 25 ng/mL; (e) insulin at a final concentration of about 20 µg/mL, wherein the medium supports undifferentiated growth and/or proliferation of human ovarian & fallopian tube epithelial cells for at least about 4 weeks or at least about 15 population doubling (PD) in vitro, without a significant decrease in differentiation potential.

Another aspect of the invention relates to a culture medium comprising: calf/fetal bovine serum at a final concentration of about 0.1%-0.2% by volume; (b) epidermal growth factor at a final concentration of about 10 ng/mL; (c) hydrocortisone at a final concentration of about 0.5 µg/mL; (d) cholera toxin at a final concentration of about 25 ng/mL; (e) insulin at a final concentration of about 20 µg/mL, wherein the medium supports undifferentiated growth and/or proliferation of human mesothelial cells for at least about 4 weeks or at least about 15 population doubling (PD) in vitro, without a significant decrease in differentiation potential.

Another aspect of the invention relates to a composition of matter comprising a mixture of solid form chemicals, the chemicals, when dissolved in a given volume of an aqueous solvent, becomes the medium of any one of the above described media.

II. Isolation and Culturing of Primary Cells

Another aspect of the invention relates to the use of the subject medium for isolating primary cells, such as primary mammalian glandular epithelial cells substantially free of other cell types, including stromal cells and myoepithelial cells.

In one embodiment, the method comprise: (a) providing tissues containing the primary cells from a mammal; (b) plating primary cells obtained from the tissue on a tissue culture container with mixed (+/−) charge surface, in culture medium for between 3 days to 4 weeks with medium change at reasonable frequency, wherein said medium change optionally occurs at least once every 12 hours to 3 days; and; (c) harvesting primary cells and transferring the harvested the primary cells to a new tissue culture container with mixed (+/−) charge surface in the medium of claim 1, thereby isolating the primary cells from the mammal.

Although not limiting, the method of the invention is particularly suitable to isolate primary glandular epithelial cells, such as mammary glandular epithelial cells. Other primary cell sources include such tissues as: breast, prostate, ovary, pancrease, stomach, intestine, colon, endocervix, kidney, skin, lung, uterus, parotid gland, or fallopian tube.

"Substantially free" as used herein refers to at least about 80% pure, preferably 85%, 90%, 95%, 99% or more pure population of the desired cells in the whole cell population. The medium of the invention not only supports the long-term growth and proliferation of the desired mammalian glandular epithelial cells, but also suppresses the growth of other major competitor cell types, including stromal cells and myoepithelial cells. Therefore, after about 1-2 weeks of culturing and passaging of the primary cells isolated from minced tissue blocks, the glandular epithelial cells are selectively enriched, and eventually become the only actively proliferating cell types in tissue culture.

In one embodiment, a tissue with the desired glandular epithelial cells (such as breast, prostate, ovary, pancrease, stomach, intestine, colon, endocervix, kidney, skin, lung, uterus, Parotid gland, or fallopian tube, etc.) is obtained from a human or non-human patient, and minced down to chunks/cubes/fragments of about 1-2 mm in dimension. Cells in the fragments are then separated by, for example, overnight collagenase digestion in suitable buffer and temperature (e.g. Hanks's buffered saline solution at 37° C. overnight). Other methods, such as mechanical means (passing the minced tissue through a steel mesh using a plunger, optionally followed by a cotton wool column, etc.) may also be used.

Glandular epithelial cells tend to form clumps of organoids. Low speed centrifugations at about 50-300 g could be used to separate these organoids from other single cells, which are mostly stromal cells and myoepithelial cells. The isolated primary cells and organoids are then plated on a tissue culture container surface that has mixed (+/−) charge surface.

Most traditional tissue culture cell container surfaces are negatively charged (see the numerous —COOH groups below, which, at neutral pH, tend to slightly dissociated and assume a negative (anionic) charge). This leads to poor attachment of the desired primary cells to the container surfaces, and thus preferably should not be used. Suitable tissue culture container with mixed charges include both positive (see the —NH$_2$ groups, which may protonate and assume a positive charge (cationic) at neutral pH) and negative charges (see the —COOH groups and above). BD Primaria™ Cultureware (BD Biosciences) manufactures such mixed-charge tissue culture containers.

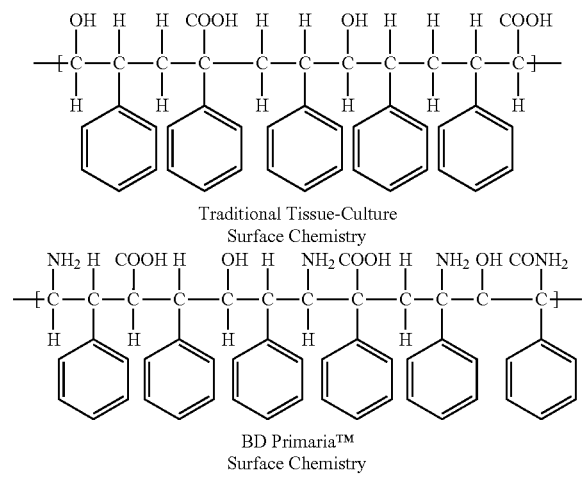

Traditional Tissue-Culture Surface Chemistry

BD Primaria™ Surface Chemistry

An alternative method is to coat the tissue culture surface with BD Matrigel™ matrix (BD Biosciences)—a solubilized basement membrane preparation extracted from EHS mouse sarcoma, a tumor rich in ECM proteins. Its major component is laminin, followed by collagen IV, heparan sulfate proteoglycans, and entactin. Other Matrigel™ equivalents may also be used.

After 7-10 days of culturing on suitable surfaces, with daily change of medium, cells can be harvested by first treating the container with a low concentration of trypsin (such as 0.025%) to remove loosely attached cells (mostly stromal cells), followed by a treatment using higher concentration of trypsin (such as 0.075%). If desired, such passage can be repeated more than once to significantly enrich for the desired primary glandular cell population. Once the enrichment step is completed, cells can be grown in secondary medium for all future culturing.

Another aspect of the invention relates to a method of subculturing primary cells, such as primary glandular epithelial cells growing in the subject media, comprising trypsinizing the attached cells with 0.075% trypsin, and harvesting cells in primary medium supplemented with trypsin inhibitor(s) such as 5% calf serum or equivalent serum. This is helpful partly because the serum-free formula of the subject medium does not contain any of the natural trypsin inhibitors in various serum preparations in other media, thus cells growing in the subject media are potentially more sensitive to the presence of trace amount of active trypsin, which may prevent effective attachment of the cells to tissue culture surfaces. As soon as the cells attach to a suitable tissue culture container, such as the BD Primaria™ containers, the serum-supplemented medium is changed back to the medium of the instant invention.

Another aspect of the invention relates to a method of subculturing primary cells, such as primary glandular epithelial cells growing in the subject media, comprising trypsinizing the attached cells with 0.15% trypsin, and harvesting cells in primary medium supplemented with trypsin inhibitor(s) such as 5% calf serum or equivalent serum. This is helpful partly because the serum-free formula of the subject medium does not contain any of the natural trypsin inhibitors in various serum preparations in other media, thus cells growing in the subject media are potentially more sensitive to the presence of trace amount of active trypsin, which may prevent effective attachment of the cells to tissue culture surfaces. Alternatively, the cells can be harvested by commercially available non-enzymatic cell dissociation buffers, or enzymes other than trypsin. As soon as the cells attach to a suitable tissue culture container, such as the BD Primaria™ containers, the serum-supplemented medium is changed back to the medium of the instant invention.

A related aspect of the invention provides a primary cell isolated using the subject media and methods, wherein the isolated primary cells grow and/or proliferate in the subject medium for at least about 4 weeks or at least about 15 population doubling (PD) in vitro, without any detectable genetic alterations, or losing differentiation potential.

In a preferred embodiment, the primary cell is a primary glandular epithelial cell, such as a primary breast/mammary epithelial cell. In other embodiments, the primary glandular epithelial cell is from a tissue/organ selected from: prostate, ovary, pancrease, stomach, intestine, colon, endocervix, kidney, skin, lung, uterus, Parotid gland, or fallopian tube.

The primary cells of the invention can proliferate in the subject media for at least about 5, 6, 7, 8, 9, 10, 11, 12, 13, 14, 15 or more weeks, or at least about 16, 20, 25, 30, 35 or more population doubling (PD) in vitro, without going into a state of senescence.

Similar primary cells, when growing in other media, such as the commercially available MEGM media, on average go into the state of senescence in about 3-4 weeks, or about 10-15 population doublings. A minor population (about $10^{-5}$) of such senesced cells might eventually escape and enter another phase of growth, but such escaped cells almost always contain additional mutations, such as p16 inactivation. In contrast, the isolated primary cells of the invention continue to grow in the subject media for much longer without incurring such mutations or entering a state of senescence.

In a related embodiment, the isolated primary cells are substantially free of stress gene (e.g. p16, p53) expression. "Substantially free" as used herein means at least about 90% free, preferably 95% free, 99% or more free as compared to that of the cells growing in other media, including the MEGM media.

In another embodiment, the isolated primary cells are substantially free of fibroblasts and stromal cells. "Substantially free" as used herein means at least about 90%, preferably 95%, 99% or more cells are the isolated primary cells (not fibroblasts or stromal cells). Alternatively, the expression level of fibroblast marker, such as vimentin, is less than 10%, preferably less than 5%, 1% or lower in the subject isolated primary cells as compared to that of primary cells growing in other media, including the MEGM media.

In another embodiment, the isolated primary cells of the invention are hormone responsive before and during culturing in the medium. For example, in the case of isolated primary mammary epithelial progenitor cells, the cells are responsive to estrogen, progesterone, and testosterone. Other isolated primary cells are responsive to hormones to which they respond before being isolated from the original tissue.

In a preferred embodiment, the primary mammalian glandular epithelial cells are isolated breast progenitor epithelial cells (BPEC) that can further differentiate into epithelial cells of luminal phenotype.

For example, the method may comprise: (1) isolating and culturing the mammary epithelial progenitor cells according to the subject method of the invention as described above; (2) inducing the differentiation of the mammary epithelial progenitor cells to epithelial cells of luminal phenotype. To illustrate, step (2) above may be effectuated by culturing cells in 3-D culture with EHS.

The differentiation may be characterized by expression of markers specific for luminal phenotype. Suitable markers may include one or more of: keratin 8, keratin 18, E-cadherin, and β-catenin.

To facilitate isolating and culturing of glandular epithelial cells from a mammal, the invention also provides a kit comprising a carrier means having in close confinement therein one or more container means: (1) wherein a first container means contains any of the subject medium described above; (2) an instruction for isolating and subculturing glandular epithelial cells from the mammal. The kit may further comprise collagenase and/or trypsin. The collagenase may be supplied in Hank's buffered saline solution (HBSS). The trypsin may be supplied in a high concentration of about 0.15% and a low concentration of about 0.025%.

Another aspect of the invention provides a method for enriching tumor stem cells in vitro, comprising culturing and subculturing tumorigenic cells of invention in culture medium comprising: (a) one or more lipid synthesis precursors; (b) one or more protein synthesis precursors; (c) one or more carbohydrate synthesis and energy metabolism precursors; (d) one or more monovalent and/or divalent cations, ions, trace metals and enzyme cofactors/vitamins; (e) one or more agents that induce increased intracellular 3'-5' cyclic adenosine monophosphate (cAMP) levels; and (f) insulin. In certain embodiment, the tumor stem cells are enriched at least 1,000 fold in vitro.

The invention also provides a kit for isolating and culturing glandular epithelial cells from a mammal, the kit comprising a carrier means having in close confinement therein one or more container means: (1) wherein a plurality of the container means, each individually contains, in proportion, solid forms of the components for any of the subject medium described above, such as that listed in Table II; (2) an instruction for making these media; (3) an instruction for isolating and subculturing glandular epithelial cells from the mammal.

In some embodiments, at least some of the components are stored at different temperatures as that for other of the components.

In some embodiments, at least some of the components are stored as liquid.

In some embodiments, at least some of the components are stored as solid powder.

In another aspect, PCT application WO 00/73420A2 describes a method of immortalizing and transforming normal somatic cells, including human mammary epithelial cells (HMEC) to immortalized and tumorigenic cells, the teaching of WO 00/73420A2 can be applied here in the isolated primary glandular cells of the invention (including BPEC). The entire content of which is incorporated herein by reference.

III. Tumor Stem Cell-Like Cells and the Uses Thereof

In addition to be suitable for culturing normal mammalian primary epithelial cells, the subject media is also suitable for culturing primary cell-derived, tumor stem cell-like cells. Thus, yet another aspect of the invention relates to isolating/establishing/purifying model tumor stem cells, and using such model tumor stem cells for screening agents specifically or preferentially targeting tumor stem cells.

The identification of a breast cancer stem cell represents a major step forward in the elucidation of the breast cancer tumor hierarchy and signals the beginning of a new era of breast cancer research. The most important outcome of these studies extend beyond the breast cancer field to cancer research in general. Although the cancer stem cell hypothesis is well established, much modern cancer research still treats tumors as homogeneous collections of cells that can be simply disrupted for biochemistry studies or for gene expression profiling. The focus of future studies in cell signaling, molecular and cellular comparisons of normal and tumorigenic pathways, gene expression profiling, and drug development must include the cancer stem cell. This in turn will require the use of primary tissue and not cell lines, functional transplantation assays for the cancer stem cell, and cell purification using cell surface or metabolic properties to isolate enriched populations.

In the breast cancer field, the BrCa-IC are key to understanding the origin and maintenance of breast cancer. With this knowledge, it is possible and desirable to design therapies targeted to the unique properties of the tumor stem cell to enable selective killing. Indeed, all of the rich information that has been gained on tumorigenic cellular pathways in cancer, including breast cancer, needs to be reevaluated in light of the functional heterogeneity that exists in the tumor clone. For example, the biological consequence of a particular signaling pathway might be different in the rare BrCa-IC compared with the more numerous non-BrCa-IC cells.

Despite the importance of cancer stem cell research, there has been no easy way of isolating and culturing cancer stem cells in vitro. In the study by Al-Hajj et al., human tumor tissues were cut up into about 2×2×2 mm cubes, and implanted directly into experimental animals. Although cell sorting using markers such as CD44 and CD24 helps to isolating/purifying such stem cells, a method of isolating or purifying such cancer stem cells to a relatively pure, homogeneous population, followed by further culturing in vitro has not been provided. In addition, partly due to the inherent characteristic of cancer such as genetic instability, the genetic composition of the tumor cells isolated based on CD44 and CD24 expression is heterogeneous and unstable.

Thus an aspect of the instant invention provides a relatively simple way to isolate, purify, enrich, and/or establish cancer stem cell-like cells derived from normal primary cells of the invention, including those derived from primary breast epithelial cells. As such it allows direct comparison of normal primary cells to tumorigenic and metastatic cancer stem cells that are directly derived from these normal cells. Such a direct comparison would not be possible for tumor stem cells that are isolated from patient samples, as the tumor initiating normal cells have been already transformed and no longer exist by definition. Moreover, high throughput drug and genetic screening requires in vitro culturing of such cells. While methods of purifying these cells are available, in vitro culture of them have not been possible. Therefore the instant invention described in this application has two advantages compared to existing technology, it provides matched normal controls for direct comparison to tumor stem cells, and it allows in vitro cultivation of both normal and tumor stem cells for drug and genetic screening.

To illustrate, normal breast tissue (or other tissues for other primary cells) obtained from a mammalian patient (e.g. human), preferably those freshly dissected from the patient (within 1-2 hours), are cut down in sterile medium (such as RPMI medium 1640) on ice to tissue fragments of 1-2 mm in size. Such tissue fragments are then digested for 3-4 hours to overnight at 37° C. with collagenase to yield a mixture of organoids and single cells (mostly stromal cells and epithelial cells). The mixture is then centrifuged 3 times, at about 20 g for 3 minutes each to enrich for the organoids, which are then plated in the subject primary media on mixed-charge tissue culture containers (e.g. Primaria™). The organoids are cultured for about 2-3 weeks, including 2-3 passages of cells to new culture containers to selectively eliminate stromal cells.

Using this method, breast epithelial progenitor cells were purified from normal breast tissues. Notably the resulting cells are largely ESA$^+$, CD44$^+$, CD24$^\pm$, similar to the breast cancer stem cells isolated from patients suggesting that this is a preexisting expression profile that was not a result of genetic events in the cancer cells, a conclusion that could not have been made by simply purifying tumor stem cells from patient samples.

Thus in one embodiment, the invention relates to a tumorigenic cell derived from a cultured mammalian primary epithelial cell isolated using the methods and media of the invention (e.g. BPEC, supra), the cell having stably incorporated therein and stably expressing exogenous DNA which, when expressed in such a cell, results in production of a tumorigenic cell that grows in an anchorage-independent manner and forms tumors in immuno-compromised animals (e.g. mice) into which the tumorigenic cell (BPLER) or its progeny are introduced. In a preferred embodiment, one or more tumors are generated in at least about 40-50% of injected animals in a xenograft transplant model, if a total of less than about 10,000, or less than about 5,000, or less than about 1,000, or less than about 500, or less than about 100 of such tumorigenic cells are injected into each animal.

Consistent with the findings of Al-Hajj at al. and similar to tumor stem cells isolated from human patient samples, the tumors that are generated as described above consist of a tumor stem cell fraction and their non-tumorigenic progeny. This was illustrated by isolating CD24$^+$ and CD24$^-$ cells from BPLER explants and re-injecting them into nude mice. As expected, the CD24$^-$ cells were tumorigenic and CD24$^+$ cells were not tumorigenic. The same phenomenon was also illustrated with cells from tissue culture; CD44$^{high}$ cells and CD44$^{low}$ cells were separated by FACS sorting and injected into nude mice and only the CD44$^{high}$ fraction was able to grow tumors.

In one embodiment, the exogenous DNA is incorporated into genomic DNA of the cultured primary glandular cell (e.g. BPEC). The exogenous DNA may comprises: (a) DNA that encodes a telomerase catalytic subunit; (b) DNA that encodes a first oncogene or suppressor/inhibitor of a tumor suppressor gene; and (c) DNA which encodes a second, distinct oncogene (or suppressor of a tumor suppressor gene), wherein the first oncogene (or the first TS gene inhibitor) and the second oncogene (or the second TS gene inhibitor) function in two different biochemical pathways in cells.

For example, the DNA of (a) may be a cDNA that encodes human telomerase catalytic subunit; the DNA of (b) may be a cDNA that encodes an oncogene which functions in a first biochemical pathway; while the DNA of (c) is a cDNA that encodes an oncogene which functions in a second biochemical pathway, wherein the first biochemical pathway and the second biochemical pathway are two distinct biochemical pathways.

In a preferred embodiment, the first biochemical pathway and the second biochemical pathway are signaling pathways and the cDNA of (b) encodes an oncogene that functions in the same signaling pathway as does the mutant H-ras oncogene product and the cDNA of (c) functions in the same signaling pathways as does the SV40 large T antigen-encoded oncoprotein, wherein the functional effects of the cDNA of (b) and the functional effects of the cDNA of (c) on their respective signaling pathways in the normal human somatic cell in which human telomerase catalytic subunit is ectopically expressed result in production of a tumorigenic epithelial cell. For example, the DNA of (b) may be a cDNA which encodes the mutant H-ras oncogene product and the DNA of (c) may be a cDNA which encodes the SV40 large T antigen oncogene product.

One type of DNA introduced into the normal cells in one embodiment of the method of the present invention is DNA encoding the telomerase catalytic subunit of a telomerase holoenzyme. The DNA can be genomic DNA or cDNA and can be from a wide variety of organisms in which it occurs naturally (e.g., human, mouse, pig, rat, dog, monkey), provided that, when it is expressed or functions in glandular epithelial cells, it produces a product which has substantially the same function as does (human) telomerase catalytic subunit. Alternatively, DNA encoding telomerase catalytic subunit can be produced using recombinant DNA methods or can be chemically synthesized. As used herein, the term "DNA encoding telomerase catalytic subunit" encompasses DNA obtained from or produced by any of these sources or methods. In one embodiment of the present invention, the DNA encodes the human telomerase catalytic subunit and, in a specific embodiment, is hTERT. (Nakamura and Cech, *Cell* 92: 587-590, 1998, Meyerson et al., *Cell* 90: 785-795, 1997). Alternatively, exogenous DNA that does not itself encode telomerase catalytic subunit, but activates or enhances expression of an endogenous gene encoding the subunit is introduced into normal human somatic cells, in which it activates a "silent" endogenous gene encoding the catalytic subunit or enhances expression of the endogenous gene encoding the catalytic subunit already being expressed in the cell.

The second type of DNA introduced into the normal cells in the present method is DNA comprising at least one oncogene. The oncogene can be any oncogene which, when expressed or functional in normal human somatic cells in which telomerase catalytic subunit is ectopically expressed, results in the production of the tumorigenic cells upon culturing/propagation of the recipient normal human cell. Preferably, the oncogene(s) introduced into normal human somatic cells is an oncogene(s) characteristics (causative) of malignant human tumors. As a result, the tumorigenic cells produced contain an oncogene(s) present in naturally occurring human malignant or cancerous tumors and are useful in methods described herein such as methods of assessing the ability of a candidate agent to inactivate or inhibit the oncogene(s) or render tumor cells more vulnerable to other agents or forms of treatment, such as radiation or laser therapy.

As used herein, the term "DNA comprising an oncogene" encompasses DNA whose expression results in production of an oncoproduct, such as an oncoprotein, and DNA which itself functions as an oncogene, such as by inactivating a resident tumor suppressor gene or by activating a resident proto-oncogene. It encompasses DNA that comprises or encodes all of the types of oncogenes described herein. The oncogene can be, for example, H-ras and K-ras, her2-neu, RET, sis, (PDGF) N-myc, L-myc, c-myc, bcl-1, bcl-2, src, and its family of related genes, MDM2 and any oncogene found in human tumor cells. The oncogene can also be a viral oncogene, such as SV40 large T, polyoma middle T, human papillomavirus E6 and E7, and the Epstein-Barr virus, and hepatitis B virus and tumor suppressor genes such as: APC, DPC4, NF-1, NF-2, p53, RB, MTS1, WT1, BRCA1, BRCA2, VHL, and PTEN. Entire oncogenes or portions thereof sufficient to result in the production of tumorigenic cells can be used. One oncogene or a combination of two or more oncogenes, such as a combination of two or more of the oncogenes listed, can be co-expressed with ectopically expressed telomerase catalytic subunit to produce tumorigenic cells.

Alternatively, instead of, or in addition to the oncogene, a suppressor of a tumor suppressor gene, such as a suppressor/inhibitor of p53, may be used to transform cells. Such suppressors/inhibitors, without limitation, may include various forms of dominant negative form of the TS (tumor suppressor) gene, antisense oligos, and various RNAi constructs (siRNA, short hairpin RNA etc.), etc.

Furthermore, in certain embodiments, additional genes such as SV40 small t antigens may be introduced into the target cell.

More than one DNA encoding an oncogene or TS gene suppressor can be used in the present method to produce tumorigenic cells. In the embodiments in which two or more oncogene-encoding DNAs are introduced, the DNAs encode oncogenes which function in biochemically distinct manners from one another. For example, each DNA can encode an oncogene that functions in a different biochemical (e.g., signaling) pathway. That is, for example, if two oncogene-encoding DNAs are used, each encodes or activates/enhances expression of an oncogene which functions in a distinct pathway. Any number of oncogene-encoding DNAs can be introduced into normal human somatic cells in which telomerase is ectopically expressed in order to render them tumorigenic. For example, in some instances it is desirable to introduce three, four, five, six or even more oncogene-encoding DNAs. The DNAs can each function in/affect a different signaling pathway or more than one can function in/affect a common pathway.

The two types of DNA introduced in the present method can be obtained from a variety of sources. For example, they can be cloned DNA, DNA obtained from a source in which they occur in nature or DNA produced by synthetic or recombinant DNA methods. They can be cDNA or genomic DNA. They can be introduced into the normal human somatic cells by a variety of techniques, such as by means of an appropriate vector (e.g., a retrovirus, such as an amphotropic retrovirus; an adenovirus vector; lentivirus); calcium phosphate-mediated transfection; lipofection; microinjection; microparticle bombardment; RNA transfection; naked DNA injection or electroporation). The resulting normal human somatic cells contain exogenous DNA encoding telomerase catalytic subunit and exogenous DNA comprising at least one oncogene; expression and/or function of the DNAs results in production of tumorigenic human somatic cells from the parental normal cells. Progeny of such cells are tumorigenic.

In one embodiment, the tumorigenic primary glandular epithelial cell (e.g. BPEC) forms tumors in immuno-compromised mice into which it is introduced, and the tumors formed are invasive and/or metastatic in the mice.

In one embodiment, the invention relates to a tumorigenic primary glandular epithelial cell (e.g. BPEC) produced by introducing into the subject normal primary glandular epithelial cells exogenous DNA comprising: (a) DNA encoding (human) telomerase catalytic subunit; (b) DNA encoding an oncogene (or TS gene suppressor) which functions in a first signaling pathway; and (c) DNA encoding an oncogene (or TS gene suppressor) which functions in a second signaling pathway, wherein the first and the second signaling pathways are not the same and the DNA of (a), the DNA of (b) and the DNA or (c) are stably incorporated into and stably expressed in the subject normal epithelial cell and progeny thereof. The exogenous DNA may be incorporated into genomic DNA of the cells.

In a preferred embodiment, the DNA of (a) is cDNA which encodes hTERT; the DNA of (b) is cDNA that encodes an oncogene that functions in the same signaling pathway as does the ras oncogene product and the DNA of (c) is cDNA that encodes an oncogene that functions in the same signaling pathways as does the SV40 LT-encoded oncoprotein, wherein function of the oncogene encoded by the cDNA of (b) and the oncogene encoded by the cDNA of (c) in their respective signaling pathways in the normal human somatic cells in which human telomerase catalytic subunit is ectopically expressed results in production of tumorigenic primary glandular epithelial cells. For example, the DNA of (b) is cDNA which encodes the H-ras oncogene product and the DNA of (c) is cDNA which encodes the SV40 LT oncogene product (or HPV E6 and E7 products). Such cells may form tumors in immuno-compromised mice into which they are introduced, and the tumors formed may be non-invasive and non-metastatic in the mice.

In certain embodiments, the exogenous DNA additionally may comprise DNA that encodes at least one oncogene in addition to the DNA of (b) and the DNA of (c). Preferably, each additional oncogene encoded by the exogenous DNA functions in a distinct biochemical pathway from the biochemical pathways in which other oncogenes encoded by exogenous DNA expressed in the cell function.

In certain embodiments, the exogenous DNA of (b), the exogenous DNA of (c) or the exogenous DNA of (b) and (c) is DNA that comprises an oncogene characteristic of malignant human tumor cells that develop in humans.

In certain embodiments, the subject modified tumorigenic epithelial cells additionally comprise exogenous DNA whose expression and/or function causes metastasis and/or invasion of the cells in an animal into which they are introduced.

In a related aspect, the invention relates to a method of producing such tumorigenic primary glandular epithelial cells (e.g. BPEC) from the corresponding subject normal primary glandular epithelial cells (e.g. BPEC), comprising introducing into such normal epithelial cells exogenous DNA which, when expressed in the normal epithelial cells, transforms the normal epithelial cells into tumorigenic epithelial cells which grow in an anchorage-independent manner in semi-solid medium and form tumors in immuno-compromised mice into which they are introduced. The invention also contemplates a tumorigenic mammalian glandular epithelial cell produced by such methods.

In one embodiment, at least about 75%, about 85%, or about 90% of such tumorigenic cells are CD44$^+$, ESA$^+$ and CD24$^±$, and there is essentially no vimentin expression in such cells. However, upon injection of sufficient amount of such tumorigenic cells into immuno-compromised mice, tumor cells isolated from these xenografted animals give rise to a mixed population of tumor cells with mixed expression of CD44, CD24, ESA, vimentin, E-cadherin, or keratin 18.

In other embodiment, such xenograft tumors arising from the injected tumorigenic cells form glandular structures similar to those seen in human tumors. In other embodiments, such xenograft tumors arising from the injected tumorigenic cells are invasive into adjacent tissues, such as skeletal muscle. In one embodiment, xenograft tumors arising from the injected tumorigenic cells are metastatic, for example, to lung in >95% of the host xenograft animals.

In one embodiment, xenograft tumors arising from the injected tumorigenic cells express progesterone, and/or estrogen receptors, and are responsive to treatment with progesterone and/or estrogen.

In one embodiment, xenograft tumors arising from the injected tumorigenic cells may express testosterone, and are responsive to treatment with testosterone.

These tumorigenic cells derived from the subject primary glandular epithelial cells (e.g. BPEC), or the tumor model established therefrom, may be used in in vitro and/or in vivo methods of identifying an agent or gene or protein or any other treatment that targets tumor cells or their environment locally or systemically which reduces proliferation of tumorigenic epithelial cells. Such method comprises propagating tumorigenic epithelial cells of the invention in the presence of an agent or drug candidate to be assessed for its ability to reduce proliferation of the tumorigenic epithelial cell, under conditions appropriate for the agent to enter the cells; determining the extent to which proliferation of the tumorigenic epithelial cells occurs in the presence of the agent to be assessed and comparing the extent determined with the extent to which proliferation of the tumorigenic epithelial cells occurs under the same conditions, but in the absence of the agent to be assessed, wherein if proliferation occurs to a lesser extent in the presence of the agent to be assessed than in its absence, the agent to be assessed is an agent which reduces proliferation of tumorigenic epithelial cells.

In a related aspect, such tumorigenic epithelial cells may be used in an in vitro method of assessing the ability of an agent or treatment which inhibits proliferation and invasive properties of tumorigenic epithelial cells to assess its ability to inhibit proliferation of such cells to a greater extent than it inhibits proliferation of parental normal epithelial cells, comprising contacting the subject tumorigenic epithelial cells with the candidate agent; determining the extent to which proliferation of the tumorigenic epithelial cells occurs in the presence of the agent and comparing the extent determined with the extent to which proliferation of corresponding normal epithelial cells cultured under the same conditions occurs, wherein if proliferation of tumorigenic epithelial cells occurs to a lesser extent than does proliferation of corresponding normal epithelial cells, the agent inhibits proliferation of tumorigenic epithelial cells to a greater extent than it inhibits proliferation of corresponding normal epithelial cells.

In one embodiment, the tumorigenic cells form a tumor in an immunocompromised xenograft animal model. In one embodiment, the tumor is invasive and/or metastatic.

In tumor cell lines that are cultured in standard tissue culture media, the frequency of tumor initiating cells (or tumor stem cells) that are maintained in the cultured cell population is extremely low (usually less than one tumor stem cell among a million cells in the culture plate). Thus a typical culture plate that is used in routine anti-cancer drug screens will contain 1 million cells at a maximum (in most cases much less than that). An agent that kills >90% of the cells in a plate is typically scored as a positive "hit". Therefore, an agent that has no effect on tumor stem cells would routinely score as positive hit in the current drug screens. In many cases such agents do not turn out to have any effect when tested against tumor in mice, since unlike tissue culture failing to kill tumor stem cells will result in treatment failure. In fact, an NIH review (http://cancernet.nci.nih.gov/newscenter/benchmarks-vol2-issue3/page2) showed that from 1990 through October 1998, 70,702 compounds were selected for screening by Access and Information Group; 6,452 of those showed potential activity 1,546 of those were chosen by the Biological Evaluation Committee for testing in mice; 79 of those were effective in killing or slowing the growth of human tumor cells, and 10 were approved by the DDG for human testing after further toxicity studies in animals. Thus only about one to two out of every 10,000 drugs screened in human tumor lines is tested in human trials. Typically, only 20 percent of those tested in early human trials (phase I) are finally approved by FDA for commercial use.

The data clearly demonstrate that routine tissue culture screens have a tremendous "false-positive" rate. In contrast to routine tumor cell line cultures, the combination of tumor cell lines and culture media described herein provides about 10,000-fold enrichment in the frequency of tumor initiating stem cells in the culture plate. Thus, the high frequency of tumor initiating cells in the medium described herein solves a major obstacle in drug discovery by potentially reducing the "false-positive" rates in anti-cancer drug screens.

In another related aspect, such tumorigenic epithelial cells may be used in an in vivo method of identifying an agent, treatment or cellular or genetic modification which reduces the proliferation, invasion or metastasis of tumorigenic epithelial cells, comprising introducing the subject tumorigenic epithelial cells into an appropriate animal, in which such cells proliferate and result in formation of a tumor; administering an agent to be assessed for its ability to reduce proliferation of tumorigenic epithelial cells to the animal, referred to as a test animal, and determining whether proliferation of tumor cells is less in the test animal than in a control animal, in which introduction of such cells resulted in formation of a tumor and to which the agent was not administered, wherein if proliferation of tumorigenic epithelial cells is less in the test animal than in the control animal, the agent is an agent which reduces proliferation of tumorigenic epithelial cells in vivo.

The subject tumorigenic epithelial cells can also be used in a method of identifying an agent which selectively inhibits the ras oncogene product, comprising: a) culturing tumorigenic epithelial cells, referred to as a first variety of tumorigenic cells, produced by introducing into genomic DNA of the subject normal epithelial cells DNA comprising: (1) cDNA which encodes human telomerase catalytic subunit; (2) cDNA which encodes the H-ras oncogene product and (3) cDNA which encodes the SV40 LT oncogene product, thereby transforming the subject normal epithelial cells into tumorigenic human somatic cells, with an agent to be assessed for its ability to inhibit the ras oncogene product; b) culturing tumorigenic epithelial cells, referred to as a second variety of tumorigenic cells, produced by introducing into genomic DNA of normal somatic cells DNA comprising: (1) cDNA which encodes telomerase catalytic subunit; (2) cDNA which encodes an oncogene other than H-ras oncogene product or the SV40 large T antigen oncogene product and (3) cDNA which encodes the SV40 large T antigen oncogene product with the agent to be assessed for its ability to inhibit the ras oncogene product; c) determining the extent to which the agent inhibits proliferation of the first variety of tumorigenic cells and the second variety of tumorigenic cells; d) comparing the extent to which the agent inhibits proliferation of the first variety of tumorigenic cells with the extent to which the agent inhibits proliferation of the second variety of tumorigenic cells, wherein if proliferation of the first variety of tumorigenic cells is inhibited and proliferation of the second variety of tumorigenic cells is not inhibited, the agent is an agent which selectively inhibits the H-ras oncogene product.

The subject tumorigenic epithelial cells can also be used in a method of identifying a gene whose expression in a tumorigenic cell is related to/involved in metastasis of such cells in vivo, comprising: a) introducing a candidate gene into the subject tumorigenic epithelial cells, thereby producing modified tumorigenic epithelial cells; b) introducing the modified tumorigenic epithelial cells into an animal; c) maintaining the animal into which the modified tumorigenic epithelial cells were introduced under conditions appropriate for formation of tumors and metastasis to occur; and d) determining whether metastasis of the modified tumorigenic epithelial cells occurs, wherein, if metastasis occurs, the candidate gene is a gene whose expression in a tumorigenic cell is related to/involved in metastasis of such cells in vivo.

The subject tumorigenic epithelial cells can also be used in a method of identifying a gene whose expression in a tumorigenic cell is related to/involved in invasiveness of such cells in vivo, comprising: a) introducing a candidate gene into the subject tumorigenic epithelial cells, thereby producing modified tumorigenic epithelial cell; b) introducing the modified tumorigenic epithelial cells into an animal; c) maintaining the animal into which the modified tumorigenic epithelial cells were introduced under conditions appropriate for formation of tumors and invasion of the tumor into tissues of the animal to occur; and d) determining whether invasion of the modified tumorigenic epithelial cells occurs, wherein, if invasion occurs, the candidate gene is a gene whose expression in a tumorigenic cell is related to/involved in invasion of such cells in vivo.

The subject tumorigenic epithelial cells can also be used in a method of identifying a gene product which is expressed in tumor cells but not in normal cells of the same type or a gene product which is not expressed in tumor cells but is expressed in normal cells, comprising analyzing the subject tumorigenic epithelial cells expressing exogenous DNA comprising (a) DNA encoding subunit telomerase catalytic; (b) DNA encoding a first oncogene; and (c) DNA encoding a second, distinct oncogene for gene products; analyzing normal parental epithelial cells of which the tumorigenic cells are a variant for gene products and comparing gene products produced by the tumorigenic cells and the normal parental cells, whereby a gene product which is expressed in tumorigenic cells but not in normal parental cells or a gene product which is not expressed in tumorigenic cells but is expressed in normal parental cells is identified, thereby identifying a gene product which is expressed in tumor cells but not in normal cells of the same type or a gene product which is not expressed in tumorigenic cells but is expressed in normal cells of the same type.

The invention also provides an in vitro method of identifying an agent which inhibits or negatively affects one or more characteristics of tumorigenic cells, the characteristics including: cell viability, growth, differentiation, proliferation, invasiveness, ability to metastasize, anchorage-independent growth, angiogenesis, and response to drugs, hormones, peptides, lipids, nucleic acids, radiation, gene expression modifiers, other cells (immune, stromal etc.) the method comprising: (1) contacting tumorigenic cells of the subject invention as described above with a candidate agent to be assessed for its ability to inhibit or negatively affect the one or more characteristics of the tumorigenic cells, under conditions appropriate for the agent to enter cells; (2) determining the extent to which the characteristics is inhibited or negatively affected in the presence of the candidate agent to be assessed; and, (3) comparing the extent determined with the characteristics of the tumorigenic cells under the same conditions, but in the absence of the candidate agent to be assessed, wherein if the characteristics is substantially inhibited or negatively affected in the presence of the candidate agent to be assessed than in its absence, the candidate agent to be assessed is an agent which inhibits or negatively affects one or more the characteristics of the tumorigenic cells. In one embodiment, the one or more characteristics is inhibited or negatively affected by at least about 20%, 40%, 50%, 60%, 70%, 80%, 90%, or 100% in the presence of the candidate agent to be assessed than in its absence. In one embodiment, the method further comprises using the identified agent as a lead molecule to identify additional agents that more potently inhibits or negatively affects the characteristics.

The invention also provides a pharmaceutical composition comprising an effective amount of the agent so identified, and one or more pharmaceutically acceptable excipient or salt.

The invention also provides an in vitro method of identifying an agent which enhances or positively affects one or more characteristics of tumorigenic cells, the characteristics including: differentiation, apoptosis, sensitivity to chemotherapy/radiotherapy, or senescence, the method comprising: (1) contacting tumorigenic cells of the subject invention with a candidate agent to be assessed for its ability to enhance or positively affect the one or more characteristics of the tumorigenic cells, under conditions appropriate for the agent to enter cells; (2) determining the extent to which the characteristics is enhanced or positively affected in the presence of the candidate agent to be assessed; and, (3) comparing the extent determined with the characteristics of the tumorigenic cells under the same conditions, but in the absence of the candidate agent to be assessed, wherein if the characteristics is substantially enhanced or positively affected in the presence of the candidate agent to be assessed than in its absence, the candidate agent to be assessed is an agent which enhances or positively affects one or more the characteristics of the tumorigenic cells.

The invention also provides an in vivo method of identifying an agent which inhibits or negatively affects one or more characteristics of tumor generated by tumorigenic cells in a tumor model, the characteristics including: tumor stem cell frequency, tumor growth, tumor differentiation invasiveness, metastasis, or angiogenesis, the method comprising:

(1) introducing to test animals tumorigenic cells of the subject invention to generate tumors; (2) administering a candidate agent to the test animals to assess its ability to inhibit or negatively affect the one or more characteristics of the tumor; and, (3) determining the extent to which the characteristics is inhibited or negatively affected in the presence of the candidate agent; wherein if the characteristics is substantially inhibited or negatively affected in the presence of the candidate agent to be assessed than in its absence, the candidate agent to be assessed is an agent which inhibits or negatively affects one or more the characteristics of the tumor.

Another aspect of the invention provides an in vivo method of determining the effect of at least two candidate agents which potentially affect one or more characteristics of tumor generated by tumorigenic cells in a tumor model, the characteristics including: tumor growth, invasiveness, metastasis, or angiogenesis, the method comprising: (a) associating each candidate agent with a unique detectable marker, wherein presence of the detectable marker substantially matches the presence of the candidate agent; (b) dividing tumorigenic cells of claim 14 into separate groups according to the number of candidate agents to be tested; (c) contacting one group of tumorigenic cells with one candidate agent; (d) introducing to test animals tumorigenic cells of step (c) to generate tumors; (e) determining the extent to which the one or more characteristics is affected in the presence of the candidate agent; (f) determining the presence of detectable markers; wherein the presence of a candidate agent is determined by the presence of its associated detectable marker, and wherein if the one or more characteristics is substantially affected in the presence of the candidate agent than in its absence, the candidate agent is an agent which affects one or more the characteristics of the tumor. In certain embodiments, each group of tumorigenic cells comprises 100 or less tumorigenic cells. In certain embodiments, the detectable marker is a DNA bar code. In certain embodiments, the detectable marker is a fluorescent marker. In certain embodiments, the agent is an RNAi molecule. In certain embodiments, the agent is an siRNA molecule. In certain embodiments, the agent is a chemical compound.

In a typical mouse xenograft experiment 1 to 10 million cells are injected into an animal model (such as mouse) in order to form a tumor. In contrast, our system allows tumor formation using as low as 10 cells. Therefore, instead of the traditional one reagent (or one condition) per animal model, our system can screen a plurality of reagents or conditions an single animal model. For example, each batch, comprising about 10-100 cells, may be treated with a biological agent or a chemical agent. Exemplary biological agents can be an RNAi molecule, an siRNA construct, or a genetic inhibitor that targets a particular gene; exemplary chemical agent may be a small molecule compound. Each candidate agent should be associated with a unique detectable marker (such as a DNA bar code), so that the presence of the detectable marker substantially matches the presence of the candidate agent. Multiple batches of cells, each treated with a different candidate agent, can then be pooled and injected into a single animal model. Thus multiple candidate agents may be screened in a single xenograft experiment, greatly increasing the efficiency of drug screening and making in vivo high throughput screening possible.

Techniques of DNA bar code tagging of chemical libraries is known in the art. The construction of libraries of compounds which carry a unique DNA sequence as a "bar-code" for each library member can facilitate the identification of binding molecules and to speed-up and miniaturize screening procedures. In principle, very large libraries of compounds can be panned with the target protein of interest immobilized on a suitable support, followed by the identification of the preferentially enriched compounds by procedures which may involve PCR amplification of the DNA codes, sequencing, and/or hybridization to a DNA microarray. DNA-encoded libraries of small organic molecules also facilitate the construction of large, encoded self-assembling chemical libraries for the identification of high-affinity binders to protein targets. For example, Dumelin et al. (Bioconjugate Chem., 17 (2), 366-370, 2006; the teaching of which is incorporated herein) describes the construction a library of 477 chemical compounds, coupled to 48mer-oligonucleotides, each containing a unique six-base sequence serving as "bar-code" for the identification of the chemical moiety. The functionality of the library was confirmed by selection and amplification of both high- and low-affinity binding molecules specific to streptavidin. Gartner et al. (2004 Sep. 10; 305(5690):1601-5; the teaching of which is incorporated herein) describes using multistep DNA-templated organic synthesis to translate libraries of DNA sequences, each containing three "codons," into libraries of sequence-programmed synthetic small-molecule macrocycles. The resulting DNA-macrocycle conjugates were subjected to in vitro selections for protein affinity. The identity of a single macrocycle possessing known target protein affinity was inferred through the sequence of the amplified DNA template surviving the selection. Brummelkamp et al. (Nature Chemical Biology 2, 202-206 (2006); the teaching of which is incorporated herein) describes the application of a large-scale RNA interference-based short hairpin RNA (shRNA) barcode screen to gain insight in the mechanism of action of nutlin-3. Noren and Noren (Methods. 2001 February; 23(2): 169-78; the teaching of which is incorporated herein) teaches a method for construction of high-complexity ($\geq 10^9$ independent clones) random peptide libraries. Scheuermann et al. (J Biotechnol. 2006 Dec. 1; 126(4):568-81. Epub 2006 Jun. 9; the teaching of which is incorporated herein) summarizes various techniques of DNA-encoded chemical libraries. Takahashi et al. (Trends Biochem Sci. 2003 March; 28(3): 159-65; the teaching of which is incorporated herein) describes libraries in which mRNA molecules are covalently attached to the peptide or protein they encode. These mRNA-protein fusions enable in vitro selection of peptide and protein libraries of >$10^{13}$ different sequences.

The invention also provides a method of identifying a gene whose expression in a tumorigenic cell is related to/involved in metastasis of such cells in vivo, comprising: (1) introducing a candidate gene into tumorigenic cells of the subject invention, thereby producing modified tumorigenic cells; (2) introducing the modified tumorigenic cells to test animals; (3) maintaining the test animals under conditions appropriate for formation of tumors and metastasis to occur; and (4) determining whether metastasis of the modified tumorigenic cells occurs, wherein, if metastasis occurs, the candidate gene is a gene whose expression in a tumorigenic cell is related to/involved in metastasis of such cells in vivo.

The invention also provides a method of identifying a gene whose expression in a tumorigenic cell is related to/involved in invasion of such cells in vivo, comprising: (1) introducing a candidate gene into tumorigenic cells of the subject invention, thereby producing modified tumorigenic cells; (2) introducing the modified tumorigenic cells to test animals; (3) maintaining the test animals under conditions appropriate for formation of tumors and invasion to occur; and (4) determining whether invasion of the modified tumorigenic cells occurs, wherein, if invasion occurs, the candidate gene is a gene whose expression in a tumorigenic cell is related to/involved in invasion of such cells in vivo.

The invention also provides a method of identifying a gene product which is expressed in tumor cells but not in normal or non-tumorigenic cells of the same type, or a gene product which is not expressed in tumor cells but is expressed in normal or non-tumorigenic cells of the same type, comprising: (1) analyzing tumorigenic cells of the subject invention; (2) analyzing normal parental cells of which the tumorigenic cells are a variant for gene products; and, (3) comparing gene products produced by the tumorigenic cells and the normal parental cells, whereby a gene product which is expressed in tumorigenic cells but not in normal parental cells, or a gene product which is not expressed in tumorigenic cells but is expressed in normal parental cells is identified, thereby identifying a gene product which is expressed in tumor cells but not in normal cells of the same type, or a gene product which is not expressed in tumorigenic cells but is expressed in normal cells of the same type.

The invention also contemplates equivalent embodiments in the cancer stem cells, all genetically and otherwise modified derivatives, and metastatic derivatives isolated/purified using the methods and media of the instant invention.

IV. Isolation of Mammary Epithelial Cells:

One embodiment of the invention provides methods to isolate a specific type of glandular epithelial cells—mammary epithelial cells, especially those exhibiting luminal epithelial cell phenotype (e.g. BPEC), although similar procedures may be used for the isolation of other glandular epithelial cells from other tissues.

Taylor-Papadimitriou and Stampfer (Culture of Human Mammary Epithelial Cells, in *Culture of Epithelial Cells*, pp. 107-133, R. Ian Freshney, Ed., Wiley-Liss, Inc., New York, N.Y.) described various procedures and reagents useful for isolation and culturing of human mammary epithelial cells, the entire content of which is incorporated herein by reference.

One source of mammary epithelial cells comes from milk. Early lactation and post-weaning milks give the highest yield of epithelial cells. In a typical protocol for milk collection, 2-7 days postpartum milk (about 5-20 mL per patient) is collected by expressing milks manually into a sterile container. The milks are pooled and diluted 1:1 with RPMI 1640 medium to facilitate centrifugation at 600-1000 g for about 20 minutes. The supernatant is carefully removed without disrupting the cell pellet, which is then washed 2-4 times with RPMI 1640 with 5% FCS until supernatant is not turbid. Resuspend the packed cell volume in growth medium and plate 50 µL packed cells in 5-cm dishes in 6 mL the subject (primary) growth medium. Incubate at 37° C. in 5% $CO_2$. Follow the rest of the subject methods to isolate/subculture glandular epithelial cells.

In an alternative embodiment, mammary epithelial cells can be isolated from reduction mammoplasty tissue, or other surgical procedures. An enzymatic dissociation technique, (modified from Hallowes et al., Cancer Res. 37: 2492-2505, 1977) coupled with crude dissection, yields large amount of pure epithelial tissues from each individual donor.

Human mammary tissue can be obtained as discarded tissues from mammoplasty surgery. Such material (preferably freshly dissected within 1-2 hours, no more than 5 hours) is placed in sterile containers with sterile buffer or Ham's F-12 medium with insulin, antibiotics, and 10% FBS (e.g. 10 µg/mL insulin, 100 U/mL penicillin, 100 µg/mL streptomycin, 50 U/mL polymixin B, and 5 µg/mL fungizone in Ham's F12 medium). If not used immediately as above, tissues can be stored at 4° C. for up to 72 hours.

Transfer cut pieces of the tissue into a Petri dish. Separate the epithelial areas (appear as embedded white strands) from the stromal matrix and the grossly fatty material in sterile 150 mm Petri dishes using a combination of sterile scalpel, forceps, and scissors. Then transfer the minced epithelium-containing tissue into a conical centrifuge tube (50 or 15 mL) with the tissue making up no greater than ⅓ of the volume of the tube. Bring the tube to full volume with tissue digesting medium (final concentration of 150 U/mL collagenase, 100 U/mL hyaluronidase, and 10% FBS in tissue mix medium), leaving only a small air space to allow for gentle mixing during rotation overnight at 37° C. Centrifuge the tubes at 600 g for 5 minutes. Discard the supernatant fat and medium. Optionally, dilute a small volume of the pellet in medium to check for degree of digestion. Digestion is complete when microscopic examination shows clumps of cells (organoids) with ductal, alveolar, or ductal-alveolar structures free from attached stroma. If digestion is incomplete, repeat the digestion for another 4-12 hours until completion. When digestion is complete, centrifuge tubes at 600 g for 5 minutes, carefully aspirate supernatant, and resuspend pellet in tissue mix medium (about 15 mg/50-mL, 5 mL/15-mL). Optionally, filter the mixture, a few milliliters a time, through a sterile 150 µL pore-size filter, and wash the organoids left on the filter a few times with 2-3 mL of medium. Flip the filter and wash the organoids off into a sterile container to collect the 150 µL organoid pool, which contains mostly ductal structures. The filtering step is often not necessary in many cases.

Repeat the same procedure using 95 µL pore-size filter to collect 95 µL organoid pool, which contains mostly smaller ductal and alveolar structures. The filtrate contains mostly small epithelial clumps and stromal cells. Transfer the 150 µL and the 95 µL organoids collections, and the final filtrate to 50-mL tubes and centrifuge at 600 g for 5 minutes. Aspirate the supernatant, resuspend the pellets in each tube by adding 1 mL medium for each 0.1 mL of packed pellet. Transfer the resuspended materials, drop by drop, onto culture surfaces to cover different areas of the dish. Then add the subject primary medium and follow the rest of the protocol.

In yet another embodiment, the tissues are minced down to fragments about 1-2 mm in size, and digested with collagenase in Hank's buffered saline solution (HBSS) at 37° C. overnight. The resulting mixture of organoids that contain organoids which are separated from single cells that are mostly stromal and myoepithelial by three consecutive rounds of centrifugation (5 min. at 200×g, 100× g and 20× g). The pellets and supernatants are collected in six fractions (200 g, 100 g and 20 g) and filtered through a 75 µm mesh, and subsequently a 45 µm mesh. All filtered fractions are plated in Primaria™ tissue culture dishes (or similar mixed-charged surfaces) in the subject culture medium. The cells are grown for 7 days during which medium is changed every day. On day 8 and 9 plates are trypsinized with 0.025% trypsin removing all stromal cells. Epithelial cells are harvested with 0.15% trypsin and transferred to new Primaria™ plates in the subject medium. After one week, cells are transferred to PWI medium and subcultured in the same medium.

In some embodiments, the cells are plated at a density of at least $0.5 \times 10^3$ cells/$cm^2$ up to about $10^6$ cells/$cm^2$. In some embodiments the cells are plated at a density of at least $10^4$ cells/$cm^2$, e.g., between $1-2 \times 10^4$ cells/$cm^2$ or between 1-5×

$10^4$ cells/cm$^2$ In some embodiments the cells are plated at between $0.5\times10^3$ cell/cm$^2$ and $5\times10^5$ cells/cm$^2$. It will be appreciated that optimal density may vary for different cell types. The tissue culture medium may be changed at varying intervals, e.g., at intervals of between 12 and 72 hours. In some embodiments, the tissue culture medium is changed relatively frequently, e.g., every 12-24 hours. In some embodiments the tissue culture medium is changed at longer intervals, e.g., every 24-72 hours. The cells may be transferred or passaged at varying intervals, e.g., between 3 days to 4 weeks, e.g., on average once a week, once every two weeks, etc. The afore-mentioned embodiments are exemplary and are not intended to limit the invention.

In a specific embodiment, small organoids from breast tissues, rather than larger ones, are used as cell sources, since they tend to yield better results than larger ones. While not wishing to be bound by any particular theory, it is possible that smaller organoids come from smaller lobules of the breast tissues, from where about 99% of breast cancers originate, instead of from larger ducts. It is also possible that the smaller organoids from small lobules are biologically distinct from the larger organoids from large ducts.

Fibroblast cell growth is generally not a problem since the subject medium does not support fibroblast cell growth effectively. However, if fibroblast growth is observed, especially in the 150 µL and 95 µL organoid fraction, fibroblasts can be removed by differential trypsinization as follows. When the epithelial patches are large, aspirate medium, wash once with saline-typsin-versene (STV), and then add 0.5 mL STV per 60-mm dish. Leave STV on cells at room temperature for about 1-2 minutes, with continued observation under the microscope. Knock the dish gently. When the fibroblasts are observed to detach while the epithelial cells remain adherent, remove the STV. Wash cells 2-3 times with sterile PBS and refeed with fresh growth medium.

The isolated mammary epithelial cells can be further characterized by immunostaining using marker protein antibodies. This may be necessary since the breast is a complex tissue with many different cell types whose lineages are not well defined. For example, fibroblast from stromal tissues may be present in the culture. In addition, one or both of the major breast epithelial cells, luminal and basal epithelial cells, could be proliferating in the culture. All these could be further complicated by phenotypic modulation that occurs in culture.

Fortunately, many monoclonal antibodies against various immunological markers have been development over the years to at least partially solve these problems. Such markers can be used not only to define specific phenotypes in vivo, but also to identify phenotypes of cultured cells. Among them, the expression profiles of various epithelial keratins have been extremely useful, since the expression profiles are maintained in culture as compared to in vivo expression profiles.

Specifically, all luminal epithelial cells express keratin 8 and 18 and most express 19, whereas all the basal cells express keratins 5 and 14, and do not express keratins 8 and 18. Keratin 7 is expressed in both cell types throughout the gland and keratin 19 and 14 are also expressed by both cell types in the large ducts, but not in the TDLU (terminal ductal lobular units). Some of the keratin antibodies are listed below in Table IV, which also lists antibodies directed to a polymorphic epithelial mucin (PEM) that is expressed by luminal epithelial cells (Burchell et al., 1983; Gendler et al., 1988), to smooth muscle actin, and to CALLA (common leukocytic leukemia antigen), which is specifically expressed by myoepithelial cells.

TABLE IV

Monoclonal Ab Useful for Characterizing Cultured Mammary Epithelial Cells

| Antibody | Target Antigen | Reference |
|---|---|---|
| HMFG-1 | Polymorphic | Burchell et al., J. Immunol. 131: 508-513, 1983. |
| HMFG-2 | Epithelial mucin | Burchell et al., J. Immunol. 131: 508-513, 1983. |
| SM-3 | (PEM) | Burchell et al., Cancer Res. 47: 5476-5482, 1987. |
| BA16 | Keratin 19 | Bartek et al., J. Cell. Sci. 75: 17-33, 1985. |
| BA17 | Keratin 19 | Bartek et al., J. Cell. Sci. 75: 17-33, 1985. |
| CO4 | Keratin 18 | Bartek et al., in Abelev (ed.): "Monoclonal Antibodies to Tumor Associated Antigens and Their Clinical Application." Budapest: Akademai Kiado. |
| DA7 | Keratin 18 | Laueroval et al., Hybridoma 7: 495-504, 1988. |
| LE61 | Keratin 18 | Lane, J. Cell. Biol. 92: 665-673, 1982. |
| LL001 | Keratin 14 | Taylor-Papadimitriou and Lane, in Neville MC Daniel CW (eds.) The Mammary Gland." New York: Plenum Publishing Corp. pp. 181-215. |
| 12C8-1 | Keratin 14 | Dairkee et al., Proc. Natl., Acad. Sci. U.S.A. 82: 7409-13, 1985. |
| M20 | Keratin 8 | Van Muijan et al., Exp. Cell. Res. 171: 331-345, 1987. |
| C-15 | Keratin 8 | Bartek, et al., in Lapis K, Eckhardt S (eds.) Molecular Biology and Differentiation of Cancer Cells." Vol. 2, Basel: Karger; Budapest: Akademai Kiado. |
| RCK 105 | Keratin 7 | Ramaekers et al., Exp. Cell. Res. 170: 235-249, 1987. |
| C-18 | Keratin 7 | Bartek, et al., in Lapis K, Eckhardt S (eds.) Molecular Biology and Differentiation of Cancer Cells." Vol. 2, Basel: Karger; Budapest: Akademai Kiado. |
| V9 | Vimentin | Osborn et al., Eu. J. Cell. Biol. 34: 137-143, 1984. |
| FN-3 | Fibronectin | Keen et al, Mol. Biol. Med. 2: 15-27, 1984. |
| A12 | CALLA | Gusterson et al., J. Natl. Cancer Inst. 77: 343-349, 1986. |
| SM1 | α-actin | Skalli et al., J. Cell. Biol. 103: 2787-2796, 1986; Gugliotta et al., J. Histochem. Cytochem. 36: 659-663, 1988. |

The mammary epithelial cells isolated using the subject methods predominantly differentiate into epithelial cells of luminal phenotype in 3-D culture. These cells express typical markers of luminal epithelial cells, as revealed by using the markers described above, and they can be cultured long-term in vitro without losing differentiation potential. Thus these cells are of the characteristics of true breast progenitor epithelial cells (BPEC). The subject BPEC cells can be used to establish a tumor model that recapitulates many aspects of breast ductal carcinoma.

U.S. Patent Application Ser. No. 60/569,005 describes a human mammary breast cancer model HMLER, in which isolated human epithelial cells (usually of basal but not luminal phenotype) are transformed (e.g., with retroviral vectors) with telomerase (e.g., hTERT), SV40 early region genes (Large T and small t antigens), and a ras pathway gene (e.g., H-ras). The HMLER cells, when injected into immunosuppressed mice, are tumorigenic.

Tumors derived from human mammary epithelial cells (HMECs) had an undifferentiated morphology with focal squamous differentiation, were minimally invasive, exhibited little stromal recruitment, and expressed basal cytokeratins (CK14). In contrast, a novel epithelial precursor cell developed ductal adenocarcinomas that were highly invasive, induced stromal desmoplasia, expressed luminal cytokeratins (CK18) and progesterone receptor. Moreover, these tumors were hormone responsive, highly tumorigenic even at 10 cells per injection, and micrometastatic to lung in >80% of mice in 10 weeks after injection.

These results demonstrate the importance of the starting target cell type in determining morphological and biological behavior in epithelial tumors and provide a new genetically defined human breast xenograft cancer model with that mimics many features reminiscent of the most common type of breast cancer.

The HMLER model recapitulates a rare form of human breast cancer of either undifferentiated or squamous differentiation. However, there is no ductal differentiation in the HMLER model, and both estrogen receptor and progesterone receptor expression are negative (i.e. the tumor does not respond to estrogen and progesterone). The tumor is also non-metastatic, with minimal local invasion and stromal recruitment. Thus the HMLER model roughly corresponds to the human basaloid/undifferentiated/squamous carcinomas, partly because the human mammary epithelial cells used to establish the HMLER model may not be precursor cells giving rise to ductal carcinoma.

There are at least 17 histological types of human breast cancers, the majority being invasive ductal carcinoma (about 80%), followed by invasive lobular carcinoma (about 10-15%). Histologically, the squamous type represents less than 1% of the human breast cancer.

The instant invention provides a method of isolating mammary epithelial progenitor cells which can grow long-term in the subject chemically-defined medium, and subsequently, under appropriate conditions, differentiate into ductal phenotype (BPEC) while maintaining its 3D polarized luminal cell phenotype.

The subject medium supports growth of isolated glandular epithelial cells, especially the BPEC cells in culture for at least about 4 weeks, 6 weeks, 10 weeks, 12 weeks, 14 weeks, 15 weeks or more without reaching senescence. This corresponds to at least about 15, 20, 25, 30, 35 or more population doubling (PD) without reaching senescence. Similarly isolated cells growing in other media typically reach senescence after about 3 weeks, or 3-15 weeks PD in culture.

The subject medium supports growth of isolated glandular epithelial cells in culture without elevated expression of p53 and p16, which are typically signs of growth under stressed conditions. In contrast, primary cells growing in MEGM medium of Clonetics express elevated levels of p53 and p16.

In addition, isolated BPECs grow in the subject media without expressing detectable levels of vimentin (fibroblast marker) and CK14 (basal epithelial marker). While in MEGM media, prominent CK14 and vimentin expression is observed.

In another aspect, cells that survive in the subject media can differentiate into epithelial cells of luminal phenotype, similar to that observed in ductal carcinoma, but different from those of myoepithelial cells or basal cells. See Table V below.

TABLE V

Expression Profiles of Various Breast Cells

| | CK18 & 19, Claudin4 | D10 | Smooth Muscle Actin (SMA) | p63 |
|---|---|---|---|---|
| Luminal Cells | + | − | − | − |
| Ductal Carcinoma | + | − | − | −/+ |
| Myoepithelial Cells | − | + | + | + |
| Basal Cells | − | + | − | + |

HMECs express basaloid markers p63 and CD10, and some low level luminal markers CK18. In 3D in vitro culture (cells growing on 100% gelled EHS and are overlaid with media with 2% EHS), HMECs differentiate into squamous cells and express squamous specific marker CK10. In contrast, BPECs cultured in 3D form ascini resembling a hollow ball, with polarized E-cadherin and 3-catenin expressions, indicating a luminal phenotype.

Using the methods as described in the U.S. Patent Application Ser. No. 60/569,005 the subject BPECs can be similarly transformed by telomerase (e.g. hTERT), SV40 early region (Large T and small t antigens), and a ras pathway gene (e.g. H-ras). The resulting cell line, BPLER, is also tumorigenic in immunosuppressed mice, but has fundamental difference with the HMLER model.

In one respect, the histology of tumors arising from BPLER is very similar, if not identical to human ductal breast carcinoma. There is prominent luminal marker CK18 expression in BPLER cells and tumors. There is also prominent expression of E-cadherin, a marker indicating polarization of cells. Morphology wise, BPLER xenografts form glandular structures similar to those seen in human tumors. BPLER xenografts into mammary fat pads are invasive into adjacent skeletal muscle, and cause a desmoplastic reaction. BPLER xenografts also express progesterone receptors based on immunohistological staining of xenograft tumor samples. In addition, BPLER tumor sizes respond to estrogen treatment, in that xenograft tumors weighed about 70-100% more in estrogen treated animals than in control animals. BPLER tumors spread within the breast tissue of mice, and the multifocal growth is consistent with lymphovascular invasion and spread of tumors.

According to the tumor stem cell model, tumor stem cells are $CD44^+$ $ESA^+$ $CD24^{low}$. The isolated $CD44^+$ $ESA^+$ $CD24^{low}$ BPECs does not express vimentin or keratin when cultured in the subject media. However, in 3D culture, such isolated BPECs can differentiate into cells of luminal phenotypes and are $CD44^+$, $keratin^+$, and $E-cadherin^+$. This demonstrates that the subject BPECs have maintained their ability to differentiate under appropriate conditions.

Upon transformation of the subject BPECs to generate tumorigenic BPLER, such cells express CD44, ESA, CD24, vimentin, keratin 18 at similar levels to BPECs. In xenograft tumors, the BPLER cells express E-cadherin and the characteristic keratin 18 marker, progesterone receptor, BER-Ep4, EMA (keratin $18^+$, E-cadherin$^+$, CD44$^{+/-}$, CD24$^{+/-}$, vimentin$^{+/-}$), representing a model closely resembling ductal carcinoma. Moreover, the stroma of the tumors express SMA similar to desmoplastic stroma of human tumors.

Another significant difference between BPLER and HMLER cells concerns the number of cells needed to be injected into immunosuppressed animals for tumor formation. As shown in Table VI below, as few as 1,000 BPLER cells injected into immunosuppressed mice are sufficient to induce xenograft tumor formation in about 40-50% of the injected animals, while between about 100,000 to 1,000,000 HMLER cells are needed to induce tumor formation in the same proportion of injected animals.

TABLE VI

Number of Cells Needed for Effective Tumorigenesis in Immunosuppressed Mice

| HMLER | | BPLER | |
|---|---|---|---|
| $1 \times 10^6$ | 7/9 | $1 \times 10^6$ | 9/9 |
| $1 \times 10^5$ | 2/9 | $1 \times 10^5$ | 9/9 |
| $1 \times 10^4$ | 0/9 | $1 \times 10^4$ | 9/9 |
| $1 \times 10^3$ | 0/9 | $1 \times 10^3$ | 7/15 |
| $1 \times 10^2$ | 0/9 | $1 \times 10^2$ | 10/12 |
| $1 \times 10^1$ | — | $1 \times 10^1$ | 2/12 |

EXAMPLES

The following examples are for illustrative purpose only, and should not be construed to be limiting in any respect of the claimed invention.

Example I. Isolation of Primary Cells

1. Tissues are minced down to fragments about 1-2 mm in size, and digested with collagenase in Hank's buffered saline solution (HBSS) at 37° C. overnight.
2. The resulting mixture of organoids that contain glandular cells are separated from single cells that are mostly stromal and myoepithelial by three consecutive rounds of centrifugation (5 min. at 300×g, 100× g and 50× g).
3. The pellets and supernatants are collected in six fractions (300 g, 100 g and 50 g) and filtered through a 75 micrometer (tm) and 45 µm mesh.
4. All filtered fractions are plated in Primaria™ tissue culture dishes in primary culture medium PWI (see below).
5. The cells are grown for 7 days during which medium is changed every day.
6. On day 8 and 9 plates are trypsinized with 0.025% trypsin removing all stromal cells.
7. Epithelial cells are harvested with 0.15% trypsin and transferred to new Primaria™ plates in PWI medium.
8. After one week cells are transferred and subcultured with 0.075% trypsin in the subject medium.

FIG. 1 illustrates that on day 12, while primary organoid cultures result in homogenous uniform colonies in the subject medium (e.g. PWI), there are multiple cell types forming a bi-phasic appearance in MEGM. Moreover, on day 40, cells in the subject medium (e.g. PWI) are small and proliferating, while in MEGM, the cells have the typical flat, enlarged and vacuolated appearance of senescent cells.

Example II. Methods of Preparing the Media

The media disclosed herein can be made fresh every time from their individual components, which are commercially available from a variety of vendors, such as Sigma, Abott Lab., etc.

Alternatively, certain components of the media may be pre-made as high concentration stock solutions, which can be diluted to their final concentrations as listed in the Tables. The stock solutions should be appropriately stored according to the characteristics of the components, including stability at the storage temperature (e.g., liquid nitrogen, −80° C., −20° C., 4° C., room temperature or about 20-25° C., etc.), sensitiveness to light, natural half life in aqueous or organic solution, etc. Some stock solutions should be remade periodically to keep a fresh stock. The following lists at least one way of preparing several exemplary stock solutions. Other equivalent methods and similar (but not identical) concentration of stock solutions may also be used.

EGF (Epidermal Growth Factor) 100 µg/ml Stock:

Human (or other mammalian) EGF can be obtained from a variety of commercial venders, such as Upstate Biotechnology. To prepare the stock:
1. Retrieve an unopened vial of 100 µg (human) EGF from refrigerator;
2. Make a 0.1 mg/ml solution by adding 1.0 ml sterile distilled water to the vial; mix gently, but well. If necessary, vary the concentration according to the weight in the vial;
3. Aliquot 0.26 ml portions into sterile ampoules properly labeled (such as "hEGF, 'n' X stock, date, ampoule letter, i.e. A, B, C etc.");
4. Optionally, check sterility of each ampoule by adding 3 µl from each ampoule to 1.5 ml media in a 35 mm dish and incubate 3 or 4 days. Check every day for contamination;
5. Store in −20° C. freezer for up to 3 months. Discard stock after 3 months, and make fresh stocks according to steps above.

(Human) Transferrin 10 mg/ml Stock:

Human (or other mammalian) Transferrin can be obtained from a variety of commercial venders, such as Sigma CAT # T-2252 Siderophilin. To prepare the stock:
1. Dissolve 1000 mg of transferrin into 100 ml distilled water to yield a stock concentration of 10 mg/ml;
2. Filter for sterility through 0.2 µm filter;
3. Aliquot 2.6 ml and 0.30 ml portions into sterile polypropylene tubes or snap-top tubes properly labeled (such as "Transferrin, 'n' x stock, month/year, vial letter, i.e., A, B, C, etc.");
4. Optionally, check sterility by placing 10 µl from each vial into corresponding labeled 35 mm dish with 1.5 ml media, check every day for contamination 4 days.
5. Store at −20° C. freezer.

Insulin 1 mg/ml Stock:

Insulin can be obtained from a variety of commercial venders, such as Sigma CAT #I-5500. To prepare the stock:
1. Dissolve 1 g of insulin powder in 200 ml of 0.005 N HCl (1 ml 1 N HCl with 199 ml of distilled water) by stirring on a magnetic stirrer;
2. When the solution is clear*, add 800 ml of distilled water, to make the final concentration of insulin 1 mg/ml;
3. Sterilize by filtering through a 0.2 µm filter;
4. Label approximately 30 sterile snap-top tubes and enough 50-ml sterile polypropylene tubes with proper label (such as "Insulin, 'n' X stock, month/year"). Aliquot 2.8 ml and 26 ml portions into sterile polypropylene tubes;
5. Store at –20° C.
   * If the solution is not clear after a reasonable amount of stirring, add a few more drops of 1 N HCl. (The total [HCl] should not exceed 0.005 N HCl/liter of solution.) When the solution clears, bring up the total volume to 1 liter with distilled water.

O-Phosphoethanolamine (Also 'O-Phosphoroethanolamine' and 'O-Phosphorylethanolamine) Stock, 0.1 M:

O-Phosphoethanolamine can be obtained from a variety of commercial venders, such as Sigma CAT # P-0503. To prepare the stock:
1. Dissolve 789.5 mg of O-Phosphoethanolamine in 56 ml of MCDB 170 base medium to give a stock concentration of 14.1 mg/ml or 0.1M;
2. Filter through 0.2 m filter for sterility;
3. Properly label sterile polypropylene tubes (such as "phospoethanoloamine, 'n' X stock, mo./yr, vial letter") and aliquot 5 ml and 0.6 ml portions;
4. Optionally, check sterility by aliquoting 10 µl from each tube into corresponding labeled 35 mm dish with 1.5 ml media. Check every day for four days, repeat if necessary;
5. Store at –20° C.

In addition, the medium of the instant invention may be prepared by adding additional components to commercially available media. For example, to make the subject culture medium, F-12 liquid Nutrient Mixture (Ham) (IX) media (GIBCO Cat. No. 11765-054) can be mixed with M-199 media (such as CAT #: MT 10-060-CV from MediaTech, Inc.) at 50:50 ratio. The mixture can then be supplemented with glutamine, EGF, transferrin, insulin, progesterone, testosterone, 17B-estradiol, o-phosphorylethanolamine, selenious acid, lionleic acid, BSA, triiodothyronine (T3), hydrocortizone, cholera toxin, HEPES, and other components to reach the final concentrations as listed in Table I or II. The medium may also contain antibiotics if desired, such as penicillin and/or streptomycin.

Example III. Comparison of Cell Growth in the Subject Medium and Other Media

The distinct advantages of the subject medium become apparent when compared with other media, especially the only commercially available medium on the market (i.e., the MEGM medium), in terms of the ability to support undifferentiated growth of isolated primary cells for substantial population doublings without going into senescence.

Figure 2:
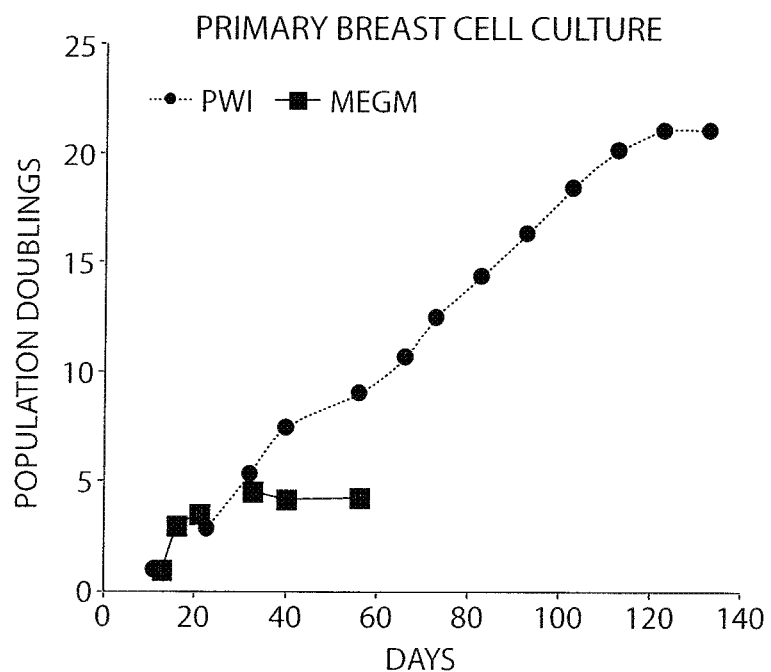
FIG. 2 shows results (growth curve) of identical primary breast cells in the subject medium (e.g. PWI) and one of the tested alternative media for such primary cells—the only commercially available medium MEGM.

FIG. 2 shows a representative result of one of such growth comparison experiments. It shows that primary cells grow in the subject media (e.g., PWI) can proliferate robustly for at least about 4 weeks, or about 15 population doublings, when identical cells from the same donor grow in other media, including the commercially available MEGM media, have largely or completely senesced. At least four types of media were compared to the subject medium. Only the MEGM result was shown, although none of the other tested media fair any better than the MEGM medium. In one typical experiment, growth in the subject medium continued till at least about the $17^{th}$ week, or about 22 population doublings. In contrast, identical cells growing in other media, including MEGM, typically stop at about the $3^{rd}$ week, or about 4 population doublings. It will be appreciated that "PWI Medium" and "PWI+ Medium" refer to certain embodiments of the inventive media in which concentrations of certain components lie within the listed ranges, wherein said concentration ranges are suitable, e.g., for culturing primary cells of various types such as those listed in Table VII (optionally transformed, e.g., with telomerase catalytic subunit). Media containing the components listed in Table VII in approximately the listed ranges or amounts (optionally containing one or more optional components listed in Table II) are aspects of the invention.

When such cells were transformed by telomerase catalytic subunit by, for example, a retroviral vector, the transformed cells became immortalized, but were not tumorigenic in immuno-compromised xenografted animals (results not shown). Such telomerase-transformed primary cells could continue to grow in the subject media till at least about the $16^{th}$ month, when the experiment was discontinued (results not shown). Once transformed, however, the cells can be grown in medium without certain components, such as agents that induce increased intracellular 3'-5' cyclic adenosine monophosphate (cAMP) levels.

Figure 3:
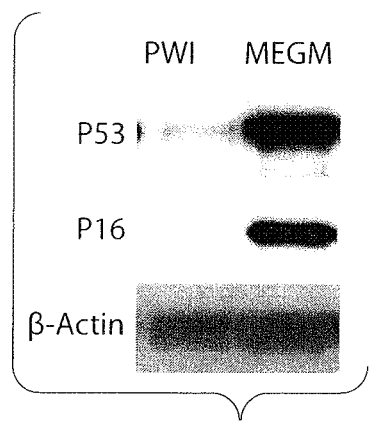
FIG. 3 shows that the isolated primary cells (e.g. primary mammary epithelial progenitors) grow in the subject media (e.g. PWI) relatively stress-free, in that these cells do not express appreciable amount of p53 or p16 gene products. In contrast, similar cells growing in the MEGM medium express large amount of p53 and p16 proteins in Western blot.

FIG. 3 shows that the isolated primary cells (e.g. primary mammary epithelial progenitors) grow in the subject media (e.g., PWI) relatively stress-free, in that these cells do not express appreciable amount of p53 or p16 gene products. In contrast, similar cells growing in MEGM medium express large amount of p53 and p16 proteins in Western blot.

Figure 4:
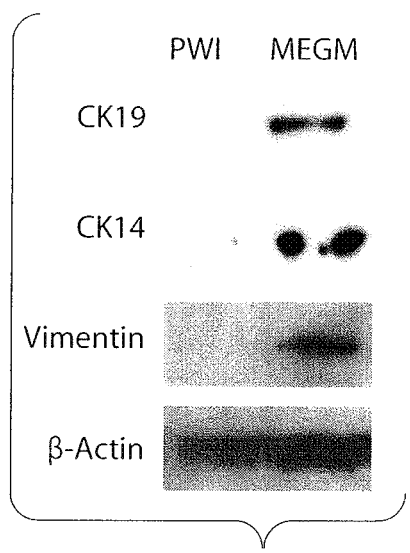
FIG. 4 indicates that the isolated primary mammary epithelial progenitor cells do not express epithelial differentiation markers (such as basal keratin 14 and luminal keratin 19) or mesenchymal differentiation markers (such as vimentin) in the subject medium (e.g. PWI), indicating that the population of isolated primary mammary epithelial cells are basically free of contamination by mesenchymal cells, such as fibroblast and other stromal cells. The result also demonstrates that the isolated mammary progenitor cells are growing in an undifferentiated state. In contrast, in the MEGM medium, cells express all these proteins in matched samples.

FIG. 4 indicates that the isolated primary mammary epithelial progenitor cells do not express epithelial differentiation markers (such as basal keratin 14 and luminal keratin 19) or mesenchymal differentiation markers (such as vimentin) in the subject media (e.g., PWI). This result indicates that the population of isolated primary mammary epithelial cells are basically free of contamination by mesenchymal cells, such as fibroblast and other stromal cells. The result also demonstrates that the isolated mammary progenitor cells are growing in an undifferentiated state. In contrast, in MEGM media, cells express all these proteins in matched samples.

Example IV. Test Different Ranges of Medium Components for Different Cell Types

The components listed in Table II above are meant to be a general guide for different cell types, thus certain components have a range of suitable concentrations. This Example demonstrates that the concentration of at least certain components of the medium may be varied, sometimes more than 1000-fold, when different cells are cultured.

Three types of cells were used in this experiment: primary breast epithelial progenitors (BEPC) isolated from normal breast tissue; such BEPC cells immortalized by telomerase catalytic subunit (BPE); and such BEPC cells stably transformed by: telomerase catalytic subunit and SV40 early region (or Human Papilloma Virus E6 and E7 genes)—BPLE cells, or telomerase catalytic subunit, SV40 early region (or HPV E6 and E7), and H-ras—BPLER cells.

Using the optimization procedure outlined above, the BEPC cells, BPE cells, BPLE cells, and BPLER cells were tested for growth in media with a large variation of concentrations for a number of components. The Table below lists representative results of such a test.

TABLE VII

| Components (mg/L) | Organoids Primary Cells (BEPC) PWI+ MEDIUM | Primary Cells + telomerase (BPE) PWI MEDIUM | Transformed Cells (BPLE and BPLER) WIT MEDIUM |
|---|---|---|---|
| Hypoxanthine Na | 3-15 | 3-15 | 3 |
| Alpha-tocopherol acetate | 0-2 | 0-2 | 0 |

TABLE VII-continued

| Components (mg/L) | Organoids Primary Cells (BEPC) PWI+ MEDIUM | Primary Cells + telomerase (BPE) PWI MEDIUM | Transformed Cells (BPLE and BPLER) WIT MEDIUM |
|---|---|---|---|
| Glutathione (reduced) | 0.025-1 | 0.025-1 | 0.025 |
| 17 beta estradiol | 0.004 | 0.004 | 0.0004 |
| Epidermal Growth Factor | 0.01 | 0.01-0.0005 | 0.0005 |
| Hydrocortisone | 0.5 | 0.5-0.0005 | 0.5-0.0005 |
| D-Glucose | 1000 | 1000 | 1000-2000 |
| Cholera toxin | 0.1 | 0.025 | 0 |
| Insulin | 20 | 10 | 10 |

Compared to BEPC cells, it is evident that BPLE and BPLER cells (tumorigenic) need much less of the most of the tested compositions, with the exception of a 2-fold increase in D-Glucose. In the extreme cases, the BPLE and BPLER cells can grow without any alphatocopherol acetate and cholera toxin. Among the other components, the largest decrease is hydrocortisone, where a 1163-fold decrease was measured. Most other components were reduced between 1-50 folds.

In contrast, the telomerase-expressing, immortal but not tumorigenic BPE cells require essentially the same medium as the parental BEPC cells, with a large decrease in hydrocortisone (500-fold), and relatively mild decreases in cholera toxin (4-fold decrease) and EGF (about 7-fold decrease).

The same experimental procedures can be used to optimize medium compositions for other cell types, even outside the range specified in Table II.

Figure 5:
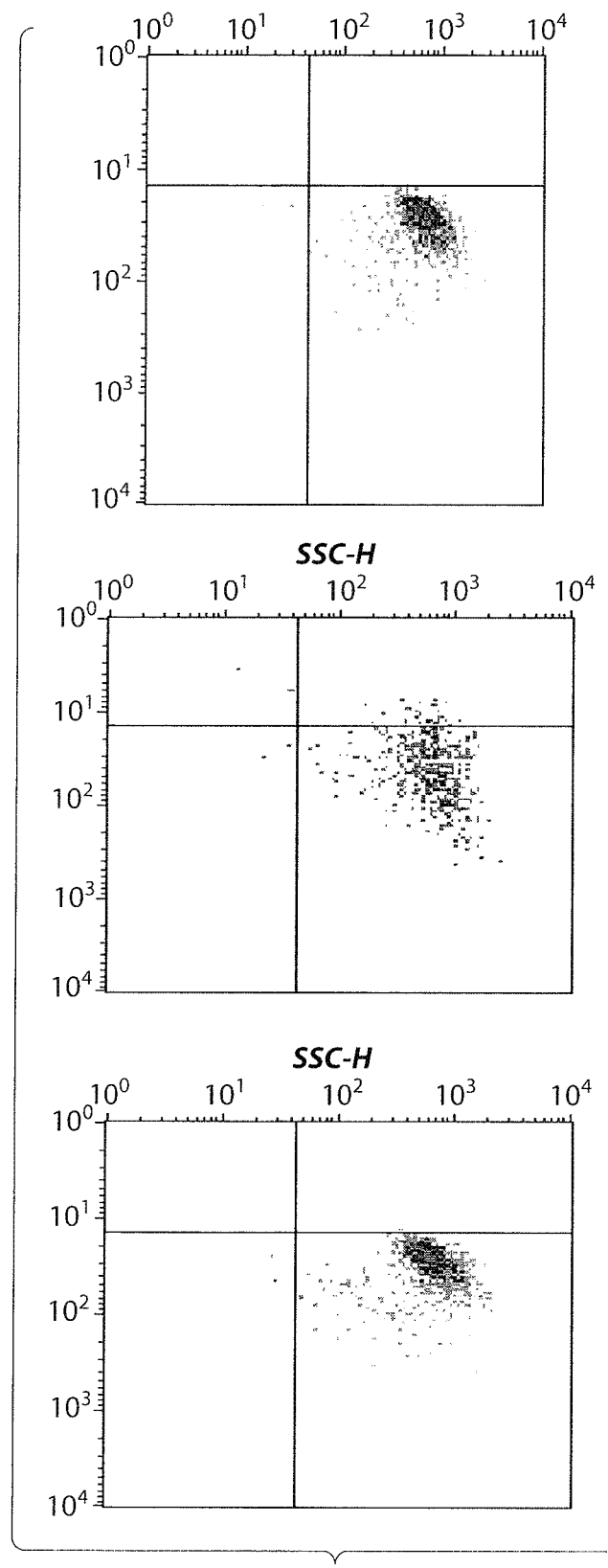
FIG. 5 shows expression profiles of CD44, CD24, and ESA in isolated primary mammary epithelial progenitors cultured in the subject medium.

Example V. CD44 and CD24 Expression Profile in Cultured Primary Mammary Epithelial Progenitors It is evident that above 85% (typically above 88%) of the isolated primary mammary epithelial progenitors expressed CD44, CD24, and Epithelial Surface Antigen (ESA). See one typical FACS analysis result shown in FIG. 5. This molecular profile is identical to breast cancer stem cells isolated from human tumor samples.

Figure 6:
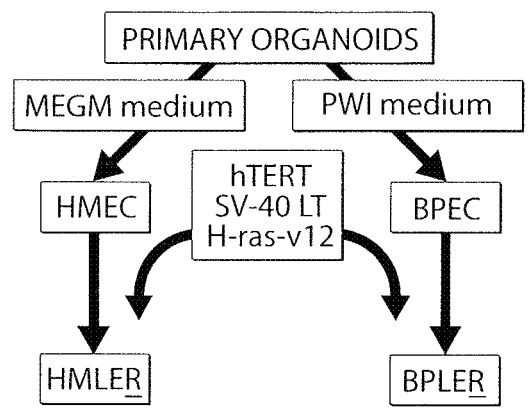
FIG. 6 is a schematic drawing showing the transformation of primary mammary epithelial progenitors to stem cell-like tumorigenic cells.

Example VI. Transformation of Primary Mammary Epithelial Progenitors to Stem Cell-Like Tumorigenic Cells FIG. 6 is a schematic drawing showing the general steps that may be used to transform primary mammary epithelial progenitors isolated using the subject medium and methods, into stem cell-like tumorigenic cells. In one particular example, primary breast cells (BPEC) grown in the subject medium (e.g. PWI) were infected successively with replication defective amphotropic retroviruses generated from Maloney-based expression constructs, each encoding a distinctive selection marker. To generate these viruses, 293T cells were transfected with 2 µg each of the amphotropic packaging plasmid pCL-10A1 and a retroviral construct expressing a desired gene. The retroviral constructs were in order of infection: a) pMIG-hTERT; expressing catalytic subunit of human telomerase and green-fluorescent protein gfp, b) pBabe-zeo-SVER; expressing SV40 early region (LT-Ag and st-Ag) and zeomycin resistance gene, and, c) pBabe-Ras-puro; expressing oncogenic H-rasV12 and puromycin resistance gene. Viral supernantants were harvested and used to infect BPECs with 8 µg/ml polybrene. Drug selection was performed by using 100 µg/ml zeocin and 0.25 µg/ml puromycin. The tumorigenic BPLER cells are grown in WIT medium.

Primary breast cells (HMECs) from the same patient cultured in the modified MCDB-170 medium (MEGM; the standard available medium for breast cells) were infected with the same plasmids. The resulting tumorigenic cells are referred to as HMLER. The generation of cells is illustrated in the figure below.

TABLE VIII

Genotype and Tumorigenicity of Various Cell Types.

| Cell Name | Genotype | | | Tumorigenicity |
|---|---|---|---|---|
| BPEC | | | | 0 |
| BPE | hTERT | | | 0 |
| BPLE | hTERT | SV40-LT/st | | 0 |
| BPLER | hTERT | SV40-LT/st | H-ras-V12 | 100% |

Subcutaneous tumorigenicity was tested in 6-8 week old immunocompromised athymic nude mice by injecting about $1\times10^6$ cells resuspended in 100 µl of 50% matrigel (EHSS). Nude mice were irradiated with 400 rad 12 hr prior to injections. Orthotopic tumorigenicity was tested by injecting about $1\times10^6$ cells into the mammary fat pad of Nod/Skid mice. All mice were sacrificed on day 70. Both orthotopic and subcutaneous injections developed tumors 100% of the time within 50 days. In total over 20 mice in each group have been tested for tumorigenicity in three separate experiments.

The table below shows that the tumorigenic BPLER cells of the invention are much more potent than HMLER cells in terms of tumorigenesis. HMLER cells reliably generate tumor in xenografted animal models only when more than $1\times10^6$ cells are injected into each animal. At $1\times10^5$ cells/animal, less than half of the animals actually develop tumor. There was not a single observed tumors in all 9 experimental animals when only $1\times10^4$ tumorigenic cells were used.

In contrast, $1\times10^4$ BPLER cells generates tumors in 100% of the experimental animals. In fact, with 10-fold lesser tumorigenic BPLER cells ($1\times10^3$ cells/animal), about 50% of the animals still develop tumor. Thus the BPLER cells are at least about 1000-fold more potent than HMLER cells in tumorigenesis.

TABLE IX

Comparison of Tumorigenic HMLER cells and BPLER cells

| HMLER | | BPLER | |
|---|---|---|---|
| $1\times10^6$ | 7/9 | $1\times10^6$ | 9/9 |
| $1\times10^5$ | 2/9 | $1\times10^5$ | 9/9 |
| $1\times10^4$ | 0/9 | $1\times10^4$ | 9/9 |
| $1\times10^3$ | 0/9 | $1\times10^3$ | 7/15 |
| $1\times10^2$ | 0/9 | $1\times10^2$ | 10/12 |
| $1\times10^1$ | — | $1\times10^1$ | 2/12 |

Example VII. Characterization of Tumors Generated by Transformed Stem Cell-Like Tumorigenic Primary Mammary Epithelial Progenitors A series of experiments were conducted to characterize the tumors formed by those transformed stem cell-like tumorigenic primary mammary epithelial progenitors.

Figure 7A:
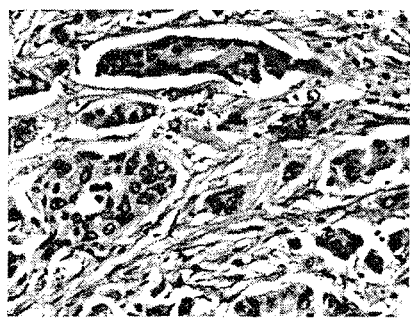
FIGS. 7A-7D show microscopic examinations of the tumors.
Figure 7C:
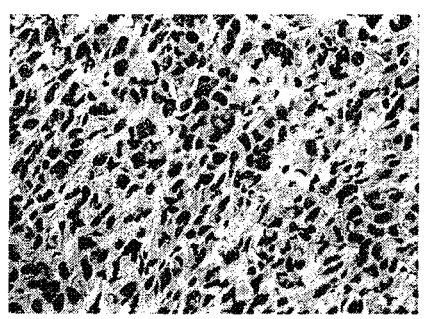
Figure 7B:
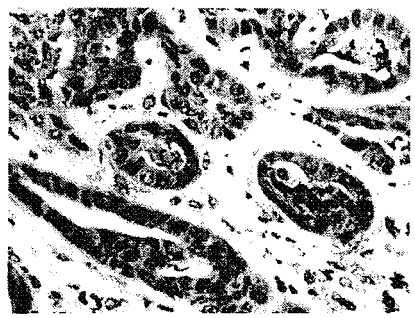
Figure 7D:
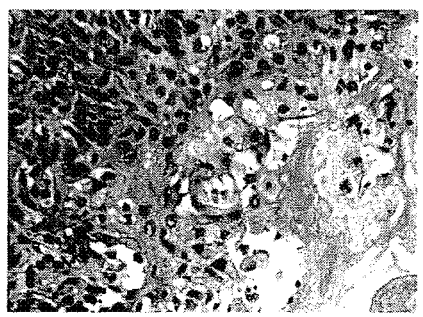

In a first experiment, tumors generated by transformed stem cell-like tumorigenic primary mammalian epithelial progenitors were excised from the animals after the animals were sacrificed. Microscopic examination of the tumors show that BPLER tumors recapitulate glandular structures (FIG. 7b) similar to Invasive Ductal Carcinoma of the breast from a human tumor sample (FIG. 7a). In contrast, HMLER tumors were either undifferentiated (FIG. 7c) due to complete lack of ductal structures or clear epithelial morphology; or focally Squamous Carcinomas due to presence of extracellular keratinization (FIG. 7d). This indicates that the subject tumor model is a close approximation of clinical tumor.

Figure 8:
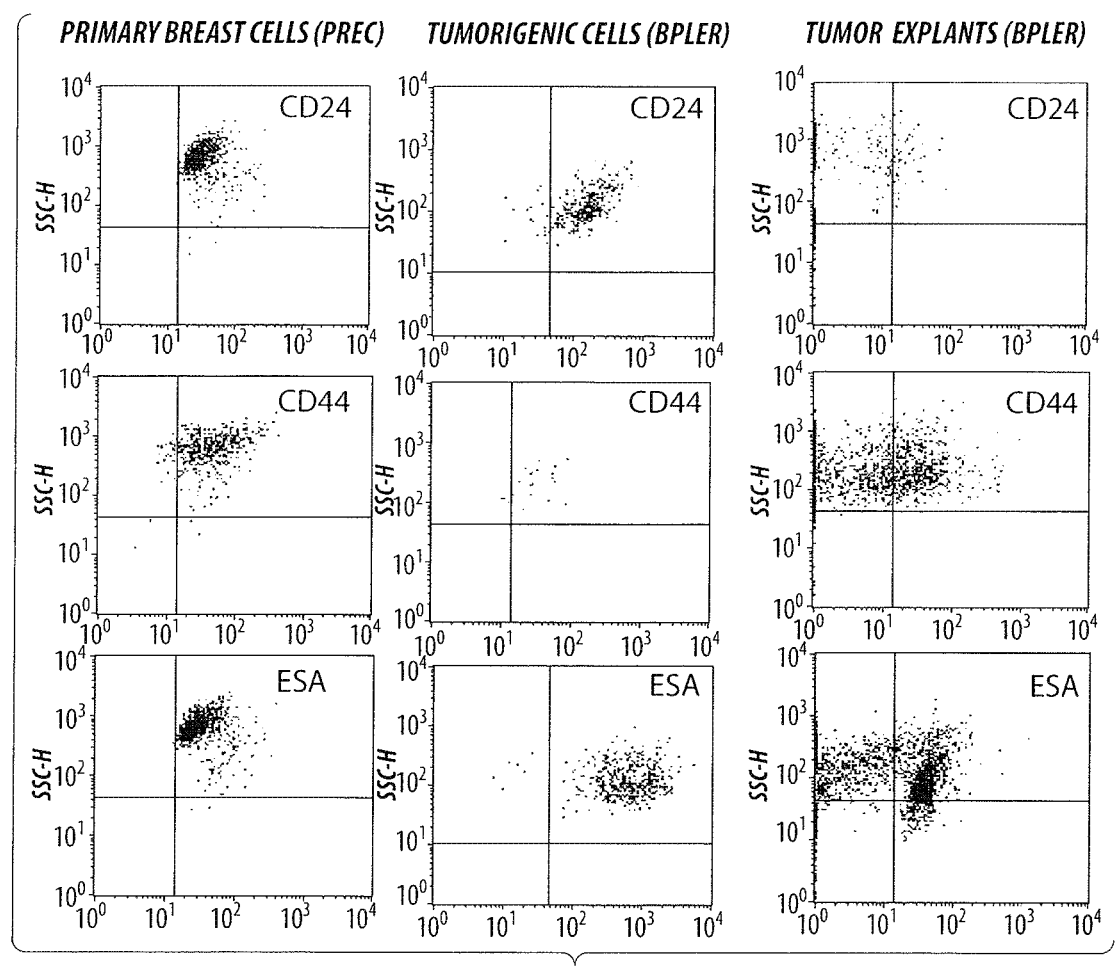
FIG. 8 is FACS analysis of CD44, CD24 and ESA expression on isolated primary breast cells, tumorigenic cells BPLER, and cells from tumor explants generated from implanted BPLER cells. The results indicate that the subject tumor model can recreate in the subject tumor model the breast cancer stem cell marker expression pattern both in vitro and in vivo.

To determine the expression of certain cell-surface antigens, BPLER tumors were isolated from mice, minced and digested into single cells with collagenase (as described for breast organoids above). The single cells from the tumors were incubated with human specific antibodies such as APC-conjugated CD24 Ab, PE-congugated CD44 Ab, ESA Ab, and control antibodies. Since only the tumor cells are green fluorescent protein positive, they can be easily identified by FACS. The expression of CD24, CD44 and ESA were analyzed by FACS. The primary breast cells and BPLER cells in tissue culture are homogenous in their expression of all three markers with over 90% of cells expressing CD44, CD24 and ESA. In contrast, the tumor explants exhibited a mixed phenotype of CD44, ESA, and CD24 expression (FIG. 8). This is consistent with the notion that the original tumorigenic cells are stem cell-like, in that they not only "regenerate" themselves ($CD44^+$, $ESA^+$, $CD24^{low}$) during the process of tumorigenesis, but also generates less-tumorigenic $CD44^-$, $ESA^-$, $CD24^{high}$) tumor cells. This indicates that the subject tumor model can recreate in the subject tumor model the breast cancer stem cell marker expression pattern both in vitro and in vivo. Moreover, this pattern is not merely the product of the genetic manipulation of the normal cells that were isolated, since the expression pattern is already present in primary cells. Therefore, the property of "stemness" resides with the original cell population that has been isolated and expanded in the subject medium, rather than any genetic manipulation of the cells. Moreover, while previous results from human tumors were able to identify the expression pattern of the tumor stem cells, they were not able to address whether this pattern preceded the malignant transformation, or it was acquired during transformation. The results of the subject tumor model identify BPEC cells as the likely normal target cells that give rise to human breast cancer stem cells by virtue of their identical CD44, ESA, CD24 expression to tumor stem cells.

The explanted BPLER tumor cells were FACS sorted into $CD24^+$ and $CD24^-$ fractions and re-injected into nude mice. If the BPLER tumor stem cell marker expression were to be functional in these cells, only $CD24^-$ fraction would be tumorigenic. The table below shows the results of such an experiment with BPLER tumor explants that confirms this prediction. Therefore, subject tumor model not only recapitulates the breast cancer stem cell marker expression pattern, but also has its functional properties in creating tumorigenic and non-tumorigenic populations in vivo.

TABLE X

Only CD24⁻ Cells Were Tumorigenic

| Number of cells injected | CD24 negative cells | CD24 positive cells |
|---|---|---|
| $1 \times 10^3$ | 5/15 | 0/12 |
| $1 \times 10^4$ | 8/15 | 0/6 |

Figure 9:
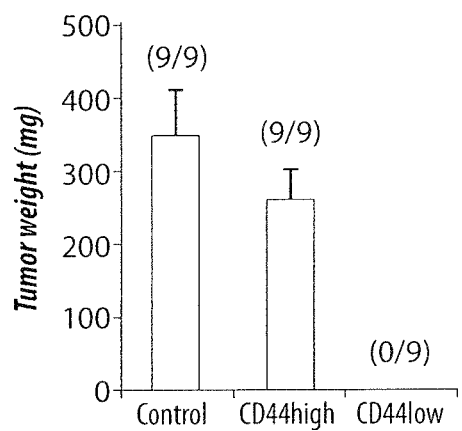
FIG. 9 demonstrates that only CD44$^{high}$ cells induced tumor formation in immuno-compromised host animals, while CD44$^{low}$ cells failed to induce tumor formation.

In vitro, there is at least a 10-fold difference in CD44 expression in BPLER cells. By cell sorting using, for example, FACS, cells falling within the top 20 percentile of all CD44-expressing cells ($CD44^{high}$) and the remaining $CD44^{low}$ cell fractions were separately injected into nude athymic mice. As expected from the human tumor data, only $CD44^{high}$ cells induced tumor formation in immunocompromised host animals (see FIG. 9), while $CD44^{low}$ cells failed to induce tumor formation. Since these cells were only expanded in tissue culture these results suggest that tumor stem cell-like properties are present already during in vitro cultivation and not limited to in vivo growth.

Figure 10:
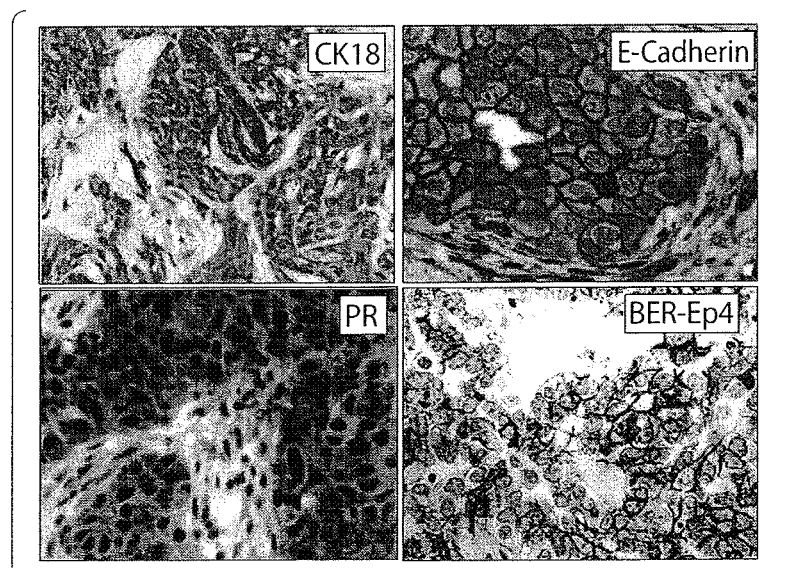
FIG. 10 Immunohistochemical characterization of the subject tumor model show that the tumor cells express breast cancer specific genes; keratin 18 (breast luminal marker), E-cadherin (epithelial marker), progesterone receptor and BER-Ep4 (marker that is positive in adenocarcinomas and negative in squamous carcinomas).

Immunohistochemical characterization of the subject tumor model show that the tumor cells express breast cancer specific genes; keratin 18 (breast luminal marker), E-cadherin (epithelial marker), progesterone receptor and BER-Ep4 (marker that is positive in adenocarcinomas and negative in squamous carcinomas). See FIG. 10. Expression of CK18 and BER-Ep4 both confirm the adenocarcinoma features and exclude a squamous tumor. E-cadherin excludes a mesenchymal tumor. BPLER xenografts express progesterone receptor, which is consistent with the notion that BPLER xenografts are hormone-responsive. This was confirmed by experiments in which estrogen-progesterone treatment of mice increased subject tumor size approximately two-fold compared to untreated mice. In addition, treatment of BPEC, BPE, and BPLE cells with a specific estrogen-antagonist ICI 182,780 resulted in >80% growth inhibitions in vitro (data not shown). Similar tumor xenografts from cells cultured in the MEGM media was negative for progesterone receptor expression and the in vitro growth inhibition of the cells with ICI 182,780 was less than 20% (data not shown).

Figure 11:
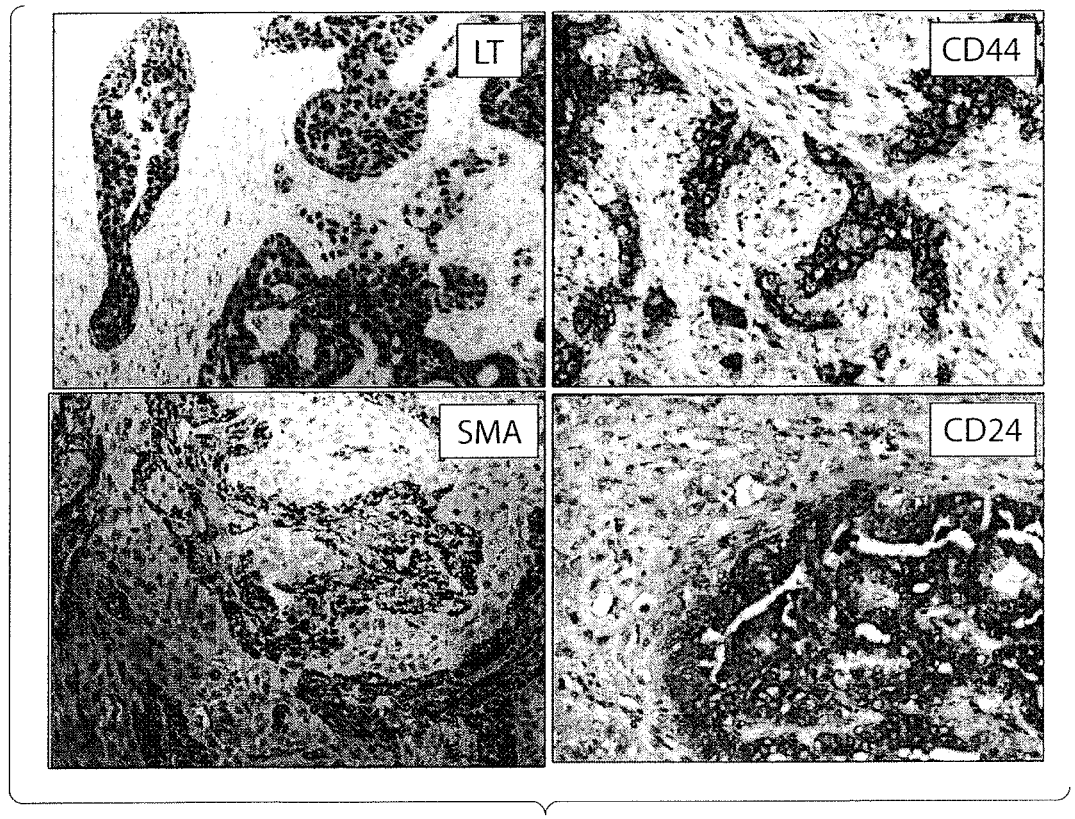
FIG. 11 Immunohistochemical analysis demonstrates that the subject tumor model mimics human breast tumors in every respect very closely, both at the morphologic and molecular level.

Staining with Large T Ag (LT) highlights the glandular morphology and presence of abundant stromal cells that are recruited to the tumor which are smooth muscle actin (SMA) positive, another typical feature of human breast cancers. CD44 and CD24 immunostains confirm the pattern seen in FACS analysis of the same tumors and show a spectrum of staining intensity (FIG. 11). These immunostains overall demonstrate that the subject tumor model mimics human breast tumors in every respect very closely both at the morphologic and molecular level.

Figure 12:
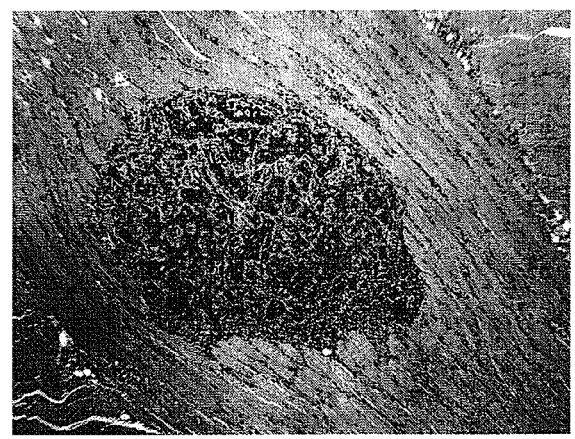
FIG. 12 indicates that BPLER xenografts into mammary fat pads are invasive into adjacent skeletal muscle, and causes a desmoplastic reaction.

FIG. 12 indicates that BPLER xenograft into mammary fat pads are invasive into adjacent skeletal muscle, and causes a desmoplastic reaction. Thus, just like clinical tumors, the BPLER tumors are invasive, a feature seldom seen in HMLER tumors.

Figure 13:
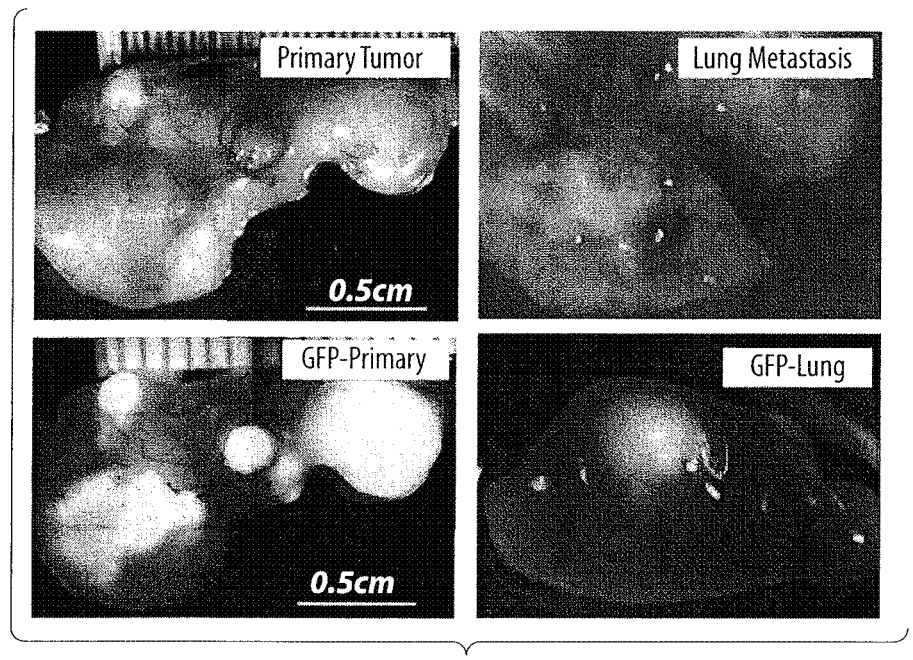
FIG. 13 shows multifocal growth in BPLER xenografts.

Consistent with the invasive behavior in FIG. 12, multi-focal growth is observed in BPLER xenografts (FIG. 13). The GFP⁺ tumor cells were injected into the mammary fat pat of Nod/skid mice and tumors were harvested at 8 weeks. The GFP image highlights that the tumor spread in the fat pad forming discontinuous and separate nodules, which was also confirmed by microscopic examinations of H&E stains (data not shown), consistent with lymphovascular invasion and spread of the tumor. This type of spread pattern is not present in HMLER tumors that grow as a single nodule (data not shown). Moreover, when lungs of the same animals are examined numerous micro-metastatic nodules were identified in 16 out of 18 mice confirming high metastatic potential of the subject tumor model. In one case the metastatic nodule was macroscopic. The lung metastasis was also confirmed microscopically in H&E stains (data not shown).

Example VIII. Differentiation of Isolated Primary Mammary Epithelial Progenitors to Luminal Epithelial Cells Isolated primary mammary epithelial progenitors may be induced to differentiate into luminal epithelial cells in 3D culture.

Figure 14:
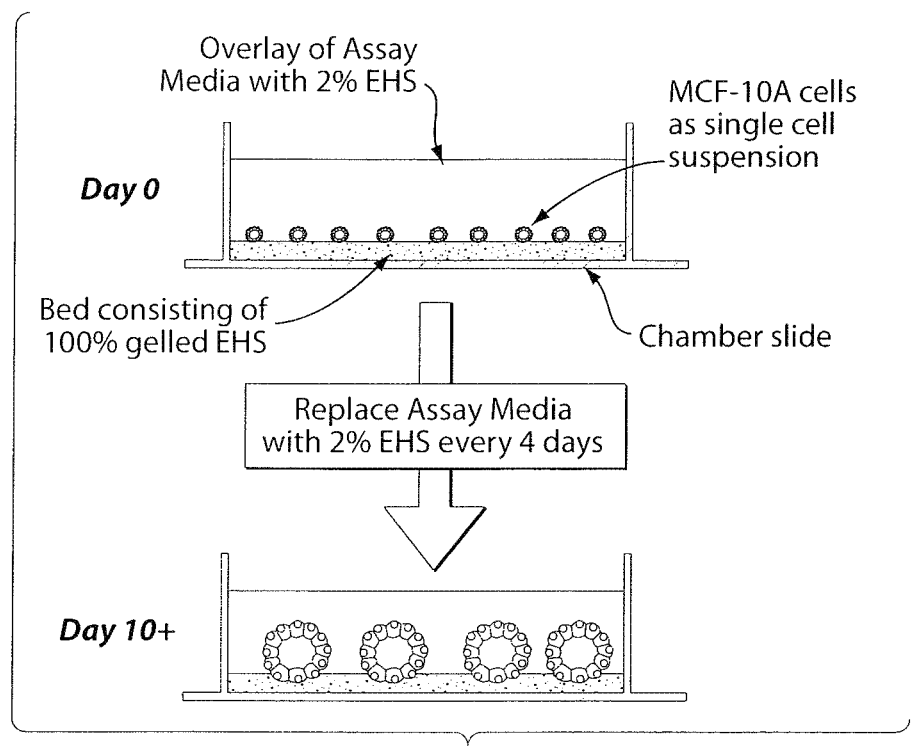
FIG. 14 is a schematic drawing of the 3D culturing methods (adapted from Debnath et al., Methods. 30(3): 256-268, 2003).

FIG. 14 (adapted from Debnath et al., Methods. 30(3): 256-268, 2003) is a schematic drawing of the 3D culturing methods. Briefly, cells to be differentiated are plated at appropriate (low) density on a bed consisting of 100% gelled EHS. A medium with about 2% EHS is then laid upon the cells, such that the EHS will eventually sediment on the cells and stimulate their differentiation into hollow ball-like structures (acini). Such structures resemble the lumen of epithelial ducts in breast.

Figure 15:
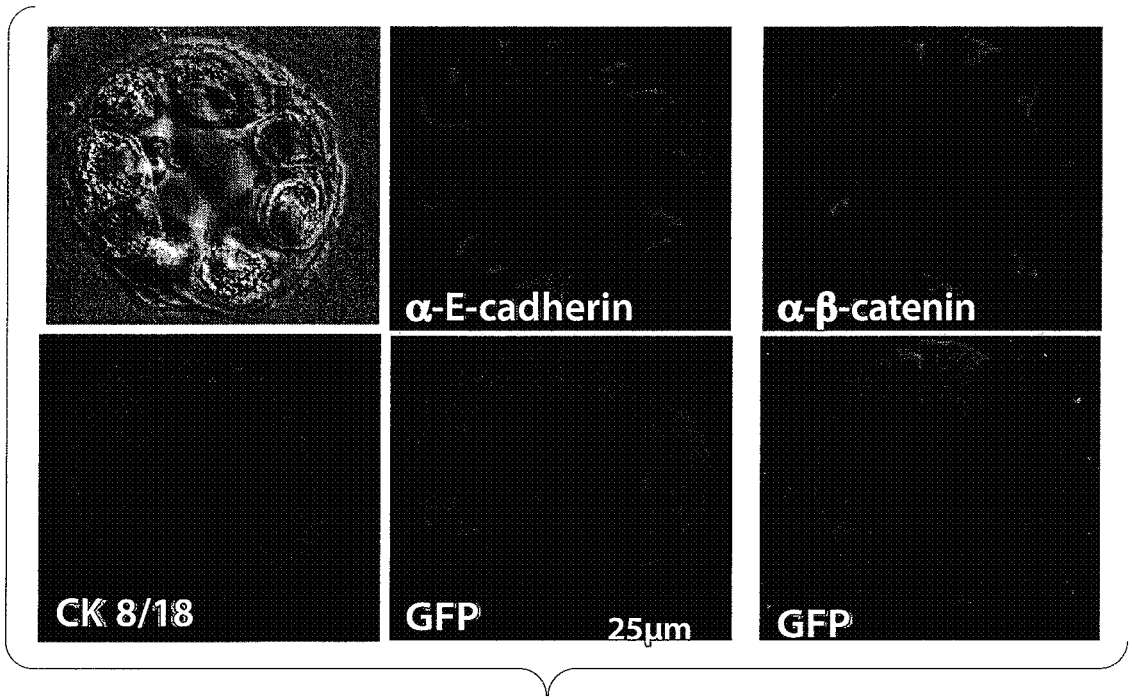
FIG. 15 indicates that primary mammary epithelial progenitors isolated using the subject media may be differentiated in 3D culture, and the developed acini express luminal epithelial cell markers E-cadherin and beta-catenin. Other luminal epithelial cell markers, keratins 8 and 18, are also expressed.

Acini may be fixed and stained to show expression of certain epithelial cell differentiation markers, such as E-cadherin and beta-catenin. FIG. 15 indicates that primary mammary epithelial progenitors isolated using the subject media may be differentiated in 3D culture, and the developed acini express luminal epithelial cell markers E-cadherin and beta-catenin. Other luminal epithelial cell markers, keratins 8 and 18, are also expressed (FIG. 15). These results demonstrated that the isolated primary mammary epithelial progenitors, when induced to differentiate in 3-D culture, could properly differentiate into epithelial cells of luminal (but not basoid) phenotype, which cells are more similar to the cells the majority of human carcinomas arise. Thus such a tumor model is biologically more relevant to the real disease in human.

Example IX. Isolation of Two Normal Human Mammary Epithelial Cell Types

To culture normal human mammary epithelial cell types other than the MEGM-derived HMECs, applicants developed a novel serum-free, chemically defined medium termed WIT (Example XIX, Supplemental Experimental procedures). Normal breast tissue from disease-free reduction mammoplasties was digested with collagenase, and the resulting multi-cellular structures (mammary organoids) were either plated directly in WIT medium on a modified plastic surface (Primaria, Becton-Dickinson), or in MEGM medium on standard tissue culture plastic; dissociation of organoids into single-cell suspensions at this stage precluded establishment of successful cultures.

Figure 16A:
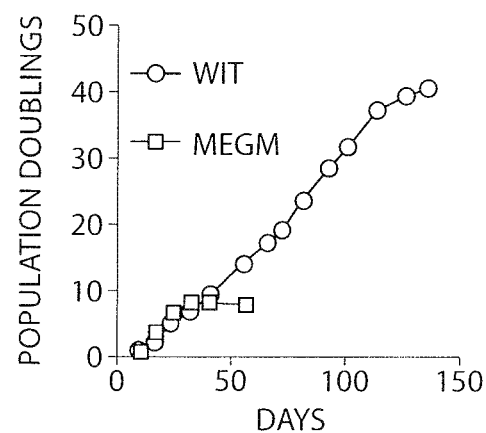
FIGS. 16A-16C compare primary culture of normal human mammary epithelial cells cultured in WIT medium and MEGM medium.
Figure 16B:
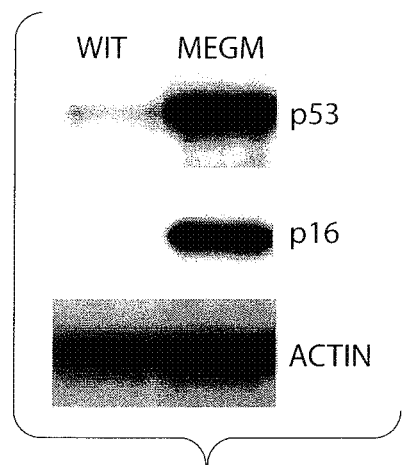
Figure 16C:
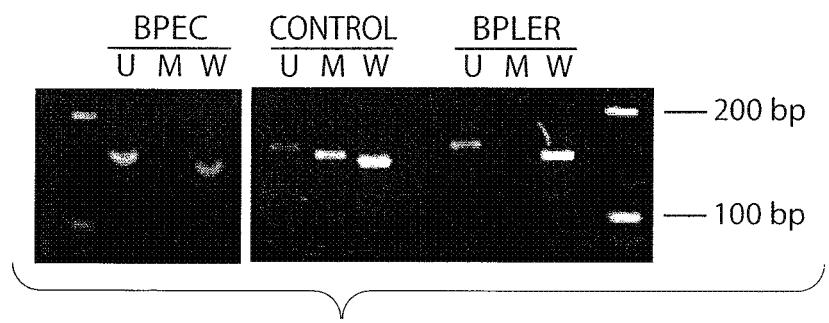

As reported previously, the majority of cells that grew out of organoids underwent growth arrest within three weeks of in vitro propagation in MEGM; in contrast there was no significant growth arrest in WIT cultures (FIG. 16A). It has been previously shown that during the first several passages in MEGM expression of the p16INK4A tumor suppressor protein is increased 10-15 fold in HMECs, causing replicative arrest referred to as MO (Romanov et al., 2001; Sandhu et al., 2000; Yaswen et al., 2001), which was not seen in the WIT medium (FIGS. 16A, 16B). This result is reminiscent of the behavior of HMECs grown on feeder layers, whose presence also allowed propagation in the absence of p16 induction (Herbert et al., 2002). Other studies have shown that MO arrest imposes a severe in vitro selection step on HMECs propagation and permits only a rare subset (<1× $10_{-5}$ cells) with an already in vivo methylated $p16_{INK4A}$ promoter to proliferate past MO arrest (Holst et al., 2003; Tlsty et al., 2004). In contrast, the p16 protein is not significantly induced in cells propagated in WIT medium on Primaria plates (FIG. 16B), allowing long-term propagation of a population of mammary cells that do not exhibit $p16_{INK4A}$ promoter methylation (FIG. 16C). Hereafter, applicants refer to human mammary epithelial cells growing in the WIT medium as BPECs (breast primary epithelial cells) in order to distinguish them from the HMECs selected for growth in MEGM medium.

Figure 23A:
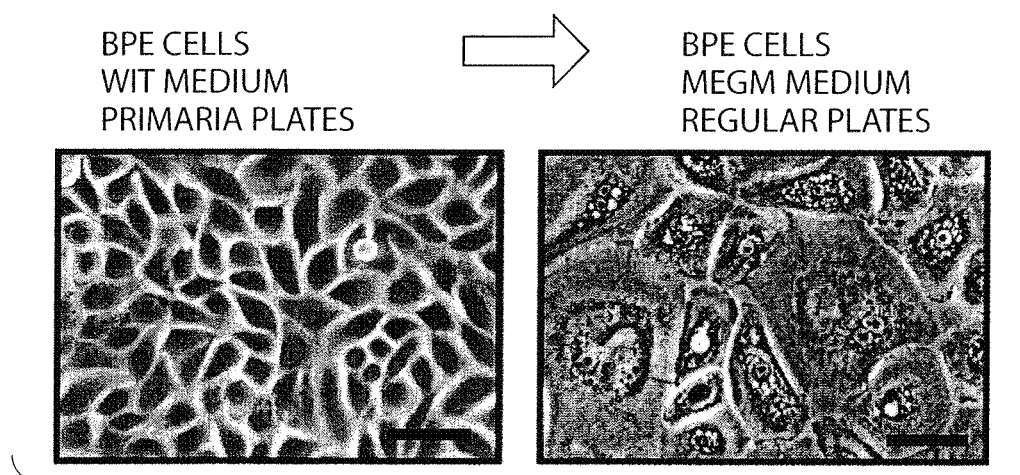
FIGS. 23A-23C illustrate that MEGM and WIT media select for distinct subpopulations of mammary epithelial cells with differing growth medium and attachment requirements.
Figure 23B:
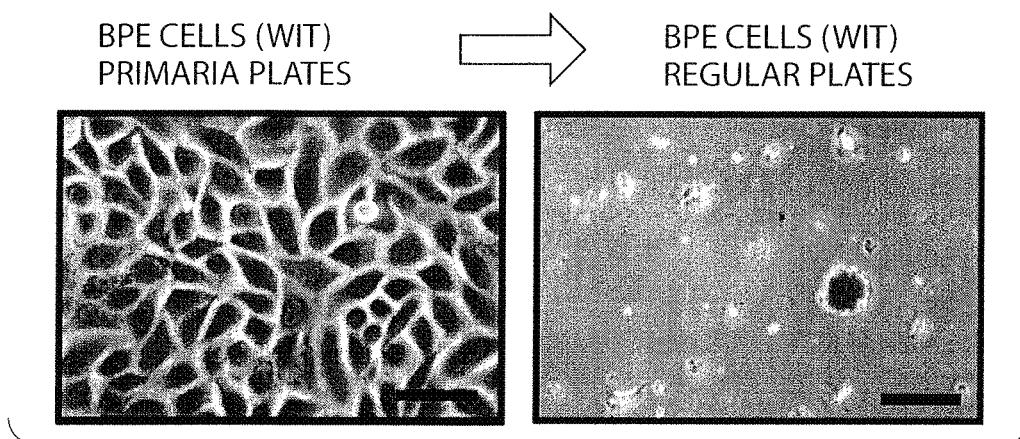
Figure 23C:
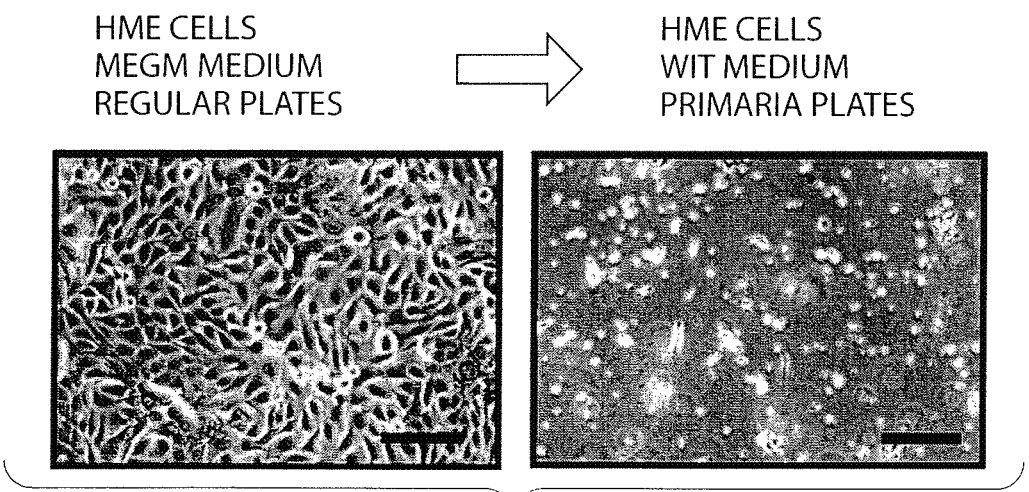

The two mammary epithelial cell populations that proliferated in the WIT and MEGM media have distinct growth requirements. When primary BPECs that had been cultured in WIT medium on Primaria plates during the initial three weeks in vitro were subsequently transferred into MEGM medium and on a regular plastic surface, all of these cells entered into permanent growth arrest within 7-10 days (FIG. 23A). Moreover, these BPECs could not be successfully propagated on regular plastic surfaces even in WIT medium (FIG. 23B). Conversely, it was not possible to transfer early passage HMECs that had been propagated in MEGM medium on regular plates during the initial three weeks in vitro into WIT medium. None of the HMEC cells survived beyond a few days due to widespread cell death; this was observed within several days on either on Primaria or regular plastic tissue culture surfaces (FIG. 23C).

Applicants note that in addition to the differing attachment surfaces, these two cell populations are propagated in substantially different media formulations: 37 of the 78 components that are present in WIT medium are either completely absent or present at >5-fold different concentration in MEGM medium (see, Example XIX, Supplemental Experimental procedures, Freshney 2000; Freshney et al., 2002). In addition, the standard MEGM medium is supplemented with bovine pituitary extract, which contains numerous undefined components, unlike the WIT medium, which is chemically defined. Hence, the combination of these two sets of distinct media and physical substrates appeared to encourage the outgrowth of cell populations that were unable to readily interconvert into the other type simply by switching from one set of growth conditions to the other.

Example X. Differentiation State of BPE and HME Cells

Applicants examined the mRNA expression profiles of BPECs and HMECs to investigate the differences between these two cell populations and found that there were nearly 2,000 mRNA transcripts in each cell population that were differentially expressed ≥2-fold compared to the other cell population (FIG. 31). Some of these differences suggested that there might be a difference in the relative luminal-myoepithelial differentiation state of these cell populations. The mammary epithelium consists of an inner, luminal layer of milk producing cells and an outer myoepithelial cell layer. The two cell types forming these two epithelial layers have distinct functions and gene expression profiles. Recently, a set of transcripts that are differentially expressed between these cell types was identified following immuno-magnetic separation of these two cell populations isolated directly from normal human breast tissue (Grigoriadis et al., 2006; Jones et al., 2004). Applicants compared these reported luminal- and myoepithelial-specific expression signatures with mRNA transcripts that are 2-fold or more differentially expressed between HMEC and BPEC populations.

Figure 17A:
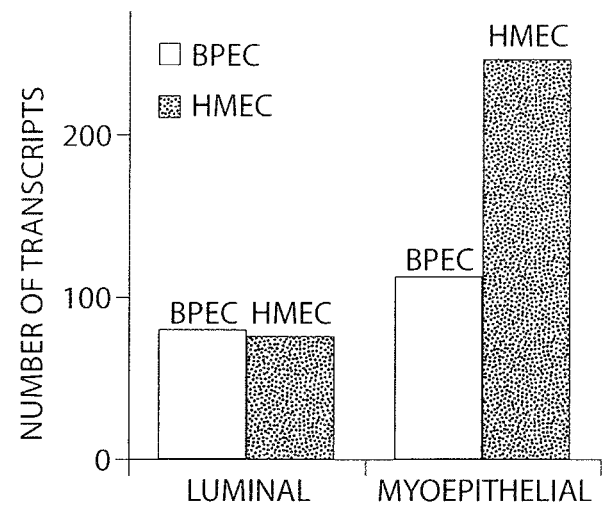
FIGS. 17A-17E show the differentiation state of BPE and HME cells.
Figure 17B:
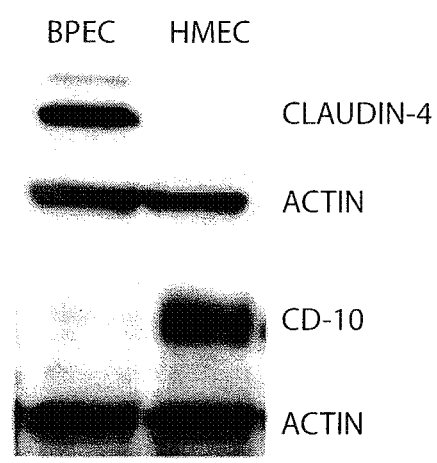
Figure 17C:
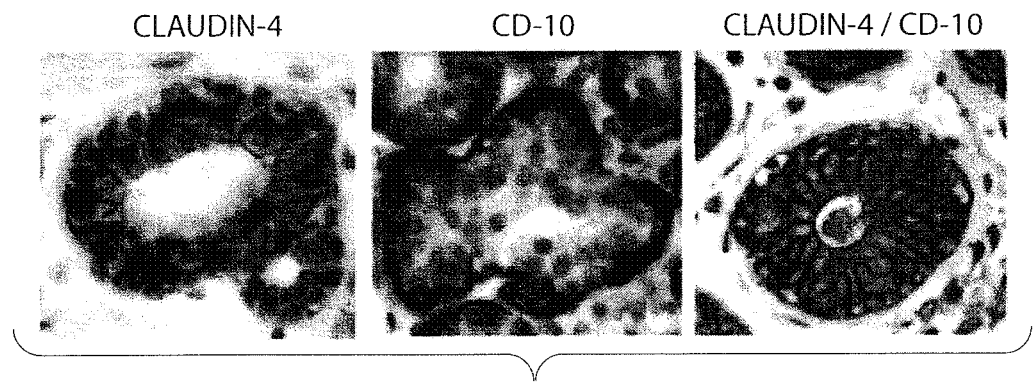

While neither cell population showed a gene expression program characteristic of fully differentiated luminal or myoepithelial cells, there was a significant difference in the relative number of myoepithelial-specific gene expression. In particular, HMECs over-expressed more than twice as many myoepithelial-specific genes relative to BPECs (FIG. 17A; FIG. 32A-32C). The differential expression of several of these genes was also confirmed at the protein level. For example, claudin-4, a protein that is exclusively expressed in the inner luminal layer of normal breast epithelium, is highly expressed in BPECs and is absent in HMECs (FIGS. 17B, 17C). Conversely, CD-10, which is exclusively expressed in the outer myoepithelial layer of the normal mammary epithelium, is highly expressed in HMECs, but is absent in BPECs (FIG. 17B, 17C). These results indicated that BPECs and HMECs differ in their differentiation state, revealing that HMECs are considerably more myoepithelial-like than BPECs.

Figure 17D:
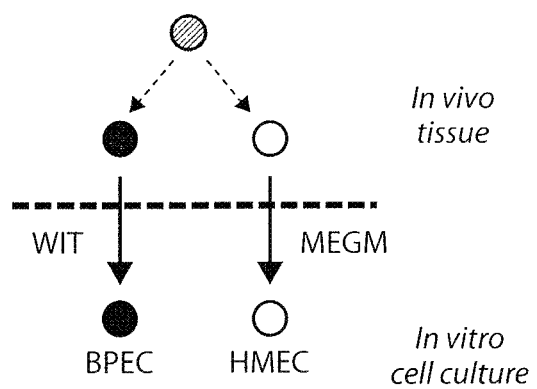
Figure 17E:
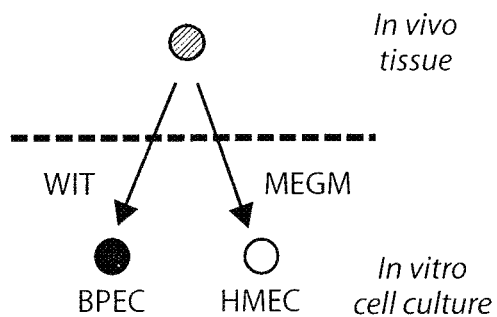

Not wishing to be bound by a particular theory, applicants postulate that these two cell phenotypes—BPECs and HMECs—arose either because of selection of two preexisting cell types within the normal breast tissue (FIG. 17D), or through in vitro differentiation from a common oligopotential in vivo precursor (FIG. 17E). In either case, based on their mutually exclusive growth requirements and differences in their differentiation state, BPECs and HMECs isolated from the same donor provided us with an experimental platform with which applicants could examine prospectively whether differences in the phenotype of normal cells from the same epithelium have lasting influences on the behavior of their transformed, tumorigenic derivatives.

Example XI. Immortalization and Transformation of BPE and HME Cell Types

To examine the influence of normal cell phenotype on that of derived transformants, applicants determined whether transformation of the BPECs growing in WIT medium on Primaria plates would give rise to tumors that were biologically different from those arising following transformation of the HMECs grown in MEGM on regular culture plates. BPECs and HMECs were transformed in three separate consecutive steps using retroviral vectors expressing hTERT, SV40-LT and H-ras respectively, as previously described (Elenbaas et al., 2001; Hahn et al., 1999). Prior to complete transformation with SV40-LT and H-ras, applicants determined the differentiation state of hTERT-expressing cells by comparing their gene expression pattern with the set of previously reported luminal- and myoepithelial-specific human breast genes (Grigoriadis et al., 2006; Jones et al., 2004).

Figure 18A:
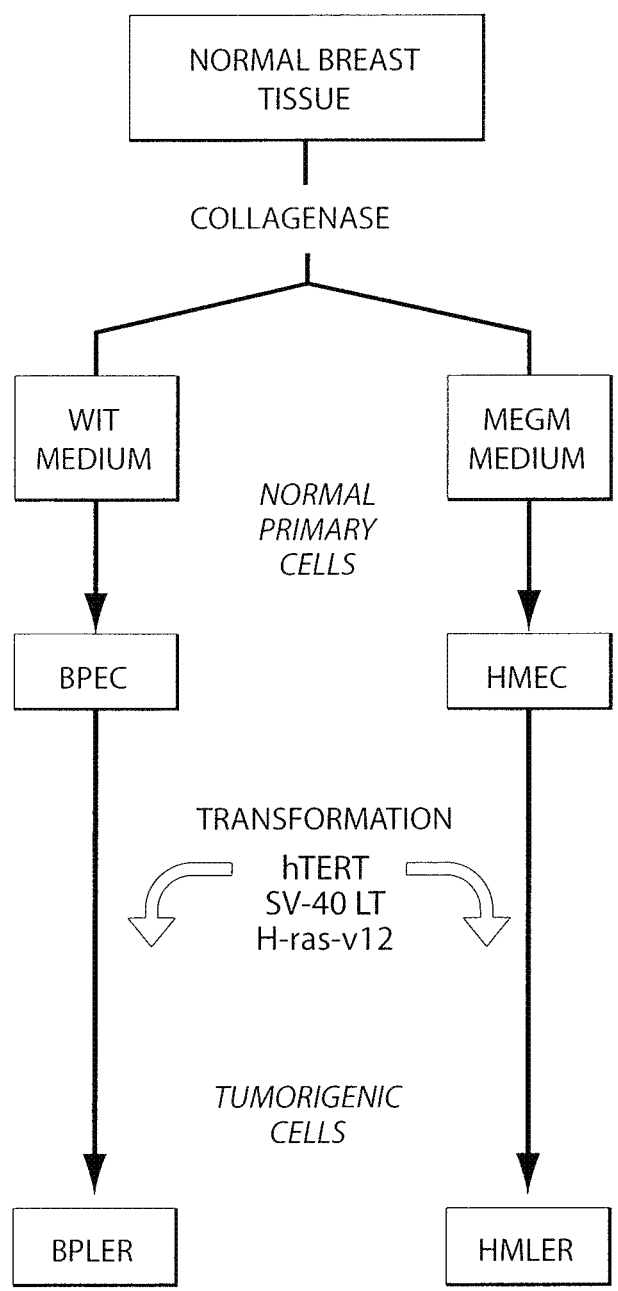
FIGS. 18A-18D show tumorigenic transformation of normal breast epithelial cells.
Figure 18B:
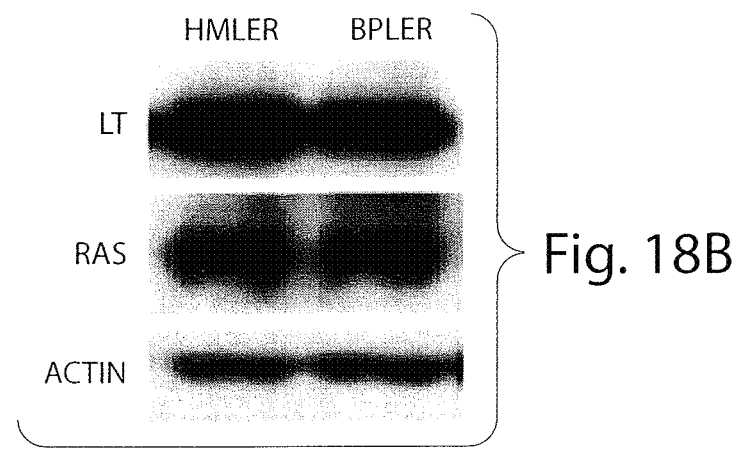
Figure 18C:
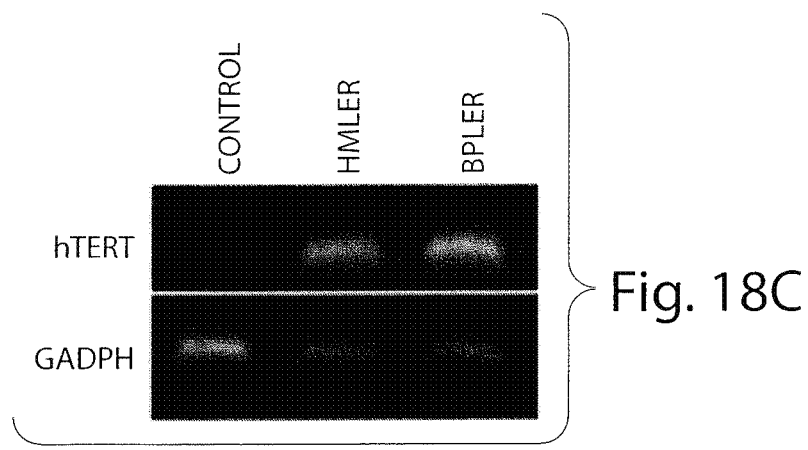
Figure 18D:
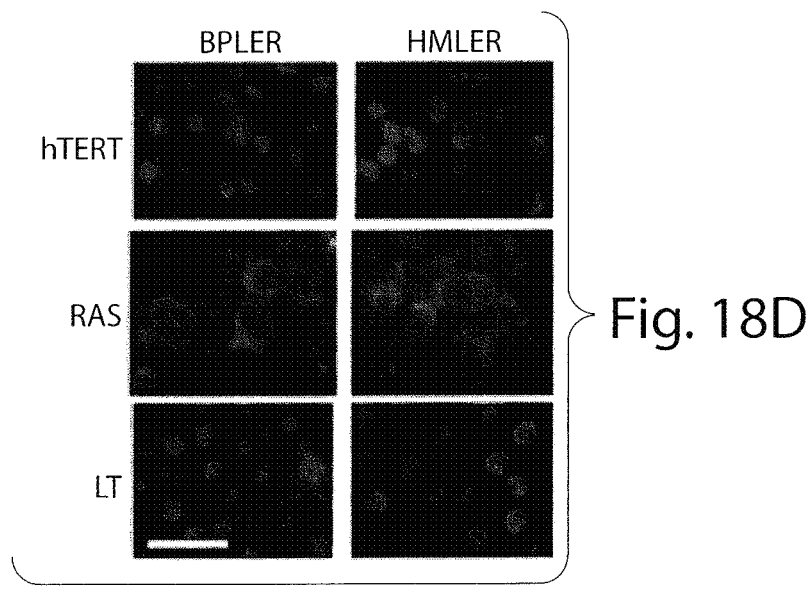
Figure 24A:
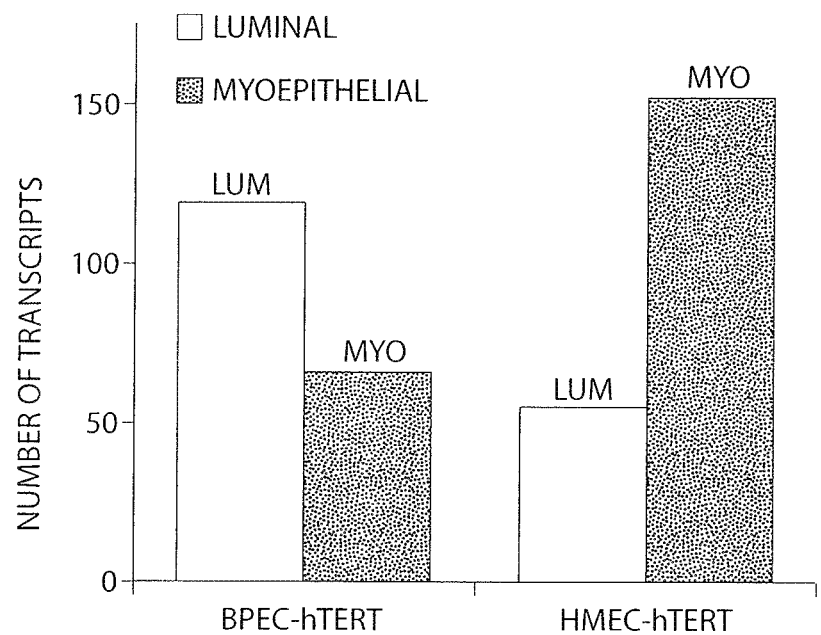
FIG. 24A shows a comparison of luminal- and myoepithelial-specific expression signatures with genes that are differentially expressed ≥2-fold between untransformed BPEC hTERT and HMEC-hTERT populations. Each bar represents the number of luminal or myoepithelial specific transcripts expressed at a higher level (≥2-fold) in one cell type relative to the other: open bar (luminal-specific genes), filled bar (myoepithelial-specific genes). The mRNA from BPEC-hTERT and HMEC-hTERT populations derived from three different individuals was analyzed, and compared to luminal- vs. myoepithelial-specific gene expression profile in the supplemental online data in "additional File 9" from Grigoriadis et. al., 2006. A full list of genes that are differentially expressed between BPECs and HMECs, and the list of genes that correspond to each specific bar in this figure is available in FIG. 33.
Figure 24B:
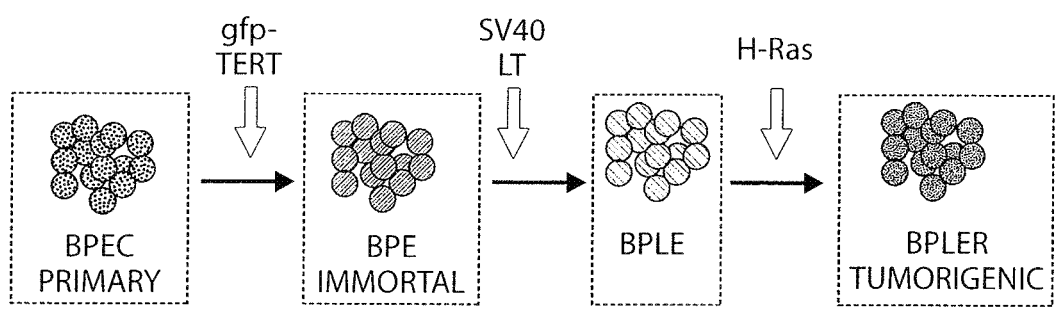
FIG. 24B shows derivation of tumorigenic human mammary epithelial cells with defined genetic elements. BPECs and HMECs were transformed in three separate consecutive steps using retroviral vectors expressing hTERT, SV40-LT and H-ras, as previously described (Elenbaas et al., 2001; Hahn et al., 1999). BPEC (primary cells), BPE (untransformed hTERT-expressing cells), BPLE (hTERT+SV-40 large T transformed, non-tumorigenic cells), BPLER (hTERT+SV-40 large T+H-Ras transformed tumorigenic cells).
Figure 24C:
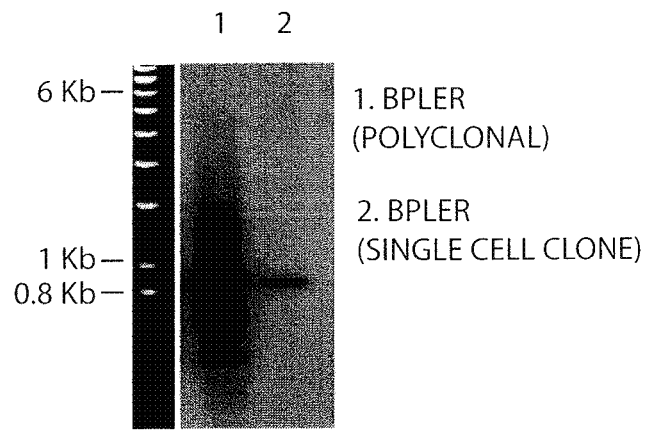
FIG. 24C shows a southern blot of polyclonal BPLER population and single cell-derived BPLER clones. Genomic DNA from the polyclonal BPLER population (lane 1) and a single cell-derived BPLER clone (lane 2) were both digested with NDE-I and probed with pBABE-puro-ras plasmid that was $_{32}$P-labeled with a random prime labeling system. The presence of a single band in the single cell-derived clone confirms low infection multiplicity. Southern blot analyses of other single-cell-derived clones also showed low number of integration sites (mostly 1-3 integration sites per vector in each infected cell). The presence of a strong merged specific signal extending between ~0.3 and 2.0 Kb in lane 1 confirms that BPLER cell population is highly polyclonal.
Figure 24D:
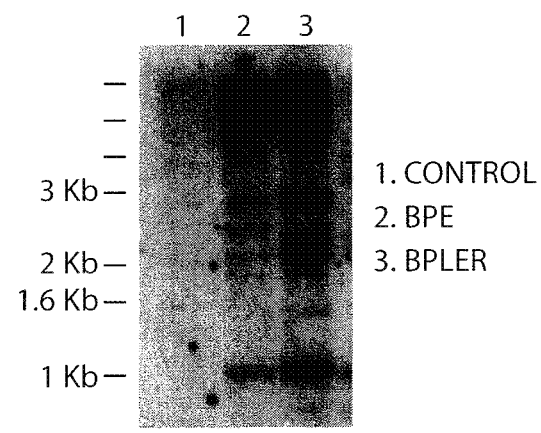
FIG. 24D shows southern blots of hTERT-immortalized BPECS and their fully transformed tumorigenic BPLER derivatives. Southern blot of genomic DNA from control BPECs with no retroviral vector expression (lane 1), BPE cells that express gfp-TERT only (lane 2), and tumorigenic BPLER cells that express all three vectors (lane 3). The genomic DNA was digested with BamHI and was probed with pmig-GFP-hTERT plasmid that was $_{32}$P-labeled with a random prime labeling system. The presence of numerous different size bands illustrates that BPLER cells remain polyclonal throughout multiple steps of transformation; most of the bands that were present after introduction of hTERT in BPE cells are still present in similar ratios in fully transformed and tumorigenic BPLER cells that had gone through two additional steps of retroviral infection and selection confirming absence of in vitro selection of rare clones during the transformation process.
Figure 25A:
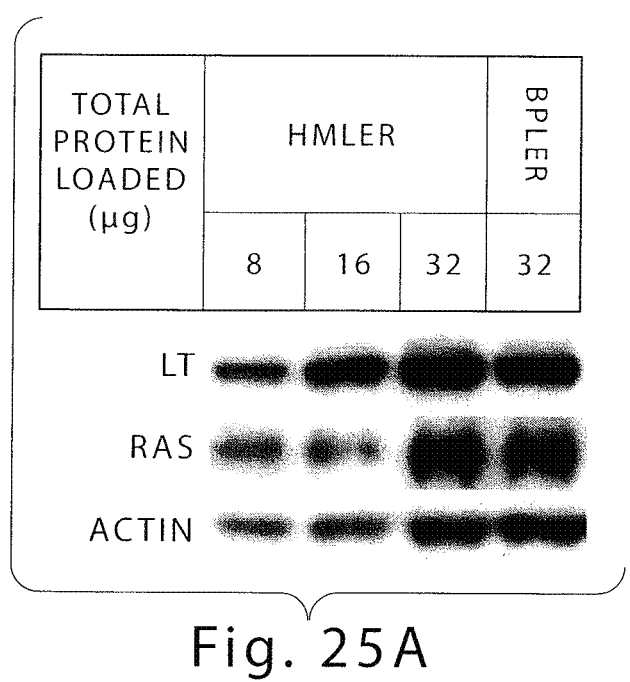
FIGS. 25A-25B show the expression of introduced genes in BPLER and HMLER cells.
Figure 25B:
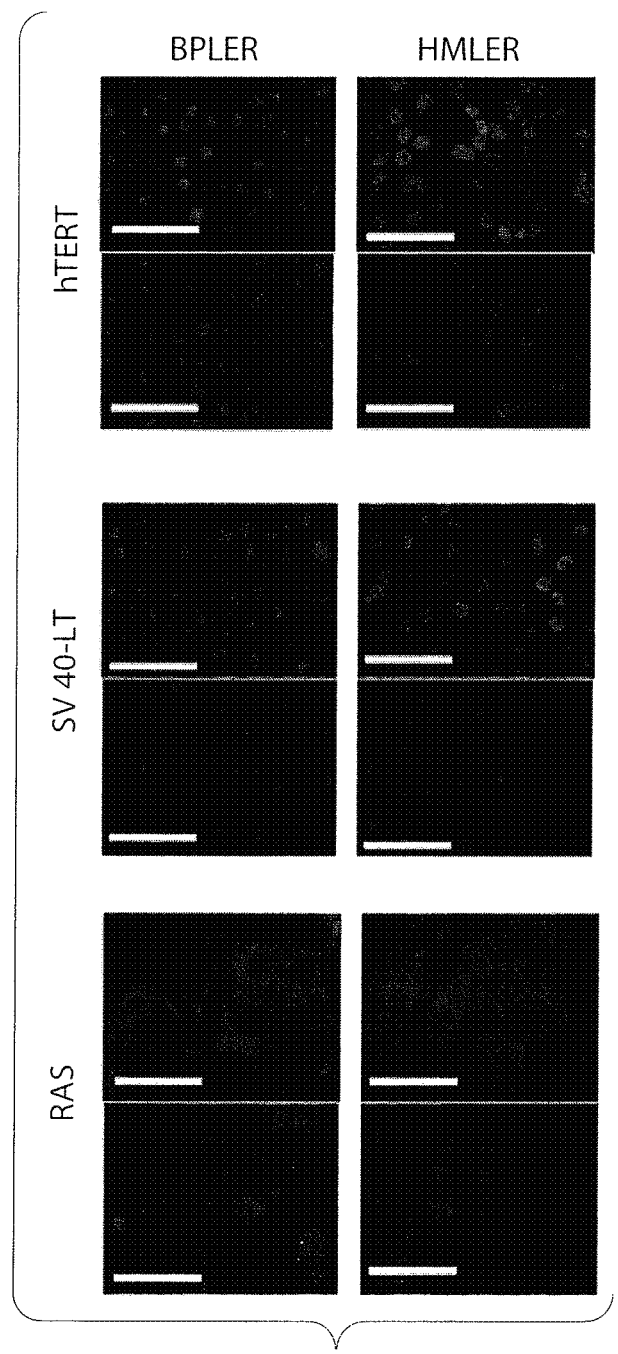
Figure 26A:
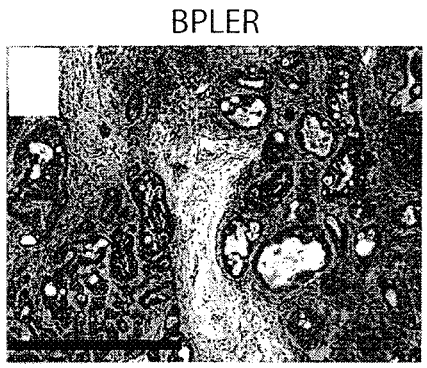
FIGS. 26A-26F are photographs showing histopathological comparison of BPLER and HMLER xenografts with human breast adenocarcinoma.
Figure 26C:
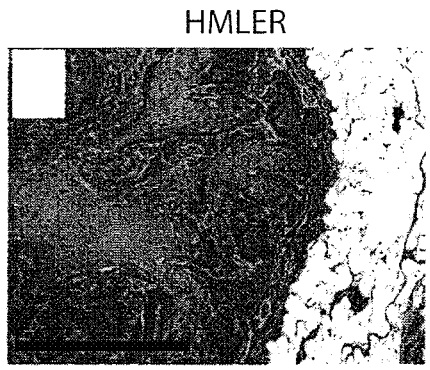
Figure 26B:
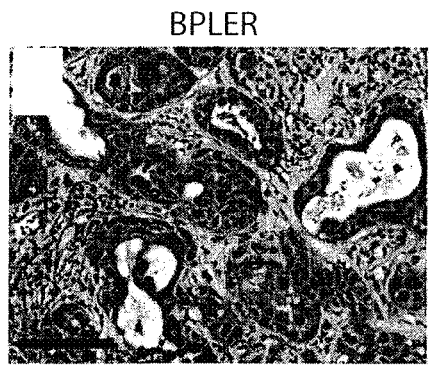
Figure 26D:
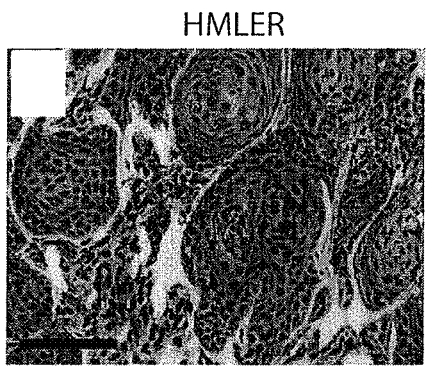
Figure 26E:
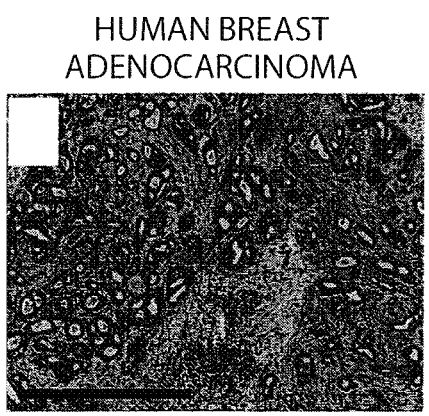
Figure 26F:
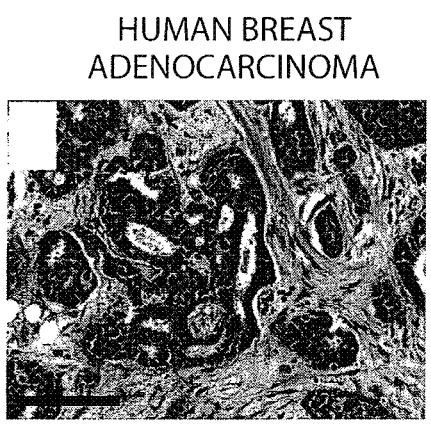
Figure 27A:
Figure 27B:
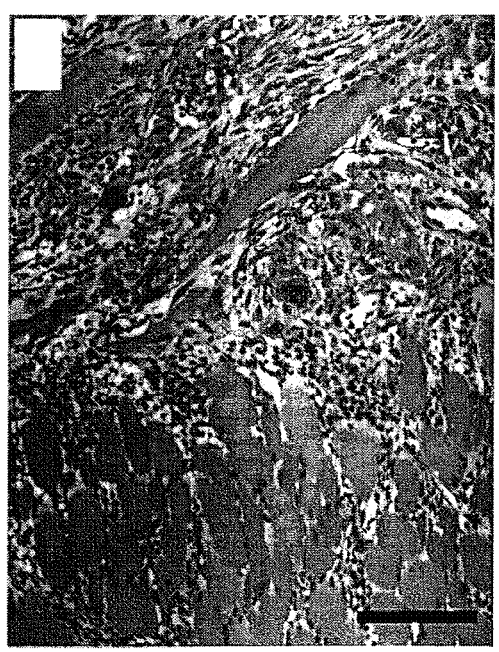

The gene expression differences indicated that, in parallel with the results described above, BPE-hTERT and HME-hTERT cells remained partially differentiated along luminal and myoepithelial pathways respectively. The BPE-hTERT cells expressed many more luminal-specific genes at a ≥2-fold higher level relative to the corresponding HME-hTERT cells; conversely, the HME-hTERT cells expressed more myoepithelial-specific genes relative to BPE-hTERT cells (FIG. 24A). Furthermore, the ratio of luminal- to myoepithelial-specific gene expression within each cell type was very different in this comparison; while BPE-hTERT cells expressed predominantly luminal-specific genes, the corresponding HME-hTERT cells predominantly expressed myoepithelial-specific genes (FIG. 24A; FIG. 33). Hence, the hTERT-expressing populations retained the relative differentiation patterns of the primary BPEC and HMEC populations. hTERT-expressing BPECs and HMECs were subsequently transformed in parallel with retroviral vectors expressing the SV40 early region and the H-ras oncogene, as described before (Elenbaas et al., 2001; Hahn et al., 1999) (FIG. 18A; FIG. 24B). The resulting transformed progeny remained polyclonal throughout multiple steps of transformation (FIGS. 24C and 24D, Hahn et al., 1999). Moreover, expression levels of the products of the introduced genes in the two cell lines were comparable, i.e., less than 2-fold different between the HMLER and BPLER cells, as determined by immunoblotting, immunofluorescence, and RT-PCR analyses (FIGS. 18B-18D, FIGS. 25A, 25B). Importantly, the continued presence of polyclonal populations of these two cell types in vitro made it unlikely that rare variant subtypes were selected during the generation of these two transformed cell populations (FIGS. 24B, 24C). The tumorigenic cells arising from HMECs following introduction of vectors expressing hTERT (L), the SV40 early region (E), and H-ras (R) are termed hereafter HMLER cells, while those arising from BPECs are termed BPLER cells (FIG. 18A).

Example XII. Histology of HMLER and BPLER Tumors

Most human breast carcinomas (>90%) retain some form of the normal glandular architecture, which explains their classification as ductal adenocarcinomas (FIGS. 26A-26F). Moreover, human breast tumors are associated with a desmoplastic stromal response, which is composed of a newly formed extracellular matrix and multiple non-neoplastic cell types, in particular, abundant alpha-smooth muscle actin (α-SMA)-positive myofibroblasts. Both the ductal architecture and the stromal response seen in human tumors are typically absent in most commonly used breast tumor xenograft models.

Significantly, the BPLER tumors focally displayed well-formed epithelial ductal structures that expressed cytokeratins 8 and 18 (FIG. 19), which were surrounded by a strong desmoplastic response composed of numerous α-SMA-positive mouse myofibroblasts; α-SMA was not expressed by the tumor cells themselves (FIGS. 27A-27H). Thus, the histopathological appearance of BPLER tumors was closer to actual human tumors compared to most xenograft models. In addition to areas of ductal differentiation, there were areas of papillary differentiation and scattered poorly differentiated regions in BPLER tumors (see FIGS. 26A-26F and FIGS. 27A-27H for additional images).

Figure 19:
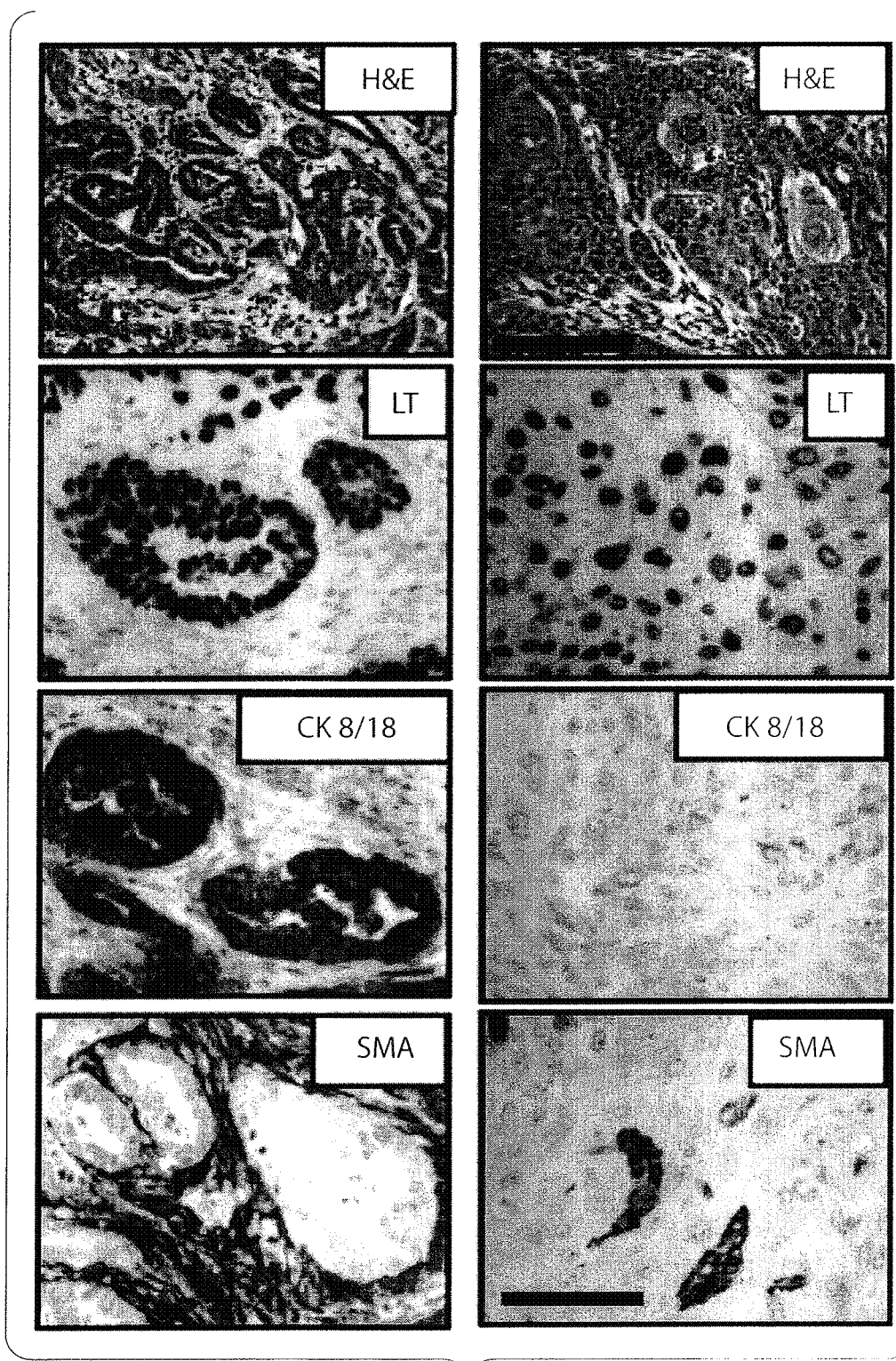
FIG. 19 are photographs showing microscopic examination of mouse mammary fat pad tumor xenografts. BPLER cells (left column) and HMLER cells (right column). (H&E): Hematoxylin-eosin staining, bar=200 micrometer. Immunoperoxidase stains of representative tumor sections: (LT): SV40-TL Ag, (SMA): α-smooth muscle actin, and (CK8/18): cytokeratin 8/18. Specific staining (brown), counter stain (blue), bar=50 micrometer. All histological sections were prepared from tumor tissue explanted 4 to 6 weeks after implantation of tumorigenic cells from tissue culture into the mammary fat pad of NOD/SCID mice.

As reported previously, HMLER cells form poorly differentiated tumors with areas of squamous cell differentiation when injected into immunocompromised mice (Elenbaas et al., 2001). Applicants observed the same results with a second independently isolated and transformed HMLER cell population (FIG. 19). Microscopic examination of representative tumor sections showed that these HMLER tumors grew as a solid mass of neoplastic cells with little desmoplastic stroma and that they formed keratin pearls—a typical feature of squamous differentiation (FIG. 19). No ductal or glandular structures that are characteristic of breast adenocarcinomas were apparent. Furthermore, HMLER tumor cells lacked cytokeratins 8 and 18 (CK 8/18), which are expressed in >85% breast adenocarcinomas but are absent in squamous cell carcinomas (FIG. 19) (Chu et al., 2002).

The histomorphology of BPLER and HMLER xenografts are reminiscent of two different classes of naturally occurring human breast tumors—adenocarcinoma and squamous cell carcinoma. Since both cell populations were transformed with the same set of introduced genetic alterations, the observed difference in tumor histomorphology appeared to be influenced by the phenotype of the starting normal cell populations.

Example XIII. Cell Type and Metastatic Ability

BPLER tumor xenografts exhibited a multifocal growth pattern in the mammary fat pad (FIG. 20A); in human breast tumors, such behavior has been ascribed to intra-mammary gland metastasis (Andea et al., 2004; Andea et al., 2002;

Norton et al., 2006). This prompted us to search for distant metastases. To do so, BPLER and HMLER cells were additionally transduced with a green fluorescent protein (GFP) gene and implanted in the mammary fat pads of NOD/SCID mice (FIGS. 20A and 20B). Ten weeks after injection, more than 70% of mice bearing BPLER tumors had lung micrometastases that generally ranged from single cells up to nodules of 20 cells, with occasional 1 mm diameter nodules (FIG. 20C), as confirmed by immunohistochemical staining of the nodules with an antibody against LT-Ag (FIG. 20D). Lung micrometastases were observed in multiple experiments using two independently derived BPLER cell lines originating from two different patients (BPLER 1 and 2, FIG. 20E). Of note, BPLER tumors were equally metastatic following subcutaneous injection in nude mice (FIG. 20E).

Despite primary tumor burdens equivalent to BPLER-injected mice, none of the HMLER-injected animals developed lung micrometastases, as ascertained by dissection microscopy as well as histological and immunohistochemical examination of the lungs, confirming previous reports that also failed to detect distant metastases in mice bearing HMLER xenograft tumors (Elenbaas et al., 2001; Kuperwasser et al., 2005). Hence, transformation of HMECs and BPECs yielded tumors with differing metastatic disposition.

Example XIV. Cell Type and Tumor-Initiating Cell Frequency

In most tumor xenograft experiments using established tumor cell lines, injection of at least $10^6$ tumor cells is required in order to observe tumor growth. Considering the rapid growth of the BPLER primary tumors, applicants injected fewer cells to allow for the long-term observations required to detect distant metastases. During the course of such experiments, applicants discovered a significant difference in the number of cells required for the seeding of tumors by the HMLER and BPLER cells: Three independent BPLER cell lines, derived from three different patients, formed tumors when as few as 100 cells were injected subcutaneously into nude mice (BPLER 1-3, Table 1, A, C). In contrast, a minimum of $2$-$3 \times 10^6$ cells was needed per inoculum in order to observe subsequent outgrowth of HMLER tumors (Table 1B). Importantly, there was no significant difference in the in vitro growth rates of BPLER and HMLER cells. Thus, in addition to histomorphology and metastatic behavior, the differences in the phenotype of normal cells also influenced tumor-initiating cell frequency observed among their transformed derivatives.

Example XV. Influence of In Vitro Growth Conditions on Tumor Initiation and Metastasis Applicants next determined whether the observed phenotypic differences in tumorigenicity and metastasis between the two transformed mammary epithelial cell types were due to adaptation to certain conditions of in vitro culture. While HMECs that had been adapted to MEGM medium could not survive in WIT medium (see above), their fully transformed derivatives proliferated equally well in both media. Accordingly, applicants tested the tumorigenicity and metastatic ability of HMLER cells that were transferred to WIT medium for three weeks prior to orthotopic or subcutaneous implantation.

The WIT-adapted HMLER cells were only slightly more tumorigenic than HMLER cells propagated exclusively in MEGM medium (Table 1, B) and, like those propagated exclusively in MEGM medium, lacked metastatic ability (data not shown). This slight increase in tumorigenicity following altered conditions of culture could not account for up to four orders of magnitude difference in the frequency of tumor-initiating cells between the HMLER and BPLER cell populations. Accordingly, these differences in behavior were apparently stably imprinted on the HMLER cells and could not be altered by propagating the HMLER cells in WIT medium.

Example XVI Influence of Normal Precursor Cell Types HME and BPE on Tumor Expression Profile To define the contribution of normal cell phenotype on tumorigenic cell phenotype, applicants compared the gene expression profiles of three independently derived primary BPECs and HMECs and their hTERT-expressing, non-tumorigenic untransformed derivatives (BPE and HME), with the profiles of their fully transformed tumorigenic derivatives (BPLER and HMLER).

Figure 21A:
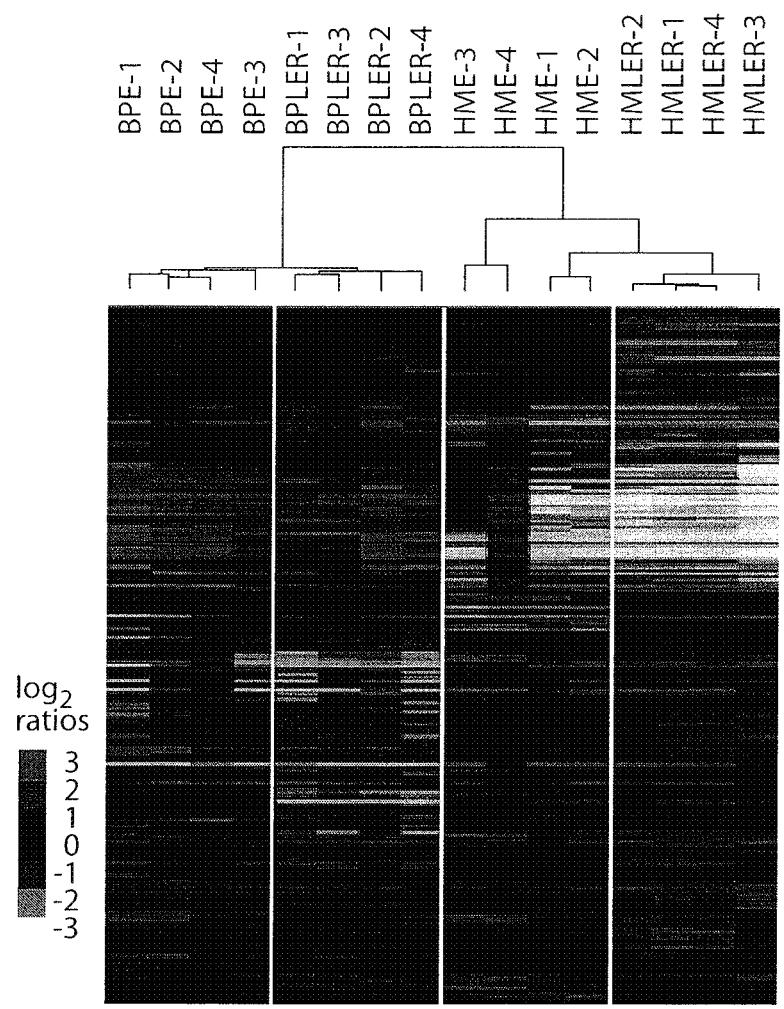
FIGS. 21A-21C show the influence of precursor cell type on gene expression signature of tumorigenic cells. The gene expression comparisons described in this figure were performed on cell populations isolated from three different individuals. The mRNA was prepared form in vitro cultured cells. The untransformed hTERT-expressing cell populations (BPE and HME) were compared with each other and with their fully transformed tumorigenic derivatives (BPLER and HMLER).

The hierarchical clustering analyses revealed that the tumorigenic cells were more similar to their untransformed parental cells than to one another. The BPE cells and their tumorigenic BPLER derivatives formed one common root cluster that is distinct form the cluster formed together by HME cells and their HMLER tumorigenic derivatives (FIG. 21A). These significant differences in gene expression patterns were in consonance with the biological differences between these various cell types that applicants described above. Comparison of the gene expression profile of each tumorigenic cell type (BPLER and HMLER) with its corresponding in vitro untransformed hTERT-expressing precursor population (BPE and HME) identified those genes that were significantly altered upon transformation. Out of a total of 15,399 expressed genes monitored in both lineages in these arrays, 1,336 genes in BPEs (vs. BPLER) and 3,022 genes in HMEs (vs. HMLER) were either increased or decreased by more than a factor of two upon transformation (FIG. 21B; see FIG. 34 for a full list of genes).

Figure 21B:
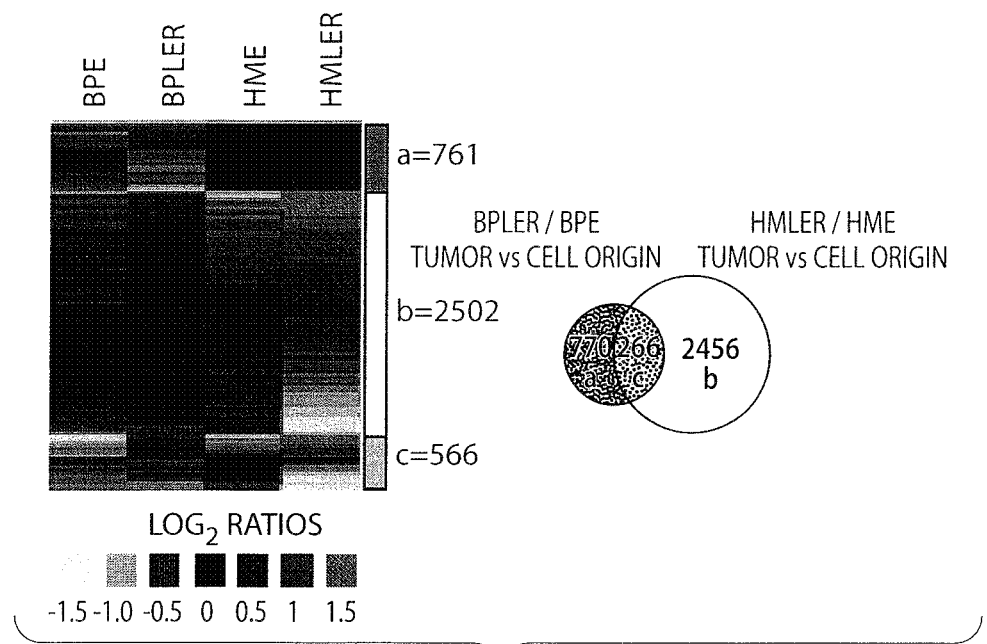
Figure 30A:
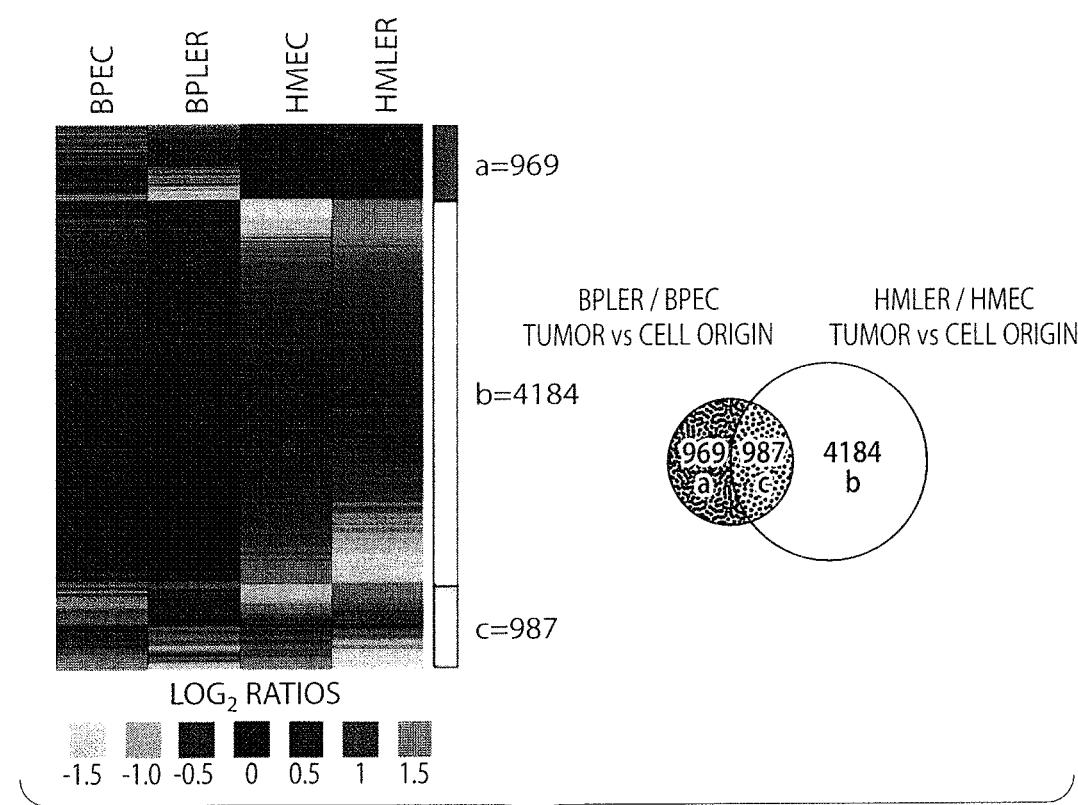
FIGS. 30A-30B show the influence of precursor cell phenotype on gene expression signature of tumorigenic cells. The gene expression comparisons described in this figure were performed on cell populations isolated form three different individuals. The mRNA was prepared form in vitro cultured cells. The primary normal mammary epithelial cell populations (BPEC and HMEC) were compared with each other and with their fully transformed tumorigenic derivatives (BPLER and HMLER). BPECs and HMECs are early passage (4-7) primary human breast epithelial cell cultures that have not been introduced with any expression vectors. BPLER and HMLER are fully transformed tumorigenic cells.

Among all of the genes altered upon transformation, only a small fraction of these genes (~15%) were altered in the same direction in both cell populations (HME vs. BPE) following transformation (FIG. 21B; group c). The remaining 85% of the genes were either altered in one lineage but not in the other, or were altered in opposite directions (increased in one lineage and decreased in the other, FIG. 21B; group a and b). The comparison of the gene expression profiles of the two transformed cell populations with those of their corresponding primary BPEC and HMEC populations that had not yet been immortalized with hTERT yielded very similar results (FIG. 30A). Hence, the same set of introduced transforming genes elicited quite different cellular-context-dependent changes in gene expression profiles following transformation.

Figure 21C:
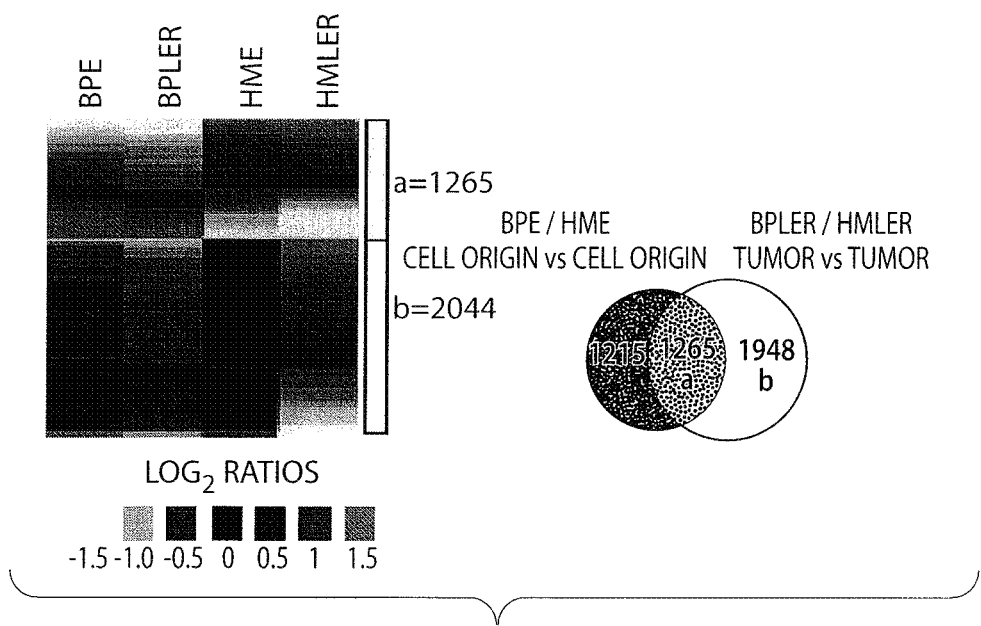
Figure 30B:
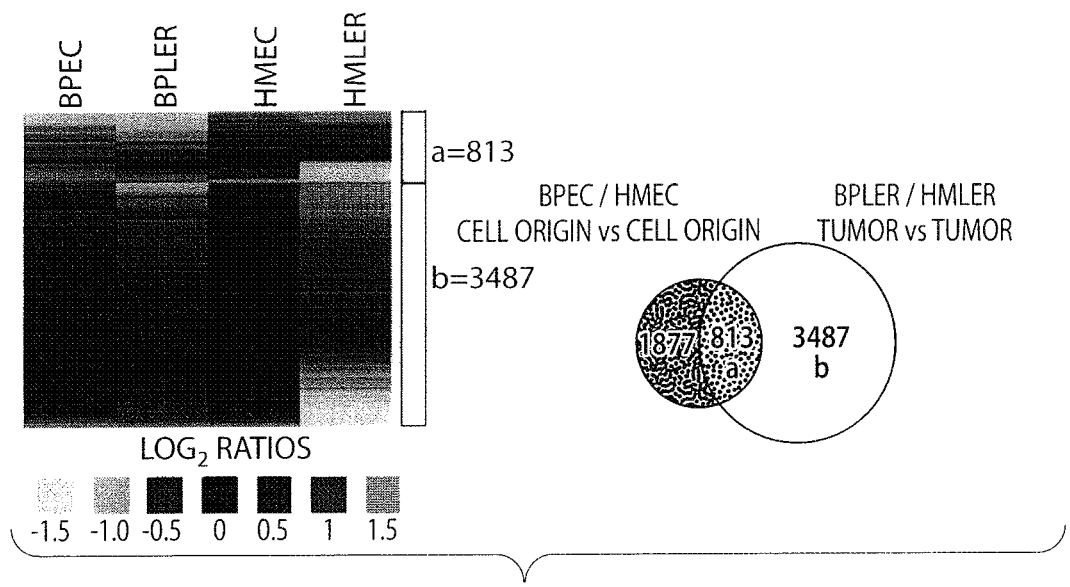

Example XVII. Contributions of Normal Precursor Cell Type to Tumor-Specific Gene Expression Applicants also examined the gene expression profiles of the transformed cell populations from another perspective. Based on the initial analyses above, it became clear that the gene expression profiles of tumor cells are partly inherited unchanged from their normal precursor cells and partly acquired due to genetic and epigenetic alterations acquired during the course of tumor pathogenesis. In order to reveal and quantify the relative contributions of these two influences on gene expression, applicants compared the gene expression profiles of the two tumorigenic cell types (BPLER and HMLER) directly with one another. This revealed 3,213 genes that were expressed significantly differently between the two tumorigenic cell populations, being increased or decreased ≥2-fold (FIG. 21C, group (a+b), BPLER/HMLER). Applicants then compared the expression levels of this set of genes in the untransformed hTERT-expressing parental cells, BPE and HME, in order to measure the scale of the contribution of the precursor cell gene expression profile to the tumor-cell-specific gene expression patterns of derived tumor cells. Interestingly, approximately 40% (1,265/3,213) of the mRNA expression differences between the BPLER and HMLER tumor cells were already apparent when the expression patterns of their respective normal precursors cells BPE and HME were compared, being increased or decreased in the same direction (1,265 genes, FIG. 21C, group a, see FIG. 34 for a full list of genes). The comparison of early passage primary BPEC and HMEC populations that had not yet been hTERT-immortalized yielded similar results, (FIG. 30B). These results further support the notion that a significant portion of the gene expression profile that distinguishes one tumor from another derives from pre-existing differences that these tumors inherit form their normal cell precursors.

The multi-step model of tumor progression emphasizes the accumulation of genetic alterations as the central mechanism driving tumorigenesis (Karakosta et al., 2005; Nowell 1976; Vogelstein et al., 1993). According to this view, the normal cell is an almost passive recipient of these mutations, and its cancer-associated phenotypes are governed largely by the somatic mutations that its descendants happen to acquire during the course of tumor progression (Cahill et al., 1999; Fearon et al., 1990). Indeed, the role of accumulated somatic mutations in determining tumor phenotype has been extensively documented and explains many of the observed differences among different tumors.

Applicants provide evidence here supporting an additional, but far less-studied, mechanism that governs tumor phenotype. HMLER and BPLER tumors that were created through introduction of the identical set of gene expression vectors differed significantly in their morphology, tumorigenicity, and metastatic behavior. Consequently, applicants conclude that in this experimental model, the observed differences between the two tumor cell types can be traced to differences inherent in their respective in vitro normal precursors, HMECs and BPECs (Olsson 2000). This observation raises the question of whether some of the clinical differences observed between subtypes of human breast cancers can be traced to their respective normal in vivo cells-of-origin.

In the presently described work, the accumulation of genetic alterations other than those introduced experimentally might, in principle, explain the observed phenotypic differences between BPLER and HMLER cells. However, applicants have previously shown in multiple human cell types, including human mammary epithelial cells, that tumors that are generated by introduction of a defined set of genetic elements do not require accumulation of additional stochastically occurring mutations in order to become tumorigenic (Hahn et al., 2002; Lundberg et al., 2000; Zimonjic et al., 2001). Furthermore, accumulation of random mutations in BPLER cells during in vitro culture is unlikely to explain the high frequency of tumor-initiating cells in BPLER cultures (~1 in $10^2$) that are present in concentrations up to four orders of magnitude higher than in HMLER cell populations (~1 in $10^6$ cells). Such a high frequency of tumor-initiating cells might well result from the positive selection of such cells during propagation in vitro. However, Southern blot analyses of the chromosomal integration sites of retroviral vector DNAs have shown that the BPLER cells remain highly polyclonal throughout the multiple steps of experimental transformation, with no evidence of in vitro selection of rare variant subclones (FIGS. 24A-D). Moreover, it is difficult to envision a single mutational event that could account for all of the multiple observed differences between BPLER and HMLER cells, including their differentiation state (adenocarcinoma vs. squamous carcinoma), tumorigenicity, stromal recruitment, and metastatic behavior.

Applicants note, as well, that BPLER tumors derived by transforming normal mammary epithelial cells (BPECs) prepared from three different donors were very similar phenotypically, excluding the influences of specific donors and their respective genetic backgrounds on the observed behavior of BPLER cells.

During the course of tumor pathogenesis, human tumor cells acquire numerous mutations that perturb multiple, centrally acting cellular regulatory pathways. This might suggest that the acquired, mutation-specific gene expression pattern would obscure or dominate the pre-existing gene expression profile of the normal precursor cells. In the present case, the expression vectors that were used to transform HMEs and BPEs deregulate many pathways known to be altered in human tumors, doing so by inhibiting p53, pRB, p130, and p107 and protein phosphatase 2A (PP2A), as well as causing overexpression of oncogenic H-Ras (Hahn et al., 2002). If the actions of the introduced transforming genes were to dominate the neoplastic cells' gene expression patterns, then the BPE and HME cells should have become more similar to one another following transformation. This was not the case, however, since the great majority (>90%) of the genes whose expression was altered following transformation were changed in a cell-type specific manner, being altered in either BPLERs or HMLERs but not in both. Furthermore, almost half of the mRNA expression differences between the BPLER and HMLER tumor cells closely reflected pre-existing differences between their corresponding untransformed precursors—the parental BPE and HME populations. Consequently, while the current practice of comparing signatures of spontaneously arising human tumors to bulk normal tissue provides some information about the pathogenesis of these tumors, applicants suggest that in the future, further interpretation of tumor expression profiles will require comparisons with the relevant normal cell-of-origin signatures.

The tumor phenotypes described here reflect one possible combination of genetic alterations that could be used to transform BPECs and HMECs to a tumorigenic state. It is therefore possible that other sets of introduced genetic alterations could lead to differing phenotypes in these two transformed cell populations. Applicants note, however, that introduction of other combinations of transforming genes into HMECs has, to date, failed to yield tumors that are phenotypically different from the HMLER tumors described here (Rangarajan et al., 2004; Watnick et al., 2003; Zhao et al., 2003).

Lastly, applicants note that the adenocarcinoma phenotype has been difficult to recapitulate in tumor xenograft models (Cardiff et al., 2000; Liu et al., 2004; Lundberg et al., 2002), even though this tumor type constitutes the great majority of the tumors arising in a variety of visceral tissues, including breast, lung, ovary, colon and prostate. Applicants point out that, in contrast, the presently described tissue culture and xenograft model system has indeed been able to phenocopy many aspects of naturally occurring human adenocarcinomas, including their metastatic behavior.

Example XVIII Experimental Procedures for Examples IX-XVII

Isolation and culture of BPECs: The normal tissue samples from reduction mammoplasty specimens of disease-free patients were minced and dissociated with collagenase (1 mg/mL, Roche) in Hank's Buffered Salt Solution at 37° C., for 6 hours. The organoids liberated from the stroma were separated from single cells by centrifugation (10×g, 5 min.) and plated on Primaria plates (Becton-Dickinson) in WIT medium (approximately 10-20 organoids/cm$_2$) at 37° C. with 5% $CO_2$; see Example XIX, Supplemental Experimental procedures for details. Nearly every organoid that attached to the plate gave rise to BPEC colonies; it was not possible to establish similar cultures following full dissociation of organoids into single cells. After 10-15 days, during which the medium was changed every two days, cells were lifted by 0.15% trypsin treatment at 37° C. and subcultures were seeded at $1$-$2 \times 10^4$ cells/cm$^2$ density, lower plating densities diminished cell survival significantly. 20% serum-containing medium (1:10) was used to inactivate trypsin, followed by centrifugation of cells in polypropylene tunes (500×g, 5 min) to remove residual trypsin and serum. The medium was replaced 24 hours after replating cells and every 48 hours thereafter. HMECs were cultured from the same organoid preparations in MEGM medium on regular tissue culture plastic ware according to established protocols (Stampfer et. al., 2000). See Example XIX, Supplemental Experimental procedures for details of cell culture medium (WIT), and retroviral infections.

Analysis of tumorigenicity and metastasis: Single-cell suspensions were prepared in a WIT:Matrigel (1:1) mixture and injected in 25 µL (orthotopic) and 100 µl (subcutaneous) volumes. Female athymic nude mice (Balb/c nu/nu, Taconic) were gamma-irradiated (400rad) 12 hours prior to subcutaneous injections. Injections of tumorigenic cells into mammary fat pads were performed in 8 week-old female Nod/Scid mice that were anesthetized with intraperitoneal Avertin and implanted with a subcutaneous 60-day release pellet containing 2 mg estrogen and 20 mg progesterone, (Innovative Research of America, FL). Metastasis to lungs and other tissues was analyzed initially under a dissecting microscope (Leica) in fresh tissues, followed by microscopic examination of hematoxylin-eosin and immunostained sections of formalin-fixed and paraffin-embedded tissues. Immunohistochemical staining was carried out by use of the conventional ABC technique. All experiments on live vertebrates were performed in accordance with relevant institutional and Federal guidelines and regulations.

Methylation-Specific PCR, RT-PCR and Southern Blots:

The genomic DNA was isolated by using columns (Qiagen). Bisulfite modification of DNA was carried out by using CpGenome™ Fast DNA Modification Kit (Chemicon). The CpG WIZ® p16 Amplification Kit (Chemicon) was used for determining the methylation status of the p16 promoter by methylation-specific PCR (MSP) (Herman et. al., 1996). In this assay, DNA-specific primers produce PCR products of different sizes following a complete chemical modification reaction; U primers amplify only unmethylated DNA (154 bp), M primers amplify only methylated DNA (145 bp), and C primers amplify only DNA that is not chemically modified, or "wild type" (142 bp). RT-PCR for hTERT mRNA was performed according to previously published methods (Dessain et al., 2000). For Southern blots, the genomic DNA digested with BamHI was probed with pmig-GFP-hTERT plasmid that was $_{32}$P-labeled with a random primer labeling system (Amersham).

Protein and RNA Expression:

The in vitro expression of proteins was confirmed by immunoblotting after separation by sodium dodecyl sulfate-7.5 to 15% gradient polyacrylamide gel electrophoresis and by immunofluorescence imaging of cells that were grown on glass cover slips preincubated with gelatin, fixed with 2% paraformaldehyde, 0.1% Triton X-100 and incubated with the following antibodies: hTERT (Bio SB, Inc.), Ras-C20 (Santa Cruz), and LT (PAb 101, Santa Cruz), E-Cadherin, cytokeratin 5, cytokeratin 8/18 (BD Pharmingen), CD-10, (Serotec, 56C6), claudin-4 (Zymed). RNA was extracted using columns according to the instructions of the vendor (Qiagen). cDNA synthesis, and hybridization to Affymetrix Human Genome U133 Plus 2.0 Arrays were performed as described previously (Signoretti et al., 2002; Wang et al., 2004). See Example XIX, Supplemental Experimental procedures for details for details of array analysis.

Example XIX. Supplemental Experimental Procedures for Examples IX-XVII

Mammary Tissue:

The normal breast tissues were collected from discarded reduction mammoplasty procedures performed for cosmetic indications at the Brigham and Women's Hospital (BWH). All samples were anonymous; no patient identifiers were associated with the collected tissues in accordance with the Institutional Review Board (IRB) for Human Research regulation. Patients were disease free, between 25-55 years old. The collected tissues were confirmed to be disease and malignancy free by histopathological examination of tissue sections. Cell culture medium: A working formulation of WIT medium for culturing transformed cells (expressing SV40 LT and Ras) can be prepared by mixing equal volumes of F12 (Sigma) and M199 media (JHR Biosciences), supplemented with the following: HEPES 10 mM (pH7.4), glutamine (2 mM), insulin (10 µg/mL), EGF (0.5 ng/mL), hydrocortisone (0.5 ng/ml), transferrin (10 µg/mL), triiodothyronine (0.2 pg/mL), 0-phosphoryl ethanolamine (5 µg/mL), selenious acid (8 ng/mL), 17β estradiol (0.5 ng/mL), linoleic acid (5 µg/mL), all-trans retinoic acid (0.025 µg/mL), hypoxanthine Na (1.75 µg/mL), lipoic acid (0.05 µg/mL), cholesterol (0.05 µg/mL), glutathione (0.012 µg/mL), xanthine (0.085 µg/mL), ascorbic acid (0.012 µg/mL), alphatocopherol phosphate (0.003 µg/mL), calciferol (vitamin D, 0.025 µg/mL), choline chloride (3.5 µg/mL), folic acid (0.33 µg/mL), vitamin B12 (0.35 µg/mL), thiamine HCl (0.08 µg/mL), i-inositol (4.5 µg/mL), uracil (0.075 µg/mL), ribose (0.125 µg/mL), para-aminobenzoic acid (0.012 µg/mL) and bovine serum albumin (1.25 mg/mL). This formulation is supplemented with cholera toxin (25 ng/mL, Calbiochem) for culturing hTERT-immortalized BPECs. The basal WIT medium is supplemented with insulin (20 µg/mL), EGF (10 ng/mL), hydrocortisone (0.5 µg/mL) and cholera toxin (100 ng/mL, Calbiochem) for culturing primary BPECs. All the concentrations listed above refers to final concentrations The primary cells were cultured in antibiotic free conditions. All chemicals were purchased from Sigma unless otherwise indicated. Tissue culture ware with a modified surface chemistry was used (Primaria, Becton-Dickinson) for BPEC and BPLER cultures. HMECs and HMLER cells were cultured in MEGM medium according to the manufacturer (Cambrex).

Retroviral Infections:

Amphotropic retroviruses were produced by transfection of the 293T producer cell line with a retroviral vector and a vector encoding a replication-defective helper virus, pCL-Ampho (Imgenex) using Fugene 6 (Roche Biochemicals), and introduced to recipient cells in individual steps in the following order; pmig-GFP-hTERT, pBABE-zeo-SV40-ER and pBABE-puro-H-ras. 50 µg/ml zeomycin (SV40 ER) and 0.5 µg/ml puromycin (G12V Hras) were used to select transformed clones (Elenbaas et al., 2001). BPECs were immortalized with hTERT between passages 4 to 7, and transformed between passages 7 to 12. HMECs were transduced with hTERT pre-MO and transformed post-MO between passages 6 to 12.

Figure 28:
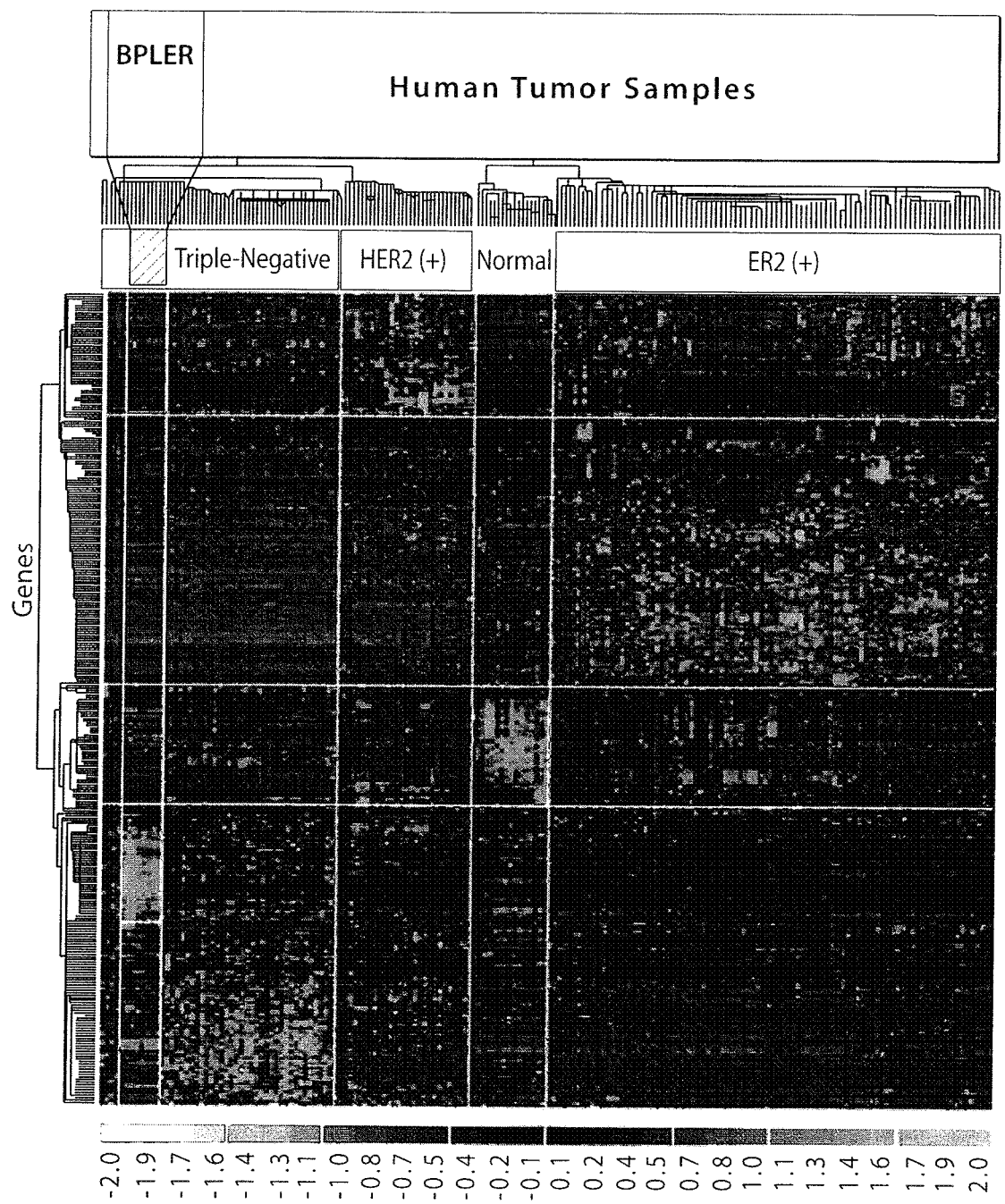
FIG. 28 shows hierarchical clustering of BPLER tumor explants with 120 human breast tumors for genes filtered for variable expression across the sample set. Each column represents a single tumor tissue sample and each row represents a single gene. Clustering orders the tumor samples according to greatest similarity of gene expression, shown by the dendrogram at the top, and orders genes by similarity of expression level among the sample set, shown by the dendrogram along the side. The dendrograms show the major tumor clusters and associated gene clusters highlighted by colored branches as follows: black, BPLER tumor explants from NOD/SCID mice; red, triple-negative human tumors; green, HER2-positive human tumors; light blue, normal breast samples; dark blue, ER-positive human tumors. Relative gene expression levels are represented as follows: mean expression in black, expression levels above the mean in progressively darker shades of red, expression levels below the mean in progressively darker shades of green. BPLER cells were injected into the mammary fat pads of NOD/SCID mice and resulting tumors were explanted 4 to 6 weeks after implantation (n=8). The human breast tumor data includes 120 cases from previously published array data sets (Matros et al., 2005; Richardson et al., 2006). Comparison of mRNA expression profiles of BPLER tumor xenografts with a collection of human breast carcinomas revealed that these experimentally created tumors were a remarkably close phenocopy of triple-negative human ductal adenocarcinomas of the breast. While HMLER tumors have a clear squamous morphological phenotype, they also clustered in such expression array analyses with the triple-negative adenocarcinomas (data not shown).
Figure 29:
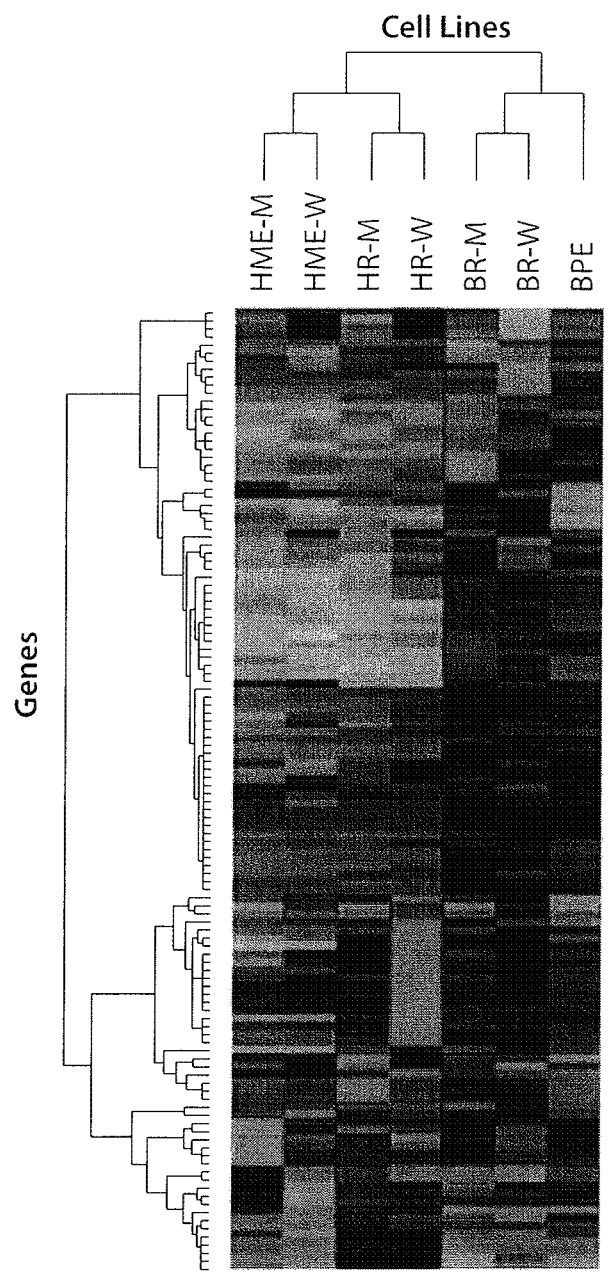
FIG. 29 shows the influence of media conditions on tumorigenic cell gene expression profiles. Each column represents a single cell type grown for at least 1 week in a different medium; HME: HMECs that express hTERT, BPE: BPECs that express hTERT, HR: HMLER, BR: BPLER, M: MEGM medium, W: WIT medium) and each row represents a different gene. Clustering orders the samples according to greatest similarity of gene expression, shown by the dendrograms at the top, and orders genes by similarity of expression level among the sample set, shown by the dendrograms along the side. Relative gene expression levels are represented as follows: mean expression in white, expression above the mean in shades of red, expression below the mean in shades of blue. The cells co-cluster based on cell type rather than the medium type they are propagated in. This result suggests that the gene expression differences between BPLER and HMLER are not readily adaptable and altered upon change in growth conditions from MEGM medium into WIT medium.

Array Analysis:

The human breast tumor Affymetrix U133p2 array data from 120 cases was a combination of two previously published array datasets (Matros et al., 2005; Richardson et al., 2006). Raw expression data obtained using Affymetrix GENECHIP software was normalized and analyzed using DNA-Chip Analyzer (dChip) custom software (Wong, W. H., Li, C. http://www.dChip.org). Array probe data was normalized to the mean expression level of each probe across the combined human tumor and cell line sample set. Unsupervised hierarchical cluster analysis (FIGS. 28 and 29) was performed using dChip hierarchical cluster function with a set of genes filtered for significant variation of expression across the sample set (standard deviation/mean expression values between 0.8 and 10). Only probe sets with RefSeq validation and annotation were used in the analyses. Duplicate probes for the same gene were excluded. Where indicated, human tumors were classified as triple-negative on the basis of their expression array characteristics, as previously described (Matros et al., 2005; Wang et al., 2004). Comparisons between cell lines (FIGS. 21A, 21B, 21C, FIGS. 30A-30B) was performed using 21 Affymetrix HG-U133 Plus 2 microarrays (4-6 biological replicates per cell type) were preprocessed and normalized with GeneChip Robust Multi-Array Analysis (GCRMA)(Wu et al., 2005). Absent/Present calls were made using 'affy' from BioConductor, and probe sets that were Absent or Marginal across all chips were removed from further analysis. Differential expression (DE) was defined as greater that 2-fold difference in expression level for each pairwise comparison. Probe set annotations were obtained from the Affymetrix web site, but regardless of annotation, all probe sets were used for the analysis, including poorly annotated sequences and duplicates for some genes. After classification based on DE and sorting by expression ratio, profiles were visualized as heatmaps with Java TreeView (Saldanha 2004) using the log 2 ratios of RNA levels of each cell type compared to the mean across all cell types. To verify statistical significance of expression patterns obtained in FIGS. 20A-20E, 16A-16C Affymetrix HG-U133 Plus 2 microarrays (4 biological replicates per cell type) were preprocessed and normalized with GeneChip Robust Multi-Array Analysis (GCRMA) (Wu et al., 2005). Differential expression was determined via a modified t-test ($p<0.05$) using Linear Models for Microarray Data (Smyth 2004) and correcting for False Discovery Rate.

TABLE XI

Medium 199 components

| Medium 199 COMPONENTS | Concentration (mg/L) |
|---|---|
| 2-deoxy-D-ribose | 0.5 |
| Adenine sulfate | 10 |
| Adenosine 5'-phosphate | 0.2 |

TABLE XI-continued

Medium 199 components

| Medium 199 COMPONENTS | Concentration (mg/L) |
|---|---|
| Adenosine 5'-triphosphate | 1 |
| Alpha-tocopherol Phosphate | 0.01 |
| Ascorbic acid | 0.05 |
| Biotin | 0.01 |
| Calciferol (Vitamin D2) | 0.1 |
| Calcium chloride (CaCl2) | 200 |
| Cholesterol | 0.2 |
| Choline chloride | 0.5 |
| D-Calcium pantothenate | 0.01 |
| D-Glucose | 1000 |
| Ferric nitrate (Fe(NO3)—9H2O) | 0.7 |
| Folic acid | 0.01 |
| Glutathione (reduced) | 0.05 |
| Glycine | 50 |
| Guanine hydrochloride | 0.3 |
| Hypoxanthine-Na | 0.4 |
| i-Inositol | 0.05 |
| L-Alanine | 25 |
| L-Arginine hydrochloride | 70 |
| L-Aspartic acid | 30 |
| L-Cysteine HCl—H2O | 0.1 |
| L-Cystine-2HCl | 26 |
| L-Glutamic Acid | 75 |
| L-Glutamine | 100 |
| L-Histidine-HCl—H2O | 21.88 |
| L-Hydroxyproline | 10 |
| L-Isoleucine | 40 |
| L-Leucine | 60 |
| L-Lysine hydrochloride | 70 |
| L-Methionine | 15 |
| L-Phenylalanine | 25 |
| L-Proline | 40 |
| L-Serine | 25 |
| L-Threonine | 30 |
| L-Tryptophan | 10 |
| L-Tyrosine 2Na 2H20 | 40 |
| L-Valine | 25 |
| Magnesium sulfate (MgSO4) | 97.67 |
| Menadione (Vitamin K3) | 0.01 |
| Niacin | 0.025 |
| Niacinamide | 0.025 |
| Para-aminobenzoic acid | 0.05 |
| Phenol red | 20 |
| Potassium chloride (KCl) | 400 |
| Pyridoxal hydrochloride | 0.025 |
| Pyridoxine hydrochloride | 0.025 |
| Riboflavin | 0.01 |
| Ribose | 0.5 |
| Sodium acetate | 50 |
| Sodium bicarbonate (NaHCO3) | 2200 |
| Sodium chloride (NaCl) | 6800 |
| Sodium phosphate, mono. (NaH2PO4—H2O) | 140 |
| Thiamine hydrochloride | 0.01 |
| Thymine | 0.3 |
| Tween 80 | 20 |
| Uracil | 0.3 |
| Vitamin A (acetate) | 0.1 |
| Xanthine-Na | 0.34 |

TABLE XII

F12 Medium Components

| F12-COMPONENTS | Concentration (mg/L) |
|---|---|
| Biotin | 0.0073 |
| Calcium chloride (Anhydrous) | 33.22 |
| Choline chloride | 14 |
| Cupric sulfate (CuSO4—5H2O) | 0.0025 |
| D-Calcium pantothenate | 0.5 |

TABLE XII-continued

F12 Medium Components

| F12-COMPONENTS | Concentration (mg/L) |
|---|---|
| D-Glucose | 1802 |
| Ferric sulfate (FeSO4—7H2O) | 0.834 |
| Folic acid | 1.3 |
| Glycine | 7.5 |
| Hypoxanthine Na | 4.77 |
| i-Inositol | 18 |
| L-Alanine | 8.9 |
| L-Arginine hydrochloride | 211 |
| L-Asparagine-H2O | 15.01 |
| L-Aspartic acid | 13.3 |
| L-Cysteine-HCl—H2O | 35.12 |
| L-Glutamic acid | 14.7 |
| L-Glutamine | 146 |
| L-Histidine-HCl—H2O | 21 |
| Linoleic Acid | 0.084 |
| Lipoic Acid | 0.21 |
| L-Isoleucine | 4 |
| L-Leucine | 13.1 |
| L-Lysine hydrochloride | 36.5 |
| L-Methionine | 4.5 |
| L-Phenylalanine | 5 |
| L-Proline | 34.5 |
| L-Serine | 10.5 |
| L-Threonine | 11.9 |
| L-Tryptophan | 2.04 |
| L-Tyrosine 2Na 2H2O | 7.81 |
| L-Valine | 11.7 |
| Magnesium chloride (Anhydrous) | 57.22 |
| Niacinamide | 0.036 |
| Phenol red | 1.2 |
| Potassium chloride (KCl) | 223.6 |
| Putrescine-2HCl | 0.161 |
| Pyridoxine hydrochloride | 0.06 |
| Riboflavin | 0.037 |
| Sodium bicarbonate (NaHCO3) | 1176 |
| Sodium chloride (NaCl) | 7599 |
| Sodium phosphate, dibas (Anhydrous) | 142 |
| Sodium Pyruvate | 110 |
| Thiamine hydrochloride | 0.3 |
| Thymidine | 0.7 |
| Vitamin B12 | 1.4 |
| Zinc sulfate (ZnSO4—7H2O) | 0.863 |

REFERENCES

1. *Epithelial cell culture protocols.* edited by Clare Wise. Totowa, N.J.: Humana Press, c2002.
2. Bocker W, Moll R, Poremba C, Holland R, Van Diest P J, Dervan P, Burger H, Wai D, Ina Diallo R, Brandt B, Herbst H, Schmidt A, Lerch M M, Buchwallow I B. Common adult stem cells in the human breast give rise to glandular and myoepithelial cell lineages: a new cell biological concept. *Lab Invest*, 82(6): 737-46, 2002.
3. http://www.cambrex.com/CatNav.catorg.17100.oid.692.navpath.411.prodoid. Mammedia http://www.cambrex.com/RelatedCatNav.catorg.17100.oid.534.prodoid.HMEC.
4. http://www.lbl.gov/LBL-Programs/mrgs/review.html #a4.
5. Speirs V, Green A R, Walton D S, Kerin M J, Fox J N, Carleton P J, Desai S B, Atkin S L. Short-term primary culture of epithelial cells derived from human breast tumors. *Br J Cancer* 78(11): 1421-9, 1998.
6. Stingl J, Eaves C J, Zandieh I, Emerman J T. Characterization of bipotent mammary epithelial progenitor cells in normal adult human breast tissue. *Breast Cancer Res Treat.* 67(2): 93-109, 2001.
7. Gudjonsson T, Villadsen R, Nielsen H L, Ronnov-Jessen L, Bissell M J, Petersen O W. Isolation, immortalization, and characterization of a human breast epithelial cell line with stem cell properties. *Genes Dev.* 16(6): 693-706, 2002.
8. Pechoux C, Gudjonsson T, Ronnov-Jessen L, Bissell M J, Petersen O W. Human mammary luminal epithelial cells contain progenitors to myoepithelial cells. *Dev Biol.* 206 (1): 88-99, 1999.
9. Wagner K U, Boulanger C A, Henry M D, Sgagias M, Hennighausen L, Smith G H. An adjunct mammary epithelial cell population in parous females: its role in functional adaptation and tissue renewal. *Development* 129(6): 1377-86, 2002.
10. Stampfer M R, Yaswen P. Culture systems for study of human mammary epithelial cell proliferation, differentiation and transformation. *Cancer Surv.* 18: 7-34, 1993.
11. Matouskova E, Dudorkinova D, Krasna L, Vesely P. Temporal in vitro expansion of the luminal lineage of human mammary epithelial cells achieved with the 3T3 feeder layer technique. *Breast Cancer Res Treat.* 60(3): 241-9, 2000.
12. Elenbaas B, Spirio L, Koerner F, Fleming M D, Zimonjic D B, Donaher J L, Popescu N C, Hahn W C, Weinberg R A. Human breast cancer cells generated by oncogenic transformation of primary mammary epithelial cells. *Genes Dev.* 15(1): 50-65, 2001.
13. Sherley J L. Asymmetric cell kinetics genes: the key to expansion of adult stem cells in culture. Stem Cells. 2002; 20(6):561-72.
14. Sherley J L, Stadler P B, Johnson D R. Expression of the wild-type p53 antioncogene induces guanine nucleotide-dependent stem cell division kinetics. Proc Natl Acad Sci USA. 1995 Jan. 3; 92(1): 136-40.
15. Rambhatla L, Bohn S A, Stadler P B, Boyd J T, Coss R A, Sherley J L. Cellular Senescence: Ex Vivo p53-Dependent Asymmetric Cell Kinetics. J Biomed Biotechnol. 2001; 1(1):28-37.
16. Lee H S, Crane G G, Merok J R, Tunstead J R, Hatch N L, Panchalingam K, Powers M J, Griffith L G, Sherley J L. Clonal expansion of adult rat hepatic stem cell lines by suppression of asymmetric cell kinetics (SACK). *Biotechnol Bioeng.* 2003 Sep. 30; 83(7):760-71.
17. Lundberg A S, Randell S H, Stewart S A, Elenbaas B, Hartwell K A, Brooks M W, Fleming M D, Olsen J C, Miller S W, Weinberg R A, Hahn W C. Immortalization and transformation of primary human airway epithelial cells by gene transfer. Oncogene. 21(29):4577-86, 2002.
18. J. Liu, G. Yang, J. A. Thompson-Lanza, A. Glassman, K. Hayes, A. Patterson, R. T. Marquez, N. Auersperg, Y. Yu, W. C. Hahn, G. B. Mills, and R. C. Bast Jr. A Genetically Defined Model for Human Ovarian Cancer Cancer Res., 64(5): 1655-1663, 2004.
19. Rangarajan A, Hong S J, Gifford A, Weinberg R A. Species- and cell type-specific requirements for cellular transformation. Cancer Cell. 6(2):171-83, 2004.
20. Andea, A. A., Bouwman, D., Wallis, T., and Visscher, D. W. (2004). Correlation of tumor volume and surface area with lymph node status in patients with multifocal/multicentric breast carcinoma. Cancer 100, 20-27.
21. Andea, A. A., Wallis, T., Newman, L. A., Bouwman, D., Dey, J., and Visscher, D. W. (2002). Pathologic analysis of tumor size and lymph node status in multifocal/multicentric breast carcinoma. Cancer 94, 1383-1390.
22. Bocker, W., Moll, R., Poremba, C., Holland, R., Van Diest, P. J., Dervan, P., Burger, H., Wai, D., Ina Diallo, R., Brandt, B., Herbst, H., Schmidt, A., Lerch, M. M., and Buchwallow, I. B. (2002). Common adult stem cells in the human breast give rise to glandular and myoepithelial cell lineages: A new cell biological concept. Lab Invest 82, 737-746.
23. Brenner, A. J., Stampfer, M. R., and Aldaz, C. M. (1998). Increased p16 expression with first senescence arrest in human mammary epithelial cells and extended growth capacity with p16 inactivation. Oncogene 17, 199-205.
24. Cahill, D. P., Kinzler, K. W., Vogelstein, B., and Lengauer, C. (1999). Genetic instability and darwinian selection in tumours. Trends Cell Biol 9, M57-60.
25. Cardiff, R. D., Anver, M. R., Gusterson, B. A., Hennighausen, L., Jensen, R. A., Merino, M. J., Rehm, S., Russo, J., Tavassoli, F. A., Wakefield, L. M., Ward, J. M., and Green, J. E. (2000). The mammary pathology of genetically engineered mice: The consensus report and recommendations from the annapolis meeting. Oncogene 19, 968-988.
26. Chu, P. G., and Weiss, L. M. (2002). Keratin expression in human tissues and neoplasms. Histopathology 40, 403-439.
27. Dessain, S. K., Yu, H., Reddel, R. R., Beijersbergen, R. L., and Weinberg, R. A. (2000). Methylation of the human telomerase gene cpg island. Cancer Res 60, 537-541.
28. Dimri, G., Band, H., and Band, V. (2005). Mammary epithelial cell transformation: Insights from cell culture and mouse models. Breast Cancer Res 7, 171-179.
29. Dontu, G., Al-Hajj, M., Abdallah, W. M., Clarke, M. F., and Wicha, M. S. (2003). Stem cells in normal breast development and breast cancer. Cell Prolif 36 Suppl 1, 59-72.
30. Elenbaas, B., Spirio, L., Koerner, F., Fleming, M. D., Zimonjic, D. B., Donaher, J. L., Popescu, N. C., Hahn, W. C., and Weinberg, R. A. (2001). Human breast cancer cells generated byoncogenic transformation of primary mammary epithelial cells. Genes Dev 15, 50-65.
31. Fearon, E. R., and Vogelstein, B. (1990). A genetic model for colorectal tumorigenesis. Cell 61, 759-767.
32. Freshney, R. I. (2000). Culture of animal cells: A manual of basic technique, 4th Edition (New York: Wiley).
33. Freshney, R. I., and Freshney, M. G. (2002). Culture of epithelial cells, 2nd Edition (New York: Wiley-Liss).
34. Grigoriadis, A., Mackay, A., Reis-Filho, J. S., Steele, D., Iseli, C., Stevenson, B. J., Jongeneel, C. V., Valgeirsson, H., Fenwick, K., Iravani, M., Leao, M., Simpson, A. J., Strausberg, R. L., Jat, P. S., Ashworth, A., Neville, A. M., and O'Hare, M. J. (2006). Establishment of the epithelialspecific transcriptome of normal and malignant human breast cells based on mpss and array expression data. Breast Cancer Res 8, R56.
35. Gusterson, B. A., Ross, D. T., Heath, V. J., and Stein, T. (2005). Basal cytokeratins and their relationship to the cellular origin and functional classification of breast cancer. Breast Cancer Res 7, 143-148.
36. Hahn, W. C., Counter, C. M., Lundberg, A. S., Beijersbergen, R. L., Brooks, M. W., and Weinberg, R. A. (1999). Creation of human tumour cells with defined genetic elements. Nature 400, 464-468.
37. Hahn, W. C., Dessain, S. K., Brooks, M. W., King, J. E., Elenbaas, B., Sabatini, D. M., DeCaprio, J. A., and Weinberg, R. A. (2002). Enumeration of the simian virus 40 early region elements necessary for human cell transformation. Mol Cell Biol 22, 2111-2123.
38. Hahn, W. C., and Weinberg, R. A. (2002). Modelling the molecular circuitry of cancer. Nat Rev Cancer 2, 331-341.
39. Hammond, S. L., Ham, R. G., and Stampfer, M. R. (1984). Serum-free growth of human mammary epithelial cells: Rapid clonal growth in defined medium and extended serial passage with pituitary extract. Proc Natl Acad Sci USA 81, 5435-5439.
40 Herbert, B. S., Wright, W. E., and Shay, J. W. (2002). P16(ink4a) inactivation is not required to immortalize human mammary epithelial cells. Oncogene 21, 7897-7900.
41 Holst, C. R., Nuovo, G. J., Esteller, M., Chew, K., Baylin, S. B., Herman, J. G., and Tlsty, T. D. (2003). Methylation of p16(ink4a) promoters occurs in vivo in histologically normal human mammary epithelia. Cancer Res 63, 1596-1601.
42. Jones, C., Mackay, A., Grigoriadis, A., Cossu, A., Reis-Filho, J. S., Fulford, L., Dexter, T., Davies, S., Bulmer, K., Ford, E., Parry, S., Budroni, M., Palmieri, G., Neville, A. M., O'Hare, M. J., and Lakhani, S. R. (2004). Expression profiling of purified normal human luminal and myoepithelial breast cells: Identification of novel prognostic markers for breast cancer. Cancer Res 64, 3037-3045.
43. Karakosta, A., Golias, C., Charalabopoulos, A., Peschos, D., Batistatou, A., and Charalabopoulos, K. (2005). Genetic models of human cancer as a multistep process. Paradigm models of colorectal cancer, breast cancer, and chronic myelogenous and acute lymphoblastic leukaemia. J Exp Clin Cancer Res 24, 505-514.
44. Kuperwasser, C., Dessain, S., Bierbaum, B. E., Garnet, D., Sperandio, K., Gauvin, G. P., Naber, S. P., Weinberg, R. A., and Rosenblatt, M. (2005). A mouse model of human breast cancer metastasis to human bone. Cancer Res 65, 6130-6138.
45. Li, Y., Welm, B., Podsypanina, K., Huang, S., Chamorro, M., Zhang, X., Rowlands, T., Egeblad, M., Cowin, P., Werb, Z., Tan, L. K., Rosen, J. M., and Varmus, H. E. (2003). Evidence that transgenes encoding components of the wnt signaling pathway preferentially induce mammary cancers from progenitor cells. Proc Natl Acad Sci USA 100, 15853-15858.
46. Liu, J., Yang, G., Thompson-Lanza, J. A., Glassman, A., Hayes, K., Patterson, A., Marquez, R. T., Auersperg, N., Yu, Y., Hahn, W. C., Mills, G. B., and Bast, R. C., Jr. (2004). A genetically defined model for human ovarian cancer. Cancer Res 64, 1655-1663.
47. Lundberg, A. S., Hahn, W. C., Gupta, P., and Weinberg, R. A. (2000). Genes involved in senescence and immortalization. Curr Opin Cell Biol 12, 705-709.
48. Lundberg, A. S., Randell, S. H., Stewart, S. A., Elenbaas, B., Hartwell, K. A., Brooks, M. W., Fleming, M. D., Olsen, J. C., Miller, S. W., Weinberg, R. A., and Hahn, W. C. (2002). Immortalization and transformation of primary human airway epithelial cells by gene transfer. Oncogene 21, 4577-4586.
49. Matros, E., Wang, Z. C., Lodeiro, G., Miron, A., Iglehart, J. D., and Richardson, A. L. (2005). Brca1 promoter methylation in sporadic breast tumors: Relationship to gene expression profiles. Breast Cancer Res Treat 91, 179-186.
50. Norton, L., and Massague, J. (2006). Is cancer a disease of self-seeding? Nat Med 12, 875-878.
51. Nowell, P. C. (1976). The clonal evolution of tumor cell populations. Science 194, 23-28.
52. Olsson, H. (2000). Tumour biology of a breast cancer at least partly reflects the biology of the tissue/epithelial cell of origin at the time of initiation—a hypothesis. J Steroid Biochem Mol Biol 74, 345-350.

53. Rangarajan, A., Hong, S. J., Gifford, A., and Weinberg, R. A. (2004). Species- and cell type specific requirements for cellular transformation. Cancer Cell 6, 171-183.
54. Richardson, A. L., Wang, Z. C., De Nicolo, A., Lu, X., Brown, M., Miron, A., Liao, X., Iglehart, J. D., Livingston, D. M., and Ganesan, S. (2006). X chromosomal abnormalities in basal-like human breast cancer. Cancer Cell 9, 121-132.
55. Romanov, S. R., Kozakiewicz, B. K., Holst, C. R., Stampfer, M. R., Haupt, L. M., and Tlsty, T. D. (2001). Normal human mammary epithelial cells spontaneously escape senescence and acquire genomic changes. Nature 409, 633-637.
56. Rosen, P. P. (2001). Rosen's breast pathology, 2nd Edition (Philadelphia: Lippincott Williams & Wilkins).
57. Saldanha, A. J. (2004). Java tree view—extensible visualization of microarray data. Bioinformatics 20, 3246-3248.
58. Sandhu, C., Donovan, J., Bhattacharya, N., Stampfer, M., Worland, P., and Slingerland, J. (2000). Reduction of cdc25a contributes to cyclin el-cdk2 inhibition at senescence in human mammary epithelial cells. Oncogene 19, 5314-5323.
59. Signoretti, S., Di Marcotullio, L., Richardson, A., Ramaswamy, S., Isaac, B., Rue, M., Monti, F., Loda, M., and Pagano, M. (2002). Oncogenic role of the ubiquitin ligase subunit skp2 in human breast cancer. J Clin Invest 110, 633-641.
60. Smyth, G. K. (2004). Linear models and empirical bayes methods for assessing differential expression in microarray experiments. Stat Appl Genet Mol Biol 3, Article 3.
61. Sorlie, T., Perou, C. M., Tibshirani, R., Aas, T., Geisler, S., Johnsen, H., Hastie, T., Eisen, M. B., van de Rijn, M., Jeffrey, S. S., Thorsen, T., Quist, H., Matese, J. C., Brown, P. O., Botstein, D., Eystein Lonning, P., and Borresen-Dale, A. L. (2001). Gene expression patterns of breast carcinomas distinguish tumor subclasses with clinical implications. Proc Natl Acad Sci USA 98, 10869-10874.
62. Sorlie, T., Tibshirani, R., Parker, J., Hastie, T., Marron, J. S., Nobel, A., Deng, S., Johnsen, H., Pesich, R., Geisler, S., Demeter, J., Perou, C. M., Lonning, P. E., Brown, P. O., Borresen-Dale, A. L., and Botstein, D. (2003). Repeated observation of breast tumor subtypes in independent gene expression data sets. Proc Natl Acad Sci USA 100, 8418-8423.
63. Stampfer, M. R., and Yaswen, P. (2000). Culture models of human mammary epithelial cell transformation. J Mammary Gland Biol Neoplasia 5, 365-378.
64. Tlsty, T. D., Crawford, Y. G., Holst, C. R., Fordyce, C. A., Zhang, J., McDermott, K., Kozakiewicz, K., and Gauthier, M. L. (2004). Genetic and epigenetic changes in mammary epithelial cells may mimic early events in carcinogenesis. J Mammary Gland Biol Neoplasia 9, 263-274.
65. Vogelstein, B., and Kinzler, K. W. (1993). The multistep nature of cancer. Trends Genet 9, 138-141.
66. Wang, Z. C., Lin, M., Wei, L. J., Li, C., Miron, A., Lodeiro, G., Harris, L., Ramaswamy, S., Tanenbaum, D. M., Meyerson, M., Iglehart, J. D., and Richardson, A. (2004). Loss of heterozygosity and its correlation with expression profiles in subclasses of invasive breast cancers. Cancer Res 64, 64-71.
67. Watnick, R. S., Cheng, Y. N., Rangarajan, A., Ince, T. A., and Weinberg, R. A. (2003). Ras modulates myc activity to repress thrombospondin-1 expression and increase tumor angiogenesis. Cancer Cell 3, 219-231.
68. Welm, B., Behbod, F., Goodell, M. A., and Rosen, J. M. (2003). Isolation and characterization of functional mammary gland stem cells. Cell Prolif 36 Suppl 1, 17-32.
69. Wu, Z., and Irizarry, R. A. (2005). Stochastic models inspired by hybridization theory for short oligonucleotide arrays. J Comput Biol 12, 882-893.
70. Yaswen, P., and Stampfer, M. R. (2001). Epigenetic changes accompanying human mammary epithelial cell immortalization. J Mammary Gland Biol Neoplasia 6, 223-234.
71. Zhao, J. J., Gjoerup, O. V., Subramanian, R. R., Cheng, Y., Chen, W., Roberts, T. M., and Hahn, W. C. (2003). Human mammary epithelial cell transformation through the activation of phosphatidylinositol 3-kinase. Cancer Cell 3, 483-495.
72. Zimonjic, D., Brooks, M. W., Popescu, N., Weinberg, R. A., and Hahn, W. C. (2001). Derivation of human tumor cells in vitro without widespread genomic instability. Cancer Res 61, 8838-8844.
73. Christoph E. Dumelin, Jörg Scheuermann, Samu Melkko, and Dario Neri, *Bioconjugate Chem.*, 17 (2), 366-370, 2006. Selection of Streptavidin Binders from a DNA-Encoded Chemical Library.
74. Gartner Z J, Tse B N, Grubina R, Doyon J B, Snyder™, Liu D R., Science. 2004 Sep. 10; 305(5690):1601-5. DNA-templated organic synthesis and selection of a library of macrocycles.
75. Thijn R Brummelkamp, Armida W M Fabius, Jasper Mullenders, Mandy Madiredjo Amo Velds, Ron M Kerkhoven, Rene Bemards and Roderick L Beijersbergen, Nature Chemical Biology 2, 202-206 (2006) An shRNA barcode screen provides insight into cancer cell vulnerability to MDM2 inhibitors.
76. Noren K A, Noren C J., Methods. 2001 February; 23(2):169-78. Construction of high-complexity combinatorial phage display peptide libraries.
77. Scheuermann J, Dumelin C E, Melkko S, Neri D, J Biotechnol. 2006 Dec. 1; 126(4):568-81. Epub 2006 Jun. 9. DNA-encoded chemical libraries.
78. Takahashi T T, Austin R J, Roberts R W., Trends Biochem Sci. 2003 March; 28(3):159-65. mRNA display: ligand discovery, interaction analysis and beyond.

All cited references, US and foreign patents or patent publications, are incorporated herein by reference. It should be understood that where the instant invention discloses a medium, the invention provides methods of making the medium, kits containing the medium, methods comprising culturing cells in the medium, cells cultured in the medium, and methods of using the cells.

What is claimed is:
1. A cell culture medium comprising:
equal volumes of F12 medium and Medium 199 supplemented with the following added components: 4-(2-hydroxyethyl)-1-piperazine ethanesulfonic acid (HEPES) pH 7.4; glutamine; insulin; epidermal growth factor (EGF); hydrocortisone; transferrin; triiodothyronine; O-phosphoryl ethanolamine; selenious acid; 17β estradiol; linoleic acid; all-trans retinoic acid; hypoxanthine monosodium (hypoxanthine (Na)); lipoic acid; cholesterol; glutathione; xanthine; ascorbic acid; alpha-tocopherol phosphate; calciferol; choline chloride; folic acid; vitamin B12; thiamine hydrochloride (thiamine HCl); i-inositol; uracil; ribose; para-aminobenzoic acid; and bovine serum albumin, wherein the insulin is added at a concentration of 20 μg/mL, the EGF is added at a concentration of 10 ng/mL, the hydrocortisone is added at a concentration of 0.5 μg/mL, and the culture medium is further supplemented with cholera toxin at a concentration of 25 ng/mL, and wherein the medium is useful for culturing tumor cells obtained from ovary, fallopian tube, or mesothelium tissue.

2. The medium of claim 1, wherein the following supplemental components are added at the following concentrations: HEPES pH 7.4 at a concentration of 10 mM; glutamine at a concentration of 2 mM; insulin at a concentration of 20 µg/mL; EGF at a concentration of 10 ng/mL; hydrocortisone at a concentration of 0.5 µg/mL; transferrin at a concentration of 10 µg/mL; triiodothyronine at a concentration of 0.2 pg/mL; O-phosphoryl ethanolamine at a concentration of 5 µg/mL; selenious acid at a concentration of 8 ng/mL; 17β estradiol at a concentration of 0.5 ng/mL; linoleic acid at a concentration of 5 µg/mL; all-trans retinoic acid at a concentration of 0.025 µg/mL; hypoxanthine Na at a concentration of 1.75 µg/mL; lipoic acid at a concentration of 0.05 µg/mL; cholesterol at a concentration of 0.05 µg/mL; glutathione at a concentration of 0.012 µg/mL; xanthine at a concentration of 0.085 µg/mL; ascorbic acid at a concentration of 0.012 µg/mL; alpha-tocopherol phosphate at a concentration of 0.003 µg/mL; calciferol at a concentration of vitamin D, 0.025 µg/mL; choline chloride at a concentration of 3.5 µg/mL; folic acid at a concentration of 0.33 µg/mL; vitamin B12 at a concentration of 0.35 µg/mL; thiamine HCl at a concentration of 0.08 µg/mL; i-inositol at a concentration of 4.5 µg/mL; uracil at a concentration of 0.075 µg/mL; ribose at a concentration of 0.125 µg/mL; para-aminobenzoic acid at a concentration of 0.012 µg/mL; and bovine serum albumin at a concentration of 1.25 mg/mL.

3. The medium of claim 1, wherein the medium contains none or trace amount of calf or fetal bovine serum.

4. The medium of claim 1, further comprising 0.1-0.2% serum.

5. The medium of claim 1, further comprising 0.1-5% serum.

6. The medium of claim 1, further comprising 1-5% serum.

* * * * *